US011578059B2

(12) United States Patent
Tapper et al.

(10) Patent No.: US 11,578,059 B2
(45) Date of Patent: Feb. 14, 2023

(54) KDM1A INHIBITORS FOR THE TREATMENT OF DISEASE

(71) Applicant: Imago Biosciences, Inc., San Carlos, CA (US)

(72) Inventors: Amy E. Tapper, San Carlos, CA (US); Cassandra Celatka, Hull, MA (US); Michael Clare, Skokie, IL (US); Hugh Y. Rienhoff, Jr., San Carlos, CA (US)

(73) Assignee: Imago Biosciences. Inc., San Carlos, CA (US)

( * ) Notice: Subject to any disclaimer, the term of this patent is extended or adjusted under 35 U.S.C. 154(b) by 132 days.

(21) Appl. No.: 17/054,126

(22) PCT Filed: May 13, 2019

(86) PCT No.: PCT/US2019/032043
§ 371 (c)(1),
(2) Date: Nov. 9, 2020

(87) PCT Pub. No.: WO2019/217972
PCT Pub. Date: Nov. 14, 2019

(65) Prior Publication Data
US 2021/0115023 A1    Apr. 22, 2021

Related U.S. Application Data

(60) Provisional application No. 62/670,323, filed on May 11, 2018.

(51) Int. Cl.
| A61K 31/497 | (2006.01) |
| C07D 403/14 | (2006.01) |
| A61K 9/00 | (2006.01) |
| A61K 31/501 | (2006.01) |
| A61K 31/506 | (2006.01) |
| A61K 31/5377 | (2006.01) |
| A61K 31/541 | (2006.01) |
| A61K 45/06 | (2006.01) |
| C07D 241/08 | (2006.01) |
| C07D 401/04 | (2006.01) |
| C07D 401/14 | (2006.01) |
| C07D 403/04 | (2006.01) |
| C07D 403/10 | (2006.01) |
| C07D 491/107 | (2006.01) |

(52) U.S. Cl.
CPC .......... *C07D 403/14* (2013.01); *A61K 9/0053* (2013.01); *A61K 31/497* (2013.01); *A61K 31/501* (2013.01); *A61K 31/506* (2013.01); *A61K 31/5377* (2013.01); *A61K 31/541* (2013.01); *A61K 45/06* (2013.01); *C07D 241/08* (2013.01); *C07D 401/04* (2013.01); *C07D 401/14* (2013.01); *C07D 403/04* (2013.01); *C07D 403/10* (2013.01); *C07D 491/107* (2013.01)

(58) Field of Classification Search
None
See application file for complete search history.

(56) References Cited

U.S. PATENT DOCUMENTS

| 9,790,195 | B2 | 10/2017 | McCall |
| 9,981,922 | B2 | 5/2018 | Rienhoff, Jr. |
| 10,370,346 | B2 | 8/2019 | Rienhoff, Jr. |
| 10,519,118 | B2 | 12/2019 | Rienhoff, Jr. |
| 10,882,835 | B2 | 1/2021 | McCall |
| 11,230,534 | B2 | 1/2022 | Rienhoff, Jr. |
| 11,390,590 | B2 | 7/2022 | Tapper |
| 2009/0162909 | A1 | 6/2009 | Campopiano |
| 2009/0191605 | A1 | 7/2009 | Liang |
| 2010/0173369 | A1 | 7/2010 | Savile |
| 2012/0108500 | A1 | 5/2012 | Sakane |
| 2013/0090386 | A1 | 4/2013 | Ortega |
| 2015/0225401 | A1 | 8/2015 | Wu |
| 2015/0232436 | A1 | 8/2015 | Baker |
| 2016/0130215 | A1 | 5/2016 | Tomita |
| 2016/0237043 | A1 | 8/2016 | Rienhoff, Jr. |
| 2016/0257662 | A1 | 9/2016 | McCall |
| 2017/0334873 | A1 | 11/2017 | McCall |
| 2018/0312474 | A1 | 11/2018 | Rienhoff, Jr. |
| 2019/0070172 | A1 | 3/2019 | Rienhoff, Jr. |
| 2020/0095214 | A1 | 3/2020 | McCall |
| 2020/0283397 | A1 | 9/2020 | Rienhoff, Jr. |

(Continued)

FOREIGN PATENT DOCUMENTS

| EP | 2177502 | 4/2010 |
| EP | 2927212 | 10/2015 |

(Continued)

OTHER PUBLICATIONS

Alvarez-Larrán, A. et al., "Red Cell Mass Measurement in Patients with Clinically Suspected Diagnosis of Polycythemia Vera or Essential Thrombocythemia", Haematologica, 97(11):1704-7, (2012).
Banker, G. et al., Modern Pharmaceutics, Marcel Dekker, New York, 3rd ed., pp. 451 & 596, (1996).
Benelkebir, H. et al., "Enantioselective Synthesis of Tranylcypromine Analogues as Lysine Demethylase (LSD1) Inhibitors", Bioorg Med Chem., 19(12):3709-16, (2011).
Binda, C. et al., "Biochemical, Structural, and Biological Evaluation of Tranylcypromine Derivatives as Inhibitors of Histone Demethylases LSD1 and LSD2", J Am Chem Soc., 132(19):6827-33, (2010).

(Continued)

*Primary Examiner* — Samantha L Shterengarts
(74) *Attorney, Agent, or Firm* — Dennis A. Bennett; Lauren L. Stevens; Cynthia Hathaway

(57) ABSTRACT

The present disclosure relates to compounds and methods which may be useful as inhibitors of KDM1A for the treatment or prevention of diseases. Methods of inhibition of KDM1A, methods of increasing gamma globin gene expression, and methods to induce differentiation in cancer cells in a human or animal subject are also provided for treatment of disease such as acute myelogenous leukemia.

30 Claims, No Drawings

(56) References Cited

U.S. PATENT DOCUMENTS

| | | |
|---|---|---|
| 2021/0147373 A1 | 5/2021 | McCall |
| 2021/0196711 A1 | 7/2021 | Rienhoff, Jr. |
| 2022/0025424 A1 | 1/2022 | Tapper |
| 2022/0073477 A1 | 3/2022 | Rienhoff, Jr. |

FOREIGN PATENT DOCUMENTS

| | | |
|---|---|---|
| WO | 2006037028 | 4/2006 |
| WO | 2008103277 | 8/2008 |
| WO | 2009001132 | 12/2008 |
| WO | 2010043721 | 4/2010 |
| WO | 2010143582 | 12/2010 |
| WO | 2011035941 | 3/2011 |
| WO | 2011042217 | 4/2011 |
| WO | 2011131576 | 10/2011 |
| WO | 2011131697 | 10/2011 |
| WO | 2012013727 | 2/2012 |
| WO | 2012013728 | 2/2012 |
| WO | 2012034116 | 3/2012 |
| WO | 2012045883 | 4/2012 |
| WO | 2012047852 | 4/2012 |
| WO | 2012071469 | 5/2012 |
| WO | 2012107498 | 8/2012 |
| WO | 2012107499 | 8/2012 |
| WO | 2012135113 | 10/2012 |
| WO | 2013057320 | 4/2013 |
| WO | 2013057322 | 4/2013 |
| WO | 2014084298 | 6/2014 |
| WO | 2014086790 | 6/2014 |
| WO | 2014164867 | 10/2014 |
| WO | 2014205511 | 12/2014 |
| WO | 2015021128 | 2/2015 |
| WO | 2015123465 | 8/2015 |
| WO | 2015162064 | 10/2015 |
| WO | 2015200843 | 12/2015 |
| WO | 2016130952 | 8/2016 |
| WO | 2017079753 | 5/2017 |
| WO | 2017116558 | 7/2017 |
| WO | 2017195216 | 11/2017 |
| WO | 2018035249 | 2/2018 |
| WO | 2018035259 | 2/2018 |
| WO | 2018106984 | 6/2018 |
| WO | 2019217972 | 11/2019 |

OTHER PUBLICATIONS

Byrn, S. et al., Solid-State Chemistry of Drugs, 2nd Ed., Ch. 11 Hydrates and Solvates, 233-47, (1999).

Contente, M. et al., "Preparation of Enantiomerically Enriched Aromatic β-Hydroxynitriles and Halohydrins by Ketone Reduction with Recombinant Ketoreductase KRED1-Pglu", Tetrahedron, 72(27-28):3974-9, (2016).

Gooden, D. et al., "Facile Synthesis of Substituted Trans-2-Arylcyclopropylamine Inhibitors of the Human Histone Demethylase LSD1 and Monoamine Oxidases A and B", Bioorg Med Chem Lett., 18(10):3047-51, (2008).

International Application No. PCT/US2014/023659; International Preliminary Report on Patentability, dated Sep. 15, 2015; 06 pages.
International Application No. PCT/US2014/023659; International Search Report and Written Opinion of the International Searching Authority, dated Jul. 29, 2014; 09 pages.
International Application No. PCT/US2014/049906; International Preliminary Report on Patentability, dated Feb. 9, 2016; 07 pages.
International Application No. PCT/US2014/049906; International Search Report and Written Opinion of the International Searching Authority, dated Oct. 27, 2016; 08 pages.
International Application No. PCT/US2016/017809; International Preliminary Report on Patentability, dated Aug. 15, 2017; 6 pages.
International Application No. PCT/US2016/017809; International Search Report and Written Opinion of the International Searching Authority, dated May 5, 2016; 8 pages.
International Application No. PCT/US2016/060847; International Preliminary Report on Patentability, dated May 8, 2018; 10 pages.
International Application No. PCT/US2016/060847; International Search Report and Written Opinion of the International Searching Authority, dated Jan. 24, 2017; 14 pages.
International Application No. PCT/US2017/047192; International Preliminary Report on Patentability, dated Feb. 19, 2019; 6 pages.
International Application No. PCT/US2017/047192; International Search Report and Written Opinion of the International Searching Authority, dated Jan. 9, 2018; 9 pages.
International Application No. PCT/US2017/047208; International Search Report and Written Opinion of the International Searching Authority, dated Oct. 30, 2017; 6 pages.
International Application No. PCT/US2019/032043; International Preliminary Report on Patentability, dated Oct. 26, 2020; 7 pages.
International Application No. PCT/US2019/032043; International Search Report and Written Opinion of the International Searching Authority, dated Aug. 23, 2019; 10 pages.
Kaluzna, I. et al., "Ketoreductases: Stereoselective Catalysts for the Facile Synthesis of Chiral Alcohols", Tetrahedron: Asymmetry, 16(22):3682-9, (2005).
Kleppe, M. et al., "Lysine-Specific Histone Demethylase, LSD1, (KDM1A) As a Novel Therapeutic Target in Myeloproliferative Neoplasms", Blood, 126(23):601; 7 pages.
Kreipe, H. et al., "Clonal Granulocytes and Bone Marrow Cells in the Cellular Phase of Agnogenic Myeloid Metaplasia", Blood, 78(7):1814-17, (1991).
Leoni, F. et al., "The Histone Deacetylase Inhibitor ITF2357 Reduces Production of Pro-Inflammatory Cytokines in Vitro and Systemic Inflammation in Vivo", Mol Med., 11(1-12):1-15, (2005).
Lerchner, A. et al., "Macrocyclic BACE-1 Inhibitors Acutely Reduce Abeta in Brain After Po Application", Bioorg Med Chem Lett., 20(2):603-7, (2010).
Lizcano, F. et al., "Epigenetic Control and Cancer: The Potential of Histone Demethylases as Therapeutic Targets", Pharmaceuticals (Basel), 5(9):963-90, (2012).
Mesa, R. et al., "The Myelofibrosis Symptom Assessment Form (MFSAF): An Evidence-Based Brief Inventory to Measure Quality of Life and Symptomatic Response to Treatment in Myelofibrosis", Leuk Res., 33(9):1199-203, (2009).
Morissette, S. et al., "High-Throughput Crystallization: Polymorphs, Salts, Co-Crystals and Solvates of Pharmaceutical Solids", Adv Drug Deliv Rev., 56(3):275-300, (2004).
Myeloproliferative Disorders: University of Maryland Medical Center. (2016). Web: <http://umm.edu/health/medical/altmed/condition/myeloproliferative-disorders>.
Ogasawara, D. et al., "Lysine-Specific Demethylase 1-Selective Inactivators: Protein-Targeted Drug Delivery Mechanism", Angew Chem Int Ed Engl., 52(33):8620-4, (2013).
Ogasawara, D. et al., "Synthesis and Biological Activity of Optically Active NCL-1, A Lysine-Specific Demethylase 1 Selective Inhibitor", Bioorg Med Chem., 19(12):3702-8, (2011).
Quintás-Cardama, A. et al., "Therapy with the Histone Deacetylase Inhibitor Pracinostat for Patients with Myelofibrosis", Leuk Res., 36(9):1124-7, (2012).
Rouhi, A., "The Right Stuff", C&EN:Science and Technology, 81(8):32-5, (2003).
Sareddy, G. et al., "KDM1 is a Novel Therapeutic Target for the Treatment of Gliomas", Oncotarget., 4(1):18-28, (2013).
Schnittger, S. et al., "FLT3 Length Mutations as Marker for Follow-Up studies in Acute Myeloid Leukaemia", Acta Haematol., 112(1-2):68-78, (2004).
Tefferi, A . . . et al., "Splenectomy in Myelofibrosis with Myeloid Metaplasia: A Single-Institution Experience with 223 Patients", Blood, 95(7):2226-33, (2000).
The Cleveland Clinic. Myelofibrosis: Prevention. Web: https//my.clevelandclinic.org/health/diseases/15672-myelofibrosis/prevention; 4 pages, (2015).
U.S. Appl. No. 14/910,423; Applicant-Intiated Interview Summary, dated Jun. 12, 2017; 2 pages.
U.S. Appl. No. 14/910,423; Applicant-Intiated Interview Summary, dated May 1, 2019; 3 pages.

(56) References Cited

OTHER PUBLICATIONS

U.S. Appl. No. 14/910,423; Final Office Action, dated Apr. 18, 2017; 7 pages.
U.S. Appl. No. 14/910,423; Non-Final Office Action, dated Sep. 16, 2016; 13 pages.
U.S. Appl. No. 14/910,423; Notice of Allowance, dated Jun. 12, 2017; 4 pages.
U.S. Appl. No. 14/910,423; Notice of Allowance, dated May 2, 2017; 7 pages.
U.S. Appl. No. 15/043,121; Examiner-Intiated Interview Summary, dated Jan. 12, 2018; 1 page.
U.S. Appl. No. 15/043,121; Examiner-Intiated Interview Summary, dated Sep. 18, 2017; 1 page.
U.S. Appl. No. 15/043,121; Non-Final Office Action, dated May 19, 2017; 12 pages.
U.S. Appl. No. 15/043,121; Notice of Allowance, dated Jan. 12, 2018; 7 pages.
U.S. Appl. No. 15/043,121; Notice of Allowance, dated Sep. 18, 2017; 9 pages.
U.S. Appl. No. 15/667,166; Corrected Notice of Allowance, dated May 8, 2019; 8 pages.
U.S. Appl. No. 15/667,166; Examiner-Initiated Interview Summary, dated May 8, 2019; 1 page.
U.S. Appl. No. 15/667,166; Non-Final Office Action, dated Aug. 23, 2018; 9 pages.
U.S. Appl. No. 15/667,166; Notice of Allowance, dated Mar. 19, 2019; 16 pages.
U.S. Appl. No. 15/773,911; Final Office Action, dated Oct. 9, 2020; 26 pages.
U.S. Appl. No. 15/773,911; Non-Final Office Action, dated Jan. 22, 2020; 38 pages.
U.S. Appl. No. 15/952,073; Applicant-Initiated Interview Summary, dated Aug. 6, 2019; 2 pages.
U.S. Appl. No. 15/952,073; Final Office Action, dated Apr. 11, 2019; 13 pages.
U.S. Appl. No. 15/952,073; Non-Final Office Action, dated Sep. 6, 2018; 31 pages.
U.S. Appl. No. 15/952,073; Notice of Allowance, dated Aug. 6, 2019; 9 pages.
U.S. Appl. No. 16/326,495; Application as filed, filed Feb. 19, 2019; 116 pages.
U.S. Appl. No. 16/326,498; Application as filed, filed Feb. 19, 2019; 61 pages.
U.S. Appl. No. 16/445,768; Application as filed, filed Jun. 19, 2019; 128 pages.
U.S. Appl. No. 16/445,768; Notice of Allowance, dated Sep. 2, 2020; 18 pages.
Wang, J. et al., "Novel Histone Demethylase LSD1 Inhibitors Selectively Target Cancer Cells with Pluripotent Stem Cell Properties", Cancer Res., 71(23)7238-49, (2011).
Wolff, M., Burger's Medicinal Chemistry and Drug Discovery, Principles and Practice, John Wiley & Sons, 5(1):975-7, (1995).
Zeppa, P. et al., "Fine-Needle Aspiration Biopsy and Flow Cytometry Immunophenotyping of Lymphoid and Myeloproliferative Disorders of the Spleen", Cancer, 99(2):118-27, (2003).
Devos, D. et al., "Practical limits of function prediction", Proteins, 41(1):98-107, (2000).
Kisselev, L., "Polypeptide Release Factors in Prokaryotes and Eukaryotes: Same Function, Different Structure", Structure, 10: 8-9, (2002).
Miyamura, S. et al., "C—H activation enables a rapid structure-activity relationship study of arylcyclopropyl amines for potent and selective LSDI inhibitors", Org Biomol Chem., 14(36):8576-85, (2016).
U.S. Appl. No. 16/326,495; Non-Final Office Action, dated Oct. 29, 2021; 28 pages.
U.S. Appl. No. 16/326,495; Notice of Allowance, dated Mar. 16, 2022; 11 pages.
U.S. Appl. No. 16/326,498; Non-Final Office Action, dated Jun. 7, 2022; 35 pages.
U.S. Appl. No. 16/326,498; Sturcture—Search pdf, pp. 1-81, (2022).
U.S. Appl. No. 16/672,083; Notice of Allowance, dated Jun. 23, 2021; 11 pages.
Whisstock, J. et al., "Prediction of protein function from protein sequence and structure", Q Rev Biophys., 36(3):307-40, (2003).
Witkowski, A. et al., "Conversion of a beta-ketoacyl synthase to a malonyl decarboxylase by replacement of the active-site cysteine with glutamine", Biochemistry, 38(36):11643-50, (1999).

KDM1A INHIBITORS FOR THE TREATMENT OF DISEASE

This application claims the benefit of priority of U.S. Provisional Application No. 62/670,323 filed 11 May 2018, the disclosure of which is hereby incorporated by reference as if written herein in its entirety.

The present disclosure relates to new compounds and compositions and their application as pharmaceuticals for the treatment of diseases.

Inhibiting the enzyme KDM1A (also known as lysine-specific demethylase 1, LSD1, Flavin-containing Amine Oxidase Domain-Containing Protein, AOF2, BRAF35-HDAC Complex Protein BHC110, FAD-Binding Protein BRAF35-HDAC Complex), may alter gene expression in cells sufficient to restore their proper physiologic function or that of the tissue, organ or the patient as a whole. This may be achieved either by enhancing transcription of a gene or genes that are pathologically silenced, e.g., as is the case in some cancer cells and heritable diseases, or decreasing transcription of a gene or genes participating in the pathological state. As such, inhibiting KDM1A would be useful for the treatment of diseases such as cancer and heritable diseases such as Wilson disease, cardiomyopathies, and hemoglobinopathies.

Gene expression is regulated through the recruitment of the RNA polymerase II transcription apparatus to the DNA template. The probability of this large multi-protein complex arriving near or at the start of DNA transcription and progressing through the entire coding region of a gene is determined in part by specific DNA sequences called promoters and enhancers, modifications of DNA sequence in the vicinity of the start of transcription, proteins bound to DNA and the topology of the DNA template itself. Factors enhancing the probability of RNA synthesis of protein-coding genes are known as transcription factors some of which participate in the transcription of all protein-coding genes and some of which are specific for the transcription of individual genes.

One major mechanism of transcription control consists of limiting the physical accessibility of the transcriptional regulatory regions to proteins that can activate or complete transcription; proteins bound to promoter or enhancer DNA sequences can occlude activating factors from binding to these DNA sequences resulting in fewer transcription initiations or extension of the activated progressing RNA polymerase complex. Likewise, topological constraints that do not allow the template DNA to unwind sufficiently to permit the steady progression of RNA polymerase on the template also serve to limit transcription rates.

The most important general factors influencing RNA synthesis using a DNA template in vivo are modifications of histones proteins that control among other factors the topology of the DNA template for transcription and its accessibility by the RNA polymerase complex. A small family of histone proteins—H2A, H2B, H3 and H4—combines to create a scaffold called the histone octamer upon which DNA is spatially and topologically organized into a regular repetitive structure called the nucleosome along the length of DNA. The conglomerate of histones, other proteins, various RNAs and DNA is called chromatin. Both DNA and histones are chemically modified in such a way as to attract and bind or repel other proteins with the effect of enhancing or repressing transcription.

The modification of DNA and associated RNAs and proteins that influence the regulation of transcription and replication that does not involve substitution of the canonical DNA bases is termed epigenetic. These epigenetic influences involve reversible chemical modifications of the four DNA bases themselves or post-translational chemical changes to the chromatin proteins and RNDs that associate with DNA. These epigenetic processes can play a pivotal role in activating or silencing the expression of a gene; in addition, the epigenetic modifications can be maintained for the life of an organism or can be dynamically modified in response to specific biochemical signals that originate either internally within the cell or extracellularly. These chromatin alterations can happen quickly or be very stable, e.g., during the hormonal induction of gene expression, chromatin structure at a specific locus can change radically within seconds to permit maximal transcription or chromatin structure can be modified to fully suppress gene expression, a state of chromatin which can be stably maintained over multiple cell divisions and even transgenerationally.

The methylation of cytosine at the 5' position is a common DNA base modification that is in turn recognized by a class of proteins most often associated with transcriptional repression. Similarly, histone proteins are chemically modified but with a wider variety of chemical adducts each of which either alone or in combination enhances or represses transcription of nearby genes. These histone modifications include, among others methylation, acetylation, sumoylation, phosphorylation, ubiquitylation, and myristoylation are recognized by other chromatin-associated proteins that in turn influence transcription rates and DNA replication. The dynamic state of gene expression and the associated chromatin states imply that histone modifications are not permanent but instead are added and removed according to the needs of the cell for specific gene products at specific times during ontogeny, adult life and the changing influences of the environment. Indeed, the specific chemical modifications of histones are each made by classes of enzymes acting at specific sites. These histone-modifying enzymes are in turn subject to tight regulation. These enzymes can potentially be targeted by compounds that inhibit their activity with the consequence of altering gene expression in a therapeutic manner.

Changes in the state of histone methylation are now known to play critical roles in normal regulation of the cell cycle and growth, the response to DNA damage and stress, and pre-natal development including differentiation. Pathological states such as cancer are associated with altered patterns of histone modifications and dysregulated histone-modifying proteins including chromatin-modifying enzymes. The need to closely regulate histone modifications is evidenced by the association of histone methylation status with human morbidity including ageing.

Histone methylation can occur on any of the three basic amino acid residues—lysine (K), arginine (R), and histidine (H). Methylation of histone H3 on lysines at positions 4 (H3K4), 9 (H3K9), 27 (H3K27), 36 (H3K36) and 79 (H3K79) are among the best studied of histone modifications that influence gene expression. Lysine tri-methylation (Kme3) on histone 3 (H3) at position 4 (H3K4me3) is a histone mark generally associated with activation of gene expression while H3K9me1 or H3K27me3 are associated with the repression of gene transcription. H3K4me1 is associated with DNA enhancers of gene transcription while H3K4me3 is associated with gene promoter activity. Likewise, loss of the methyl group at H3K4 is associated with repression of gene expression. Thus, the addition and removal of methyl groups at H3K4 constitutes a gene transcription switch. It is also evident that lysine can be modified with a mono-, di- or tri-methyl groups, each modification having a different biological effect through the attraction of different proteins recognizing those specific methylation modifications at that site.

A critical aspect of the regulation of the state of histone methylation is the recruitment of methyltransferases and demethylases to specific genetic loci. DNA sequence-specific binding proteins including transcription factors are one class of proteins responsible for this recruitment through the assemblage of protein complexes that bind these methyl-transferring enzymes. A well-studied example is the *Drosophila melanogaster* trithrorax group (TrxG) response elements (TREs) which recruit the H3K4 methyltransferase, TRX, to specific genes via transcription factors that recognize the TRE DNA sequence.

The histone methylation marks are recognized by methyl-binding domains in a diverse group of proteins; these domains include PHD fingers, WD40 and ankyrin repeats, CW and PWWP domains, and the Royal superfamily of proteins. These proteins, in turn, determine which additional activities are recruited into chromatin sites and ultimately the state of transcription at a given locus. Indeed, depending on which methyl-recognition protein binds the marked histone, the same methyl-lysine modification can have opposing effects on transcription. H3K4me2 and H3K4me3 are associated with transcriptional activation, but when bound by the PHD-domain-containing co-repressor protein Inhibitor of Growth family member 2 (ING2), an associated histone deacetylase complex is stabilized repressing gene expression. Thus, these effector proteins recognizing the methyl-lysine histone modifications significantly influence the level of transcriptional activity.

The ability to alter gene expression selectively by modifying the state of chromatin allows a novel therapeutic strategy to induce or de-repress the expression of genes that can provide a benefit, especially for genes whose expression has been suppressed by pathological mechanism as in the case of some cancers or suppressed by physiologic mechanism but who de-repression can phenotypically suppress mutations in paralogous genes with complementary function.

Many genes within a genome are members of gene families as a consequence of gene duplication. These genes are termed paralogs of one another. Following gene duplication, patterns of expression of two genes will evolve in a distinct manner in part to control the effects of gene dosage. Following gene duplication, random genetic drift arising from naturally occurring mutations and the subsequent selection of nucleotide sequence is commonly observed first in non-coding regions of duplicated genes, often in transcriptional regulatory regions. DNA changes in regulatory sequences can influence any or all aspects of gene expression: the magnitude of expression, its developmental timing, induction by stimuli outside the cell including hormonal or metabolic signals, and the cell type in which expression is restricted. In instances in which the duplication is recent in evolutionary time or where natural selection has maintained a high degree of protein-coding sequence similarity, the gene product of one paralog, gene A, can complement the pathological loss or silencing of the other paralog, gene B, if expression of gene A is not limiting in the same cell.

Altering patterns of gene expression may offer profound therapeutic benefits for genetic conditions in which enhanced expression of a paralogous gene "rescues" a phenotype caused by a mutation in a paralog. This might be called autologous gene complementation. In the case of Wilson disease caused by mutations in ATP7B, enhanced expression by pharmacologic induction of ATP7A, a closely related copper transporter protein, might rescue mutations in ATP7B, another copper transporter. The basic function of each copper transporter protein has been preserved but following the duplication of the common ancestral gene, the expression of these two genes has been separated spatially, one confined to intestinal enterocytes, the other to hepatocytes. This one of many examples of paralogous gene in which one gene can complement the loss of the second if appropriately expressed in the same cell or tissue.

A notable example of a paralogous gene family is the well-studied alpha and beta family of globin genes coding for the alpha and beta subunits of hemoglobin. Five beta-like genes each arising by gene duplication are arrayed next to each other on chromosome 16 with each gene being transcribed in a temporally-specific manner throughout the 9 months of human embryonic and fetal development. The five beta-like globin proteins share a high degree of protein sequence similarity, so much so that genetic mutations inactivating the adult beta globin gene can be clinically silent if expression of any one of the other 4 subunit members of the beta-like globin family is adequate. Activation of expression and subsequent transcriptional silencing of each specific embryonic and fetal beta-like globin gene is regulated in part by epigenetic mechanisms. The rescue of mutations in the beta globin gene, mutations which are responsible for diseases such as thalassemia major or sickle cell anemia, by transcriptional induction of one or more of the other beta-like genes through the pharmacologic manipulation of epigenetic silencing would be clinically beneficial. Autologous activation with a pharmacologic agent of a functionally complementary paralog of a mutated or pathologically silenced gene may be a more successful therapeutic strategy than replacing or repairing the mutated gene with a wild-type (normal) copy.

Interest in influencing the activity of histone modifications for therapeutic effect derive from observations that the expression of specific genes under epigenetic control could be altered by altering epigenetic marks such as methylation. In the case of cancer, loss of specific histone methylation marks concomitant with overexpression of histone demethylases is associated with the recurrence of those cancers with attendant poorer outcomes. These studies suggest that specific tumor suppressor genes are silenced by loss of methylation modifications that in turn enhance the survival and growth potential of neoplastic cells. This had led to the proposition that inhibition of histone demethylase activity might have therapeutic value.

KDM1A (also known as Lysine-Specific Demethylase 1 (LSD1) or AOF2 or BHC110) was the first enzyme with specific lysine demethylase activity to be described demonstrating unequivocally that histone modifications are reversible rather than permanent. Among its demethylase substrates, KDM1A is a histone H3 lysine demethylase that catalyzes the oxidative demethylation of H3K4me1 or me2 and H3K9me1 or me2 but not the substrate H3K4me3. The enzyme also demethylates non-histone proteins such as p53 and Gfi1. KDM1A contains an amine oxidase domain that demethylates H3Kme substrate in a flavin adenine dinucleotide (FAD)-dependent manner similar to other monoamine (MAO) and polyamine oxidase inhibitors. Indeed, non-specific inhibitors of MAO enzymes can inhibit the demethylase activity of KDM1A KDM1A is over-expressed in many human cancers including Wilm's tumor, small-cell lung, bladder, prostate, breast, head & neck, colon, and ovarian cancer and associated with more frequent relapses. KDM1A is required for transcriptional regulation mediated by the androgen receptor in prostate cancer, the estrogen receptor in breast carcinomas, and the TLX receptor in neuroblastoma. Knockdown of KDM1A expression decreases proliferation of cancer cells. KDM1A is also overexpressed in cancer cells that are nuclear hormone receptor-independent including ER-negative breast. Potent, selective small molecule inhibitors of KDM1A should be useful for treatment of these and other cancers in which KDM1A activity is overabundant.

The structure and state of chromatin can also influence the ability of a pathogenic virus to insert into host DNA, undergo transcription and replicate. Infection by the alpha herpes viruses herpes simplex virus (HSV) and varicella-zoster virus (VSV) effect the remodeling of chromatin after infection of host cells to counter the rapid deposition of nucleosomes containing histones with transcriptional repressive marks by employing virus-encoded transcription factors to recruit the host HCF-1 co-activator complex that contains KDM1A and the histone H3K4 methyltransferases Set1 or MLL family members. It has been demonstrated that inhibition of KDM1A in cells infected with HSV1 inhibits HSV IE gene expression, suppresses lytic infection and reduces viral loads. Similarly, inhibiting KDM1A causes a decrease in the expression of the immediate early genes in cells infected with human cytomegalovirus and adenovirus suggesting a broader role for KDM1A in viral pathogenesis.

The influence KDM1A activity has on the transcription of specific genes is dependent on recruitment of KDM1A to a specific gene promoter region via DNA binding proteins. In the case of androgen-dependent gene expression, KDM1A associates with the androgen steroid receptor which specifically targets DNA binding sites in the promoters of androgen-responsive genes. Thus, proteins that bind KDM1A determine where along the chromosome the demethylase activity is targeted. Many proteins have been reported to interact with KDM1A including the CoREST, CtBP, NuRD, BRAF35 complexes, DNMT1, MTA1/2, Mi2beta, RbAp46/48, HDAC1, 2, and 3, TIF1beta, Blimp-1, ZNF217 and ZNF198, a subset of which form larger and in some cases complexes that mutually exclude one another. The KDM1A/CoREST complex which may also include DNMT1 and NuRD among other factors is particularly important for the repression of expression of specific genes.

KDM1A is recruited to the promoter region of genes through site-specific transcription factors. Such factors include among others the androgen receptor, the estrogen receptor alpha, Snail1, Slug, HIV Tat, ZEB1, RBP-J, PIT1, REST, NR2C1, NR2C2 and isoforms of Gfi1b. These transcription factors can recruit KDM1A to participate in activation of gene expression or silencing of gene expression depending on the cell type and the specific transcription factors.

Many of the enzyme activities that regulate the state of chromatin are influenced allosterically or require as co-factors metabolic intermediates, mediators or end-products of cell metabolism. These intermolecular relationships between gene expression and metabolism provide cells with signaling pathways connecting the external and internal cellular environment including nutrients with mechanisms modulating gene expression. This cellular sensing can alter both short and long term adjustments to gene expression patterns constituting an epigenetic memory of historical metabolic states and environmental conditions. For example, beta-hydroxybutyrate, a product of long chain fatty acid metabolism and a major source of energy for mammals during starvation or prolonged exertion, inhibits class I histone deacetylases (HDAC) but not class 2b HDAC. Thus the effects of starvation and nutrient loss can be epigenetically coded and preserved. Acetyl-coenzyme A, nicotinamide adenine dinucleotide (NAD) and alpha-ketoglutarate also influence histone methylation and acetylation states.

Flavin adenine dinucleotide (FAD) is a required co-factor for KDM1A. FAD, in conjunction with NAD and NADP act as cellular redox sensors. KDM1A temporarily converts FAD to FADH after which an electron acceptor, likely $O_2$ and others, completes the catalytic cycle by regenerating FAD and $H_2O_2$. Thus, the cellular redox state influences KDM1A activity both by its ability to oxidize FADH and other electron acceptors. In a general sense, chromatin states, hence gene expression, can be altered by the variable concentrations of metabolic intermediates and in the specific case of KDM1A that activity is entirely dependent on FAD whose concentration fluctuates as a function of the energetic economy of the cell. In addition, it has been shown that inhibition of KDM1A can lower serum glucose, reduced hepatic glycogen, and is a powerful insulin secretogogue. Pharmaceutical manipulation of KDM1A activity may thus prove useful for the treatment of diseases that represent pathological aberrations of the energy status of the cell including metabolic syndrome, dyslipidemias, diabetes, obesity, anorexia, failure to thrive, cachexia, lipodystrophies, and steatohepatitis.

The steroid hormones estradiol and testosterone and related compound play a key role in both normal development and in pathological states such as breast and prostate cancer in which tumor cell growth is dependent on hormonal signaling. The biological effects of steroid hormones are mediated by structurally and functionally distinct ligand-binding receptors that function as a transcription factor recruited to a specific DNA binding site. The ligand-bound steroid receptors act as the principal transcriptional regulator of hormone effects. Transcriptional activation of gene expression for all steroid-dependent hormones is dependent on chromatin structure and the presence of co-factors. The estrogen receptor employs, for example, the co-factors SRC1, SRC2, AIB1, PELP1, CBP, p300, PCAF, CARM1, PRMT1 and co-repressors such as NCoR, SMRT and MTA1. The transcriptional response to hormone stimulation is dependent on the interaction of these co-factors and repressors as well as the state of chromatin, especially modification of histones by histone-modifying enzymes associated with the co-regulators. Both estrogenic and androgenic hormone stimulation induces several histone modifications at the promoters of target genes that alter the acetylation, phosphorylation and methylation state of local histones. To affect the maximal rate of transcription for a hormone-responsive gene, KDM1A activity is required. Thus, KDMA1 should prove useful as a therapeutic target of pharmaceuticals in blunting or ablating the hormone-dependence of tumor cells. This same therapeutic logic applies to other ligand-dependent transcription factors whose transcriptional activation is partly or wholly dependent on KDM1A activity to alter chromatin states sufficiently to facilitate transcription—examples of these would include the vitamin D, retinoid and lipid-activated receptors.

Numerous therapeutic agents have been identified that have the effect of altering gene expression acting either directly on proteins, generally enzymes, that alter chromatin states or indirectly. Though the precise mechanisms of their action have not all been fully elucidated, those mechanism can be inferred from our understanding of the protein complexes that participate in the activation of specific gene expression. These agents include 5'-azacytadine and 5'-aza-2' deoxycytidine (decitabine) which inhibit DNMT1 or other DNA methyltransferases known to be present and active at promoter sites of silenced genes such as gamma globin promoter; vorinostat and panobinostat or other inhibitors of histone deacetylase (HDAC) enzymes; hydroxyurea (HU), valproate and sodium butyrate and its analogues each of which may interfere with the activity of orphan nuclear receptors. All of these agents enjoy some clinical use principally in the management of neoplastic disease. Though some clinical utility of these agents for other disease states has been demonstrated, these agents have not been widely adopted because of their modest therapeutic effects and their toxicity.

The use of agents that inhibit any enzymatic activity resident in the protein complex bound to gene promoter has the potential to disrupt the repression of gamma globin gene expression and result in increased levels of fetal hemoglobin also known as hemoglobin F (HbF). Such targets include any of the interfaces of the specific protein-protein contacts, for example, the NuRD complex and KDM1A; the DNA binding recognition domains of, for example, NR2C1 and NR2C2; the ligand binding domains of, for example, NR2C1 and NR2C2; the enzyme activities such as lysine demethylase, for example, KDM1A; histone deacetylases (HDAC), for example HDAC1, 2, or 3; DNA methyltransferases, for example, DNMT1.

There remains a need for compositions and methods for altering gene expression in cells and tissues sufficient to restore the cell or tissue to normal physiologic function including, e.g., appropriate apoptosis in the case of cancer, or to alter the pathological phenotype of the cell, tissue, organ or organism by inducing the expression of one or more genes sufficiently to suppress the pathological state.

Accordingly, the inventors herein disclose new compounds, compositions and methods for treating diseases associated with KDM1A activity.

Provided herein is Embodiment 1: a compound having structural Formula I:

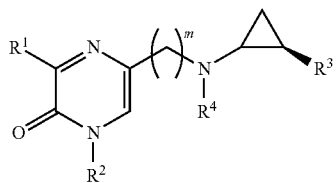

or a salt or ester thereof, wherein:
m is chosen from 0, 1, 2, 3, and 4;
$R^1$ is a nitrogen-containing heterocycloalkyl or heteroaryl, either of which is optionally substituted with 1, 2, or 3 $R^5$ groups;
$R^2$ is H, or is chosen from alkyl, cycloalkyl, haloalkyl, heterocycloalkyl, aryl, heteroaryl, cycloalkylalkyl, heterocycloalkylalkyl, arylalkyl, and heteroarylalkyl, any of which is optionally substituted with 1, 2, or 3 $R^6$ groups;
$R^3$ is chosen from aryl and heteroaryl, either of which is optionally substituted with 1, 2, or 3 $R^7$ groups;
each $R^4$ is independently chosen from hydrogen, alkyl, alkenyl, alkynyl, and cycloalkyl;
each $R^5$ is independently chosen from halogen, alkyl, alkenyl, alkynyl, hydroxy, amino, oxo, cyano, $COR^8$, $CONR^8R^9$, $COOR^8$, $NHCOR^8$, $NHCONR^8R^9$, $SOR^8$, $SO_2R^8$, $NHSO_2R^8$, and $SO_2NR^8R^9$;
each $R^6$ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, $COR^8$, $S_2R^8$, $NHSO_2R^8$, $NHSO_2NHR^8$, $SO_2NR^8R^9$, $NHCOR^8$, $NHCONHR^8$, $CONHR^8$, and $CONR^8R^9$;
each $R^7$ is independently chosen from alkyl, amino, cyano, halo, and hydroxy; and
$R^1$ and $R^9$ are independently chosen from hydrogen, aryl, and lower alkyl; or $R^8$ and $R^9$ may be taken together to form a nitrogen-containing heterocycloalkyl or heteroaryl ring, which is optionally substituted with lower alkyl.

Certain compounds disclosed herein may possess useful KDM1A inhibiting activity, and may be used in the treatment or prophylaxis of a disease or condition in which KDM1A plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting KDM1A. Other embodiments provide methods for treating a KDM1A-mediated disorder in a patient in need of such treatment, comprising administering to said patient a therapeutically effective amount of a compound or composition according to the present disclosure. Also provided is the use of certain compounds disclosed herein for use in the manufacture of a medicament for the treatment of a disease or condition ameliorated by the inhibition of KDM1A.

Also provided herein is Embodiment 2: a compound having structural Formula Ia:

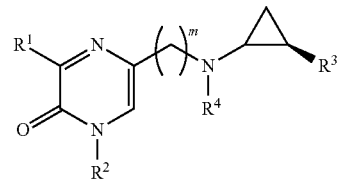

or a salt or ester thereof, wherein:
m is chosen from 0, 1, 2, 3, and 4;
$R^1$ is a nitrogen-containing heterocycloalkyl or heteroaryl, either of which is optionally substituted with 1, 2, or 3 $R^5$ groups;
$R^2$ is H, or is chosen from alkyl, cycloalkyl, haloalkyl, heterocycloalkyl, aryl, and heteroaryl, any of which is optionally substituted with 1, 2, or 3 $R^6$ groups;
$R^3$ is chosen from aryl and heteroaryl, either of which is optionally substituted with 1, 2, or 3 $R^7$ groups;
each $R^4$ is independently chosen from hydrogen, alkyl, alkenyl, alkynyl, and cycloalkyl;
each $R^5$ is independently chosen from halogen, alkyl, alkenyl, alkynyl, hydroxy, amino, oxo, cyano, $COR^8$, $CONR^8R^9$, $COOR^8$, $NHCOR^8$, $NHCONR^8R^9$, $SOR^8$, $SO_2R^8$, $NHSO_2R^8$, and $SO_2NR^8R^9$;
each $R^6$ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, $COR^8$, $SO_2R$, $NHSO_2R$, $NHSO_2NHR^8$, $SO_2NR^8R^9$, $NHCOR^8$, $NHCONHR^8$, $CONHR^8$, and $CONR^8R^9$;
each $R^7$ is independently chosen from alkyl, amino, cyano, halo, and hydroxy; and R⁸ and R⁹ are independently chosen from hydrogen, aryl, and lower alkyl; or R⁸ and R⁹ may be taken together to form a nitrogen-containing heterocycloalkyl or heteroaryl ring, which is optionally substituted with lower alkyl.

Also provided herein is Embodiment 3: a compound having structural Formula II:

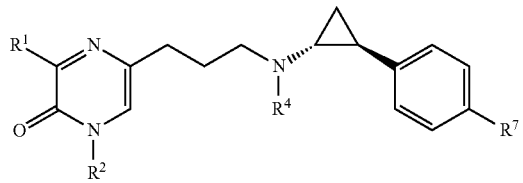

(II)

or a salt or ester thereof, wherein:

R¹ is a nitrogen-containing heterocycloalkyl or heteroaryl, either of which is optionally substituted with 1, 2, or 3 R⁵ groups;

R² is H, or is chosen from alkyl, cycloalkyl, haloalkyl, heterocycloalkyl, aryl, and heteroaryl, any of which is optionally substituted with 1, 2, or 3 R⁶ groups;

each R⁴ is independently chosen from hydrogen, alkyl, alkenyl, alkynyl, and cycloalkyl;

each R⁵ is independently chosen from halogen, alkyl, alkenyl, alkynyl, hydroxy, amino, oxo, cyano, COR⁸, CONR⁸R⁹, COOR⁸, NHCOR⁸, NHCONR⁸R⁹, SOR⁸, SO₂R⁸, NHSO₂R⁸, and SO₂NR⁸R⁹;

each R⁶ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, COR⁸, SO₂R, NHSO₂R, NHSO₂NHR⁸, SO₂NR⁸R⁹, NHCOR⁸, NHCONHR⁸, CONHR⁸, and CONR⁸R⁹;

each R⁷ is independently chosen from hydrogen, alkyl, amino, cyano, halo, and hydroxy; and each R⁸ and R⁹ is independently chosen from hydrogen, aryl, and lower alkyl; or R⁸ and R⁹ may be taken together to form a nitrogen-containing heterocycloalkyl or heteroaryl ring, which is optionally substituted with lower alkyl.

In certain embodiments, R¹ is chosen from piperidine, morpholine, thiomorpholine, piperazine, pyrrolidine, azetidine, 2-azaspiro[3.3]heptane, 2,6-diazaspiro[3.3]heptane, and 2-oxa-6-azaspiro[3.3]heptane, and is optionally substituted with 1, 2, or 3 R⁵ groups.

In certain embodiments, R¹ is chosen from piperidine, morpholine, thiomorpholine, piperazine, pyrrolidine, azetidine, 2-azaspiro[3.3]heptane, 2,6-diazaspiro[3.3]heptane, and 2-oxa-6-azaspiro[3.3]heptane, and is optionally substituted with 1 or 2 R⁵ groups.

In certain embodiments, R¹ is chosen from

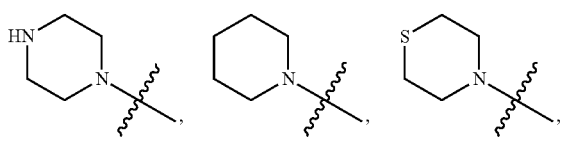

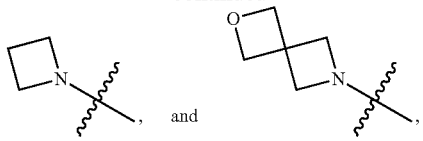

and is optionally substituted with 1, 2, or 3 R⁵ groups.

In certain embodiments, R¹ is chosen from

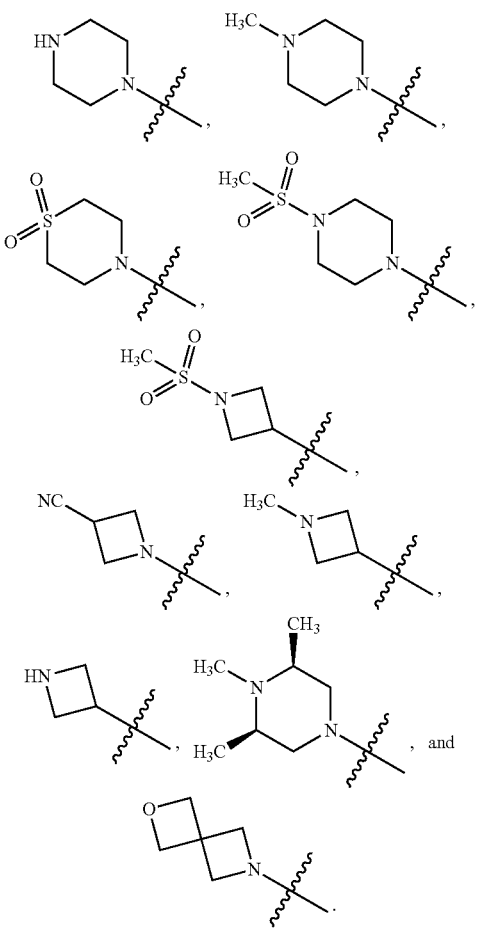

In certain embodiments, R² is chosen from aryl and heteroaryl, either of which is optionally substituted with 1 or 2 R⁶ groups.

In certain embodiments, R² is chosen from aryl and heteroaryl, either of which is optionally substituted with 1 R⁶ groups.

In certain embodiments, R² is chosen from phenyl, pyrrolyl, pyrazolyl, imidazolyl, oxazolyl, isoxazolyl, triazolyl, thiazolyl, pyridinyl, pyrazinyl, pyridazinyl, and pyrimidinyl, any of which is optionally substituted with 1 or 2 R⁶ groups.

In certain embodiments, R² is chosen from phenyl, pyridinyl, and pyrimidinyl, any of which is optionally substituted with 1 or 2 R⁶ groups.

In certain embodiments, R² is chosen from phenyl, pyridinyl, and pyrimidinyl, any of which is optionally substituted with 1 R⁶ groups.

In certain embodiments, R² is hydrogen.
In certain embodiments, R⁴ is hydrogen.

In certain embodiments, each $R^6$ is independently chosen from halogen, alkyl, cycloalkyl, heterocycloalkyl, heteroaryl, alkylheteroaryl, heteroarylalkyl, cyano, $COR^8$, $SO_2R^8$, $NHSO_2R^8$, $NHSO_2NHR^8$, $SO_2NR^8R^9$, $NHCOR^8$, and $NHCONHR^8$.

In certain embodiments, each $R^6$ is independently chosen from halogen, heteroaryl, alkylheteroaryl, $SO_2R^8$, $NHSO_2R^8$, $NHSO_2NHR^8$, $SO_2NR^8R^9$, $NHCOR^8$, and $NHCONHR^8$.

In certain embodiments, each $R^7$ is independently chosen from hydrogen and fluorine.

In certain embodiments, $R^7$ is fluorine.

Also provided are the following Embodiments:

Embodiment 4: the compound of Embodiment 1, wherein $R^3$ is chosen from phenyl, pyridinyl, pyridazinyl, pyrimidinyl, and pyrazinyl, any of which is substituted with 1, 2, or 3 $R^5$ groups.

Embodiment 5: the compound of Embodiment 4, wherein $R^3$ is phenyl, which is optionally substituted with 1, 2, or 3 $R^7$ groups.

Embodiment 6: the compound of any one of Embodiments 1, 4, and 5, wherein $R^3$ is optionally substituted with 1 or 2 $R^7$ groups.

Embodiment 7: the compound of Embodiment 6, wherein $R^3$ is substituted with 1 or 2 $R^7$ groups.

Embodiment 8: the compound of Embodiment 6, wherein $R^3$ is optionally substituted with 1 $R^7$ group.

Embodiment 9: the compound of Embodiment 6, wherein $R^3$ is chosen from

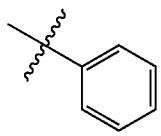 and 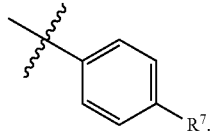

Embodiment 10: the compound of any one of Embodiments 1 and 4-9, wherein each $R^7$ is independently chosen from $NH_2$, cyano, halo, and hydroxy.

Embodiment 11: the compound of Embodiment 10, wherein each $R^7$ is independently chosen from cyano and halo.

Embodiment 12: the compound of Embodiment 11, wherein each $R^7$ is independently chosen from bromine, chlorine, and fluorine.

Embodiment 13: the compound of Embodiment 12, wherein $R^7$ is fluorine.

Embodiment 14: the compound of Embodiment 6, wherein $R^3$ is unsubstituted with an $R^7$ group.

Embodiment 15: the compound of Embodiment 3, wherein each $R^7$ is independently chosen from $NH_2$, cyano, halo, and hydroxy.

Embodiment 16: the compound of Embodiment 15, wherein each $R^7$ is independently chosen from cyano and halo.

Embodiment 17: the compound of Embodiment 16, wherein each $R^7$ is independently chosen from bromine, chlorine, and fluorine.

Embodiment 18: the compound of Embodiment 17, wherein $R^7$ is fluorine.

Embodiment 19: the compound of Embodiment 17, wherein $R^3$ is

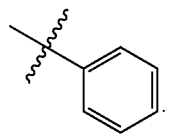 [SMILES: *c1ccccc1]

Embodiment 20: the compound of Embodiment 17, wherein $R^3$, with substitution $R^7$ where appropriate, is

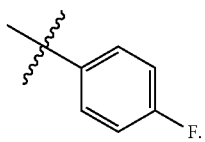 [SMILES: *c1ccc(F)cc1]

Embodiment 21: the compound of any one of Embodiments 1 and 3-20, wherein $R^2$ is chosen from alkyl, cycloalkyl, haloalkyl, heterocycloalkyl, aryl, heteroaryl, cycloalkylalkyl, heterocycloalkylalkyl, arylalkyl, and heteroarylalkyl, any of which is optionally substituted with 1, 2, or 3 $R^6$ groups.

Embodiment 22: the compound of Embodiment 21, wherein $R^2$ is chosen from alkyl, cycloalkyl, haloalkyl, heterocycloalkyl, aryl, heteroaryl, cycloalkylmethyl, heterocycloalkylmethyl, arylmethyl, and heteroarylmethyl, any of which is optionally substituted with 1, 2, or 3 $R^6$ groups.

Embodiment 23: the compound of Embodiment 22, wherein $R^2$ is chosen from cycloalkyl, aryl, heteroaryl, arylmethyl, and heteroarylmethyl, any of which is optionally substituted with 1, 2, or 3 $R^6$ groups.

Embodiment 24: the compound of Embodiment 23, wherein $R^2$ is chosen from $C_{3-6}$cycloalkyl, phenyl, pyridyl, pyridazinyl, pyrimidinyl, pyrazinyl, phenylmethyl, pyridylmethyl, pyridazinylmethyl, pyrimidinylmethyl, and pyrazinylmethyl, any of which is optionally substituted with 1, 2, or 3 $R^6$ groups.

Embodiment 25: the compound of any one of Embodiments 1-24, wherein $R^2$ is optionally substituted with 1 or 2 $R^6$ groups.

Embodiment 26: the compound of Embodiment 25, wherein $R^2$ is substituted with 1 or 2 $R^6$ groups.

Embodiment 27: the compound of Embodiment 25, wherein $R^2$ is optionally substituted with 1 $R^6$ group.

Embodiment 28: the compound of Embodiment 27, wherein $R^2$ is substituted with 1 $R^6$ group.

Embodiment 29: the compound of the compound of any one of Embodiments 1-28, wherein each $R^6$ is independently chosen from halogen, alkyl, cycloalkyl, haloalkyl, haloalkoxy, aryl, aryloxy, heterocycloalkyl, heteroaryl, cyano, alkoxy, $COR^8$, $SO_2R^8$, $NHSO_2R^8$, $NHSO_2NHR^8$, $SO_2NR^8R^9$, $NHCOR^8$, $NHCONHR^8$, $CONHR^8$, and $CONR^8R^9$.

Embodiment 30: the compound of the compound of Embodiment 29, wherein each $R^6$ is independently chosen from halogen, alkyl, haloalkoxy, aryl, heteroaryl, cyano, alkoxy, $SO_2R^8$, $NHSO_2R^8$, $SO_2NR^8R^9$, $CONHR^8$, and $CONR^8R^9$.

Embodiment 31: the compound of the compound of Embodiment 30, wherein each $R^6$ is independently chosen from fluoro, chloro, phenyl, pyridinyl, pyridazinyl, pyrimidinyl, pyrazinyl, pyrrolyl, pyrazolyl, imidazolyl, triazolyl, cyano, alkoxy, $SO_2R^8$, $SO_2NR^8R^9$, $CONHR^8$, and $CONR^8R^9$.

Embodiment 32: the compound of the compound of any one of Embodiments 1-31, wherein each $R^8$ and $R^9$ is independently chosen from hydrogen and $C_{1-4}$alkyl.

Embodiment 33: the compound of the compound of Embodiment 32, wherein each $R^8$ and $R^9$ is independently chosen from hydrogen and methyl.

Embodiment 34: the compound of Embodiment 27, wherein $R^2$ is unsubstituted with an $R^6$ group.

Embodiment 35: the compound of any one of Embodiments 1-18, wherein $R^2$, with substitution $R^6$ where appropriate, and further with substitutions $R^8$ and $R^9$ where appropriate, is chosen from:

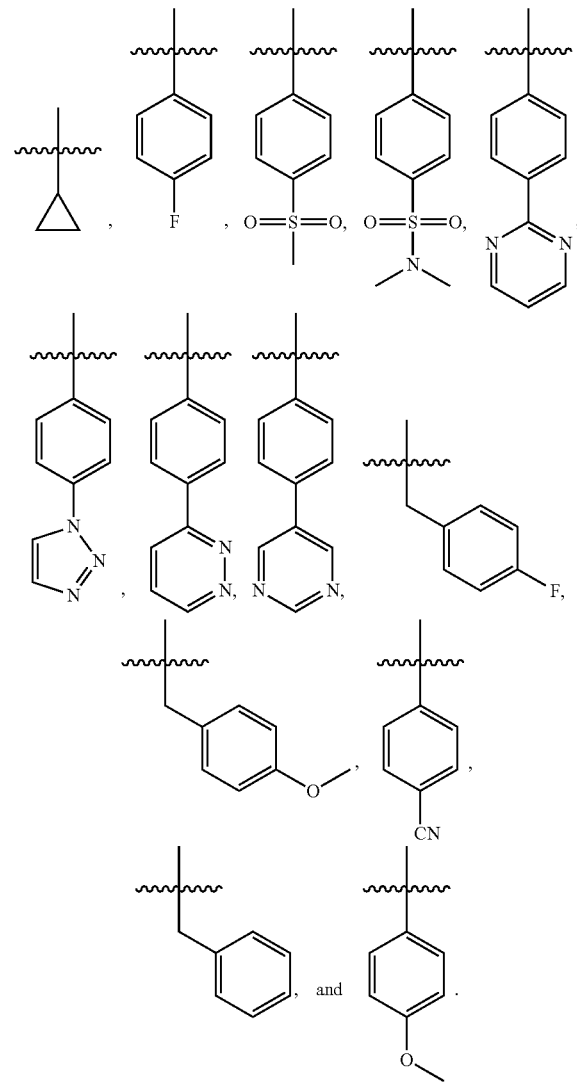

Embodiment 36: the compound of any one of Embodiments 1-18, wherein $R^2$ is H.

Embodiment 37: the compound of any one of Embodiments 1-36, wherein $R^1$ is a 5-7 membered nitrogen-containing heterocycloalkyl or heteroaryl, either of which is optionally substituted with 1, 2, or 3 $R^5$ groups.

Embodiment 38: the compound of Embodiment 37, wherein $R^1$ is a 5-7 membered heteroaryl, which is optionally substituted with 1, 2, or 3 $R^5$ groups.

Embodiment 39: the compound of Embodiment 38, wherein $R^1$ is chosen from pyridyl, pyridazinyl, pyrimidinyl, pyrazinyl, pyrrolyl, pyrazolyl, imidazolyl, and triazolyl, any of which is optionally substituted with 1, 2, or 3 $R^5$ groups.

Embodiment 40: the compound of Embodiment 39, wherein $R^1$ is chosen from pyridyl, pyrimidinyl, and pyrazolyl, any of which is optionally substituted with 1, 2, or 3 $R^5$ groups.

Embodiment 41: the compound of Embodiment 37, wherein $R^1$ is a 5-7 membered nitrogen-containing heterocycloalkyl, which is optionally substituted with 1, 2, or 3 $R^5$ groups.

Embodiment 42: the compound of Embodiment 41, wherein $R^1$ is chosen from piperidine, morpholine, thiomorpholine, piperazine, pyrrolidine, azetidine, 2-azaspiro[3.3]heptane, 2,6-diazaspiro[3.3]heptane, and 2-oxa-6-azaspiro[3.3]heptane, any of which is optionally substituted with 1, 2, or 3 $R^5$ groups.

Embodiment 43: the compound of Embodiment 42, wherein $R^1$, with substitution $R^5$ where appropriate and further with substitutions $R^8$ and $R^9$ where appropriate, is chosen from

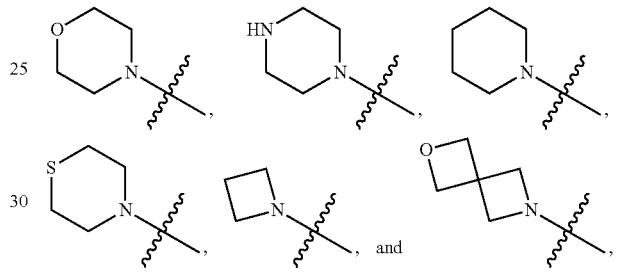

any of which is optionally substituted with 1, 2, or 3 $R^5$ groups.

Embodiment 44: the compound of Embodiment 43, wherein $R^1$ is

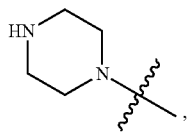

which is optionally substituted with 1, 2, or 3 $R^5$ groups.

Embodiment 45: the compound of any one of Embodiments 1-44, wherein $R^1$ is optionally substituted with 1 or 2 $R^5$ groups.

Embodiment 46: the compound of Embodiment 45, wherein $R^1$ is substituted with 1 or 2 $R^5$ groups.

Embodiment 47: the compound of Embodiment 45, wherein $R^1$ is optionally substituted with 1 $R^5$ group.

Embodiment 48: the compound of any one of Embodiments 1-47, wherein each $R^5$ is independently chosen from halogen, alkyl, hydroxy, $NH_2$, oxo, cyano, $COR^8$, $CONR^8R^9$, $COOR^8$, $NHCOR^8$, $NHCONR^8R^9$, $SOR^8$, $SO_2R^8$, $NHSO_2R^8$, and $SO_2NR^8R^9$.

Embodiment 49: the compound of Embodiment 48, wherein each $R^5$ is independently chosen from $C_{1-6}$alkyl, hydroxy, $NH_2$, oxo, cyano, $CONR^8R^9$, and $SO_2R^8$.

Embodiment 50: the compound of Embodiment 49, wherein each $R^5$ is independently chosen from $CH_3$, oxo, $CONH_2$, and $SO_2CH_3$.

Embodiment 51: the compound of Embodiment 50, wherein $R^5$ is $SO_2CH_3$.

Embodiment 52: the compound of Embodiment 45, wherein $R^1$ is not substituted with an $R^5$ group.

Embodiment 53: the compound of Embodiment 38, wherein $R^1$ is chosen from

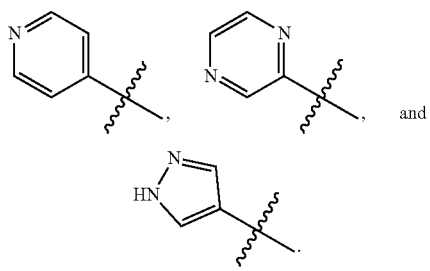

Embodiment 54: the compound of Embodiment 41, wherein $R^1$, with substitution $R^5$ where appropriate, and further with substitutions $R^8$ and $R^9$ where appropriate, is chosen from:

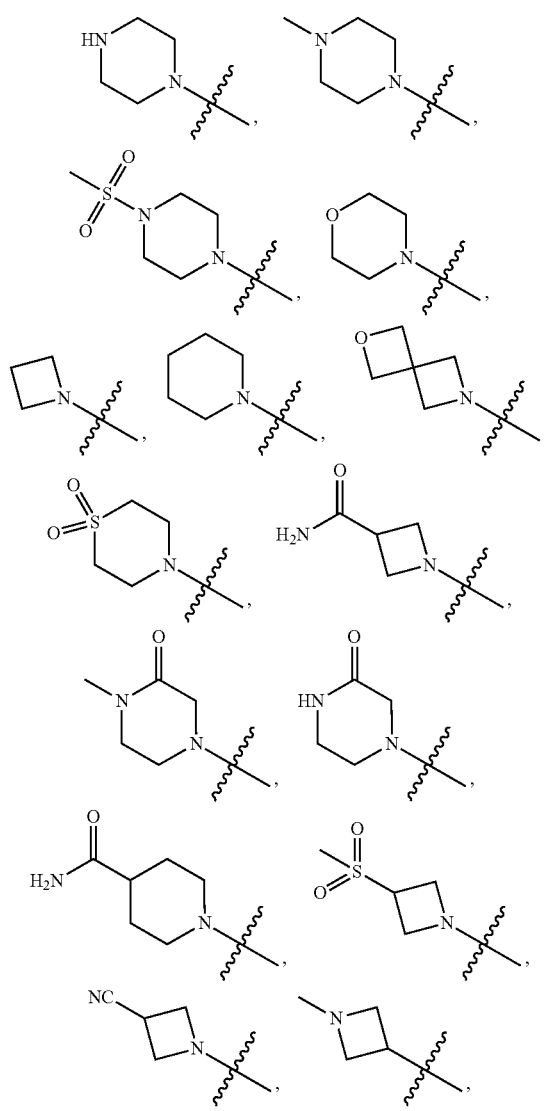

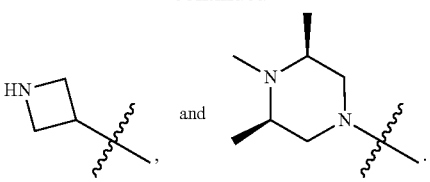

Embodiment 55: the compound of Embodiment 41, wherein $R^1$, with substitution $R^5$ where appropriate, and further with substitutions $R^8$ and $R^9$ where appropriate, is chosen from:

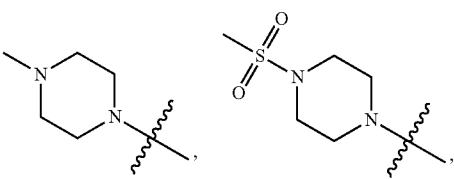

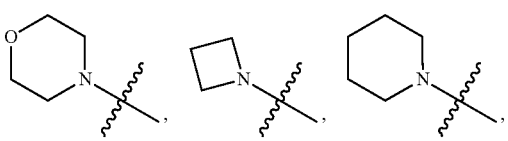

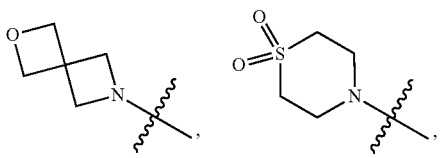

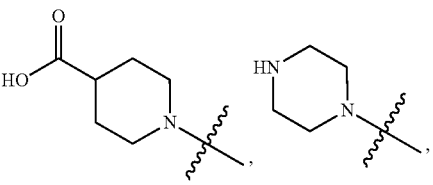

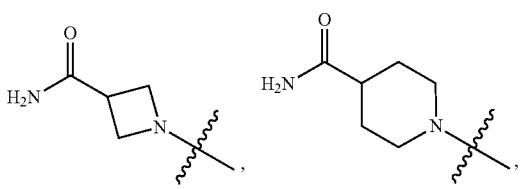

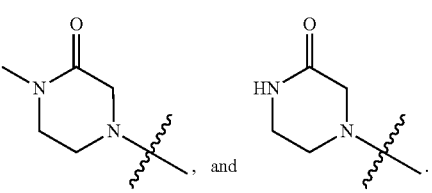

Embodiment 56: the compound of Embodiment 41, wherein $R^1$, with substitution $R_5$ where appropriate, and further with substitution $R_8$ where appropriate, is chosen from:

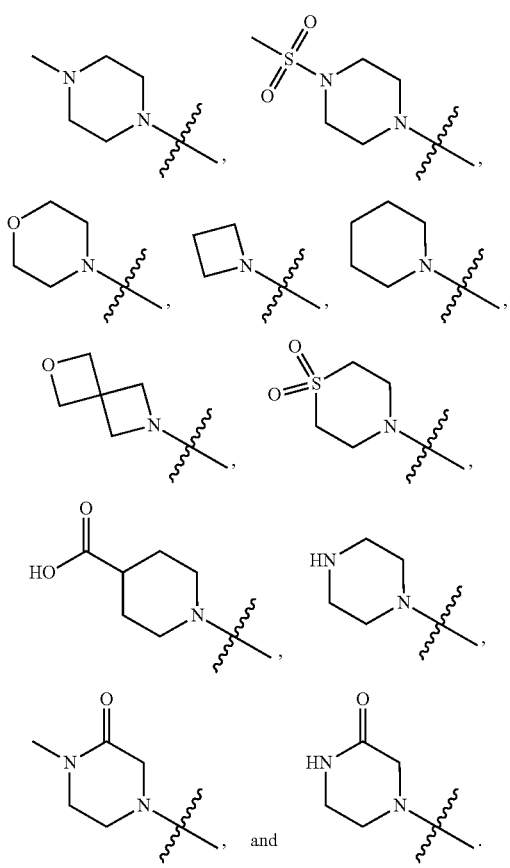

Embodiment 57: the compound of Embodiment 41, wherein R¹, with substitution R⁵ where appropriate, and further with substitutions R⁸ and R⁹ where appropriate, is chosen from:

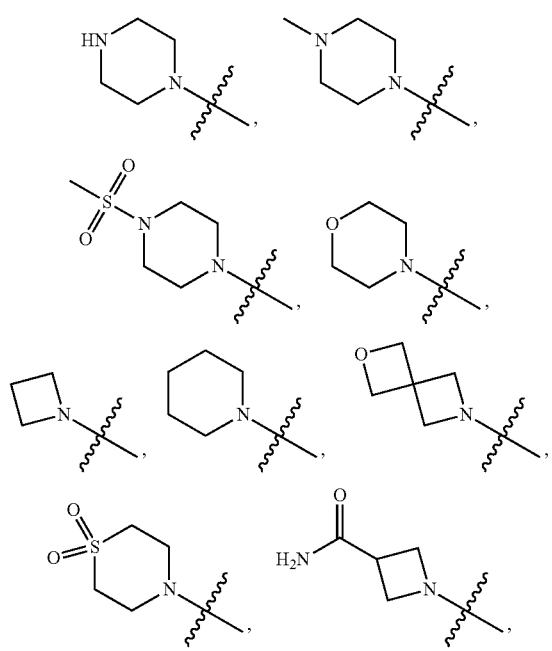

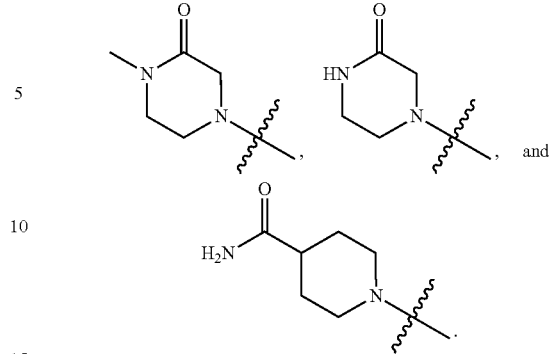

Embodiment 58: the compound of Embodiment 41, wherein R¹, with substitution R⁵ where appropriate, and further with substitutions R⁸ and R⁹ where appropriate, is chosen from:

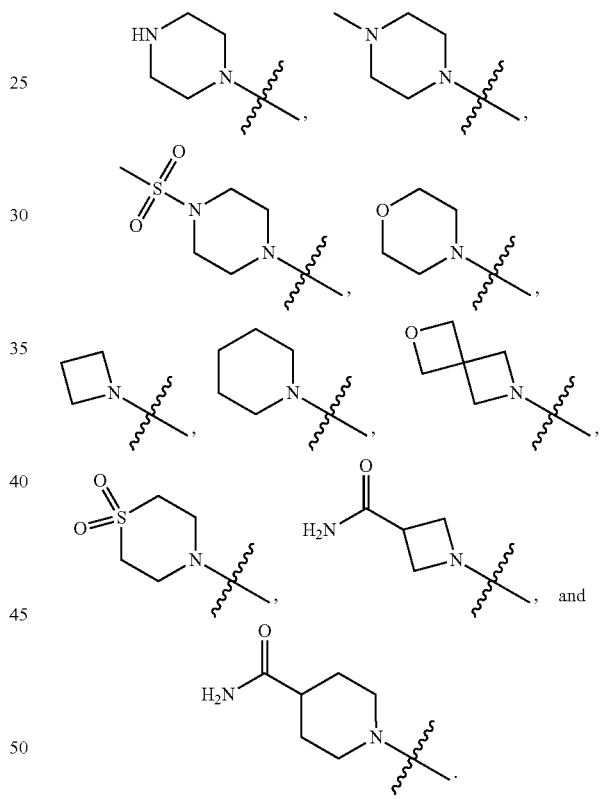

Embodiment 59: the compound of any one of Embodiments 1-58, wherein m is chosen from 1, 2, 3, and 4.

Embodiment 60: the compound of Embodiment 59, wherein m is chosen from 2 and 3.

Embodiment 61: the compound of Embodiment 60, wherein m is 2.

Embodiment 62: the compound of Embodiment 60, wherein m is 3.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present disclosure also relates to a method of inhibiting at least one KDM1A function comprising the step of contacting KDM1A with a compound as described herein. The cell phenotype, cell proliferation, activity of KDM1A, change in biochemical output produced by active KDM1A, expression of KDM1A, or binding of KDM1A with a natural binding partner may be monitored. Such methods may be modes of treatment of disease, biological assays, cellular assays, biochemical assays, or the like.

Also provided herein is a method of treatment of a KDM1A-mediated disease comprising the administration of a therapeutically effective amount of a compound as disclosed herein, or a salt thereof, to a patient in need thereof.

In certain embodiments, the disease is cancer.

In certain embodiments, the cancer is chosen from Ewing's sarcoma, multiple myeloma, T-cell luekemia, Wilm's tumor, small-cell lung cancer, bladder cancer, prostate cancer, breast cancer, head/neck cancer, colon cancer, and ovarian cancer.

Still other disorders or conditions advantageously treated by the compounds disclosed herein include the prevention or treatment of hyperproliferative diseases, especially cancers, either alone or in combination with standards of care especially those agents that target tumor growth by re-instating tumor suppressor genes in the malignant cells. Hematological and non-hematological malignancies which may be treated or prevented include but are not limited to multiple myeloma, acute and chronic leukemias and hematopoietic proliferative and neoplastic disorders including Myelodysplastic Syndrome (MDS), Acute Myelogenous Leukemia (AML), Acute Lymphocytic Leukemia (ALL), Chronic Lymphocytic Leukemia (CLL), and Chronic Myelogenous Leukemia (CML), lymphomas, including Hodgkin's lymphoma and non-Hodgkin's lymphoma (low, intermediate, and high grade), as well as solid tumors and malignancies of the brain, head and neck, breast, lung (including non-small-cell lung cancer), reproductive tract, upper digestive tract, pancreas, liver, renal system, bladder, prostate and colorectal. The present compounds and methods can also be used to treat fibrosis, such as that which occurs with radiation therapy. The present compounds and methods can be used to treat subjects having or prevent the progression of adenomatous polyps, including those with familial adenomatous polyposis (FAP) or sarcoidosis. Non-cancerous proliferative disorders additionally include psoriasis, eczema, and dermatitis.

In certain embodiments, the disease is a myeloid disease.

In certain embodiments, the myeloid disease is chosen from Myelofibrosis, Polycythemia Vera, Essential Thrombocythemia, Myelodysplastic Syndrome (MDS), Acute Myelogenous Leukemia (AML), and Chronic Myelogenous Leukemia (CML).

In certain embodiments, the myeloid disease is selected from the group consisting of polycythemia vera (PV), essential thrombocythemia (ET), myelofibrosis (MF), chronic myelogenous leukemia (CML), chronic neutrophilic leukemia (CNL), and chronic eosinophilic leukemia (CEL). In certain embodiments, the myeloid disease is selected from the group consisting of polycythemia vera (PV), essential thrombocythemia (ET), and myelofibrosis (MF). In certain embodiments, the myeloid disease is myelofibrosis selected from primary myelofibrosis (PMF) and post PV/ET myelofibrosis. In certain embodiments, the myeloid disease is primary myelofibrosis (PMF). In certain embodiments, the myeloid disease is post PV/ET myelofibrosis. In certain embodiments, the myeloid disease is essential thrombocythemia. In certain embodiments, the myeloid disease is polycythemia vera. In certain embodiments, the myeloid disease is chronic myelogenous leukemia. In certain embodiments, the myeloid disease is chronic neutrophilic leukemia. In certain embodiments, the myeloid disease is chronic eosinophilic leukemia. In certain embodiments, the patient is a human In certain embodiments, the disease is an inflammatory disease.

In certain embodiments, the inflammatory disease is chosen from inflammatory bowel disease, rheumatoid arthritis, or systemic lupus erythematosus.

Also provided herein is a compound as disclosed herein for use as a medicament.

Also provided herein is a compound as disclosed herein for use as a medicament for the treatment of a KDM1A-mediated disease.

Also provided is the use of a compound as disclosed herein as a medicament.

Also provided is the use of a compound as disclosed herein as a medicament for the treatment of a KDM1A-mediated disease.

Also provided is a compound as disclosed herein for use in the manufacture of a medicament for the treatment of a KDM1A-mediated disease.

Also provided is the use of a compound as disclosed herein for the treatment of a KDM1A-mediated disease.

Also provided herein is a method of inhibition of KDM1A comprising contacting KDM1A with a compound as disclosed herein, or a salt thereof.

Also provided herein is a method for achieving an effect in a patient comprising the administration of a therapeutically effective amount of a compound as disclosed herein, or a salt thereof, to a patient, wherein the effect is chosen from cognition enhancement.

Also provided is a method of modulation of a KDM1A-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

Terms

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system, which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination:

lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the disclosure encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present disclosure includes all cis, trans, syn, anti, entgegen (E), and zusammen (Z) isomers as well as the appropriate mixtures thereof. Additionally, compounds may exist as tautomers; all tautomeric isomers are provided by this disclosure. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "myeloid disease", as used herein, is intended to include diseases that can be classified under the term myeloproliferative neoplasm.

The term "myeloproliferative neoplasm" (MPN) refers to blood cancers that occur when the body makes too many white or red blood cells, or platelets as a consequence of somatic mutations that activate the hormone signaling pathways that control the production of these types of blood cells. They are "clonal diseases of hematopoietic stem cells" given that the neoplastic cells arise from a single mutant clone arising from bone marrow cells (Campregher et al. Rev Bras Hematol Hemoter. 2012; 34(2):150-5). MPNs include polycythemia vera (PV), myelofibrosis including primary myelofibrosis (PMF, including, in certain embodiments, both the prefibrotic/early stage and the overt fibrotic stage) and post-PV/ET myelofibrosis (PPV-MF and PET-MF), essential thrombocythemia (ET), chronic neutrophilic leukemia (CNL), chronic eosinophilic leukemia, not otherwise specified (CEL-NOS), and chronic myeloid leukemia (CML), as well as other unclassifiable MPNs. For a more thorough discussion of MPNs and related myeloid neoplasms and acute leukemia, as well as diagnostic criteria for PV, ET, PMF, and other MPNs, see Arber et al. "The 2016 revision to the World Health Organization classification of myeloid neoplasms and acute leukemia", Blood 2016, 127 (20):2391-2405. For a thorough discussion of myelofibrosis diagnostic and response criteria, see Tefferi A et al., "Revised response criteria for myelofibrosis: International Working Group-Myeloproliferative Neoplasms Research and Treatment (IWG-MRT) and European LeukemiaNet (ELN) consensus report," Blood, 122(8):1395-98 (2013).

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"KDM1A inhibitor" is used herein to refer to a compound that exhibits an $IC_{50}$ with respect to KDM1A activity of no more than about 100 μM and more typically not more than about 50 μM, as measured in the KDM1A inhibition assay described generally herein. "$IC_{50}$" is that concentration of inhibitor which reduces the activity of an enzyme (e.g., KDM1A) to half-maximal level. Certain compounds disclosed herein have been discovered to exhibit inhibition against KDM1A. In certain embodiments, compounds will exhibit an $IC_{50}$ with respect to KDM1A of no more than about 10 μM; in further embodiments, compounds will exhibit an $IC_{50}$ with respect to KDM1A of no more than about 200 nM; in yet further embodiments, compounds will exhibit an $IC_{50}$ with respect to KDM1A of not more than about 50 nM; in yet further embodiments, compounds will exhibit an $IC_{50}$ with respect to KDM1A of not more than about 10 nM; in yet further embodiments, compounds will exhibit an $IC_{50}$ with respect to KDM1A of not more than about 2 nM, as measured in the KDM1A assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts

The compounds disclosed herein can exist as therapeutically acceptable salts. The present disclosure includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present disclosure contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Formulations

While it may be possible for the compounds of the subject disclosure to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject disclosure or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

Combinations and Combination Therapies

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Alternatively, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). There is even the possibility that two compounds, one of the compounds described herein and a second compound may together achieve the desired therapeutic effect that neither alone could achieve. Alternatively, by way of example only, the benefit experienced by a patient may be increased by administering one of the compounds described herein with another therapeutic agent (which also includes a therapeutic regimen) that also has therapeutic benefit. By way of example only, in a treatment for acute myelogenous leukemia or sickle cell anemia involving administration of one of the compounds described herein, increased therapeutic benefit may result by also providing the patient with another therapeutic agent for sickle cell anemia or for acute myelogenous leukemia. In any case, regardless of the disease, disorder or condition being treated, the overall benefit experienced by the patient may simply be additive of the two therapeutic agents or the two agents may have synergistic therapeutic effects in a patient.

Effective combination therapy may be achieved with a single composition or pharmacological formulation that includes both agents, or with two distinct compositions or formulations, at the same time, wherein one composition includes a compound of the present disclosure, and the other includes the second agent(s). Alternatively, the therapy may precede or follow the other agent treatment by intervals ranging from minutes to months. Administration of the compounds of the present disclosure to a patient will follow general protocols for the administration of pharmaceuticals, taking into account the toxicity, if any, of the drug. It is expected that the treatment cycles would be repeated as necessary.

Specific, non-limiting examples of possible combination therapies include use of certain compounds of the invention with the following agents and classes of agents: agents that inhibit DNA methyltransferases such as decitabine or 5'-azacytadine; agents that inhibit the activity of histone deacetylases, histone de-sumoylases, histone de-ubiquitinases, or histone phosphatases such as hydroxyurea; antisense RNAs that might inhibit the expression of other components of the protein complex bound at the DR site in the gamma globin promoter; agents that inhibit the action of Klf1 or the expression of KLF1; agents that inhibit the action of Bcl11a or the expression of BCL11A; and agents that inhibit cell cycle progression such as hydroxyurea, ara-C or daunorubicin; agents that induce differentiation in leukemic cells such as all-trans retinoic acid (ATRA).

Inhibition of KDM1A (LSD1) activity alone may be sufficient therapy for the treatment of some diseases; for other such as cancer, combination therapies are often additive or synergistic in their therapeutic effects and may even be necessary to achieve the full clinical benefit desired. There is specific scientific evidence to rationalize the combination of an inhibitor of KDM1A with all-trans retinoic acid (ATRA), arsenic trioxide, inhibitors of DNA methyltransferases such as 5'-azacytidine or 5'-aza 2'-deoxycytidine, inhibitors of NFκB signaling such as sulindac or conventional anti-neoplastic agents such as anthracyclines or nucleoside analogues such as cytosine arabinoside. Likewise, agents that induce leukemia stem cells into the cell cycle (G-CSF, GM-CSF, stem cell factor, thrombopoietin (TPO)) or agents that negate the contributory role cytokines (TPO, CCL3(MIP-1)) play in remodeling the niche of cancer stem cells may be useful as part of a combination including an LSD1 inhibitor.

Specific, non-limiting examples of possible combination therapies include use of certain compounds of the invention with anti-cancer (chemotherapeutic) drugs. Classes of anti-cancer drugs include, but are not limited to: alkylating agents, anti-metabolites, antimitotics, checkpoint inhibitors, plant alkaloids and terpenoids, topoisomerase inhibitors, cytotoxic antibiotics, aromatase inhibitors, angiogenesis inhibitors, anti-steroids and anti-androgens, mTOR inhibitors, tyrosine kinase inhibitors, and others.

For use in cancer and neoplastic diseases a CBP/P300 inhibitor may be optimally used together with one or more of the following non-limiting examples of anti-cancer agents:

(1) alkylating agents, including but not limited to carmustine, chlorambucil (LEUKERAN), cisplatin (PLATIN), carboplatin (PARAPLATIN), oxaliplatin (ELOXATIN), streptozocin (ZANOSAR), busulfan (MYLERAN), dacarbazine, ifosfamide, lomustine (CCNU), melphalan (ALKERAN), procarbazine (MATULAN), temozolomide (TEMODAR), thiotepa, and cyclophosphamide (ENDOXAN);

(2) anti-metabolites, including but not limited to cladribine (LEUSTATIN), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), raltitrexed;

(3) antimitotics, which are often plant alkaloids and terpenoids, or derivatives thereof, including but not limited to taxanes such as docetaxel (TAXITERE) and paclitaxel (ABRAXANE, TAXOL); vinca alkaloids such as vincristine (ONCOVIN), vinblastine, vindesine, and vinorelbine (NAVELBINE);

(4) checkpoint inhibitors, such as anti-PD-1 or PD-L1 antibodies pembrolizumab (KEYTRUDA), nivolumab (OPDIVO), MEDI4736, and MPDL3280A; anti-CTLA-4 antibody ipilimumab (YERVOY); and those that target LAG3 (lymphocyte activation gene 3 protein), KIR (killer cell immunoglobulin-like receptor), 4-1BB (tumour necrosis factor receptor superfamily member 9), TIM3 (T-cell immunoglobulin and mucin-domain containing-3) and OX40 (tumour necrosis factor receptor superfamily member 4);

(5) topoisomerase inhibitors, including but not limited to camptothecin (CTP), irinotecan (CAMPTOSAR), topotecan (HYCAMTIN), teniposide (VUMON), and etoposide (EPOSIN);

(6) cytotoxic antibiotics, including but not limited to actinomycin D (dactinomycin, COSMEGEN), bleomycin (BLENOXANE) doxorubicin (ADRIAMYCIN), daunorubicin (CERUBIDINE), epirubicin (ELLENCE), fludarabine (FLUDARA), idarubicin, mitomycin (MITOSOL), mitoxantrone (NOVANTRONE), plicamycin;

(7) aromatase inhibitors, including but not limited to aminoglutethimide, anastrozole (ARIMIDEX), letrozole (FEMARA), vorozole (RIVIZOR), exemestane (AROMASIN);

(8) angiogenesis inhibitors, including but not limited to genistein, sunitinib (SUTENT) and bevacizumab (AVASTIN);

(9) anti-steroids and anti-androgens such as aminoglutethimide (CYTADREN), bicalutamide (CASODEX), cyproterone, flutamide (EULEXIN), nilutamide (NILANDRON);

(10) tyrosine kinase inhibitors, including but not limited to imatinib (GLEEVEC), erlotinib (TARCEVA), lapatininb (TYKERB), sorafenib (NEXAVAR), and axitinib (INLYTA);

(11) mTOR inhibitors such as everolimus, temsirolimus (TORISEL), and sirolimus;

(12) monoclonal antibodies such as trastuzumab (HERCEPTIN) and rituximab (RITUXAN);

(13) other agents, such as amsacrine; Bacillus Calmette-Guerin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

Thus, in another aspect, certain embodiments provide methods for treating KDM1A-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of KDM1A-mediated disorders.

Specific diseases to be treated by the compounds, compositions, and methods disclosed herein include cancer, myeloid diseases, and inflammatory diseases.

Specific cancers that can be advantageously treated by the compounds disclosed herein include Ewing's sarcoma, multiple myeloma, T-cell luekemia, Wilm's tumor, small-cell lung cancer, bladder cancer, prostate cancer, breast cancer, head/neck cancer, colon cancer, and ovarian cancer.

Specific myeloid diseases that can be advantageously treated by the compounds disclosed herein include myelofibrosis, polycythemia vera, essential thrombocythemia, myelodysplastic syndrome (MDS), acute myelogenous leukemia (AML), and chronic myelogenous leukemia (CML).

Specific inflammatory diseases that can be advantageously treated by the compounds disclosed herein include, without limitation: arthritis, including sub-types and related conditions such as rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic inflammation of the pancreas; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritus and vitiligo. In addition, compounds of invention are also useful in organ transplant patients either alone or in combination with conventional immunomodulators.

The compounds disclosed herein can be used in the treatment of diseases in which an increase in transcription through the manipulation of epigenetic regulatory factors such as inhibition of KDM1A would be beneficial to the patient. This applies to diseases including but not limited to loss of function mutations, mutations resulting in haploinsufficiency, deletions and duplications of genetic material or epigenetic regulatory mechanisms have altered the normal expression pattern of a gene or genes that has the effect of altering the dose of a gene product(s). Such diseases may include diseases both acquired and hereditary in which the expression of, for example, cytokines affecting immune function, are altered, X-linked mental retardation and other forms of compromised cognitive or motor function such as Alzheimer and Parkinson disease whether they are the acquired or hereditary forms, lipid disorders such as elevated cholesterol, low density lipoprotein, very low density lipoprotein or triglycerides, both type one and type two diabetes, and Mendelian genetic diseases.

Other disorders or conditions that can be advantageously treated by the compounds disclosed herein include inflammation and inflammatory conditions. Inflammatory conditions include, without limitation: arthritis, including sub-types and related conditions such as rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis; osteoporosis, tendonitis, bursitis, and other related bone and joint disorders; gastrointestinal conditions such as reflux esophagitis, diarrhea, inflammatory bowel disease, Crohn's disease, gastritis, irritable bowel syndrome, ulcerative colitis, acute and chronic inflammation of the pancreas; pulmonary inflammation, such as that associated with viral infections and cystic fibrosis; skin-related conditions such as psoriasis, eczema, burns, sunburn, dermatitis (such as contact dermatitis, atopic dermatitis, and allergic dermatitis), and hives; pancreatitis, hepatitis, pruritus and vitiligo. In addition, compounds of invention are also useful in organ transplant patients either alone or in combination with conventional immunomodulators.

Autoimmune disorders may be ameliorated by the treatment with compounds disclosed herein. Autoimmune disorders include Crohn's disease, ulcerative colitis, dermatitis, dermatomyositis, diabetes mellitus type 1, Goodpasture's syndrome, Graves' disease, Guillain-Barré syndrome (GBS), autoimmune encephalomyelitis, Hashimoto's disease, idiopathic thrombocytopenic purpura, lupus erythematosus, mixed connective tissue disease, multiple sclerosis (MS), myasthenia gravis, narcolepsy, pemphigus vulgaris, pernicious anemia, psoriasis, psoriatic arthritis, polymyositis, primary biliary cirrhosis, rheumatoid arthritis, Sjögren's syndrome, scleroderma, temporal arteritis (also known as "giant cell arteritis"), vasculitis, and Wegener's granulomatosis.

The compounds disclosed herein are also useful for the treatment of organ and tissue injury associated with severe burns, sepsis, trauma, wounds, and hemorrhage- or resuscitation-induced hypotension, and also in such diseases as vascular diseases, migraine headaches, periarteritis *nodosa*, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephritis, nephrotic syndrome, Behcet's syndrome, polymyositis, gingivitis, periodontis, swelling occurring after injury, ischemias including myocardial ischemia, cardiovascular ischemia, and ischemia secondary to cardiac arrest, and the like.

The compounds disclosed herein are also useful for the treatment of certain diseases and disorders of the nervous system. Central nervous system disorders in KDM1A inhibition is useful include cortical dementias including Alzheimer's disease, central nervous system damage resulting from stroke, ischemias including cerebral ischemia (both focal ischemia, thrombotic stroke and global ischemia (for example, secondary to cardiac arrest), and trauma. Neurodegenerative disorders in which KDM1A inhibition is useful include nerve degeneration or nerve necrosis in disorders such as hypoxia, hypoglycemia, epilepsy, and in cases of central nervous system (CNS) trauma (such as spinal cord and head injury), hyperbaric oxygen-induced convulsions and toxicity, dementia e.g., pre-senile dementia, and AIDS-related dementia, cachexia, Sydenham's chorea, Huntington's disease, Parkinson's Disease, amyotrophic lateral sclerosis (ALS), Korsakoffs disease, cognitive disorders relating to a cerebral vessel disorder, hypersensitivity, sleeping disorders, schizophrenia, depression, depression or other symptoms associated with Premenstrual Syndrome (PMS), and anxiety.

Still other disorders or conditions advantageously treated by the compounds disclosed herein include the prevention or treatment of hyperproliferative diseases, especially cancers, either alone or in combination with standards of care especially those agents that target tumor growth by re-instating tumor suppressor genes in the malignant cells. Hematological and non-hematological malignancies which may be treated or prevented include but are not limited to multiple myeloma, acute and chronic leukemias and hematopoietic proliferative and neoplastic disorders including Myelodysplastic Syndrome (MDS), Acute Myelogenous Leukemia (AML), Acute Lymphocytic Leukemia (ALL), Chronic Lymphocytic Leukemia (CLL), and Chronic Myelogenous Leukemia (CML), lymphomas, including Hodgkin's lymphoma and non-Hodgkin's lymphoma (low, intermediate, and high grade), as well as solid tumors and malignancies of the brain, head and neck, breast, lung (including non-small-cell lung cancer), reproductive tract, upper digestive tract, pancreas, liver, renal system, bladder, prostate and colorectal. The present compounds and methods can also be used to treat fibrosis, such as that which occurs with radiation therapy. The present compounds and methods can be used to treat subjects having or prevent the progression of adenomatous polyps, including those with familial adenomatous polyposis (FAP) or sarcoidosis. Non-cancerous proliferative disorders additionally include psoriasis, eczema, and dermatitis.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and $LTA_4$ hydrolase inhibitors. The compounds disclosed herein may also be used to prevent tissue damage when therapeutically combined with antibacterial or antiviral agents.

The compounds disclosed herein are also useful for the treatment of treat metabolic disorders. KDM1A, using flavin adenosine dinucleotide (FAD) as a cofactor, epigenetically regulates energy-expenditure genes in adipocytes depending on the cellular FAD availability. Additionally, loss of KDM1A function induces a number of regulators of energy expenditure and mitochondrial metabolism resulting in the activation of mitochondrial respiration. Furthermore, in the adipose tissues from mice fed a high-fat diet, expression of KDM1A-target genes is reduced.

Metabolic syndrome (also known as metabolic syndrome X) is characterized by having at least three of the following symptoms: insulin resistance; abdominal fat—in men this is defined as a 40 inch waist or larger, in women 35 inches or larger; high blood sugar levels—at least 110 milligrams per deciliter (mg/dL) after fasting; high triglycerides—at least 150 mg/dL in the blood stream; low HDL—less than 40 mg/dL; pro-thrombotic state (e.g., high fibrinogen or plasminogen activator inhibitor in the blood); or blood pressure of 130/85 mmHg or higher. A connection has been found between metabolic syndrome and other conditions such as obesity, high blood pressure and high levels of LDL cholesterol, all of which are risk factors for cardiovascular diseases. For example, an increased link between metabolic syndrome and atherosclerosis has been shown. People with metabolic syndrome are also more prone to developing type 2 diabetes, as well as PCOS (polycystic ovarian syndrome) in women and prostate cancer in men.

As described above, insulin resistance can be manifested in several ways, including type 2 diabetes. Type 2 diabetes is the condition most obviously linked to insulin resistance. Compensatory hyperinsulinemia helps maintain normal glucose levels often for decades before overt diabetes develops. Eventually the beta cells of the pancreas are unable to overcome insulin resistance through hypersecretion. Glucose levels rise and a diagnosis of diabetes can be made. Patients with type 2 diabetes remain hyperinsulinemic until they are in an advanced stage of disease. As described above, insulin resistance can also correlate with hypertension. One half of patients with essential hypertension are insulin resistant and hyperinsulinemic, and there is evidence that blood pressure is linked to the degree of insulin resistance. Hyperlipidemia, too, is associated with insulin resistance. The lipid profile of patients with type 2 diabetes includes increased serum very-low-density lipoprotein (VLDL) cholesterol and triglyceride levels and, sometimes, a decreased low-density lipoprotein (LDL) cholesterol level. Insulin resistance has been found in persons with low levels of high-density lipoprotein HDL). Insulin levels have also been linked to VLDL synthesis and plasma triglyceride levels.

Specific metabolic diseases and symptoms to be treated by the compounds, compositions, and methods disclosed herein are those mediated at least in part by KDM1A. Accordingly, disclosed herein are methods: for treating insulin resistance in a subject; for reducing glycogen accumulation in a subject; for raising HDL or HDLc, lowering LDL or LDLc, shifting LDL particle size from small dense to normal LDL, lowering VLDL, lowering triglycerides, or inhibiting cholesterol absorption in a subject; for reducing insulin resistance, enhancing glucose utilization or lowering blood pressure in a subject; for reducing visceral fat in a subject; for reducing serum transaminases in a subject; for inducing mitochondrial respiration in a subject; or for treating disease; all comprising the administration of a therapeutic amount of a compound as described herein, to a patient in need thereof. In further embodiments, the disease to be treated may be a metabolic disease. In further embodiment, the metabolic disease may be selected from the group consisting of: obesity, diabetes mellitus, especially Type 2 diabetes, hyperinsulinemia, glucose intolerance, metabolic syndrome X, dyslipidemia, hypertriglyceridemia, hypercholesterolemia, and hepatic steatosis. In other embodiments, the disease to be treated may be selected from the group consisting of: cardiovascular diseases including vascular disease, atherosclerosis, coronary heart disease, cerebrovascular disease, heart failure and peripheral vessel disease. In preferred embodiments, the methods above do not result in the induction or maintenance of a hypoglycemic state.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

LIST OF ABBREVIATIONS

ACN=MeCN=$CH_3CN$=acetonitrile; Boc=tert-butyloxycarbonyl; BPin=4,4,5,5-tetramethyl-1,3,2-dioxaborolan-2-yl; $Br_2$=bromine; Bu=n-butyl; t-Bu=tert-butyl=2,2-dimethylethyl; °C.=Celsius; CBz=carboxybenzyl; $CDCl_3$=deuterated chloroform; $CD_3CN$=deuterated acetonitrile; DBN=1,5-Diazabicyclo(4.3.0)non-5-ene; DBU=1,8-diazabicyclo(5.4.0)undec-7-ene; DCM=$CH_2Cl2$=dichloromethane; DDTT=3-((dimethylaminomethylidene)amino)-3H-1,2,4-dithiazole-5-thione; DIPEA=iPr2NEt=diisopropylethylamine; DMAP=4-Dimethylaminopyridine; DMEDA=N,N'-dimethyl ethylenediamine; DMF=dimethylformamide; DMF-$d_7$=dimethylformamide-$d_7$; DMSO=dimethyl sulfoxide; DMSO-$d_6$=dimethyl sulfoxide-$d_6$; DMTr=dimethoxytrityl=(4-methoxyphenyl)$_2$(phenyl)methyl; $D_2O$=deuterated water; dppf=1,1'-bis(diphenylphosphino)ferrocene; EA=EtOAc=ethyl acetate; ES+=electrospray positive ionization; ES−=electrospray negative ionization; Et=ethyl; EtOH=ethanol; h=hour; H=hydrogen; HCl=hydrogen chloride; $HCO_2NH_4$=ammonium formate; $H_2O$=water; HPLC=high pressure liquid chromatography, also known as preparative high performance liquid chromatography; int.=intermediate; iPr=isopropyl=2-propyl; IPA=iPrOH=isopropanol=2-propanol; M=molar; mCPBA=m-chloroperbenzoic acid; MeOH=methanol; MHz=megahertz; mL=milliliter; min=minute; MS=mass spectrometry; MsCl=methanesulfonyl chloride; MW=microwave; $N_2$=nitrogen; $NH_3$=ammonia; $NH_4OH$=ammonium hydroxide; NMP=N-Methyl-2-pyrrolidone; $^1$H-NMR=proton nuclear magnetic resonance; $^{31}$P-NMR=phosphorous nuclear magnetic resonance; PBS=phosphate buffered saline; PE=petroleum ether; Pin=pinacol=2,3-dimethylbutane-2,3-diol; $Pin_2B_2$=4,4,4',4',5,5,5',5'-octamethyl-2,2'-bi(1,3,2-dioxaborolane); Piv=pivaloyl=$(CH_3)_3C—C(=O)—$; prep-HPLC=preparative high pressure liquid chromatography, also known as preparative high performance liquid chromatography; RT=room temperature; NaOH=sodium hydroxide; $Pd(dppf)Cl_2$=[1,1'-bis(diphenylphosphino)ferrocene]palladium(II) dichloride; RuPhos=dicyclohexyl(2',6'-diisopropoxy-[1,1'-biphenyl]-2-yl)phosphine; THF=tetrahydrofuran; Py=pyridine; SFC=supercritical fluid chromatography; TBSCl=tert-butyldimethylsilyl chloride; TEA=triethylamine; TEAB=tetraethyl ammonium bicarbonate; TfOH=trifluoromethanesulfonic acid; TMSCl=trimethylsilyl chloride; TFA=trifluoroacetic acid; $K_2CO_3$=potassium carbonate; μL=ul=microliter.

General Synthetic Methods for Preparing Compounds

The following schemes can be used to practice the present disclosure.

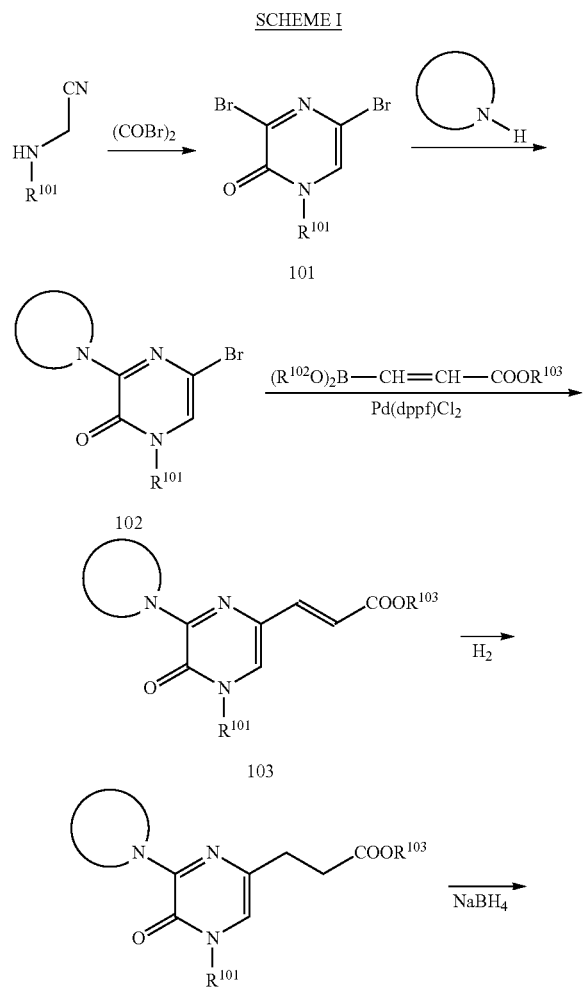

Certain examples disclosed herein can be synthesized using the following general synthetic procedure set forth in Scheme I. An appropriately substituted aminoacetonitrile is reacted with oxalyl bromide to construct a pyrazinone 101. Nucleophilic substitution with a cyclic amine provides selectively monosubstituted pyrazinone 102. The side chain is incorporated via a Pd(II)-mediated coupling with a functionalized vinylboronate reagent to give doubly substituted pyrazinone 103. A series of reduction and oxidation steps affords aldehyde 104, which is coupled with a substituted cyclopropylamine under reductive amination conditions to give 105.

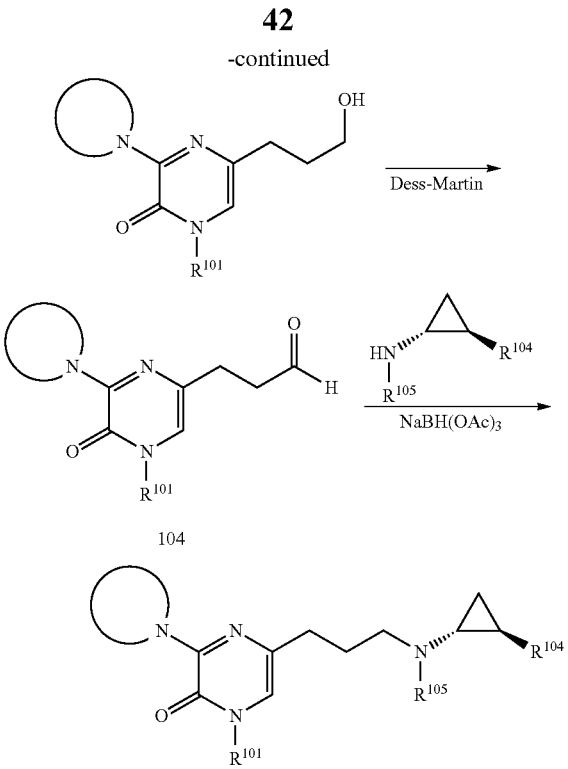

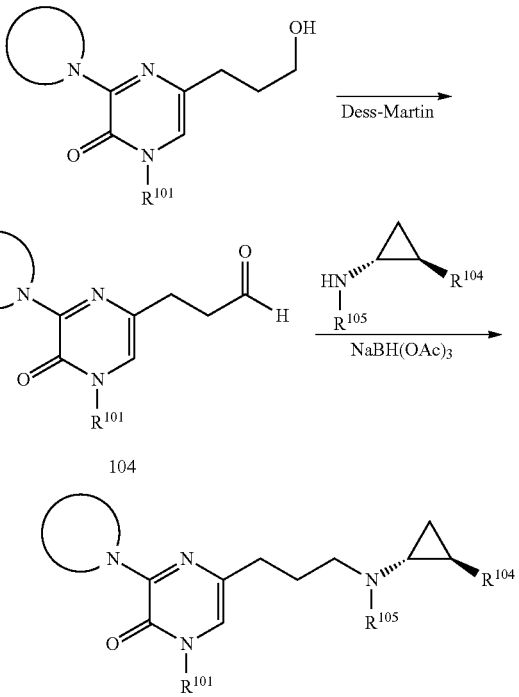

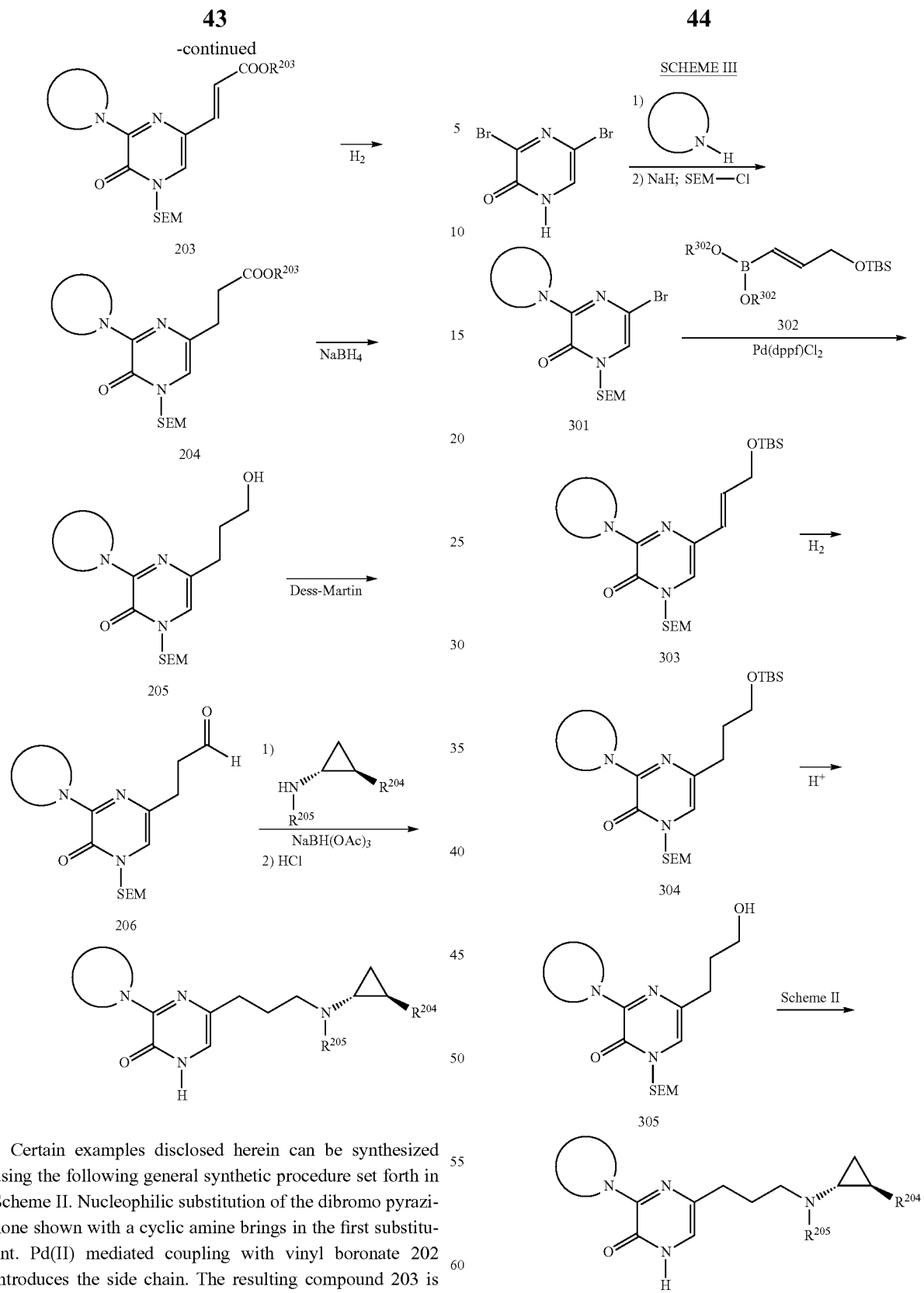

Certain examples disclosed herein can be synthesized using the following general synthetic procedure set forth in Scheme II. Nucleophilic substitution of the dibromo pyrazinone shown with a cyclic amine brings in the first substituent. Pd(II) mediated coupling with vinyl boronate 202 introduces the side chain. The resulting compound 203 is converted to aldehyde 206 via a three-step sequence consisting of hydrogenation, hydride reduction, and Dess-Martin oxidation. Aldehyde 206 is coupled with a substituted cyclopropylamine under reductive amination conditions. Finally, the SEM group is removed under acidic conditions.

Certain examples disclosed herein can be synthesized using the following general synthetic procedure set forth in Scheme III. Nucleophilic substitution of the dibromo pyrazinone shown with a cyclic amine brings in the first substituent. Pd(II) mediated coupling with vinyl boronate 302 introduces the side chain. The resulting compound 303 is converted to aldehyde 305 via a two-step sequence consisting of hydrogenation and silyl ether deprotection. Conversion of 305 to the desired product is accomplished as described for Scheme II.

SCHEME IV

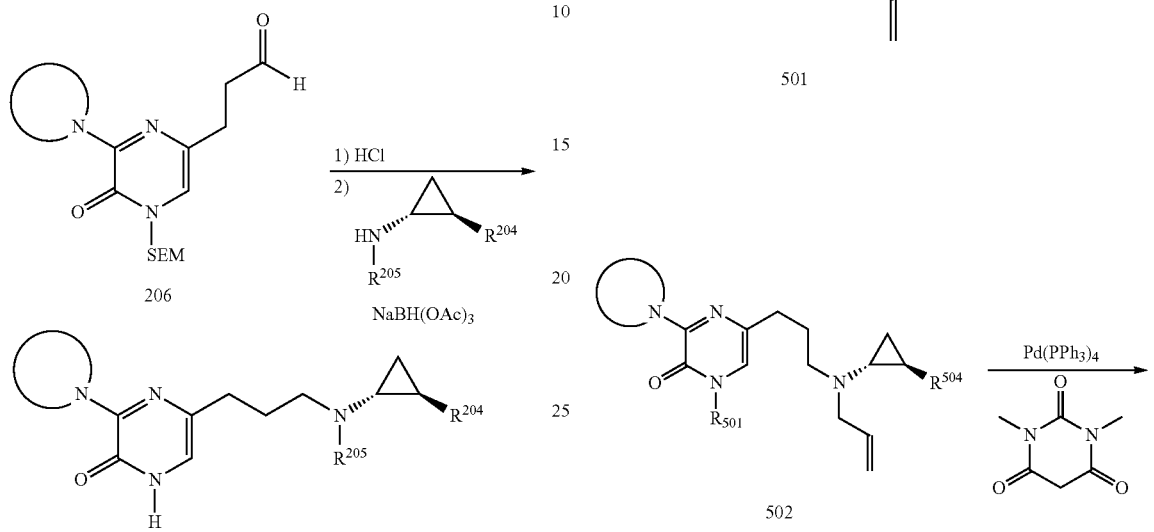

Certain examples disclosed herein can be synthesized using the following general synthetic procedure set forth in Scheme IV. Aldehyde 206, prepared with the methods of Scheme II or Scheme III, or using other methods available in the art, is reacted with acid to remove the SEM group. The resulting material is then coupled with a substituted cyclopropylamine under reductive amination conditions.

SCHEME V

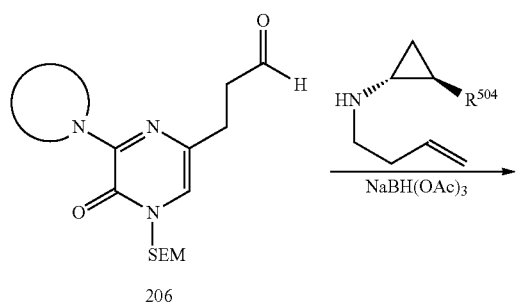

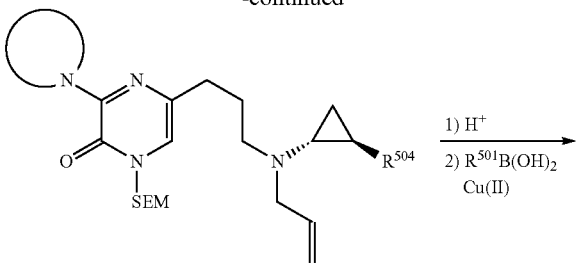

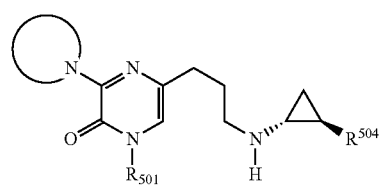

Certain examples disclosed herein can be synthesized using the following general synthetic procedure set forth in Scheme V. Aldehyde 206, prepared with the methods of Scheme II or Scheme III, or using other methods available in the art, is then coupled with an allyl cyclopropylamine under reductive amination conditions. The amine product 501 is reacted with acid to remove the SEM group, and then coupled with a suitable boronic ester in the presence of Cu(II) to give 502. Synthesis completed by removal of the allyl group with Pd(II) catalyst.

SCHEME VI(a)(b)(c)

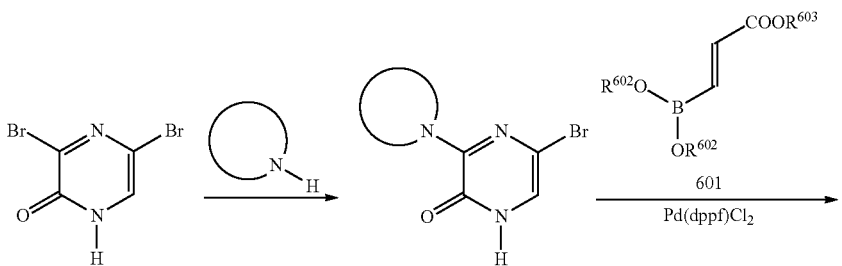

-continued

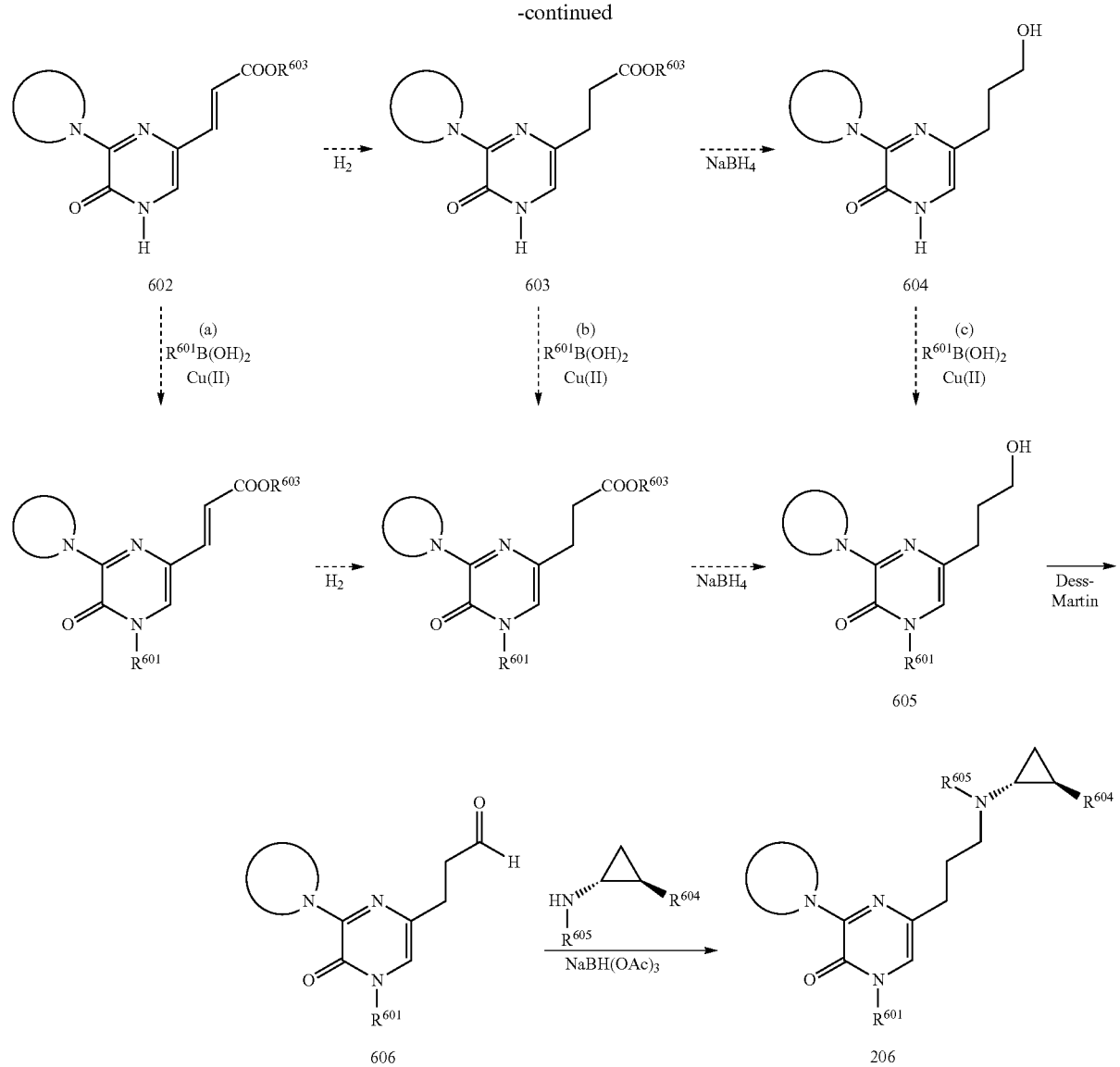

Certain examples disclosed herein can be synthesized using the following general synthetic procedure set forth in Scheme VI. Nucleophilic substitution of the dibromo pyrazinone shown with a cyclic amine brings in the first substituent. Pd(II) mediated coupling with vinyl boronate 601 introduces the side chain. At this stage, three opportunities are available for Cu(II) mediated coupling of the pyrazinone nitrogen with an organoboronic acid reagent: (a) before catalytic hydrogenation of the alkene, i.e., coupling with 602, (b) after catalytic hydrogenation of the alkene and before hydride reduction of the ester, i.e., coupling with 603, or (c) after both catalytic hydrogenation of the alkene and hydride reduction of the ester, i.e., coupling with 604. These pathways are indicated in the Scheme II diagram. The product of any of the three pathways is carried forth to provide alcohol 605, which is transformed to the desired cyclopropylamine product via Dess-Martin oxidation to aldehyde 606, followed by reductive amination.

SCHEME VII(a)(b)

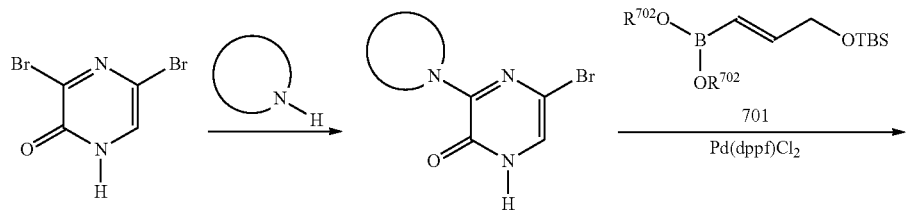

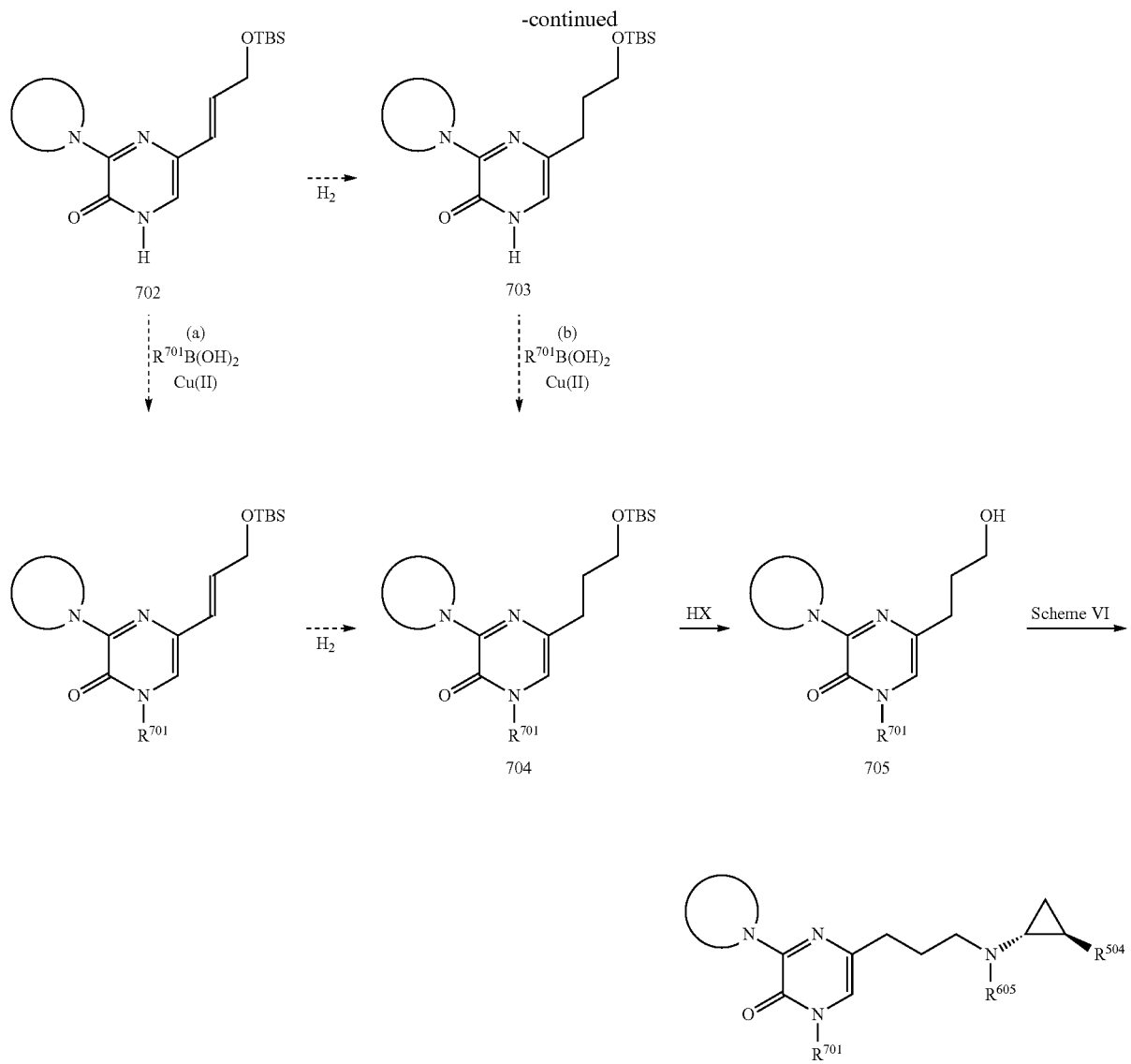

Certain examples disclosed herein can be synthesized using the following general synthetic procedure set forth in Scheme VII. Nucleophilic substitution of the dibromo pyrazinone shown with a cyclic amine brings in the first substituent. Pd(II) mediated coupling with vinyl boronate 701 introduces the side chain. At this stage, two opportunities are available for Cu(II) mediated coupling of the pyrazinone nitrogen with an organoboronic acid reagent: (a) before catalytic hydrogenation of the alkene, i.e., coupling with 702, or (b) catalytic hydrogenation of the alkene, i.e., coupling with 703. These two pathways are indicated in the Scheme VII diagram. In either case, TBS ether 704 is deprotected with acid, or with other techniques available in the art. The resulting alcohol 705 is transformed to the desired cyclopropylamine product via the route as disclosed for Scheme VI.

SCHEME VIII(a)(b)(c)

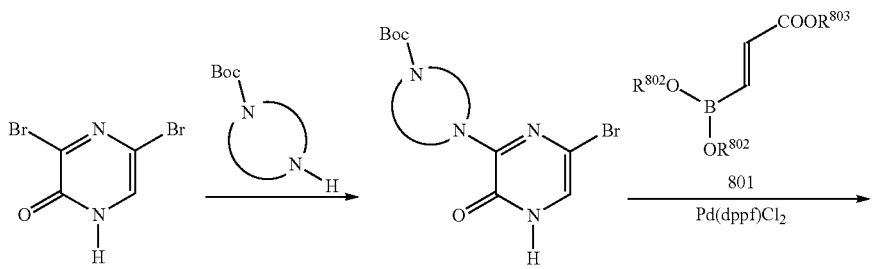

-continued

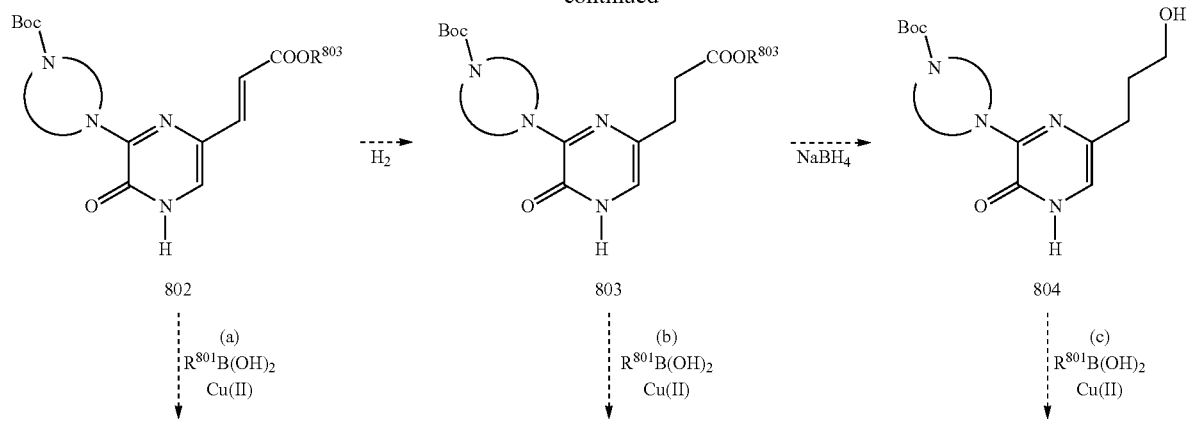

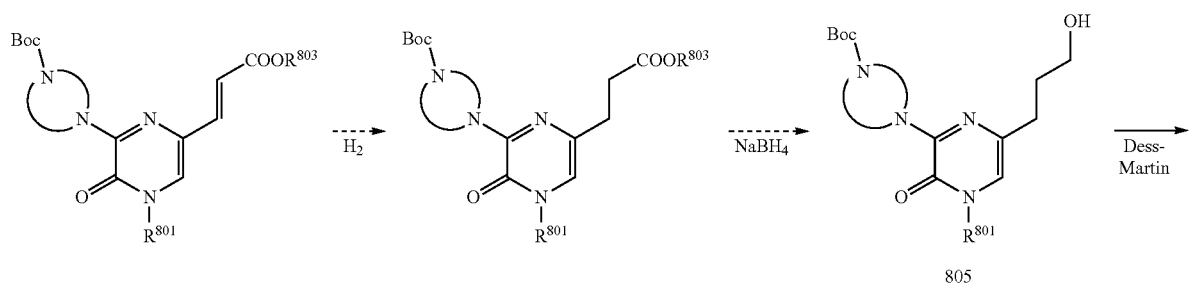

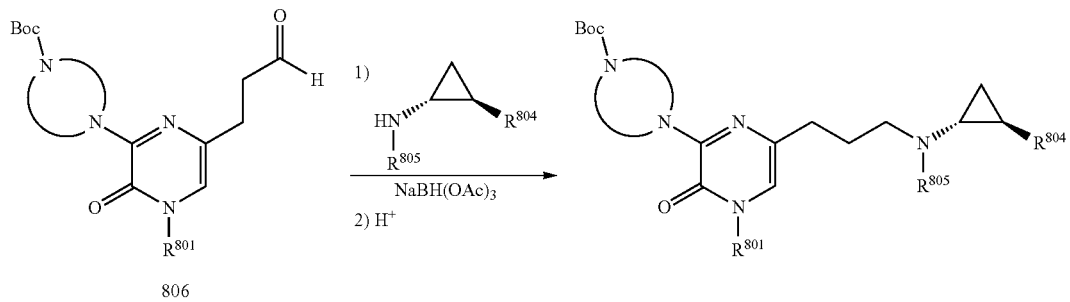

Certain examples disclosed herein can be synthesized using the following general synthetic procedure set forth in Scheme VIII. Nucleophilic substitution of the dibromo pyrazinone shown with a cyclic amine, which has a Boc-protected amino functionality, brings in the first substituent. Pd(II) mediated coupling with vinyl boronate 801 introduces the side chain. As with Scheme II, three opportunities are available for Cu(II) mediated coupling of the pyrazinone nitrogen with an organoboronic acid reagent, and are indicated in the Scheme III diagram. The resulting alcohol 805 is converted to aldehyde 806, which in turn is subjected to reductive amination conditions. Synthesis completed by removal of the Boc protecting group with acid.

SCHEME IX(a)(b)

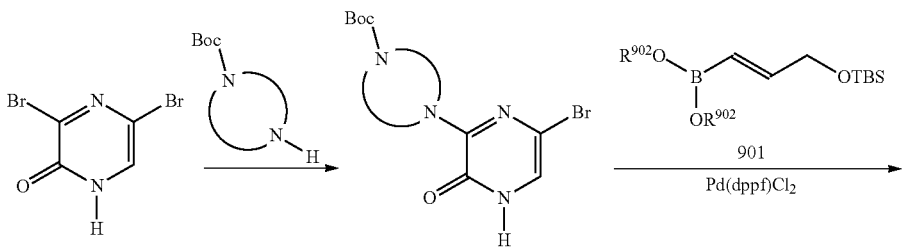

-continued

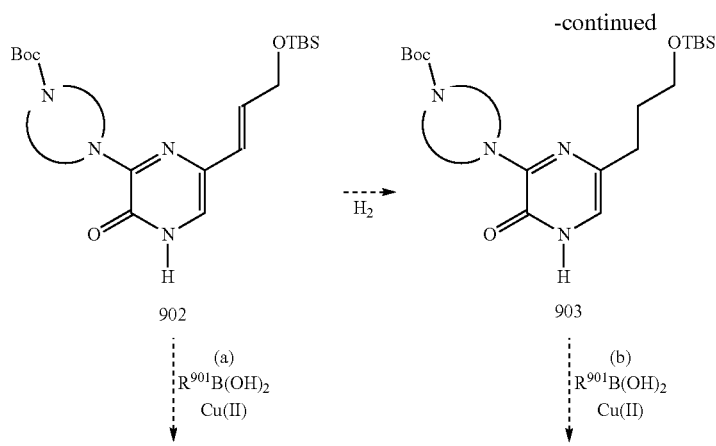

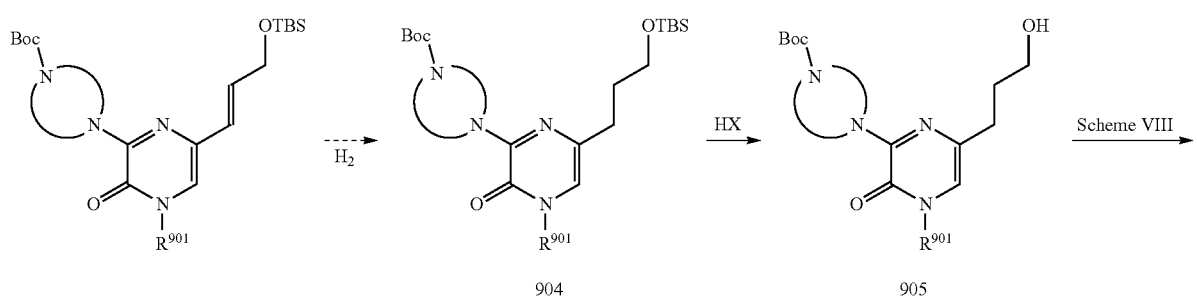

Certain examples disclosed herein can be synthesized using the following general synthetic procedure set forth in Scheme IX. Nucleophilic substitution of the dibromo pyrazinone shown with a cyclic amine, which has a Boc-protected amino functionality, brings in the first substituent. Pd(II) mediated coupling with vinyl boronate 901 introduces the side chain. As in Scheme VII, two opportunities are available for Cu(II) mediated coupling of the pyrazinone nitrogen with an organoboronic acid reagent: (a) before catalytic hydrogenation of the alkene, i.e., coupling with 902, or (b) catalytic hydrogenation of the alkene, i.e., coupling with 903. These two pathways are indicated in the Scheme IX diagram. In either case, TBS ether 904 is deprotected with acid, or with other techniques available in the art. The resulting alcohol 905 is converted to the desired cyclopropylamine via the methods disclosed in Scheme VIII.

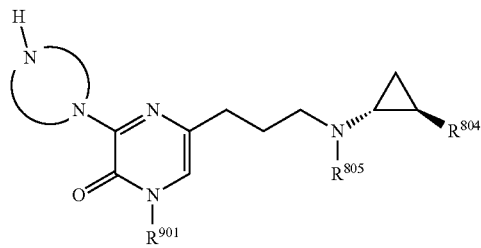

SCHEME X

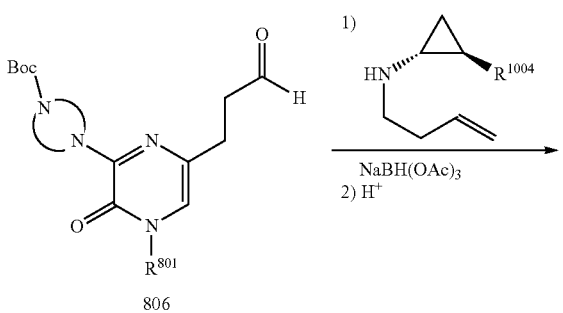

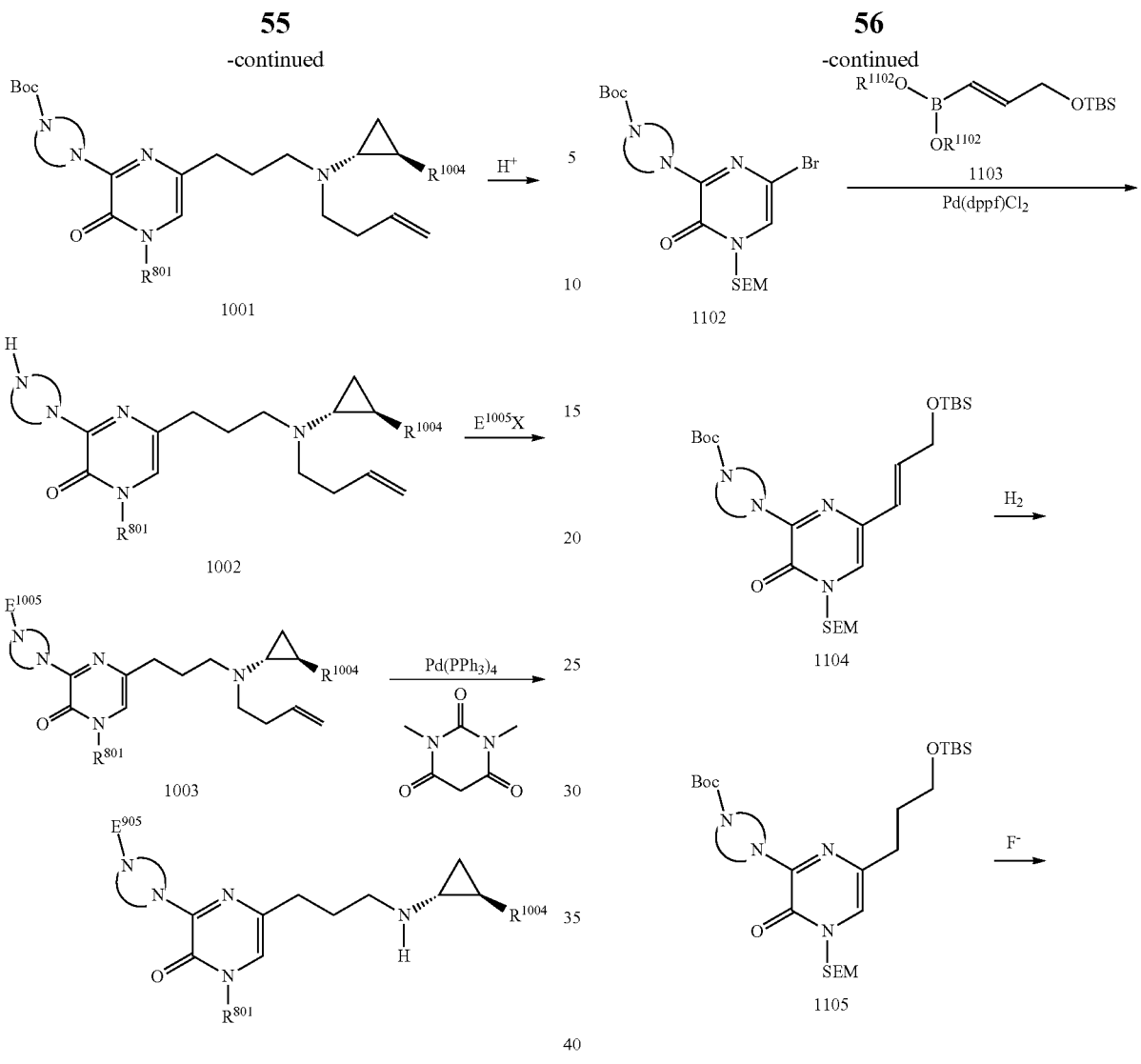

Certain examples disclosed herein can be synthesized using the following general synthetic procedure set forth in Scheme X. Synthesis of aldehyde 806 is accomplished as in Scheme VIII, or using other methods available in the art. Aldehyde 806 is subjected to reductive amination conditions with the allyl amine shown above. The Boc group is selectively removed with acid to give amine 1002, and can be functionalized with an electrophilic species, indicated as $E^{405}X$, to give 1003. Finally, the allyl group can be removed in the presence of a suitable Pd(0) catalyst.

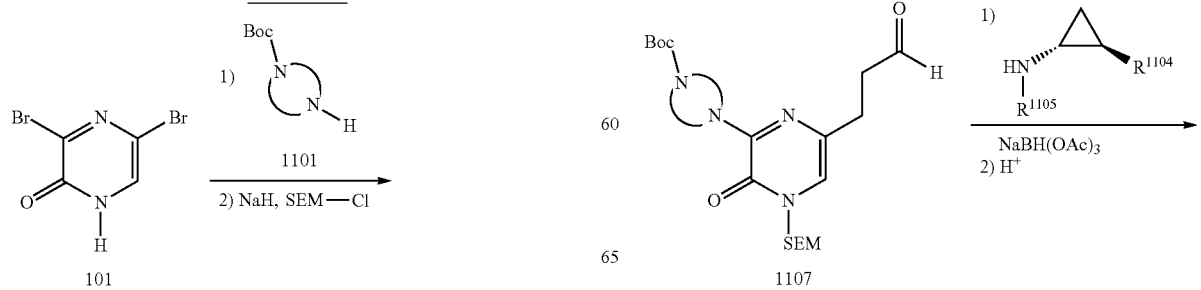

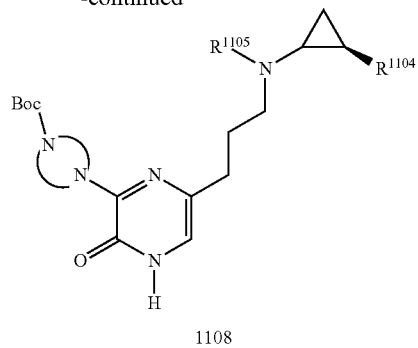

1108

Certain examples disclosed herein can be synthesized using the following general synthetic procedure set forth in Scheme XI. Dibromo precursor 101 is reacted with monoprotected diamine 1101 to give the selectively substituted pyrazinone 1102. Coupling with boronic ester 1103 gives disubstituted pyrazinone 1104. Functional group manipulation proceeds as before, to give aldehyde 1107, which is then coupled under reductive amination condition to give 1108.

The disclosure is further illustrated by the following examples.

EXAMPLES

Chromatographic Procedures

The following chromatographic procedures may be employed to purify the compounds disclosed below.

Procedure A: Sunfire Prep C18 OBD Column, 10 μm, 19×250 mm, mobile phase $H_2O$ (0.05% TFA)/$CH_3CN$, flow rate: 20 mL/min, detector, UV 254/210 nm.

Procedure B: (2 #-AnalyseHPLC-SHIMADZU (HPLC-10)), XBridge C18 OBD Prep column, pore size: 100 Å, particle size: 10 μm, column size: 19 mm×250 mm, mobile phase: $H_2O$ (0.05% TFA)/$CH_3CN$, detector, UV 254/220 nm.

Procedure C: (2 #-AnalyseHPLC-SHIMADZU (HPLC-10)), XBridge C18 OBD Prep column, pore size: 100 Å, particle size: 10 μm, column size: 19 mm×250 mm, mobile phase: $H_2O$ (10 mM $NaHCO_3$)/$CH_3CN$, detector, UV 254/220 nm.

Procedure D: (2 #-AnalyseHPLC-SHIMADZU (HPLC-10)), XBridge Shield RP18 OBD column, pore size: 130 Å, particle size 10 μm, column size: 19×250 mm, mobile phase: $H_2O$ (0.05% TFA)/$CH_3CN$, flow rate: 25 mL/min, detector, UV 254/220 nm.

Procedure E: (2 #-AnalyseHPLC-SHIMADZU (HPLC-10)), XBridge Shield RP18 OBD column, pore size: 130 Å, particle size 10 μm, column size: 19×250 mm, mobile phase: $H_2O$ (10 mM $NaHCO_3$)/$CH_3CN$, flow rate: 25 mL/min, detector, UV 254/220 nm.

Procedure F: (2 #SHIMADZU (HPLC-01)): Column, Xselect CSH OBD Column, particle size 5 μm, column size: 30×150 mm; mobile phase, $H_2O$ (0.05% TFA) and $CH_3CN$, flow rate 60 mL/min, Detector, UV 220/254 nm.

Procedure G: (2 #SHIMADZU (HPLC-01)): Column: Xselect CSH Fluoro Phenyl OBD Column, particle size 5 μm, column size: 19×250 mm, 5 um; mobile phase $H_2O$ (0.05% TFA) and $CH_3CN$, flow rate: 25 mL/min, Detector 254/210 nm.

Example 1

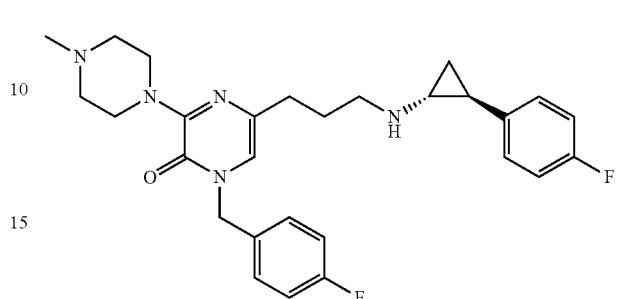

1-[4-Fluorobenzyl]-5-[3-([(1R,2S)-2-(4-fluorophenyl)cyclopropyl]amino)propyl]-3-[4-methylpiperazin-1-yl]pyrazin-2(1H)-one

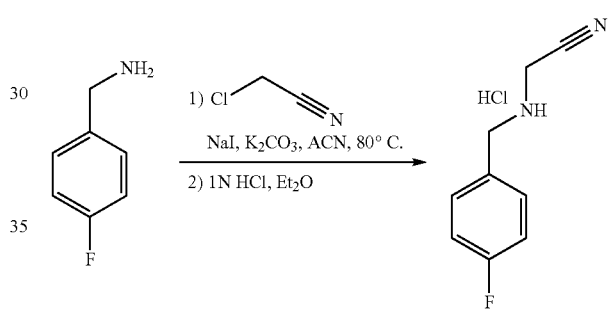

2-[(((4-Fluorophenyl)methyl)amino]acetonitrile A mixture of 2-chloroacetonitrile (6.6 g, 87.90 mmol, 1.1 equiv), (4-fluorophenyl)methanamine (10 g, 79.91 mmol, 1 equiv), $K_2CO_3$ (33.1 g, 239.72 mmol, 3 equiv), and NaI (119.8 mg, 0.80 mmol, 0.01 equiv) in $CH_3CN$ (200 mL) was stirred for 16 hr at 80° C. The solids were removed by filtration, and the filtrate was concentrated under vacuum. The residue was dissolved in 200 mL of $Et_2O$. The resulting solution was diluted with 50 mL of HCl in dioxane. The solid that formed was collected by filtration, affording 10 g (62.37%) of the title compound as a yellow solid.

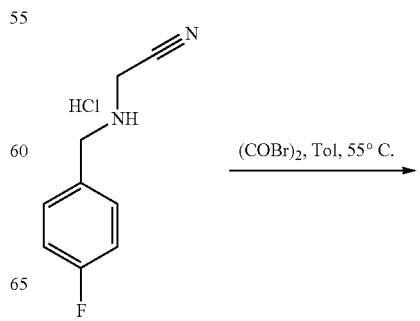

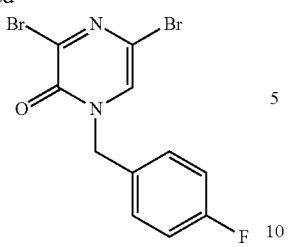

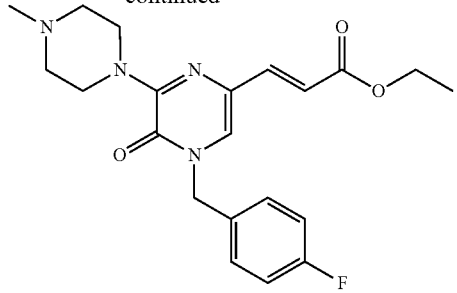

1-((4-Fluorophenyl)methyl)-3,5-dibromopyrazin-2(1H)-one A solution of the product from the previous step (12 g, 59.81 mmol, 1 equiv) and oxalyl bromide (64.5 g, 299.04 mmol, 5 equiv) in toluene (200 mL) was stirred for 16 hr at 55° C., then concentrated under vacuum. The residue was dissolved in 200 mL of CH$_2$Cl$_2$, washed with 2×100 ml of aq Na$_2$CO$_3$, and dried over anhydrous Na$_2$SO$_4$. The residue was purified with silica gel chromatography using EtOAc/petroleum ether (1:3) to afford 10 g (46.19%) of the title compound as a yellow oil.

Ethyl (2E)-3-[6-(4-methylpiperazin-1-yl)-5(4H)-oxo-4-((4-fluorophenyl)-methyl)pyrazin-2-yl]propenoate (Intermediate 1-4) A mixture of the product from the previous step (6 g, 15.75 mmol, 1 equiv), ethyl (2E)-3-(tetramethyl-1,3,2-dioxaborolan-2-yl)prop-2-enoate (5.34 g, 23.62 mmol, 1.5 equiv), K$_2$CO$_3$ (6.52 g, 47.24 mmol, 3 equiv), Pd(dppf)Cl$_2$ (1.15 g, 1.57 mmol, 0.1 equiv), dioxane (300 mL), and H$_2$O (100 mL) was stirred overnight at 90° C. under N$_2$. The residue was purified with silica gel chromatography using EtOAc/petroleum ether to afford 3 g (48%) of the title compound as a yellow oil.

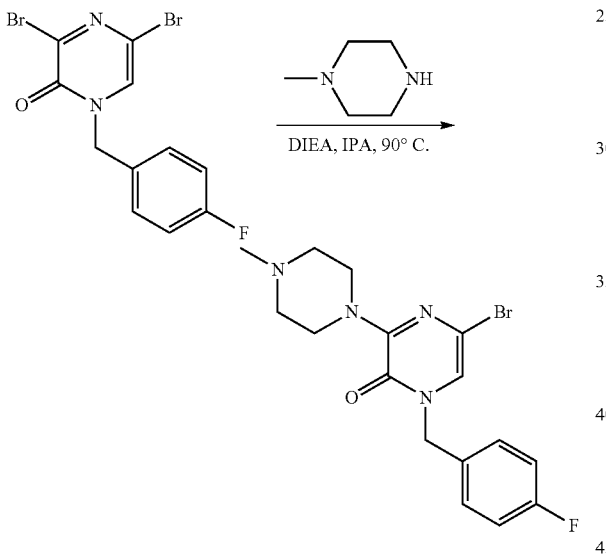

3-(4-Methylpiperazin-1-yl)-5-bromo-1-((4-fluorophenyl)methyl)pyrazin-2(1H)-one (Intermediate 1-3) A solution of the product from the previous step (10 g, 27.62 mmol, 1.00 equiv) in IPA (500 mL), 1-methylpiperazine (3.31 g, 33.15 mmol, 1.20 equiv), and DIEA (7.13 g, 55.25 mmol, 2.01 equiv) was stirred overnight at 90° C. The residue was purified with silica gel chromatography using EtOAc/petroleum ether (5:1), affording 10 g (95%) of the title compound as a yellow oil.

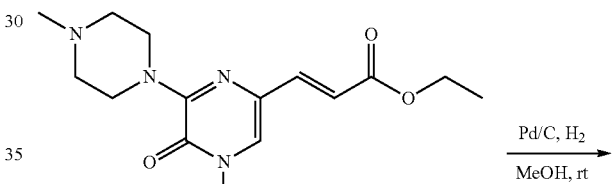

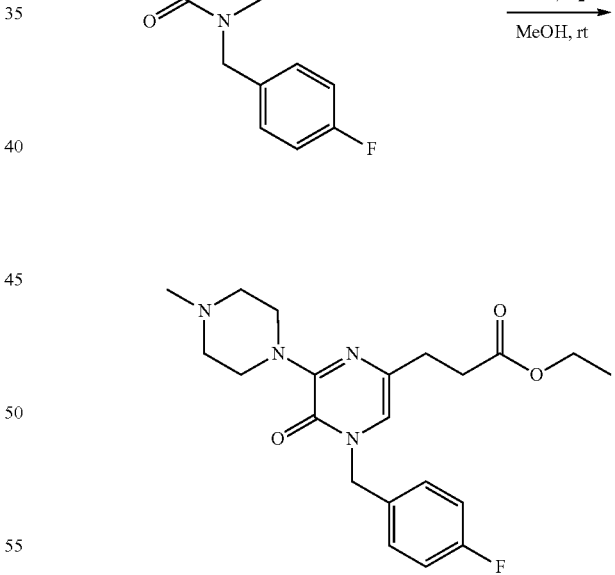

Ethyl 3-[6-(4-methylpiperazin-1-yl)-5(4H)-oxo-4-((4-fluorophenyl)methyl)-pyrazin-2-yl]propanoate (Intermediate 1-5) A solution of the product from the previous step (3 g, 7.5 mmol, 1.00 equiv) in MeOH (50 mL) was stirred for 1 h over Pd/C (1.0 g) under an H$_2$ atmosphere at rt. The solids were removed by filtration, and the filtrate was concentrated under vacuum to afford 2.6 g (86%) of the title compound as a yellow oil.

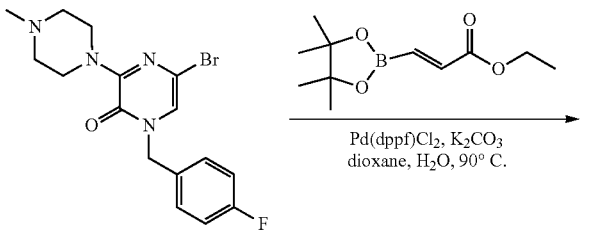

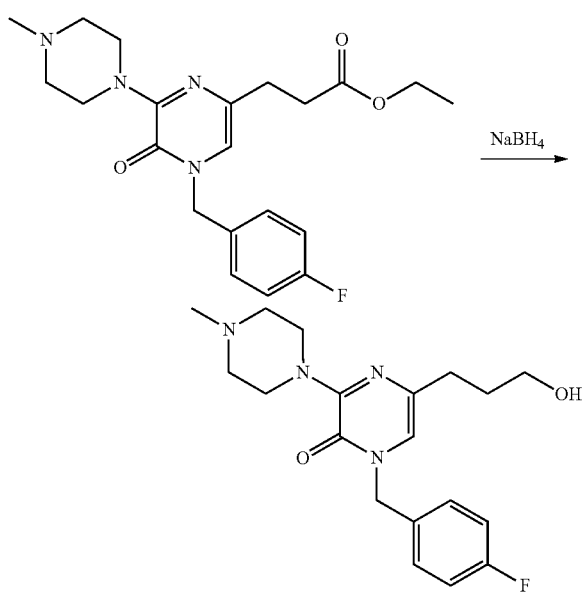

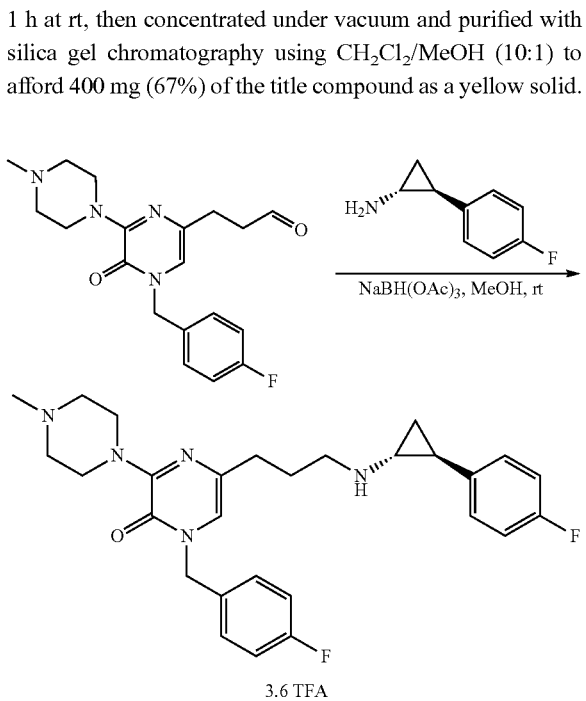

3-[6-(4-Methylpiperazin-1-yl)-4-((4-fluorophenyl)methyl)-5(4H)-oxopyrazin-2-yl]propan-1-ol (Intermediate 1-6) To a stirred solution of the product from the previous step (1.3 g, 3.23 mmol, 1 equiv) in MeOH (50 mL) was added NaBH₄ (2.46 g, 64.68 mmol, 20 equiv) in portions. The resulting solution was stirred for 16 hr at rt. The reaction was then quenched by the addition of 200 mL of H₂O. The resulting solution was extracted with 3×100 ml of CH₂Cl₂, then concentrated under reduced pressure. The residue was purified with silica gel chromatography using CH₂Cl₂/MeOH (10:1) to afford 700 mg (60%) of the title compound as a yellow solid.

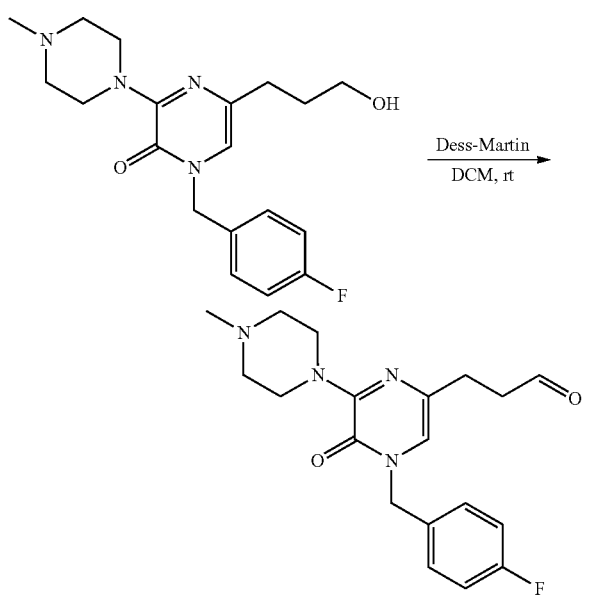

3-[6-(4-Methylpiperazin-1-yl)-4-((4-fluorophenyl)methyl)-5(4H)-oxopyrazin-2-yl]propanal (Intermediate 1-7) A solution of the product from the previous step (600 mg, 1.67 mmol, 1.00 equiv) and Dess-Martin reagent (848 mg, 2.00 mmol, 1.20 equiv) in CH₂Cl₂ (30 mL) was stirred for 1 h at rt, then concentrated under vacuum and purified with silica gel chromatography using CH₂Cl₂/MeOH (10:1) to afford 400 mg (67%) of the title compound as a yellow solid.

1-[4-Fluorobenzyl]-5-[3-([(1R,2S)-2-(4-fluorophenyl)cyclopropyl]amino)-propyl]-3-[4-methylpiperazin-1-yl]pyrazin-2(1H)-one (Example 1) A solution of the product from the previous step (400 mg, 1.12 mmol, 1 equiv) and (1R,2S)-2-(4-fluorophenyl)-cyclopropan-1-amine (202 mg, 1.34 mmol, 1.2 equiv) in MeOH (20 mL) was stirred for 30 min at rt. To the solution was then added NaBH(OAc)₃ (568 mg, 2.68 mmol, 2.4 equiv) at rt. The resulting solution was stirred for 30 min at rt. The reaction was then quenched by the addition of 30 mL of H₂O. The resulting solution was extracted with 3×30 ml of CH₂Cl₂. The organic layers were combined, concentrated under reduced pressure, and purified using chromatographic Procedure A (30% to 33% CH₃CN in 9 min), to afford 88.2 mg (9%) of the title compound as a yellow oil.

LC-MS: (ES, m/z): 494 [M+H]⁺. ¹H NMR (400 MHz, MeOD-d₄) δ ppm: 7.39-7.36 (m, 2H), 7.18-7.15 (m, 2H), 7.07-7.01 (m, 5H), 5.04 (s, 2H), 4.87-4.81 (m, 2H), 3.52-3.47 (m, 2H), 3.21-3.12 (m, 6H), 2.94-2.90 (m, 4H), 2.53-2.42 (m, 3H), 2.06-1.98 (m, 2H), 1.49-1.32 (m, 2H).

Example 2

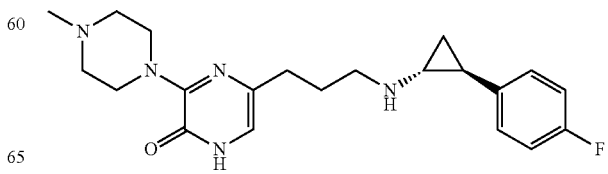

5-[3-([(1R,2S)-2-(4-fluorophenyl)cyclopropyl]amino)propyl] 3-[4-methylpiperazin-1-yl]-pyrazin-2(1H)-one

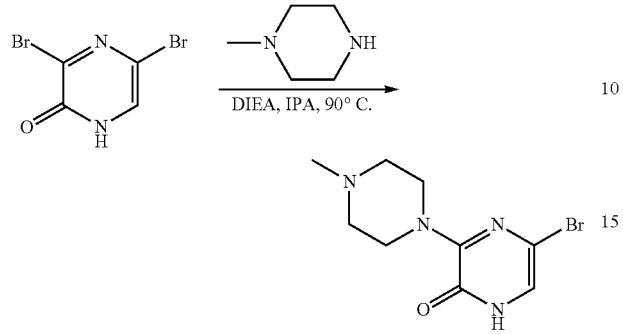

5-Bromo-3-(4-methylpiperazin-1-yl)-pyrazin-2(1H)-one (Intermediate 2-1)

A solution of 3,5-dibromo-1,2-dihydropyrazin-2-one (10 g, 39.84 mmol, 1.00 equiv), 1-methylpiperazine (4.38 g, 1.1 eq), and DIEA (15.41 g, 3.0 equiv) in IPA (50 mL) was stirred for 16 h at 90° C., then cooled and concentrated under vacuum, to afford 10 g (91%) of the title compound as an off-white solid.

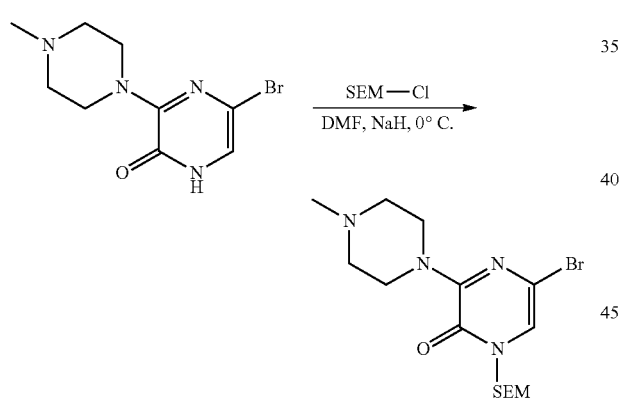

5-Bromo-3-(4-methylpiperazin-1-yl)-1-[(2-(trimethylsilyl)ethoxy)methyl]-pyrazin-2(1H)-one (Intermediate 2-2)

To a solution of the product from the previous step (10 g, 36.76 mmol, 1 equiv), in DMF (500 mL) was added NaH (60%) (2.21 g, 55.25 mmol, 1.5 equiv). The resulting solution was stirred for 1 hr at 0° C., then a solution of [2-(chloromethoxy)ethyl]trimethylsilane (9.15 g, 55.12 mmol, 1.5 equiv) in DMF (100 mL) was added dropwise with stirring over 30 min. The resulting solution was stirred for an additional 4 hr at rt, then diluted 500 ml of H₂O and extracted with 3×500 ml of EtOAc. The combined organic layers were concentrated and purified with silica gel chromatography using EtOAc/petroleum ether (1:3) to afford 10.5 g (55.08%) of the title compound as a yellow oil.

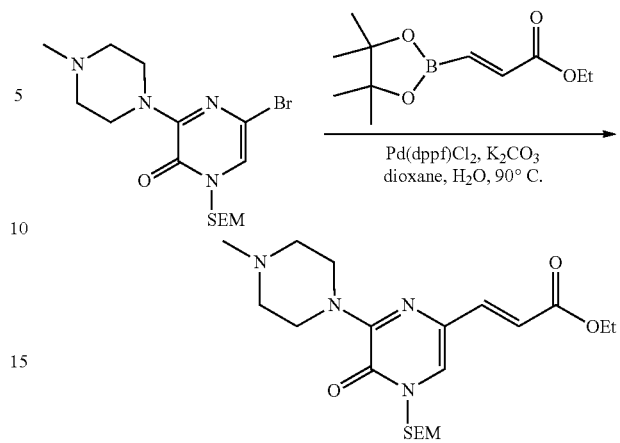

Ethyl (2E)-3-[6-(4-methylpiperazin-1-yl)-5(4H)-oxo-4-[(2-(trimethylsilyl)-ethoxy)methyl]-pyrazin-2-yl]propenoate (Intermediate 2) The procedure for preparing Intermediate 1-4 was used with the product from the previous step (5 g, 12.39 mmol). The crude product was purified with silica gel chromatography using EtOAc/petroleum ether (1:3) to afford 2.5 g (55%) of the title compound as a light yellow solid.

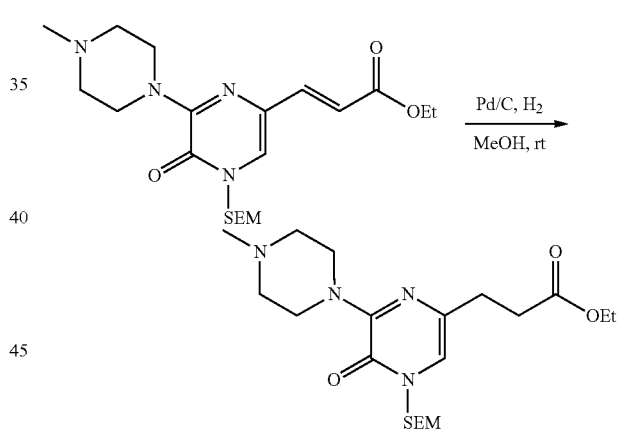

Ethyl 3-[6-(4-methylpiperazin-1-yl)-5(4H)-oxo-4-[(2-(trimethylsilyl)ethoxy)-methyl]-pyrazin-2-yl]propanoate (Intermediate 2-4) The procedure for preparing Intermediate 1-5 was used with Intermediate 2-3 (2.5 g, 5.92 mmol, 1.00 equiv) to afford 2.2 g (93%) of the title compound as a solid.

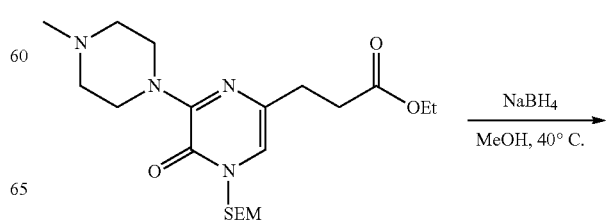

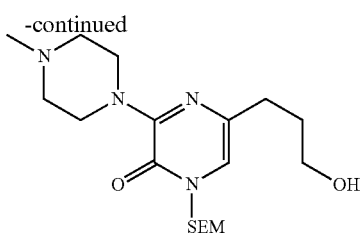

3-[6-(4-Methylpiperazin-1-yl)-5(4H)-oxo-4-[[2-(trimethylsilyl)ethoxy]methyl]pyrazin-2-yl]propan-1-ol (Intermediate 2-5) The procedure for preparing Intermediate 1-6 was used with Intermediate 2-4 (2.2 g, 5.92 mmol, 1.00 equiv). The crude product was purified with silica gel chromatography using CH$_2$Cl$_2$/MeOH (1:10) to afford 1.3 g (52%) of the title compound as a solid.

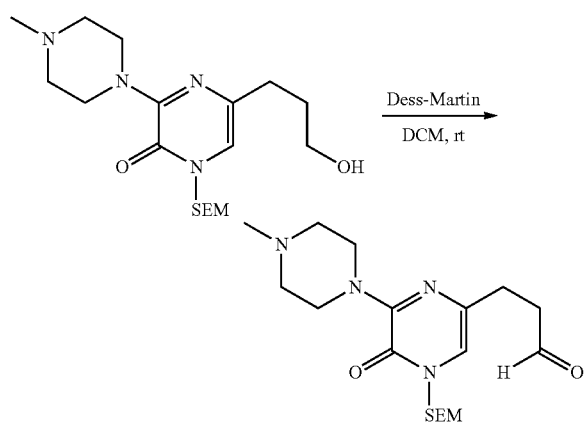

3-[6-(4-Methylpiperazin-1-yl)-5(4H)-oxo-4-[[2-(trimethylsilyl)ethoxy]methyl]pyrazin-2-yl]propanal (Intermediate 2-6) The procedure for preparing Intermediate 1-7 was used with Intermediate 2-5 (1.3 g, 3.40 mmol, 1.00 equiv). The crude product was purified with silica gel chromatography using EtOAc/petroleum ether (1:3) to afford 700 mg (74%) of the title compound as a light yellow solid.

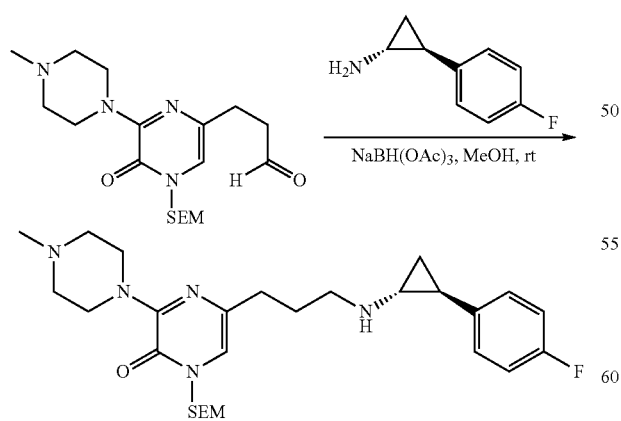

5-(3-[[(1R,2S)-2-(4-Fluorophenyl)cyclopropyl]amino]propyl)-3-(4-methyl-piperazin-1-yl)-1-[[2-(trimethylsilyl)ethoxy]methyl]pyrazin-2(1H)-one (Intermediate 2-7) The reductive amination step for preparing Example 1 from Intermediate 1-7 was used with Intermediate 2-6 (700 mg, 1.84 mmol, 1.00 equiv). The residue was purified using silica gel chromatography using EtOAc/petroleum ether (1:3) to afford 400 mg (69%) of the title compound as a light yellow solid.

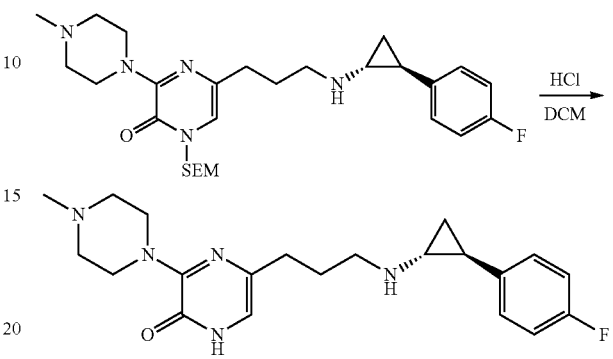

5-[3-([[(1R,2S)-2-(4-fluorophenyl)cyclopropyl]amino)propyl] 3-[4-methylpiperazin-1-yl]-pyrazin-2(1H)-one (Example 2) A solution of Intermediate 2-7 (300 mg, 0.58 mmol, 1.00 equiv) in aq HCl (25 mL)/CH$_2$Cl$_2$ (25 mL) was stirred for 1 h at rt. The resulting mixture was concentrated under vacuum, then purified using chromatographic Procedure E (28% to 60% CH$_3$CN in 7 min), Rt: 6.20 min, to afford 44.1 mg (20%) of the title compound as an off-white solid.

LC-MS: (ES, m/z): 386 [M+H]$^+$. $^1$H NMR (400 MHz, Methanol-d$_4$) δ 7.06-7.03 (m, 2H), 6.97-6.93 (m, 2H), 6.65-6.62 (s, 1H), 3.82-3.72 (s, 4H), 2.78-2.72 (m, 2H), 2.58-2.50 (m, 4H), 2.48-2.42 (m, 2H), 2.36-2.30 (m, 4H), 1.90-1.85 (m, 3H), 1.10-1.02 (m, 1H), 1.02-0.95 (m, 1H).

Example 3

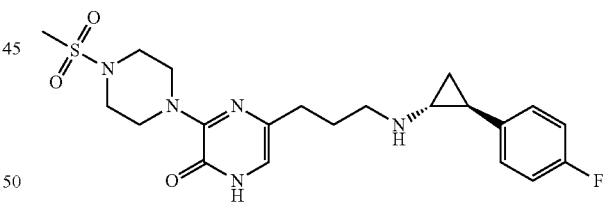

5-[3-([[(1R,2S)-2-(4-fluorophenyl)cyclopropyl]amino)propyl]-3-[4-(methylsulfonyl)piperazin-1-yl]pyrazin-2(1H)-one

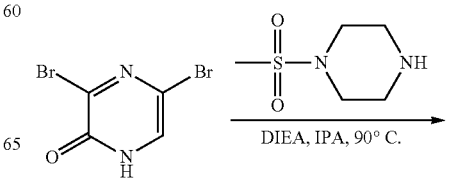

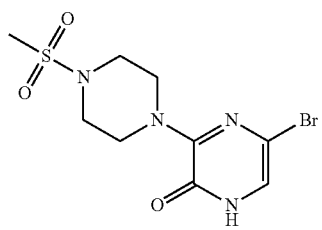

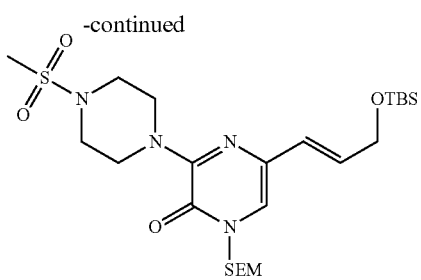

5-Bromo-3-(4-(methylsulfonyl)piperazin-1-yl)-pyrazin-2(1H)-one (Intermediate 3-1) The procedure for preparing Intermediate 2-1 was used with 3,5-dibromo-1,2-dihydropyrazin-2-one (10 g, 39.39 mmol, 1.00 equiv) and 1-(methylsulfonyl)-piperazine (7.80 g, 47.56 mmol, 1.21 equiv). The crude product was purified with silica gel chromatography using EtOAc/petroleum ether (4:1) to afford 10 g (75%) of the title compound as a off-white solid.

(E)-5-[[3-((tert-butyldimethyl)silyl)oxy]propen-1-yl]-3-(4-(methylsulfonyl)-piperazin-1-yl)-1-[(2-(trimethylsilyl)ethoxy)methyl]-pyrazin-2(1H)-one (Intermediate 3-3) A mixture of Intermediate 3-2 (8.2 g, 17.56 mmol, 1 equiv), tert-butyldimethyl[([2E]-3-[tetramethyl-1,3,2-dioxaborolan-2-yl]prop-2-en-1-yl)oxy]silane (7.85 g, 26.34 mmol, 1.5 equiv), K₂CO₃ (7.27 g, 52.68 mmol, 3 equiv), Pd(dppf)Cl₂ (1.28 g, 1.74 mmol, 0.1 equiv), dioxane (450 mL), and H₂O (150 mL) was stirred overnight at 90° C., concentrated under vacuum, and purified with silica gel chromatography using EtOAc/petroleum ether (1:2) to afford 3.2 g (33%) of the title compound as a yellow oil.

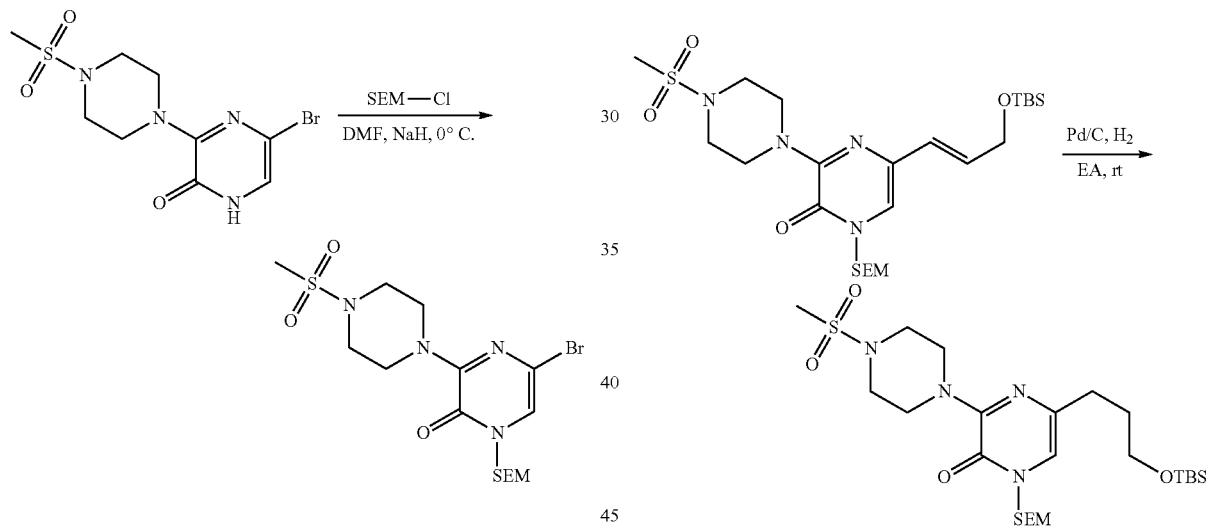

5-Bromo-3-(4-(methylsulfonyl)piperazin-1-yl)-1-[(2-(trimethylsilyl)ethoxy)-methyl]-pyrazin-2(1H)-one (Intermediate 3-2) The procedure for preparing Intermediate 2-2 was used with Intermediate 3-1. The crude product was purified with silica gel chromatography using EtOAc/petroleum ether (1:3) to afford 8.2 g (59%) of the title compound as a yellow oil.

5-[[3-((tert-butyldimethyl)silyl)oxy]propyl]-3-(4-(methylsulfonyl)piperazin-1-yl)-1-[(2-(trimethylsilyl)ethoxy)methyl]-pyrazin-2(1H)-one (Intermediate 3-4) A solution of Intermediate 3-3 (1.5 g, 2.68 mmol, 1.00 equiv) in EtOAc (100 mL) was stirred over Pd/C (0.15 g) under an H₂ atmosphere for 2 h at rt. The solids were removed by filtration, and the filtrate was concentrated under vacuum, to afford 1.2 g (80%) of the title compound as a yellow oil.

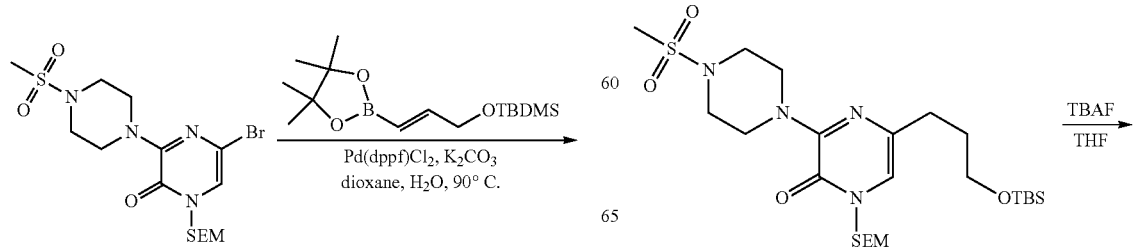

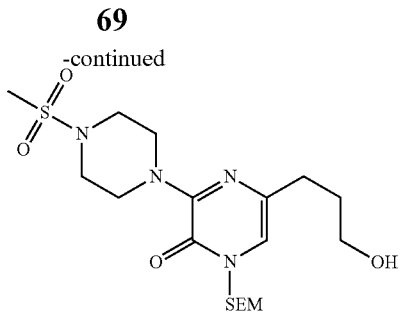
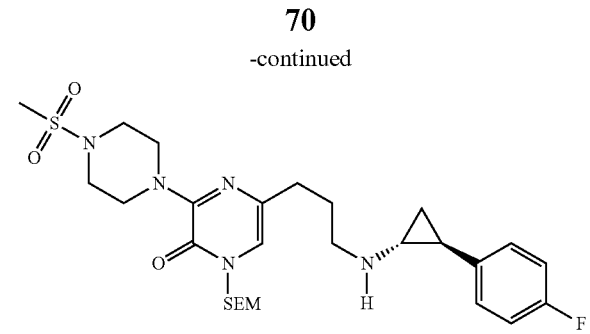

3-[6-(4-(methylsulfonyl)piperazin-1-yl)-5(4H)-oxo-4-[(2-(trimethylsilyl)-ethoxy)methyl]-pyrazin-2-yl]-propan-1-ol (Intermediate 3-5) A solution of Intermediate 3-4 (1.2 g, 2.14 mmol, 1 equiv) and TBAF (10 mL, THF) in THF (50 mL) was stirred for 2 hr at rt. The residue was purified with silica gel chromatography using CH$_3$CN/H$_2$O (1:3) to afford 750 mg (78%) of the title compound as an off-white solid.

5-(3-[[(1R,2S)-2-(4-Fluorophenyl)cyclopropyl]amino]propyl)-3-(4-(methyl-sulfonyl)piperazin-1-yl)-1-[[2-(trimethylsilyl)ethoxy]methyl]pyrazin-2 (1H)-one The reductive amination step for preparing Example 1 from Intermediate 1-7 was used with the product from the previous step (400 mg, 0.899 mmol, 1 equiv). The crude reaction product was purified with silica gel chromatography using EtOAc/petroleum ether (2:1) to afford 300 mg (58%) of the title compound as a yellow solid.

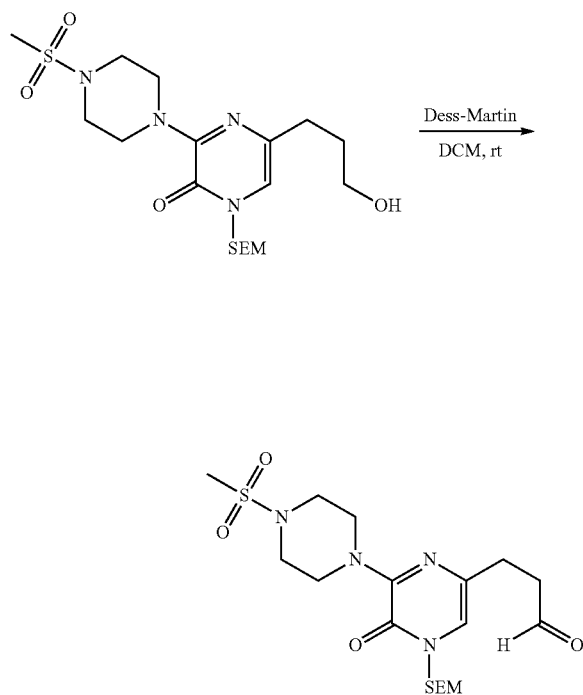

3-[6-(4-(methylsulfonyl)piperazin-1-yl)-5(4H)-oxo-4-[(2-(trimethylsilyl)-ethoxy)methyl]-pyrazin-2-yl]-propanal The procedure for preparing Intermediate 1-7 was used with Intermediate 3-5 (600 mg, 1.34 mmol) to afford 400 mg (67%) of the title compound as a yellow oil.

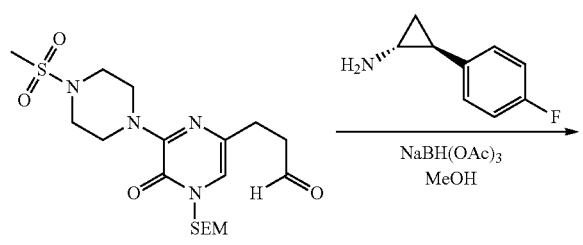

5-[3-([(1R,2S)-2-(4-fluorophenyl)cyclopropyl]amino)propyl]-3-[4-(methylsulfonyl)piperazin-1-yl]pyrazin-2 (1H)-one A solution of the product from the previous step (300 mg, 0.52 mmol, 1 equiv) and TFA (2 mL) in CH$_2$Cl$_2$ (10 mL) was stirred for 1 h at rt. The crude product (5 mL) was purified using chromatographic Procedure B (10.0% to 29.0% CH$_3$CN in 9 min), to afford 49.1 mg (21%) of the title compound as a yellow oil.

LC-MS: (ES, m/z): 450 [M+H]$^+$. $^1$H NMR (400 MHz, MeOD-d$_4$) δ ppm: 7.20-7.17 (m, 2H), 7.07-7.02 (m, 2H), 6.69 (s, 1H), 3.89-3.80 (m, 4H), 3.30-3.27 (m, 4H), 3.26-3.22 (m, 2H), 2.98-2.94 (m, 1H), 2.85 (s, 3H), 2.55-2.51 (m, 2H), 2.47-2.42 (m, 1H), 2.08-2.01 (m, 2H), 1.50-1.46 (m, 1H), 1.40-1.34 (m, 1H).

Example 4

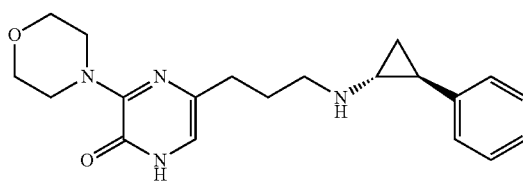

5-[3-([(1R,2S)-2-(4-fluorophenyl)cyclopropyl]amino)propyl]-3-morpholinopyrazin-2(1H)-one

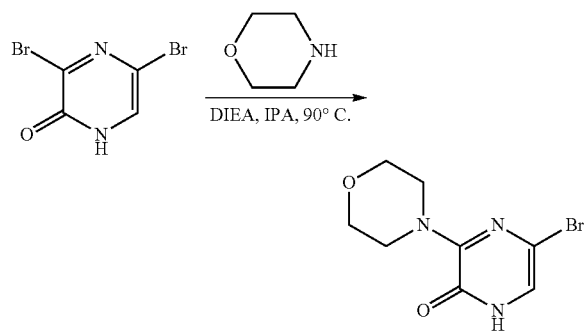

5-Bromo-3-(morpholin-4-yl)-pyrazin-2(1H)-one (Intermediate 4-1) The procedure for preparing Intermediate 2-1 was used with 3,5-dibromo-1,2-dihydropyrazin-2-one (10 g, 39.39 mmol, 1.00 equiv) and morpholine (5.1 g, 58.54 mmol, 1.50 equiv), using 2 h of reaction time at 90° C., affording 9 g (88%) of the title compound as a light yellow solid.

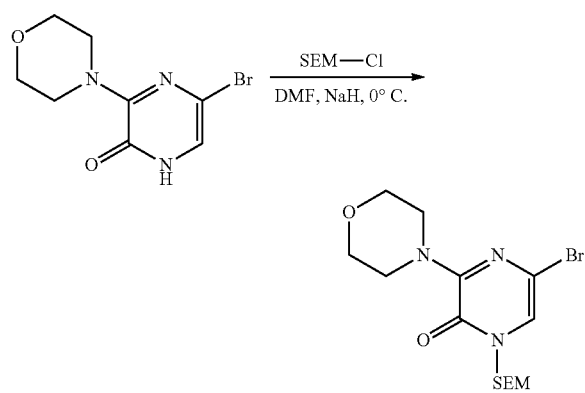

5-Bromo-3-(morpholin-4-yl)-1-[(2-(trimethylsilyl)ethoxy)methyl]-pyrazin-2(1H)-one (Intermediate 4-2) A mixture of Intermediate 4-1 (9 g, 34.60 mmol, 1.00 equiv), NaH (2.4 g, 100.00 mmol, 3.00 equiv), and [2-(chloromethoxy)ethyl]trimethylsilane (8.6 g, 51.58 mmol, 1.50 equiv) in DMF (80 mL) was stirred for 3 h at 0-10° C. The reaction was quenched and diluted with 500 mL of EtOAc. The resulting mixture was washed with 5×200 mL of $H_2O$.

The organic phase was dried over $Na_2SO_4$ and concentrated under vacuum, to afford 7 g (52%) of the title compound as light yellow oil.

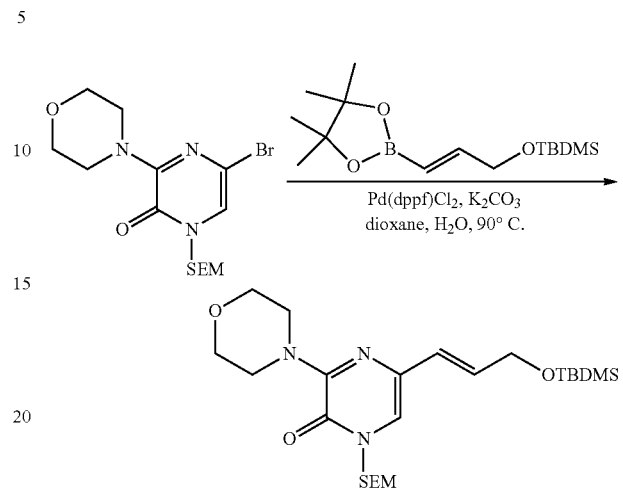

(E)-5-[[3-((tert-butyldimethyl)silyl)oxy]propen-1-yl]-3-(morpholin-4-yl)-1-[(2-(trimethylsilyl)ethoxy)methyl]-pyrazin-2(1H)-one (Intermediate 4-3 The procedure for preparing Intermediate 3-3 was used with Intermediate 4-2 (7 g, 17.93 mmol), using 2 hr of reaction time at 90° C., to afford 3.6 g (42%) of the title compound as a light yellow oil.

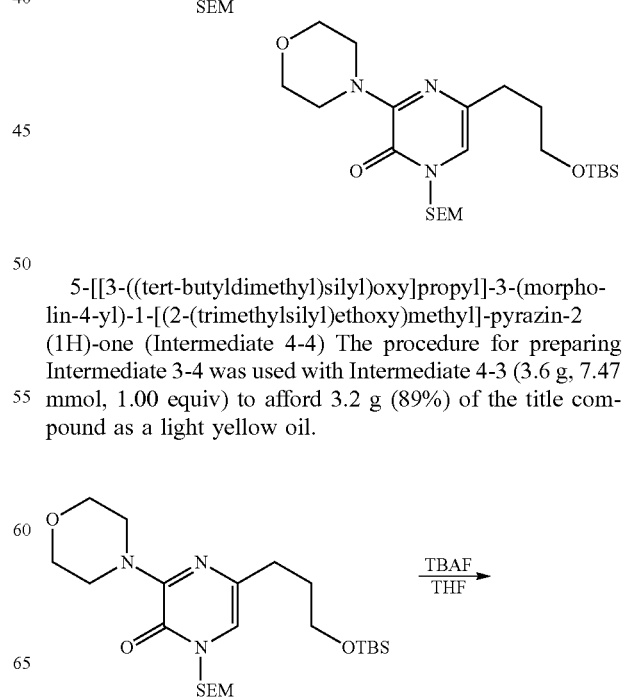

5-[[3-((tert-butyldimethyl)silyl)oxy]propyl]-3-(morpholin-4-yl)-1-[(2-(trimethylsilyl)ethoxy)methyl]-pyrazin-2(1H)-one (Intermediate 4-4) The procedure for preparing Intermediate 3-4 was used with Intermediate 4-3 (3.6 g, 7.47 mmol, 1.00 equiv) to afford 3.2 g (89%) of the title compound as a light yellow oil.

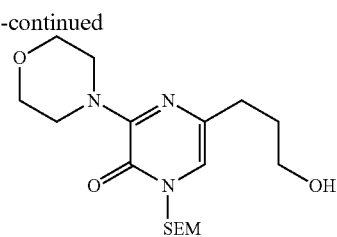

3-[6-(morpholin-4-yl)-5(4H)-oxo-4-[(2-(trimethylsilyl)ethoxy)methyl]-pyrazin-2-yl]-propan-1-ol (Intermediate 4-5) A solution of Intermediate 4-4 (1.4 g, 2.89 mmol, 1.00 equiv) and TBAF (5 mL, 1.20 equiv) in THF (30 mL) was stirred for 2 h at 25° C. The residue was purified with silica gel column using H$_2$O/MeCN (2:1) to afford 0.73 g (68%) of the title compound as a light yellow oil.

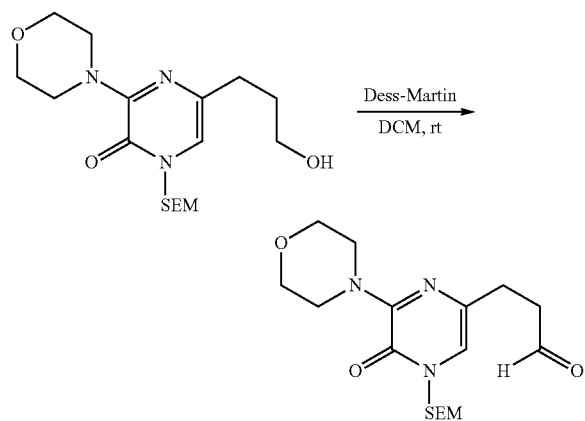

3-[6-(morpholin-4-yl)-5(4H)-oxo-4-[(2-(trimethylsilyl)ethoxy)methyl]-pyrazin-2-yl]-propanal (Intermediate 4-6) The procedure for preparing Intermediate 1-7 was used with Intermediate 4-5 (700 mg, 1.89 mmol, 1.00 equiv) to afford 0.35 g (50%) of the title compound as a light yellow solid.

5-(3-[[(1R,2S)-2-(4-Fluorophenyl)cyclopropyl]amino]propyl)-3-(morpholin-4-yl)-1-[[2-(trimethylsilyl)ethoxy]methyl]pyrazin-2(1H)-one (Intermediate 4-7) A mixture of Intermediate 4-6 (350 mg, 0.95 mmol, 1.00 equiv), (1R,2S)-2-(4-fluoro-phenyl)cyclopropan-1-amine (170 mg, 1.12 mmol, 1.10 equiv), NaBH(OAc)$_3$ (480 mg, 2.26 mmol, 2.40 equiv), and MeOH (20 mL) was stirred for 2 h at 25° C., then diluted with 100 mL of CH$_2$Cl$_2$, washed with 3×20 mL of H$_2$O, dried over Na$_2$SO$_4$, and concentrated under reduced pressure to afford 0.32 g (67%) of the title compound as a light yellow oil.

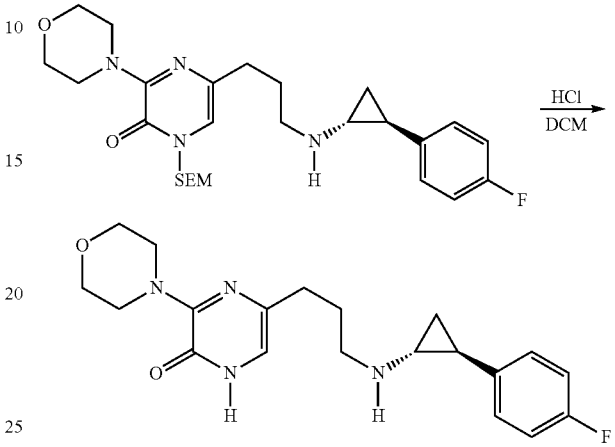

5-[3-([(1R,2S)-2-(4-fluorophenyl)cyclopropyl]amino)propyl]-3-morpholinopyrazin-2(1H)-one The deprotection step for preparing Example 2 from Intermediate 2-7 was used with the product from the previous step (320 mg, 0.64 mmol). The crude product (5 mL) was purified using chromatographic Procedure B (30.0% to 50.0% CH$_3$CN in 8 min), to afford 115.4 mg (49%) of the title compound as a white solid.

LC-MS: (ES, m/z): 373 [M+H]$^+$. $^1$H NMR (300 MHz, MeOD-d$_4$) δ ppm: 7.23-7.13 (m, 2H), 7.13-6.96 (m, 2H), 6.70-6.60 (s, 1H), 3.80-3.68 (m, 8H), 3.22-3.18 (m, 1H), 3.00-2.82 (m, 1H), 2.59-2.36 (m, 3H), 2.07-1.97 (m, 3H), 1.52-1.30 (m, 2H).

Example 5

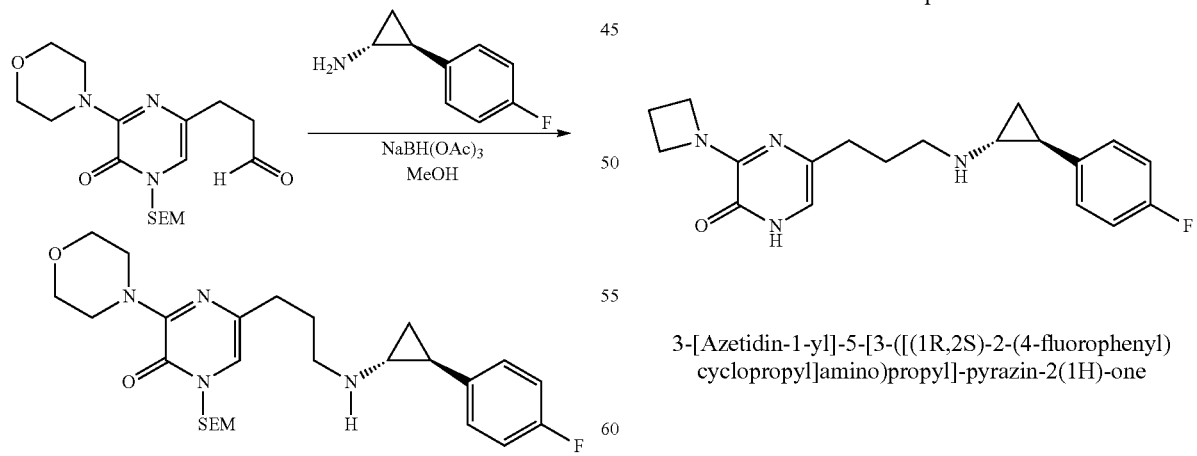

3-[Azetidin-1-yl]-5-[3-([(1R,2S)-2-(4-fluorophenyl)cyclopropyl]amino)propyl]-pyrazin-2(1H)-one

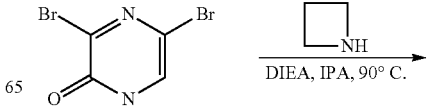

-continued

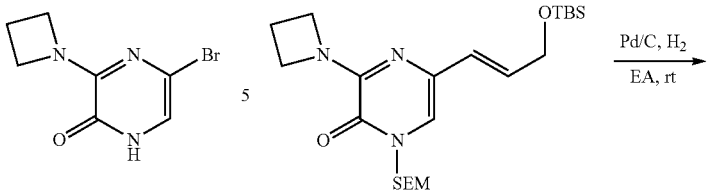

5-Bromo-3-(azetidin-1-yl)-pyrazin-2(1H)-one The procedure for preparing Intermediate 2-1 was used with 3,5-dibromo-1,2-dihydropyrazin-2-one (10 g, 39.39 mmol, 1.00 equiv) and azetidine (2.75 g, 47.56 mmol, 1.21 equiv). The crude product was purified with silica gel chromatography using EtOAc/petroleum ether (4:1) to afford 7.1 g (78.1%) of the title compound as a white solid.

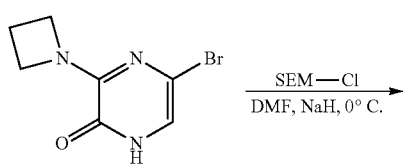

5-Bromo-3-(azetidin-1-yl)-1-[(2-(trimethylsilyl)ethoxy)methyl]-pyrazin-2(1H)-one The procedure for preparing Intermediate 2-2 was used with the product from the previous step (7.1 g, 30.87 mmol, 1 equiv), to afford 7.2 g (64.8%) of the title compound as a yellow oil.

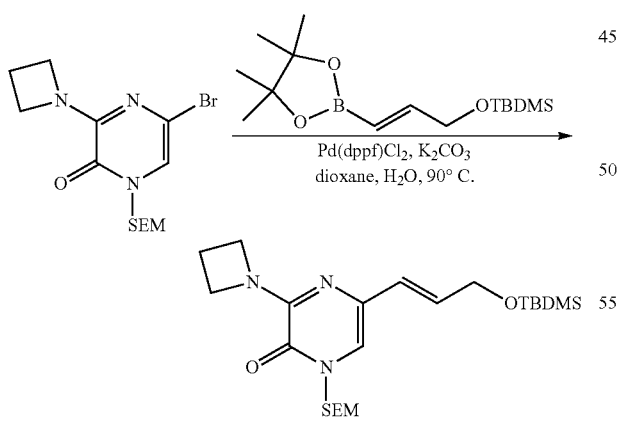

(E)-5-[[3-((tert-butyldimethyl)silyl)oxy]propen-1-yl]-3-(azetidin-1-yl)-1-[(2-(trimethylsilyl)ethoxy)methyl]-pyrazin-2(1H)-one The procedure for preparing Intermediate 3-3 was used with the product from the previous step (7.2 g, 20.0 mmol) to afford 3.30 g (36.4%) of the title compound as a yellow oil.

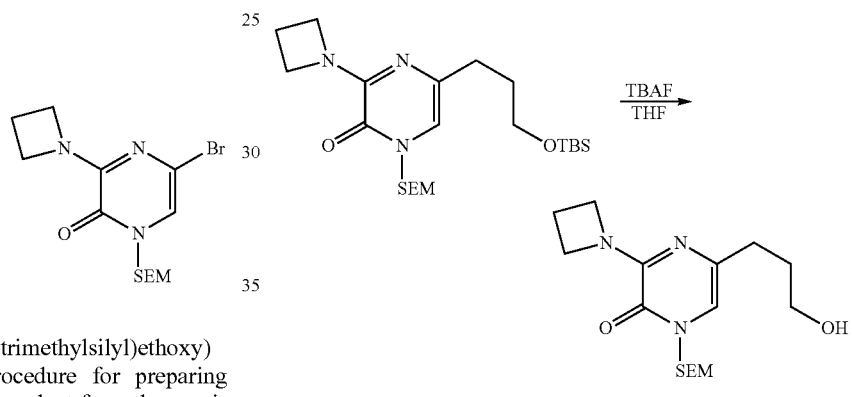

5-[[3-((tert-butyldimethyl)silyl)oxy]propyl]-3-(azetidin-1-yl)-1-[(2-(trimethylsilyl)ethoxy)methyl]-pyrazin-2(1H)-one The procedure for preparing Intermediate 3-4 was used with the product from the previous step (3.30 g, 7.30 mmol, 1.00 equiv) to afford 3.10 g (94%) of the title compound as an orange oil.

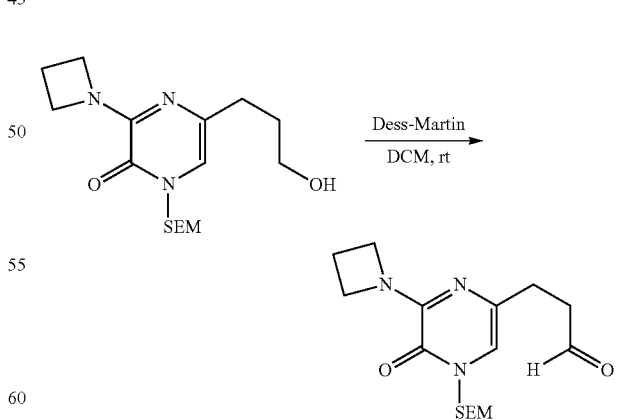

3-[6-(azetidin-1-yl)-5(4H)-oxo-4-[(2-(trimethylsilyl)ethoxy)methyl]-pyrazin-2-yl]-propan-1-ol The procedure for preparing Intermediate 3-5 was used with the product from the previous step (3.0 g, 6.61 mmol, 1 equiv) to afford 1.5 g (66.76%) of the title compound as an off-white solid.

3-[6-(azetidin-1-yl)-5(4H)-oxo-4-[(2-(trimethylsilyl)ethoxy)methyl]-pyrazin-2-yl]-propanal The procedure for preparing Intermediate 1-7 was used with the product from the previous step (1.00 g, 2.94 mmol, 1.00 equiv) to afford 0.6 g (60.35%) of the title compound as a yellow oil.

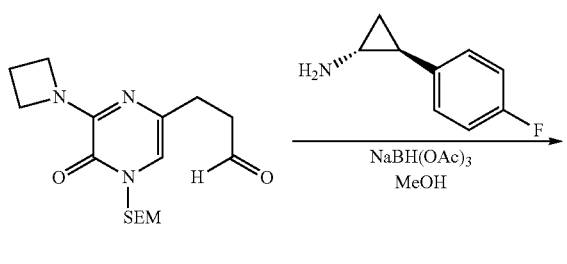

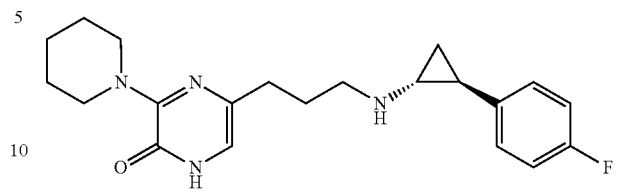

Example 6

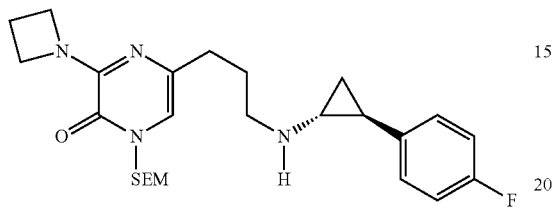

5-[3-([(1R,2S)-2-(4-fluorophenyl)cyclopropyl]amino)propyl]-3-[piperidin-1-yl]pyrazin-2(1H)-one 5-(3-[[(1R,2S)-2-(4-Fluorophenyl)cyclopropyl]amino]propyl)-3-(azetidin-1-yl)-1-[[2-(trimethylsilyl)ethoxy]methyl]pyrazin-2(1H)-one The reductive amination step for preparing Example 1 from Intermediate 1-7 was used with the product from the previous step (600 mg, 1.78 mmol). The crude product was purified with silica gel chromatography using EtOAc/petroleum ether (2:1) to afford 500 mg (59.6%) of the title compound as a yellow solid.

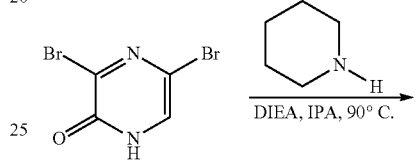

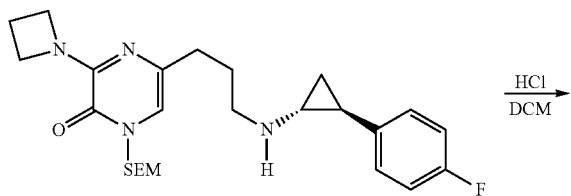

5-Bromo-3-(piperidin-1-yl)-pyrazin-2(1H)-one (Intermediate 6-1) The procedure for preparing Intermediate 2-1 was used with 3,5-dibromo-1,2-dihydropyrazin-2-one (15 g, 59.08 mmol, 1 equiv) and piperidine (7.5 g, 88.62 mmol, 1.5 equiv), to afford 12 g (78.69%) of the title compound as an off-white solid.

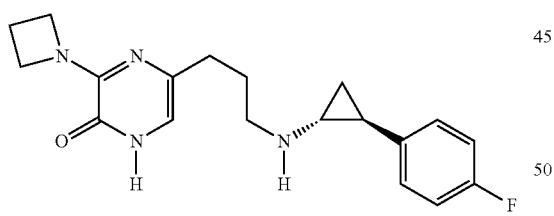

3-[Azetidin-1-yl]-5-[3-([(1R,2S)-2-(4-fluorophenyl)cyclopropyl]amino)propyl]-pyrazin-2(1H)-one The deprotection step for preparing Example 2 from Intermediate 2-7 was used with the product from the previous step (500 mg, 1.06 mmol, 1 equiv). The crude product (5 mL) was purified using chromatographic Procedure A (10% to 58% CH$_3$CN), to afford 39.1 mg (10.81%) of the title compound as a white solid.

LC-MS: (ES, m/z): 343 [M+H]$^+$. $^1$H NMR (400 MHz, MeOD-d$_4$) δ ppm: 7.23-7.18 (m, 2H), 7.05 (t, J=8.6 Hz, 2H), 6.42 (s, 1H), 4.61 (s, 4H), 3.22 (t, J=8.6 Hz, 2H), 2.98-2.94 (m, 1H), 2.55-2.42 (m, 5H), 2.04-1.96 (m, 2H), 1.54-1.47 (m, 1H), 1.40-1.33 (m, 1H).

5-Bromo-3-(piperidin-1-yl)-1-[(2-(trimethylsilyl)ethoxy)methyl]-pyrazin-2(1H)-one The procedure for preparing Intermediate 4-2 was used with the product from the previous step (3.9 g, 15.11 mmol). The crude product was purified with silica gel chromatography using EtOAc/petroleum ether (1:30) to afford 4.2 g (71.6%) of the title compound as a light yellow oil.

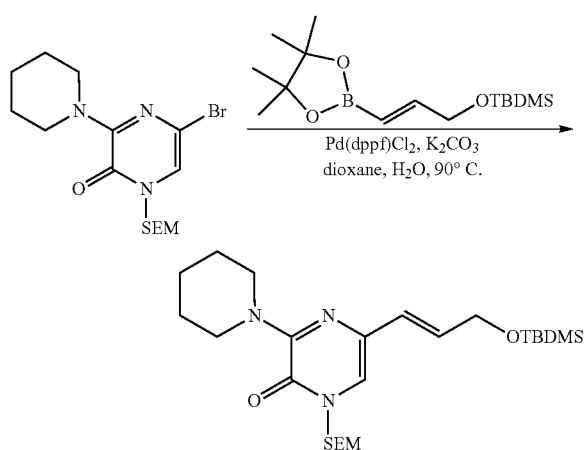

(E)-5-[[3-((tert-butyldimethyl)silyl)oxy]propen-1-yl]-3-(piperidin-1-yl)-1-[(2-(trimethylsilyl)ethoxy)methyl]-pyrazin-2(1H)-one The procedure for preparing Intermediate 3-3 was used with the product from the previous step (4 g, 10.30 mmol), using 12 hr of reaction time at 90° C., to afford 1.2 g (24.3%) of the title compound as a light yellow oil.

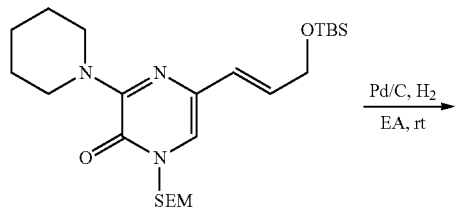

5-[[3-((tert-butyldimethyl)silyl)oxy]propyl]-3-(piperidin-1-yl)-1-[(2-(trimethylsilyl)ethoxy)methyl]-pyrazin-2(1H)-one The procedure for preparing Intermediate 3-4 was used with the product from the previous step (1.2 g, 2.50 mmol, 1 equiv) to afford 1.1 g (91.28%) of the title compound as a light yellow oil.

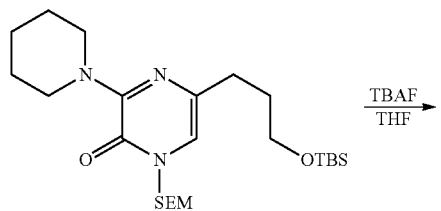

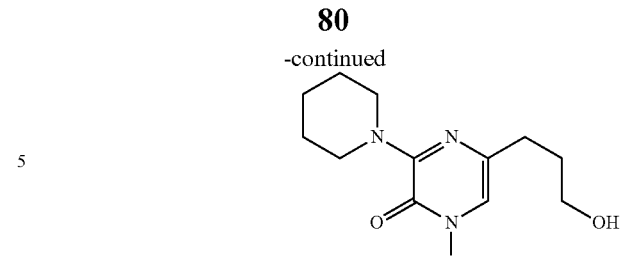

3-[6-(piperidin-1-yl)-5(4H)-oxo-4-[(2-(trimethylsilyl)ethoxy)methyl]-pyrazin-2-yl]-propan-1-ol The procedure for preparing Intermediate 3-5 was used with the product from the previous step (1.1 g, 2.28 mmol, 1 equiv) to afford 0.51 g (60.78%) of the title compound as a light yellow solid.

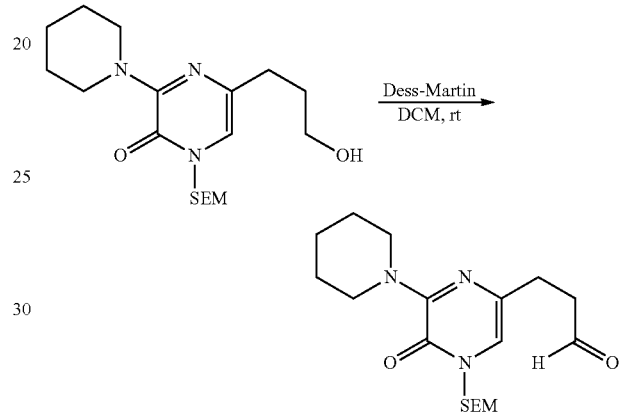

3-[6-(piperidin-1-yl)-5(4H)-oxo-4-[(2-(trimethylsilyl)ethoxy)methyl]-pyrazin-2-yl]-propanal The procedure for preparing Intermediate 1-7 was used, with 2 hr of stirring, with the product from the previous step (510 mg, 1.39 mmol) to afford 300 mg (59%) of the title compound as a light yellow oil.

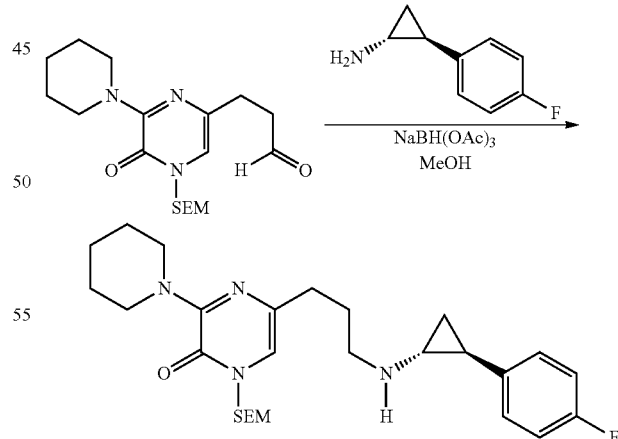

5-(3-[[(1R,2S)-2-(4-Fluorophenyl)cyclopropyl]amino]propyl)-3-(piperidin-1-yl)-1-[[2-(trimethylsilyl)ethoxy]methyl]pyrazin-2(1H)-one The procedure for preparing Intermediate 4-7 was used with the product from the previous step (300 mg, 0.82 mmol, 1 equiv) to afford 210 mg (51.10%) of the title compound as a light yellow oil.

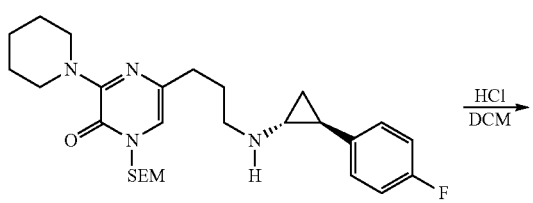

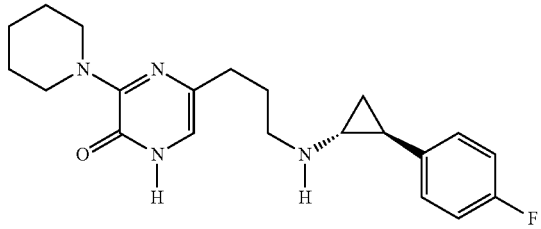

5-[3-([(1R,2S)-2-(4-fluorophenyl)cyclopropyl]amino)propyl]-3-[piperidin-1-yl]pyrazin-2(1H)-one The deprotection step for preparing Example 2 from Intermediate 2-7 was used with the product from the previous step (210 mg, 0.42 mmol, 1 equiv). The crude product (5 mL) was purified using chromatographic Procedure D (10% to 51% CH$_3$CN in 7 min), to afford 19.2 mg (9.77%) of the title compound as a light yellow oil.

LC-MS: (ES, m/z): 371 [M+H]$^+$. $^1$H NMR (300 MHz, MeOD-d$_4$) δ ppm: 7.28-7.15 (m, 2H), 7.15-6.99 (m, 2H), 6.70-6.61 (m, 1H), 3.86-3.65 (m, 4H), 3.28-3.20 (m, 2H), 3.02-2.98 (m, 1H), 2.66-2.36 (m, 3H), 2.16-1.96 (m, 2H), 1.80-1.59 (m, 6H), 1.59-1.31 (m, 2H).

Example 7

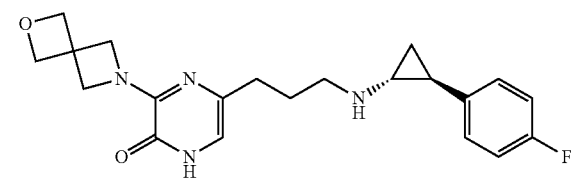 [SMILES: O=c1[nH]cc(CCCN[C@@H]2C[C@H]2c2ccc(F)cc2)nc1N1CC2(COC2)C1]

5-[3-([(1R,2S)-2-(4-fluorophenyl)cyclopropyl]amino)propyl]-3-[2-oxa-6-azaspiro[3.3]heptan-6-yl]pyrazin-2(1H)-one

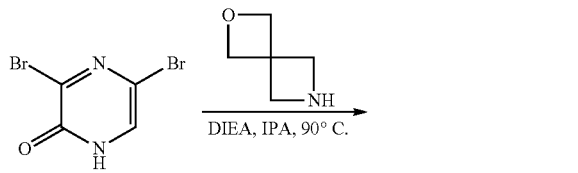

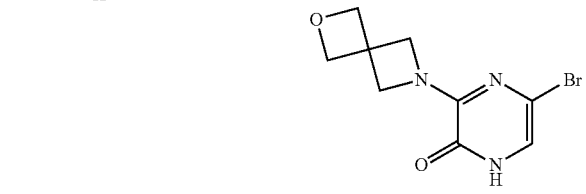

5-Bromo-3-(2-Oxa-6-azaspiro[3.3]heptan-6-yl)-pyrazin-2(1H)-one (Intermediate 7-1) The procedure for preparing Intermediate 2-1 was used with 3,5-dibromo-1,2-dihydropyrazin-2-one (10 g, 39.39 mmol, 1.00 equiv) and 2-oxa-6-azaspiro[3.3]heptane (5.9 g, 59.52 mmol, 1.50 equiv), using 6 hr reaction time at 90° C. The crude product was purified with silica gel chromatography using EtOAc/petroleum ether (4:1) to afford 9 g (84%) of the title compound as a yellow solid.

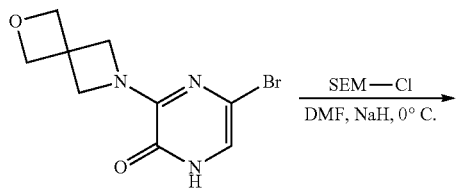

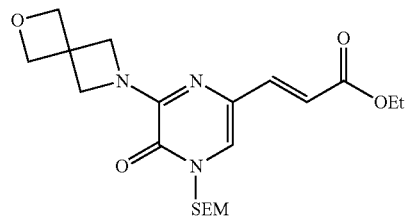

5-Bromo-3-(2-oxa-6-azaspiro[3.3]heptan-6-yl)-1-[(2-(trimethylsilyl)ethoxy)-methyl]-pyrazin-2(1H)-one The procedure for preparing Intermediate 2-2 was used with Intermediate 7-1 (9 g, 33.08 mmol, 1.00 equiv) to afford 3.6 g (27%) of the title compound as off-white oil.

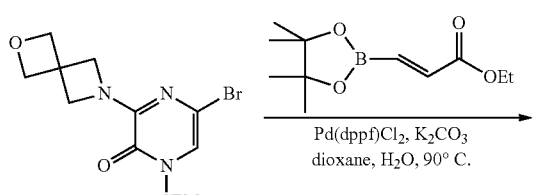

Ethyl (2E)-3-[6-(2-oxa-6-azaspiro[3.3]heptan-6-yl)-5(4H)-oxo-4-[(2-(trimethylsilyl)ethoxy)methyl]-pyrazin-2-yl]propenoate The procedure for preparing Intermediate 1-4 was used with the product from the previous step (3.6 g, 8.95 mmol, 1.00 equiv) to afford 2.8 g (74%) of the title compound as a yellow oil.

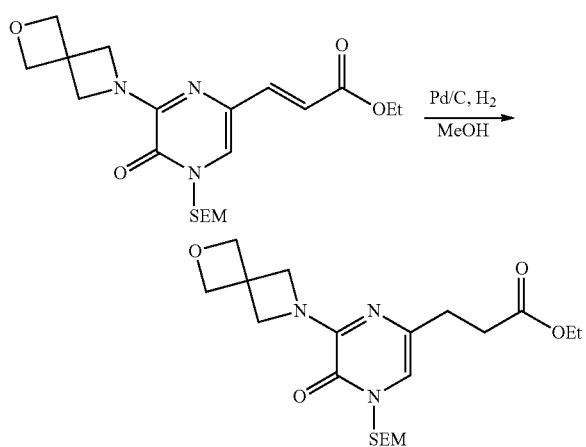

Ethyl 3-[6-(2-oxa-6-azaspiro[3.3]heptan-6-yl)-5(4H)-oxo-4-[(2-(trimethylsilyl)ethoxy)methyl]-pyrazin-2-yl]propanoate The procedure for preparing Intermediate 1-5 was used with the product from the previous step (2.8 g, 6.64 mmol, 1.00 equiv) to afford 2.7 g (96%) of the title compound as a yellow oil.

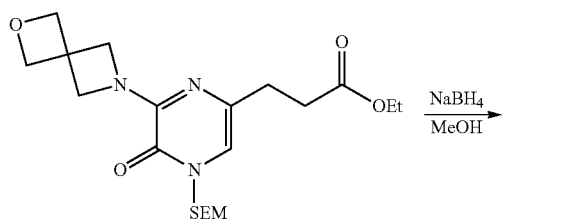

3-[6-(2-Oxa-6-azaspiro[3.3]heptan-6-yl)-5(4H)-oxo-4-[(2-(trimethylsilyl)-ethoxy)methyl]-pyrazin-2-yl]-propan-1-ol The procedure for preparing Intermediate 1-6 was used with the product from the previous step (2.7 g, 6.37 mmol, 1.00 equiv) to afford 1.8 g (74%) of the title compound as a yellow oil.

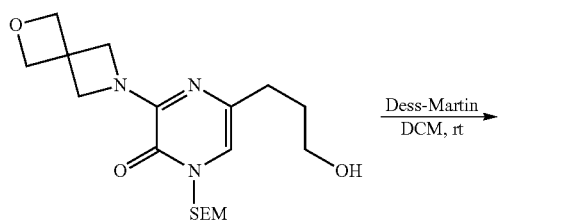

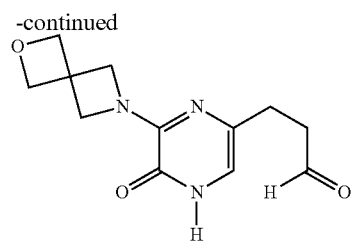

3-[6-(2-Oxa-6-azaspiro[3.3]heptan-6-yl)-5(4H)-oxo-4-[(2-(trimethylsilyl)-ethoxy)methyl]-pyrazin-2-yl]-propanal The procedure for preparing Intermediate 1-7 was used with the product from the previous step (1.8 g, 4.72 mmol, 1.00 equiv) to afford 0.5 g (28%) of the title compound, for which the SEM group had been cleaved under the reaction conditions, as a white solid.

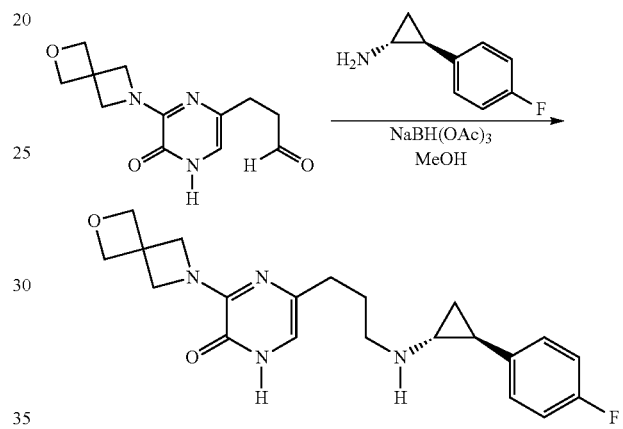

5-[3-([(1R,2S)-2-(4-fluorophenyl)cyclopropyl]amino) propyl]-3-[2-oxa-6-azaspiro[3.3]heptan-6-yl]pyrazin-2 (1H)-one The reductive amination step for preparing Example 1 from Intermediate 1-7 was used with the product from the previous step (500 mg, 1.32 mmol, 1.00 equiv). The crude product (3 mL) was purified by Prep-HPLC (Column: XBridge Prep Phenyl OBD, particle size: 5 m, column size 19×150 mm, H$_2$O (20 mM NH$_4$HCO$_3$)/CH$_3$CN, flow rate: 20 mL/min, gradient: 25% to 30% CH$_3$CN in 10 min, Rt: 11.3 min, detector, UV 254 nm), to afford 50 mg (10%) of the title compound as a white solid.

LCMS: (ES, m/z): 385 [M+H]$^+$. $^1$H NMR (300 MHz, Methanol-d$_4$) δ ppm: 7.09-6.97 (m, 2H), 7.03-6.87 (m, 2H), 6.37 (s, 1H), 4.83-4.78 (m, 4H), 4.45-4.25 (m, 4H), 2.74-2.63 (m, 2H), 2.35 (m, 2H), 2.3-2.2 (m, 1H), 1.93-1.63 (m, 3H), 1.09-0.88 (m, 2H).

Example 8

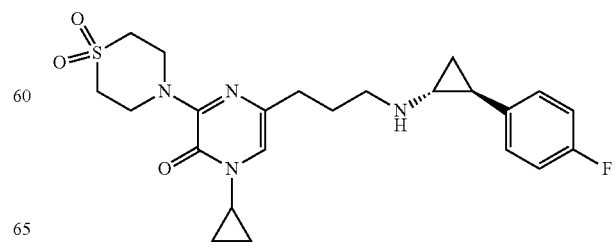

1-Cyclopropyl-3-[1,1-dioxidothiomorpholino]-5-[3-([(1R,2S)-2-(4-fluorophenyl)cyclopropyl]amino)propyl]pyrazin-2(1H)-one

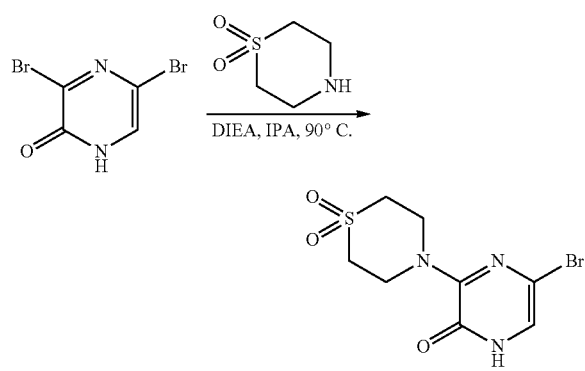

5-Bromo-3-(1,1-dioxothiomorpholin-4-yl)-pyrazin-2(1H)-one (Intermediate 8-1) The procedure for preparing Intermediate 2-1 was used with 3,5-dibromo-1,2-dihydropyrazin-2-one (10 g, 39.39 mmol, 1.00 equiv) and 4-thiomorpholine-1,1-dione (6.43 g, 47.56 mmol, 1.21 equiv). The crude product was purified with silica gel chromatography using EtOAc/petroleum ether (4:1) to afford 4.0 g (33%) of the title compound as a white solid.

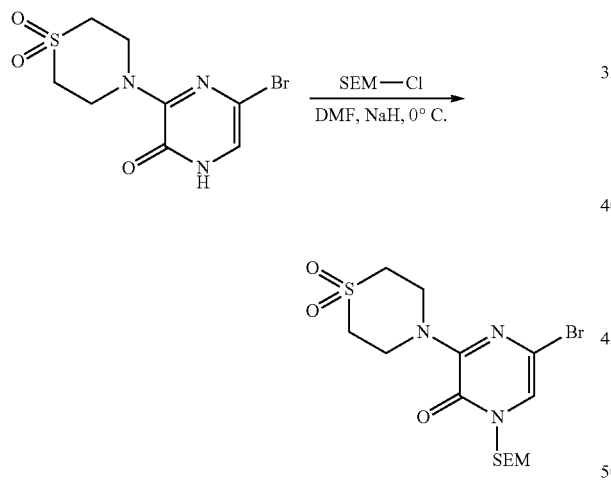

5-Bromo-3-(1,1-dioxothiomorpholin-4-yl)-1-[(2-(trimethylsilyl)ethoxy)-methyl]-pyrazin-2(1H)-one (Intermediate 8-2) The procedure for preparing Intermediate 2-2 was used with Intermediate 8-1 (3.0 g, 9.74 mmol, 1 equiv) to afford 2.35 g (55.08%) of the title compound as a yellow oil.

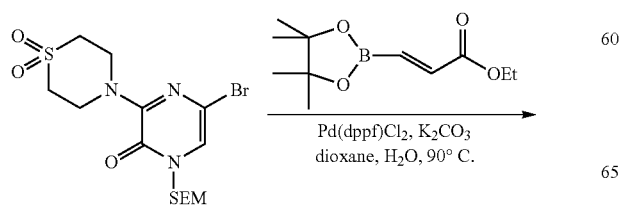

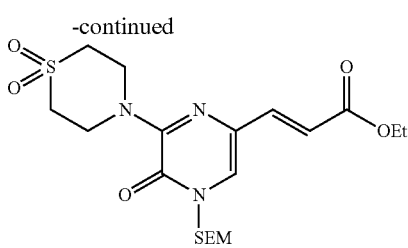

Ethyl (2E)-3-[6-(1,1-dioxothiomorpholin-4-yl)-5(4H)-oxo-4-[(2-(trimethylsilyl)ethoxy)methyl]-pyrazin-2-yl]propenoate (Intermediate 8-3 The procedure for preparing Intermediate 1-4 was used with Intermediate 8-2 (2.35 g, 5.36 mmol, 1 equiv) to afford 1.80 g (73.25%) of the title compound as an orange oil.

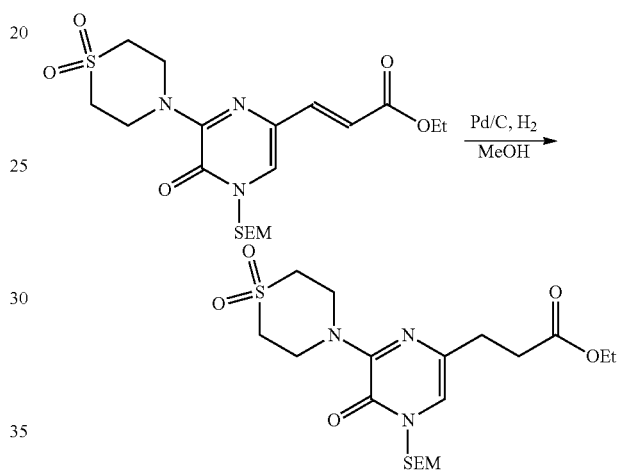

Ethyl 3-[6-(1,1-dioxothiomorpholin-4-yl)-5(4H)-oxo-4-[(2-(trimethylsilyl)-ethoxy)methyl]-pyrazin-2-yl]propanoate (Intermediate 8-4) The procedure for preparing Intermediate 1-5 was used with Intermediate 8-3 (1.80 g, 3.93 mmol, 1.00 equiv) to afford 1.80 g (99%) of the title compound as an orange oil.

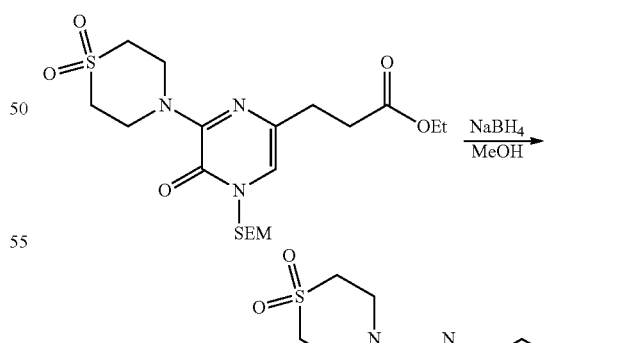

3-[6-(1,1-dioxothiomorpholin-4-yl)-5(4H)-oxo-4-[(2-(trimethylsilyl)ethoxy)-methyl]-pyrazin-2-yl]-propan-1-ol (Intermediate 8-5) The procedure for preparing Intermediate 1-6 was used with Intermediate 8-4 (1.8 g, 3.92 mmol, 1 equiv) with 2 hr reaction time. The crude product was purified with silica gel chromatography using EtOAc/petroleum ether (3:2) to afford 1.3 g (79.47%) of the title compound as an off-white solid.

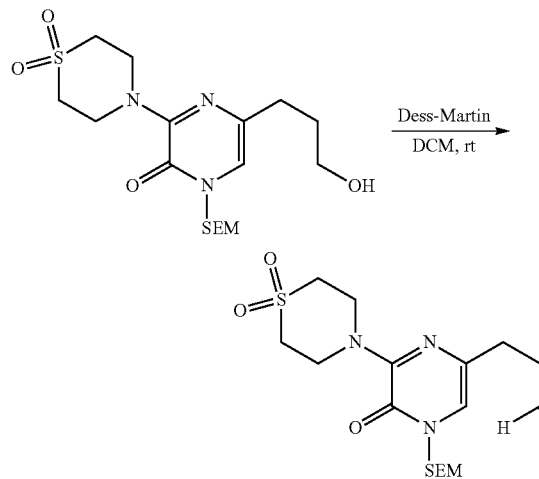

3-[6-(1,1-dioxothiomorpholin-4-yl)-5(4H)-oxo-4-[(2-(trimethylsilyl)ethoxy)-methyl]-pyrazin-2-yl]-propanal (Intermediate 8-6) The procedure for preparing Intermediate 1-7 was used with Intermediate 8-5 (1.30 g, 3.11 mmol, 1.00 equiv) to afford 1.0 g (77.29%) of the title compound as a yellow oil.

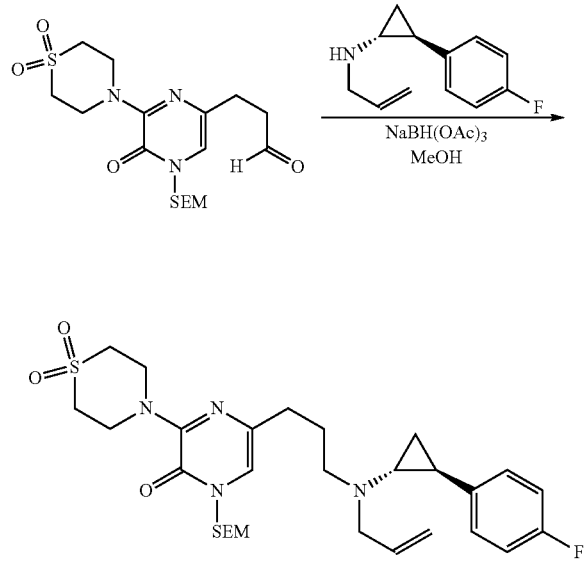

5-(3-[[(1R,2S)-2-(4-Fluorophenyl)cyclopropyl] (2-propen-1-yl)amino]propyl)-3-(1,1-dioxothiomorpholin-4-yl)-1-[[2-(trimethylsilyl)ethoxy]methyl]pyrazin-2(1H)-one (Intermediate 8-7) The reductive amination step for preparing Example 1 from Intermediate 1-7 was used with Intermediate 8-6 (1.0 g, 2.40 mmol, 1 equiv) to afford 900 mg (63.35%) of the title compound as an orange oil.

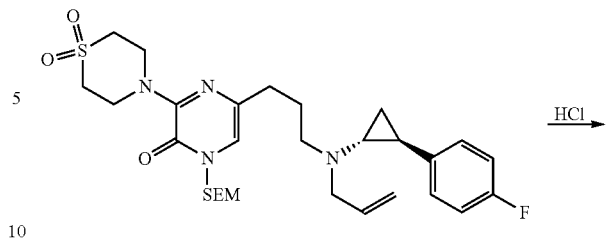

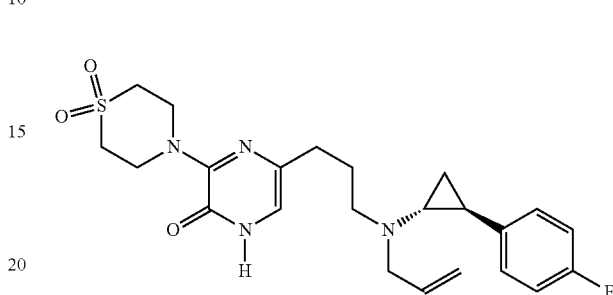

5-(3-[[(1R,2S)-2-(4-Fluorophenyl)cyclopropyl] (2-propen-1-yl)amino]propyl)-3-(1,1-dioxothiomorpholin-4-yl)-pyrazin-2(1H)-one (Intermediate 8-8) The deprotection step for preparing Example 2 from Intermediate 2-7 was used with Intermediate 8-7 (900 mg, 1.52 mmol, 1 equiv). The crude product was purified with silica gel chromatography using $CH_2Cl_2$/MeOH (15:1) to afford 700 mg (99.71%) of the title compound as an orange solid.

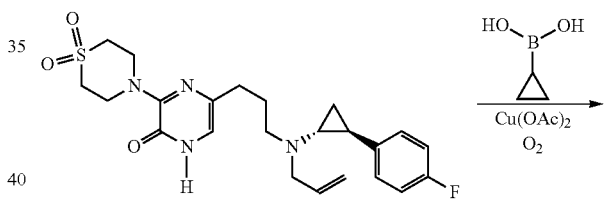

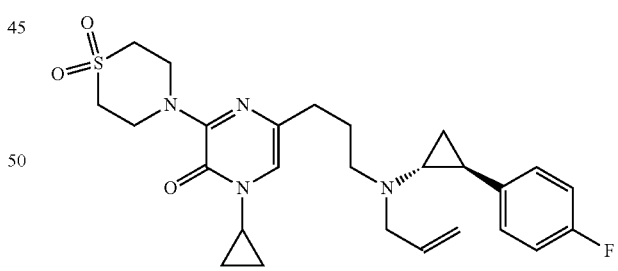

5-(3-[[(1R,2S)-2-(4-Fluorophenyl)cyclopropyl] (2-propen-1-yl)amino]propyl)-3-(1,1-dioxothiomorpholin-4-yl)-1-cyclopropylpyrazin-2(1H)-one (Intermediate 8-9 Intermediate 8-8 (700 mg, 1.52 mmol, 1 equiv) was combined with cyclopropylboronic acid (196 mg, 2.28 mmol, 1.5 equiv), Cu(OAc)$_2$ (276.0 mg, 1.52 mmol, 1 equiv), and TEA (461.5 mg, 4.56 mmol, 3 equiv) in $CH_2Cl_2$ (40 mL). Oxygen was added to the mixture, and the resulting solution was stirred for 16 h at rt, then purified with silica gel chromatography using EtOAc/petroleum ether (1:1) to afford 300 mg (39.43%) of the title compound as a yellow oil.

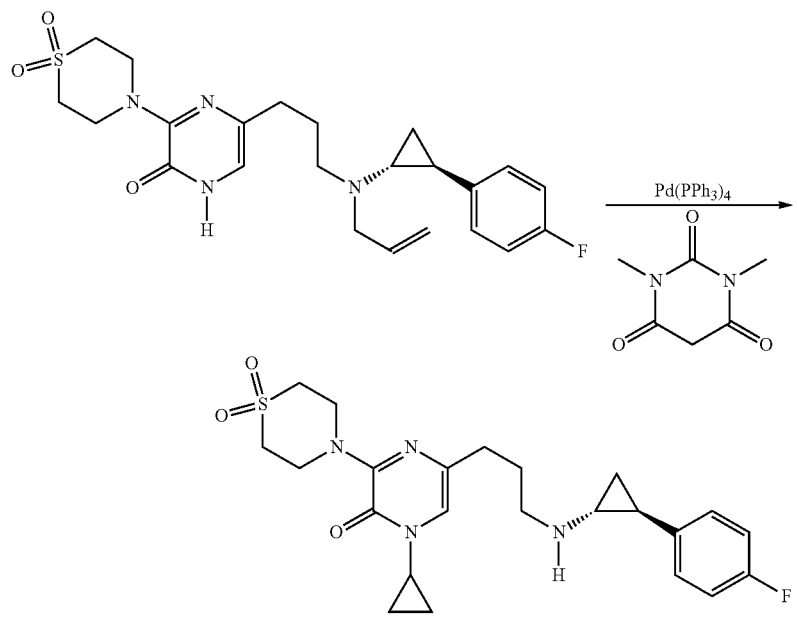

1-Cyclopropyl-3-[1,1-dioxidothiomorpholino]-5-[3-([(1R,2S)-2-(4-fluorophenyl)cyclopropyl]amino)propyl]pyrazin-2(1H)-one A solution of the product from the previous step (300 mg, 0.60 mmol, 1 equiv), 1,3-dimethyl-1,3-diazinane-2,4,6-trione (280.5 mg, 1.80 mmol, 3 equiv), and Pd(PPh$_3$)$_4$ (140 mg, 0.12 mmol, 0.2 equiv) in THF (30 mL) was stirred for 2 hr under N$_2$ at 50° C. The crude product was purified using chromatographic Procedure A (10% to 58% CH$_3$CN in 9 min), to afford 52.1 mg (18.88%) of the title compound as a light yellow solid.

LC-MS: (ES, m/z): 461 [M+H]$^+$. $^1$H NMR (300 MHz, MeOD-d$_4$) δ ppm: 7.18-7.14 (m, 2H), 7.05-6.99 (m, 2H), 6.87 (s, 1H), 4.28-4.26 (m, 4H), 3.28-3.19 (m, 3H), 3.16-3.11 (m, 4H), 2.96-2.91 (m, 1H), 2.53-2.48 (m, 2H), 2.45-2.38 (m, 1H), 2.06-1.98 (m, 2H), 1.46-1.34 (m, 2H), 1.08-1.03 (m, 2H), 0.87-0.82 (m, 2H).

Example 9

3-(1,1-Dioxidothiomorpholino)-5-(3-(((1R,2S)-2-phenylcyclopropyl)amino)propyl)pyrazin-2(1H)-one

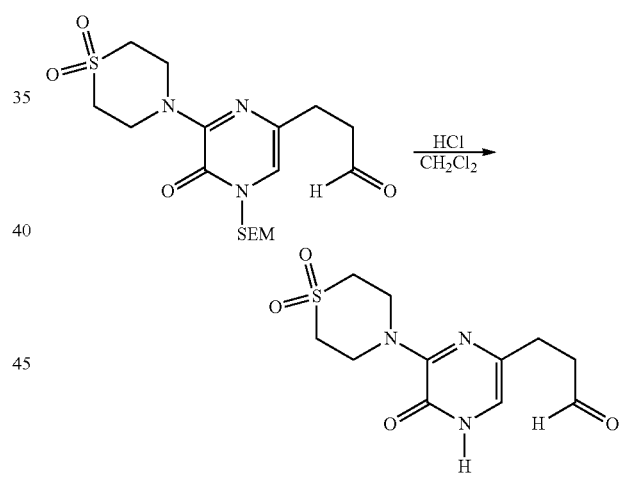

3-[6-(1,1-dioxothiomorpholin-4-yl)-5(4H)-oxopyrazin-2-yl]-propanal The deprotection step for preparing Example 2 from Intermediate 2-7 was used with Intermediate 8-6 (600 mg, 1.44 mmol). The crude product was purified with silica gel chromatography using CH$_2$Cl$_2$/MeOH (15:1) to afford 400 mg (96.97%) of the title compound as an orange oil.

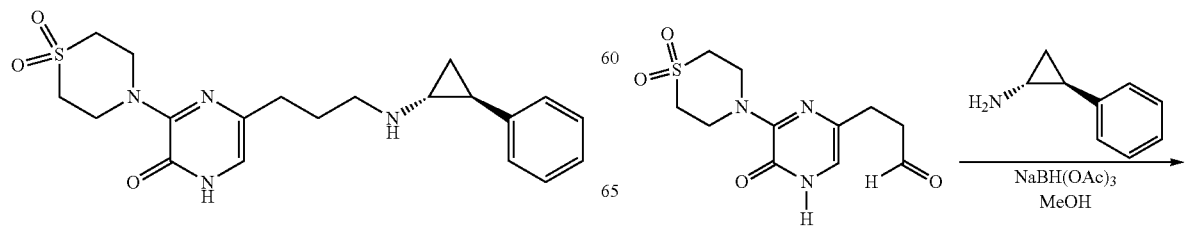

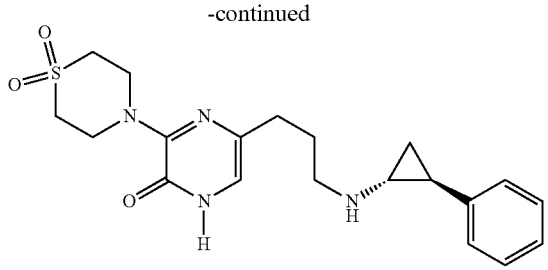

3-(1,1-Dioxidothiomorpholino)-5-(3-(((1R,2S)-2-phenyl-cyclopropyl)amino)-propyl)pyrazin-2(1H)-one The reductive amination step for preparing Example 1 from Intermediate 1-7 used with the product from the previous step (400 mg, 1.40 mmol, 1 equiv). The crude product (5 mL) was purified using chromatographic Procedure E (28% to 50% CH$_3$CN in 8 min, Rt: 7.02 min), to afford 85.3 mg (15%) of the title compound as a white solid.

LC-MS: (ES, m/z): 403 [M+H]$^+$. $^1$H NMR (300 MHz, MeOD-d$_4$) δ ppm: 7.27-7.17 (m, 2H), 7.13-7.06 (m, 1H), 7.02-6.99 (m, 2H), 6.66 (s, 1H), 4.27-4.24 (m, 4H), 3.11-3.04 (m, 4H), 2.73-2.68 (m, 2H), 2.46-2.40 (m, 2H), 2.30-2.25 (m, 1H), 1.90-1.80 (m, 3H), 1.06-0.94 (m, 2H).

Example 10

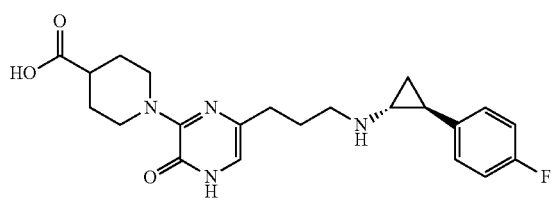 [SMILES: O=C(O)C1CCN(c2nc(CCCN[C@@H]3C[C@H]3c3ccc(F)cc3)c[nH]c2=O)CC1]

1-[6-(3-[([1R,2S]-2-[4-fluorophenyl]cyclopropyl)amino]propyl)-3-oxo-3,4-dihydropyrazin-2-yl]piperidine-4-carboxylic acid

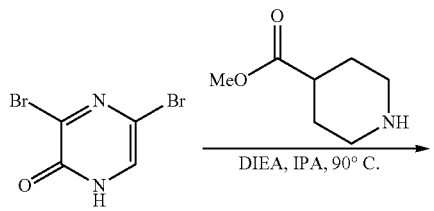

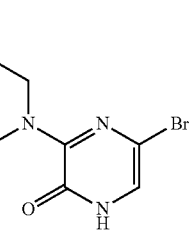

Methyl 1-(6-bromo-3(4H)-oxopyrazin-2-yl)piperidine-4-carboxylate (Intermediate 10-1) The procedure for preparing Intermediate 2-1 was used with 3,5-dibromo-1,2-dihydropyrazin-2-one (10 g, 39.39 mmol, 1.00 equiv) and methyl piperidine-4-carboxylate (8.4 g, 58.67 mmol, 1.49 equiv), using 12 h of reaction time at 90° C., affording 10 g (80%) of the title compound as a light yellow solid.

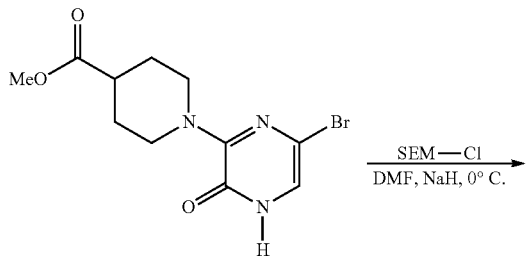

Methyl 1-(6-bromo-3(4H)-oxo-4-[[2-(trimethylsilyl)ethoxy]methyl]-pyrazin-2-yl)piperidine-4-carboxylate The procedure for preparing Intermediate 4-2 was used with Intermediate 10-1 (5 g, 15.82 mmol, 1.00 equiv) to afford 4 g (57%) of the title compound as a light yellow oil.

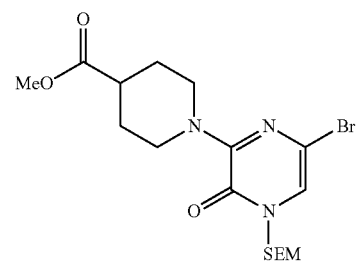

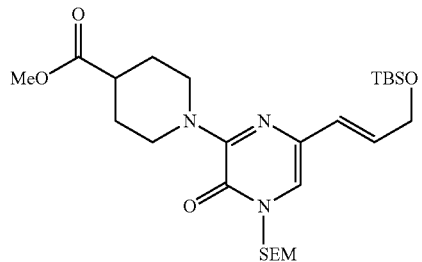

Methyl 1-[6-[(1E)-3-[(tert-butyldimethylsilyl)oxy]prop-1-en-1-yl]-3(4H)-oxo-4-[[2-(trimethylsilyl)ethoxy]methyl]-3,4-dihydropyrazin-2-yl]piperidine-4-carboxylate The procedure for preparing Intermediate 3-3 was used with the product from the previous step (4 g, 8.96 mmol), using 2 hr reaction time, to afford 1.7 g (35%) of the title compound as a light yellow oil.

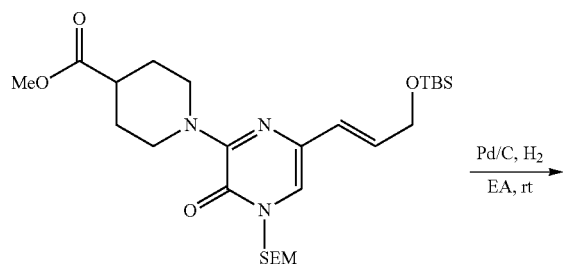

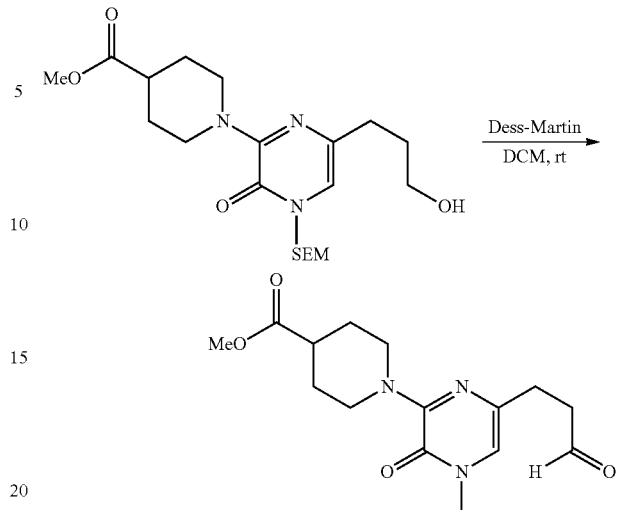

Methyl 1-(6-[3-[(tert-butyldimethylsilyl)oxy]propyl]-3 (4H)-oxo-4-[[2-(trimethylsilyl)ethoxy]methyl]-pyrazin-2-yl)piperidine-4-carboxylate The procedure for preparing Intermediate 3-4 was used with the product from the previous step (1.8 g, 3.35 mmol, 1.00 equiv) to afford 1.7 g (94%) of the title compound as a light yellow oil.

Methyl 1-(3(4H)-oxo-6-(3-oxopropyl)-pyrazin-2-yl) piperidine-4-carboxylate

The procedure for preparing Intermediate 1-7 was used with the product from the previous step (800 mg, 1.88 mmol, 1.00 equiv) to afford 0.45 g (82%) of the title compound as a light yellow oil.

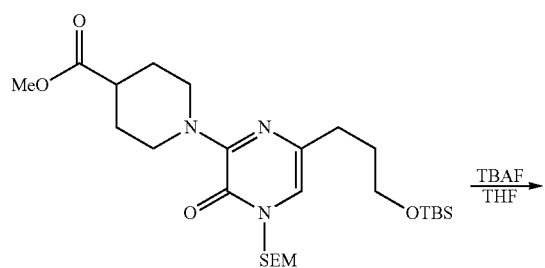

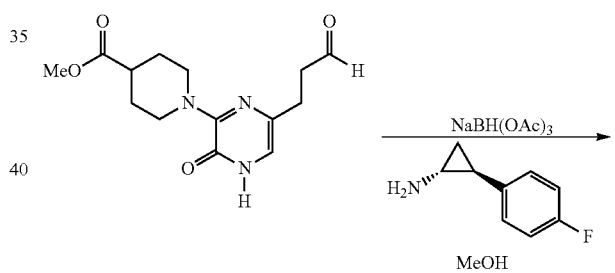

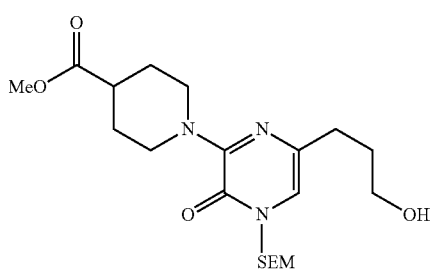

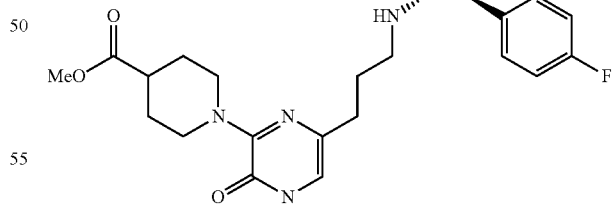

Methyl 1-[6-(3-hydroxypropyl)-3(4H)-oxo-4-[[2-(trimethylsilyl)ethoxy]methyl]-pyrazin-2-yl]piperidine-4-carboxylate The procedure for preparing Intermediate 3-5 was used with the product from the previous step (1.7 g, 3.15 mmol, 1.00 equiv) to afford 0.8 g (60%) of the title compound as a light yellow oil.

Methyl 1-[6-(3-[[(1R,2S)-2-(4-fluorophenyl)cyclopropyl]amino]propyl)-3(4H)-oxopyrazin-2-yl]piperidine-4-carboxylate The procedure for preparing Intermediate 4-7 was used with the product from the previous step (450 mg, 1.53 mmol, 1.00 equiv) afford 0.3 g (46%) of the title compound as a light yellow oil, which was carried forward without further purification.

95

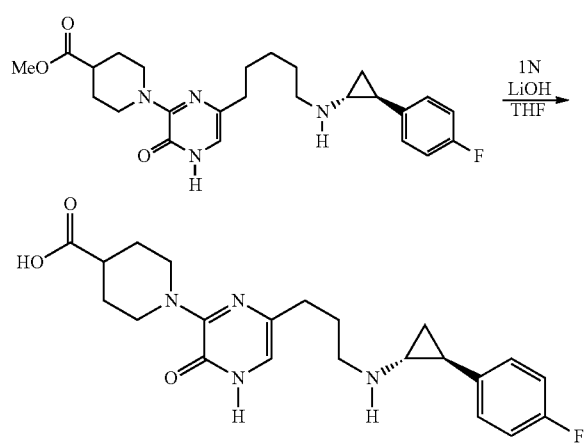

1-[6-(3-[([1R,2S]-2-[4-fluorophenyl]cyclopropyl)amino]propyl)-3-oxo-3,4-dihydropyrazin-2-yl]piperidine-4-carboxylic acid A solution of the product from the previous step (300 mg, 0.70 mmol, 1.00 equiv) and LiOH (80 mg, 3.34 mmol, 5.00 equiv) in THF (20 mL) and H$_2$O (3 mL) was stirred for 2 h at 25° C., then concentrated under vacuum and purified using chromatographic Procedure C (38.0% to 50.0% CH$_3$CN in 8.2 min), to afford 82.6 mg (28%) of the title compound as a light yellow solid.

LC-MS: (ES, m/z): 415 [M+H]$^+$. $^1$H NMR (300 MHz, MeOD-d$_4$) δ ppm: 7.23-7.07 (m, 2H), 7.07-6.93 (m, 2H), 6.82-6.69 (s, 1H), 4.78-4.32 (m, 2H), 3.02-2.78 (m, 4H), 2.72-2.55 (m, 1H), 2.52-2.28 (m, 3H), 2.27-2.02 (m, 1H), 2.02-1.81 (m, 4H), 1.81-1.51 (m, 2H), 1.38-1.01 (m, 2H).

Example 11

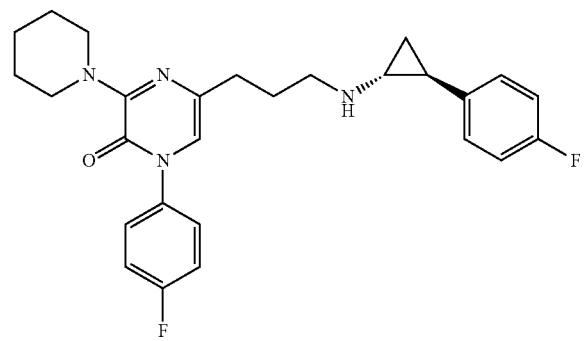 [SMILES: O=c1c(N2CCCCC2)nc(CCCN[C@@H]2C[C@H]2c2ccc(F)cc2)cn1-c1ccc(F)cc1]

1-[4-Fluorophenyl]-3-[piperidin-1-yl]-5-[3-([(1R,2S)-2-(4-fluorophenyl)cyclopropyl]amino)propyl]-pyrazin-2(1H)-one

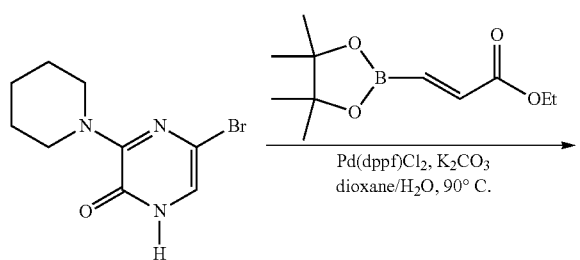

96

-continued

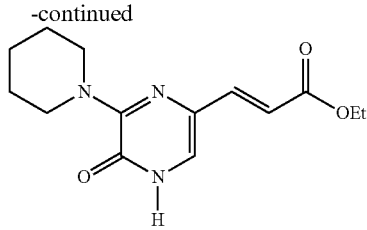

Ethyl (2E)-3-[6-(piperidin-1-yl)-5(4H)-oxopyrazin-2-yl]propenoate The procedure for preparing Intermediate 1-4 was used with Intermediate 6-1 to afford 2 g (47%) of the title compound as a yellow oil.

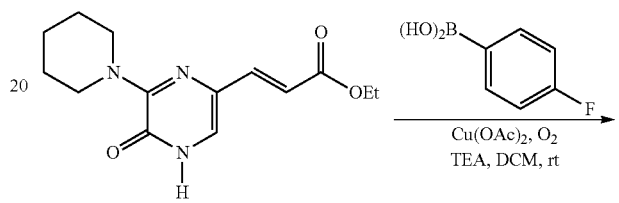

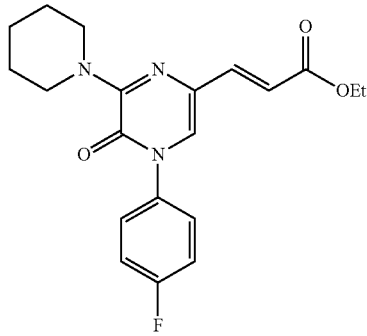

Ethyl (2E)-3-[4-(4-fluorophenyl)-6-(piperidin-1-yl)-5(4H)-oxopyrazin-2-yl]-propenoate The procedure for preparing Intermediate 8-9 was used with the product from the previous step (2 g, 7.22 mmol, 1 equiv) and 4-fluorophenylboronic acid to afford 1 g (37%) of the title compound as a yellow oil.

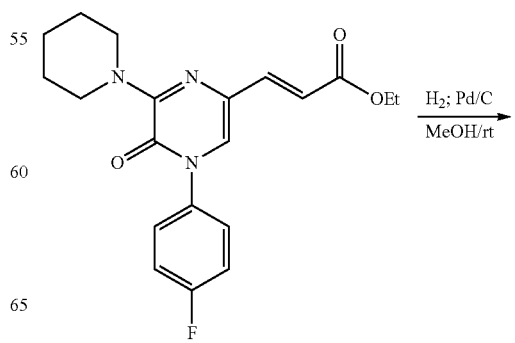

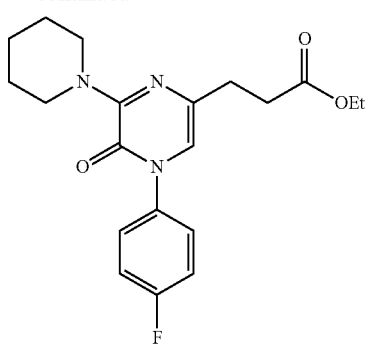

Ethyl (2E)-3-[4-(4-fluorophenyl)-6-(piperidin-1-yl)-5(4H)-oxopyrazin-2-yl]-propanoate The procedure for preparing Intermediate 3-4 was used with the product from the previous step (1 g, 2.70 mmol, 1.00 equiv) to afford 1 g (99%) of the title compound as a yellow oil.

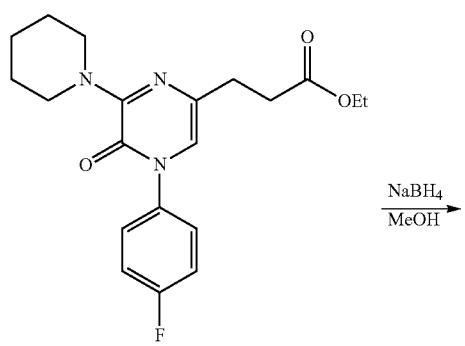

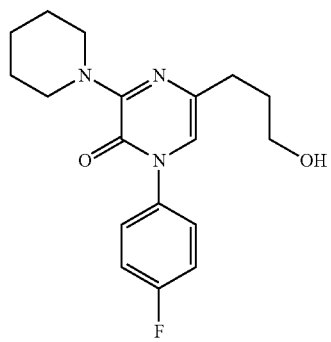

(2E)-3-[4-(4-Fluorophenyl)-6-(piperidin-1-yl)-5(4H)-oxopyrazin-2-yl]propan-1-ol The procedure for preparing Intermediate 1-6 was used with the product from the previous step (1 g, 2.68 mmol, 1 equiv), with 6 hr reaction time, to afford 500 mg (56%) of the title compound as a yellow solid.

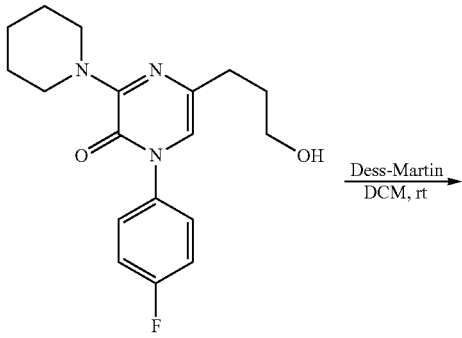

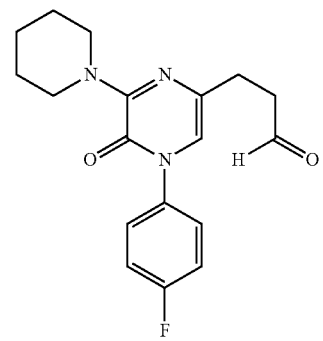

(2E)-3-[4-(4-Fluorophenyl)-6-(piperidin-1-yl)-5(4H)-oxopyrazin-2-yl]-propanal The procedure for preparing Intermediate 1-7 was applied to the product from the previous step (500 mg, 1.51 mmol, 1.00 equiv) to afford 300 mg (60%) of the title compound as a yellow oil.

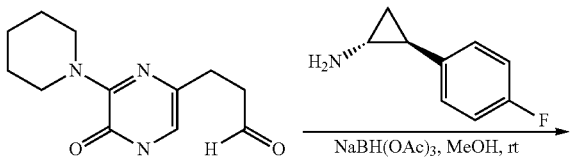

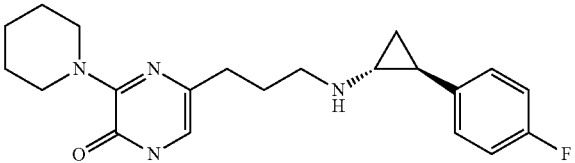

1-[4-Fluorophenyl]-3-[piperidin-1-yl]-5-[3-({[(1R,2S)-2-(4-fluorophenyl)-cyclopropyl]amino)propyl]-pyrazin-2(1H)-one The reductive amination step for preparing Example 1 from Intermediate 1-7 was used with the product from the previous step (300 mg, 0.912 mmol, 1 equiv). The crude product (5 mL) was purified using chromatographic Procedure A (35% to 40% CH₃CN in 10 min, Rt: 8.12 min), to afford 68.9 mg (11%) of the title compound as a yellow oil.

LC-MS: (ES, m/z): 465 [M+H]⁺. ¹H NMR (400 MHz, MeOD-d₄) δ ppm: 7.45-7.42 (m, 2H), 7.30-7.26 (t, J=17.2 Hz, 2H), 7.23-7.20 (m, 2H), 7.09-7.04 (t, J=17.2 Hz, 2H), 6.81 (s, 1H), 3.77-3.75 (m, 4H), 3.30-3.28 (m, 2H), 3.02-2.98 (m, 1H), 2.58-2.54 (m, 2H), 2.49-2.46 (m, 1H), 2.12-2.08 (m, 2H), 1.67-1.65 (m, 6H), 1.53-1.48 (m, 1H), 1.41-1.36 (m, 1H).

Example 12

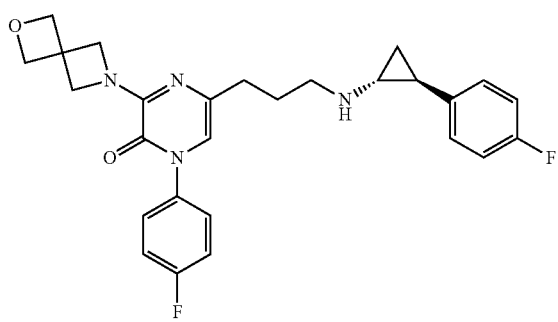 [SMILES: O=c1c(N2CC3(COC3)C2)nc(CCCN[C@@H]2C[C@H]2c2ccc(F)cc2)cn1-c1ccc(F)cc1]

1-[4-Fluorophenyl]-5-[3-([(1R,2S)-2-(4-fluorophenyl)cyclopropyl]amino)propyl]-3-[2-oxa-6-azaspiro[3.3]heptan-6-yl]pyrazin-2(1H)-one

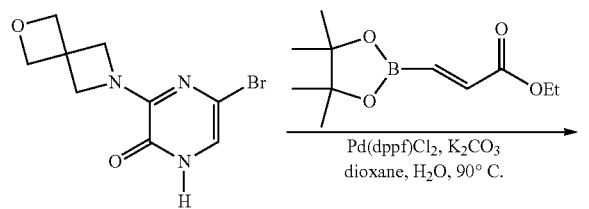

Ethyl (E)-3-(6-[2-oxa-6-azaspiro[3.3]heptan-6-yl]-5(4H)-oxopyrazin-2-yl)prop-2-enoate (Intermediate 12-1) The procedure for preparing Intermediate 1-4 was used with Intermediate 7-1 (3.6 g, 13.23 mmol) with 2 h of reaction time at 90° C. The crude product was purified with silica gel chromatography using EtOAc/petroleum ether (1:1) to afford 1.7 g (44%) of the title compound as a yellow solid.

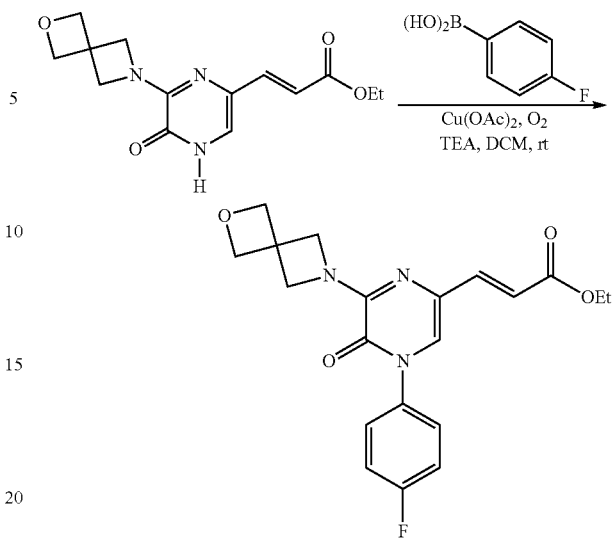

Ethyl (E)-3-[4-(4-fluorophenyl)-6-[2-oxa-6-azaspiro[3.3]heptan-6-yl]-5(4H)-oxopyrazin-2-yl]prop-2-enoate The procedure for preparing Intermediate 8-9 was used with Intermediate 12-1 (2 g, 6.87 mmol, 1.00 equiv) and 4-fluorophenylboronic acid (1.4 g, 10.01 mmol, 1.50 equiv). The crude product was purified using silica gel chromatography using EtOAc/petroleum ether (1:1) to afford 0.7 g (26%) of the title compound as a yellow solid.

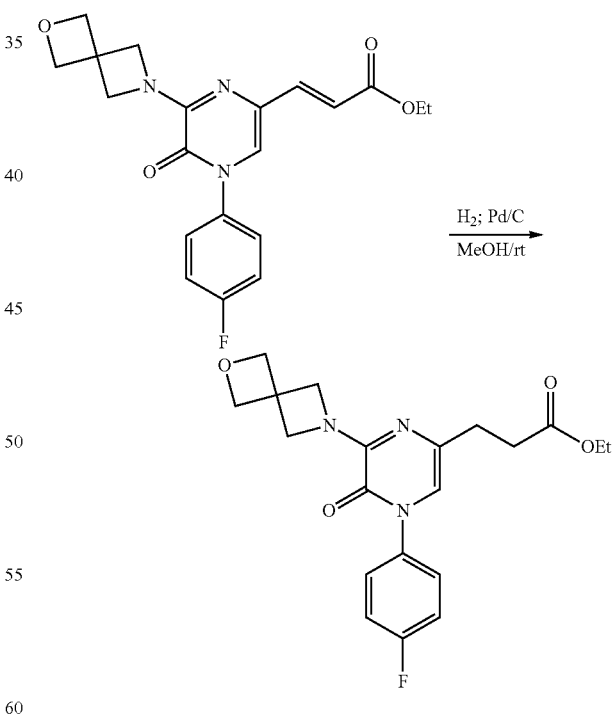

Ethyl 3-[4-(4-fluorophenyl)-6-[2-oxa-6-azaspiro[3.3]heptan-6-yl]-5(4H)-oxo-pyrazin-2-yl]propanoate The procedure for preparing Intermediate 1-5 was used with the product from the previous step (850 mg, 2.21 mmol, 1.00 equiv) to afford 0.7 g (82%) of the title compound as a yellow oil.

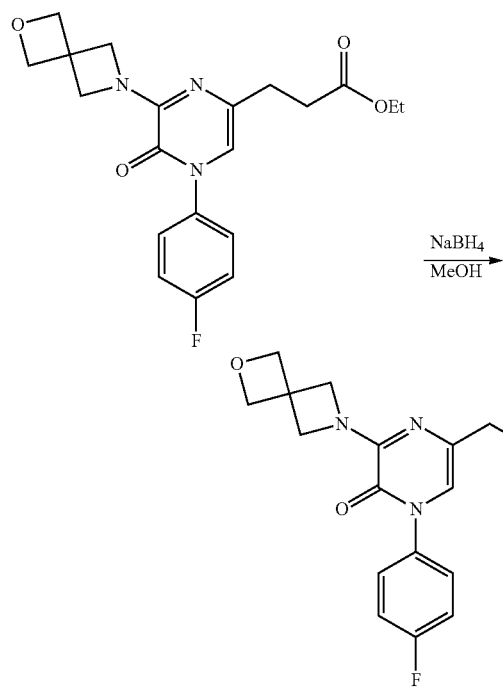

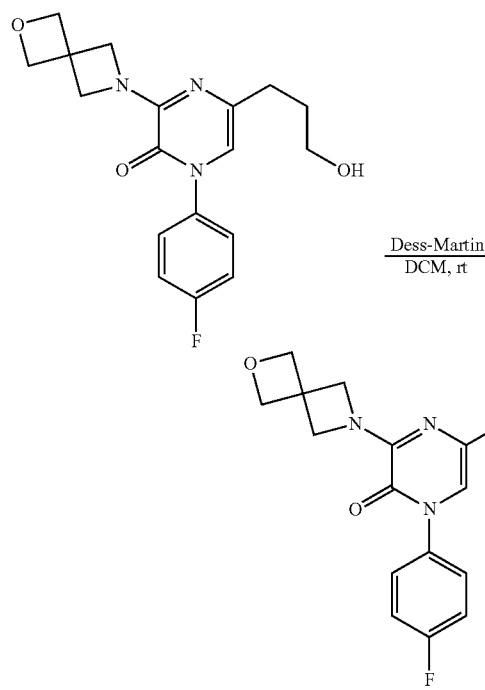

3-[4-(4-Fluorophenyl)-6-[2-oxa-6-azaspiro[3.3]heptan-6-yl]-5(4H)-oxo-pyrazin-2-yl]propan-1-ol The procedure for preparing Intermediate 1-6 was used with the product of the previous step (700 mg, 1.81 mmol, 1.00 equiv), to afford 0.4 g (64%) of the title compound as colorless oil.

3-[4-(4-Fluorophenyl)-6-[2-oxa-6-azaspiro[3.3]heptan-6-yl]-5(4H)-oxo-pyrazin-2-yl]propanal The procedure for preparing Intermediate 1-7 was used with the product from the previous step (500 mg, 1.45 mmol, 1.00 equiv) to afford 0.28 g (56%) of the title compound as a yellow oil.

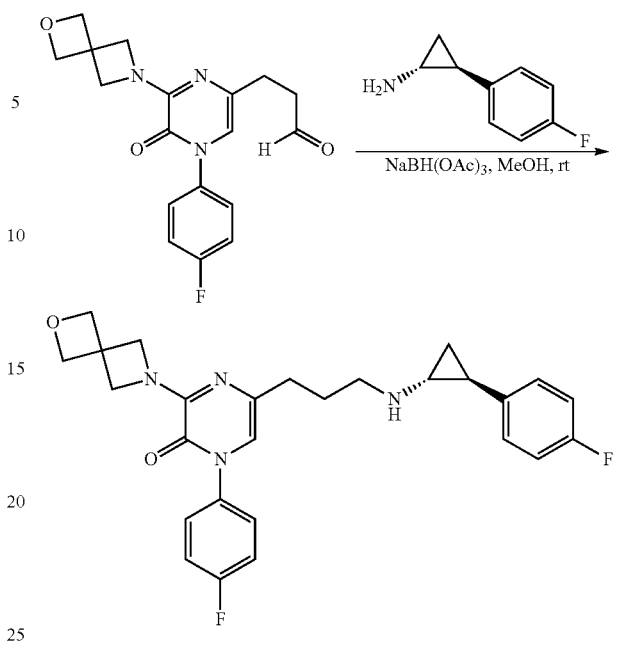

1-[4-Fluorophenyl]-5-[3-([(1R,2S)-2-(4-fluorophenyl)cyclopropyl]amino)propyl]-3-[2-oxa-6-azaspiro[3.3]heptan-6-yl]pyrazin-2(1H)-one The reductive amination step for preparing Example 1 from Intermediate 1-7 was used with the product from the previous step (280 mg, 0.82 mmol, 1.00 equiv). The crude product (5 mL) was purified using chromatographic Procedure C (35.0% to 52.0% $CH_3CN$ in 8.8 min), to afford 75.9 mg (19%) of the title compound as a light yellow solid.

LCMS: (ES, m/z): 479 [M+H]⁺. $^1$H NMR (300 MHz, Methanol-$d_4$) δ ppm: 7.45-7.31 (m, 2H), 7.29-7.14 (m, 2H), 7.09-6.98 (m, 2H), 7.00-6.85 (m, 2H), 6.55 (s, 1H), 4.70 (s, 4H), 4.40 (s, 4H), 2.79-2.68 (m, 2H), 2.38 (t, J=7.2 Hz, 2H), 2.33-2.23 (m, 1H), 1.95-1.74 (m, 3H), 1.10-0.89 (m, 2H).

Example 13

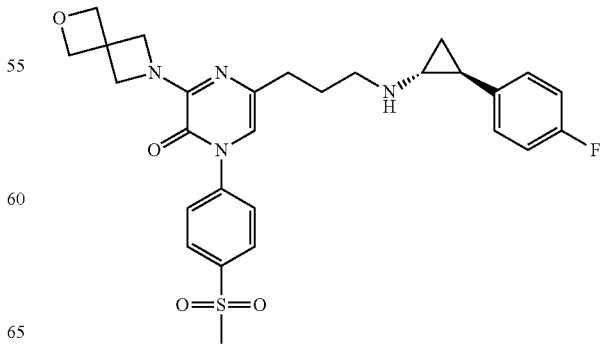

103

5-[3-([(1R,2S)-2-(4-fluorophenyl)cyclopropyl]amino)propyl]-1-[4-(methylsulfonyl)phenyl]-3-[2-oxa-6-azaspiro[3.3]heptan-6-yl]pyrazin-2(1H)-one

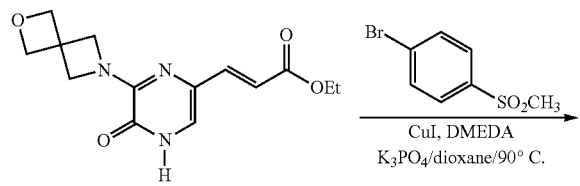

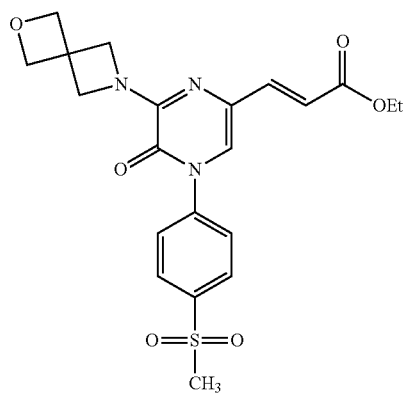

Ethyl (E)-3-[4-(4-methylsulfonylphenyl)-6-[2-oxa-6-azaspiro[3.3]heptan-6-yl]-5(4H)-oxopyrazin-2-yl]prop-2-enoate (Intermediate 13-1) A solution of Intermediate 12-1 (2 g, 6.87 mmol, 1.00 equiv), 1-bromo-4-methanesulfonylbenzene (2.4 g, 10.21 mmol, 1.50 equiv), N,N-dimethylethylenediamine (480 mg, 5.45 mmol, 0.80 equiv), $K_3PO_4$ (4.3 g, 20.26 mmol, 3.00 equiv), CuI (520 mg, 2.73 mmol, 0.40 equiv) in dioxane (100 mL) was stirred for 6 h at 90° C. The resulting mixture was concentrated under vacuum, and purified with silica gel chromatography using EtOAc/petroleum ether (1:1) to afford 1.3 g (43%) of the title compound as a yellow solid.

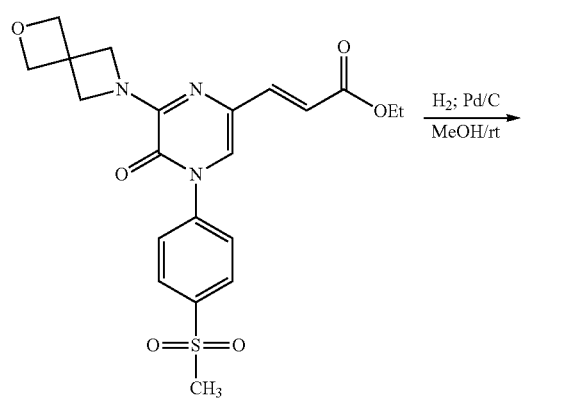

104

-continued

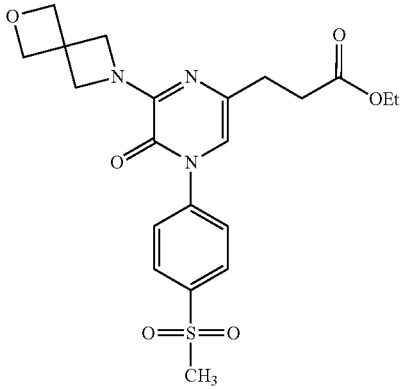

Ethyl 3-[4-(4-methylsulfonylphenyl)-6-[2-oxa-6-azaspiro[3.3]heptan-6-yl]-5(4H)-oxopyrazin-2-yl]propanoate The procedure for preparing Intermediate 1-5 was used with the product from the previous step (1.3 g, 2.92 mmol, 1.00 equiv) to afford 1.0 g (77%) of the title compound as a yellow solid.

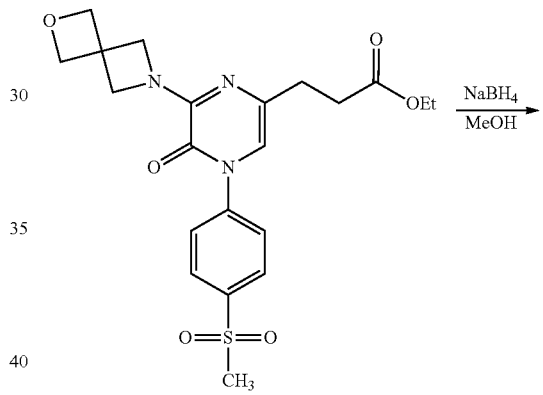

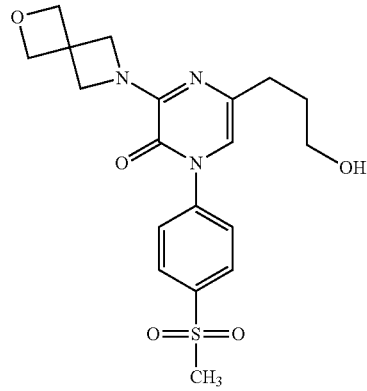

3-[4-(4-Methylsulfonylphenyl)-6-[2-oxa-6-azaspiro[3.3]heptan-6-yl]-5(4H)-oxopyrazin-2-yl]propan-1-ol The procedure for preparing Intermediate 1-6 was used with the product of the previous step (1.0 g, 2.23 mmol, 1.00 equiv), using 4 hr of reaction time at rt, to afford 0.4 g (44%) of the title compound as a yellow oil.

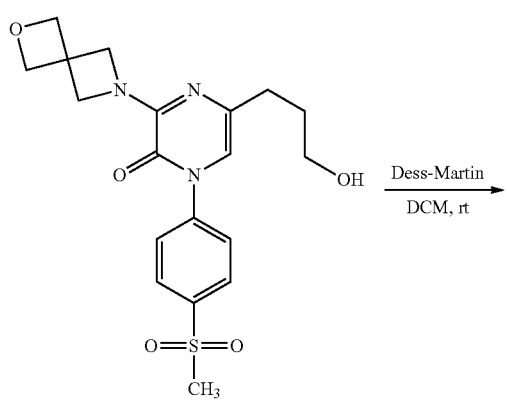

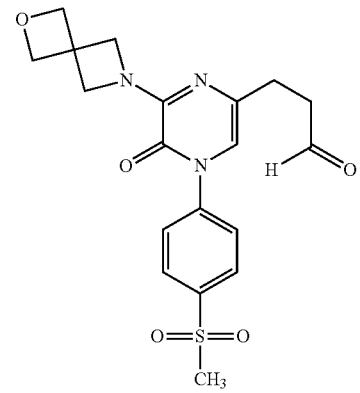

3-[4-(4-Methylsulfonylphenyl)-6-[2-oxa-6-azaspiro[3.3]heptan-6-yl]-5(4H)-oxopyrazin-2-yl]propanal The procedure for preparing Intermediate 1-7 was used with the product from the previous step (400 mg, 0.99 mmol, 1.00 equiv) to afford 150 mg (38%) of the title compound as a colorless oil.

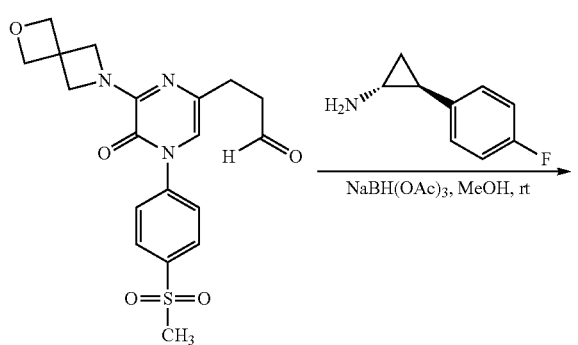

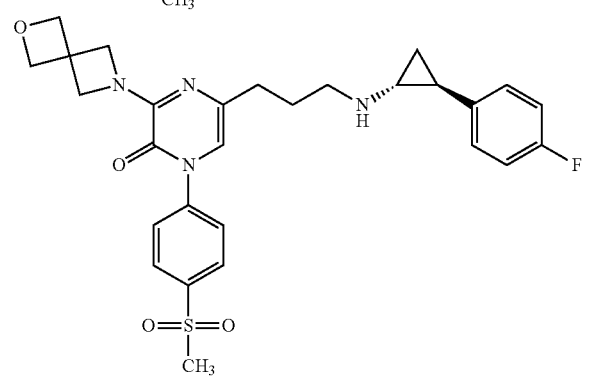

5-[3-([(1R,2S)-2-(4-fluorophenyl)cyclopropyl]amino) propyl]-1-[4-(methyl-sulfonyl)phenyl]-3-[2-oxa-6-azaspiro [3.3]heptan-6-yl]pyrazin-2(1H)-one The procedure for preparing Intermediate 4-7 was used with the product from the previous step (150 mg, 0.37 mmol). The crude product was purified using chromatographic Procedure E (42% to 45% CH$_3$CN in 7 min, Rt: 6.7 min) to afford 11.1 mg (6%) of the title compound as a light yellow solid.

LCMS: (ES, m/z): 539 [M+H]$^+$. $^1$H NMR (300 MHz, Methanol-d$_4$) δ ppm: 8.12-8.01 (m, 2H), 7.72-7.62 (m, 2H), 7.09-6.86 (m, 4H), 6.62 (s, 1H), 4.72 (s, 4H), 4.42 (s, 4H), 3.14 (s, 3H), 2.73 (t, J=7.5 Hz, 2H), 2.39 (t, J=7.2 Hz, 2H), 2.31-2.22 (m, 1H), 1.89-1.79 (m, 3H), 1.10-0.88 (m, 2H).

Example 14

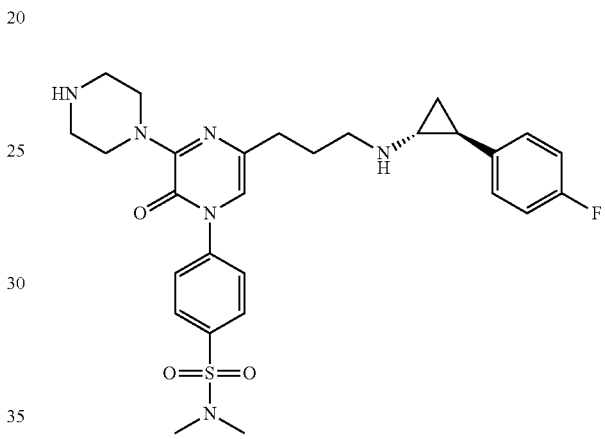

4-[5-(3-[([1R,2S]-2-[4-fluorophenyl]cyclopropyl) amino]propyl)-2-oxo-3-(piperazin-1-yl)pyrazin-1 (2H)-yl]-N,N-dimethylbenzenesulfonamide

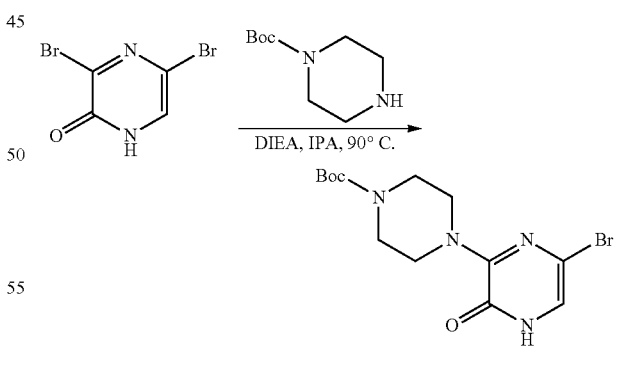

tert-Butyl 4-(6-bromo-3(4H)-oxopyrazin-2-yl)piperazine-1-carboxylate (Intermediate 14-1) The procedure for preparing Intermediate 2-1 was used with 3,5-dibromo-1,2-dihydropyrazin-2-one (20 g, 78.78 mmol, 1.00 equiv) and tert-butyl piperazine-1-carboxylate (22 g, 118.12 mmol, 1.50 equiv). The crude product was purified with silica gel chromatography using EtOAc/petroleum ether (1:20) to afford 25 g (88%) of the title compound as a yellow solid.

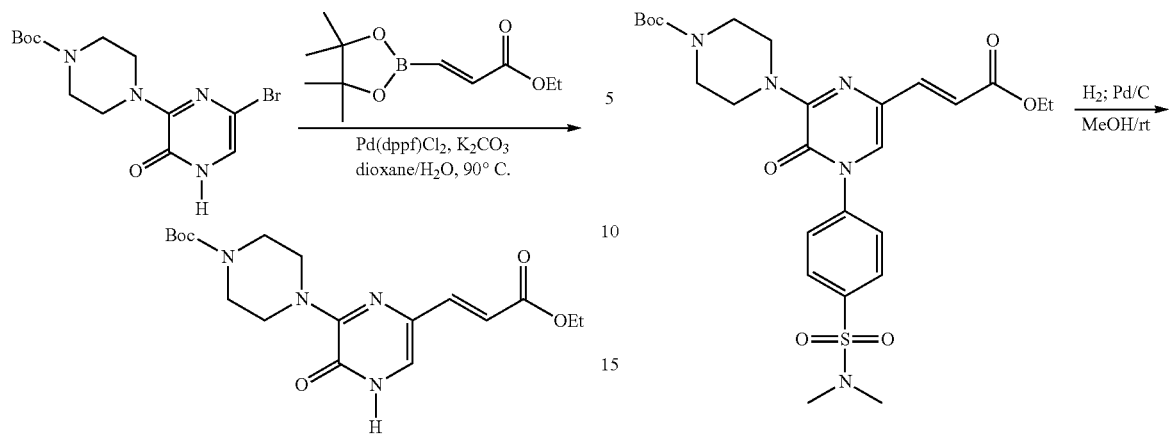

tert-Butyl 4-[6-[(E)-3-ethoxy-3-oxoprop-1-en-1-yl]-3 (4H)-oxopyrazin-2-yl]-piperazine-1-carboxylate (Intermediate 14-2) The procedure for preparing Intermediate 1-4 was used with Intermediate 14-1 (4 g, 11.14 mmol). The crude product was purified with silica gel chromatography using EtOAc/petroleum ether (1:10) to afford 1 g (24%) of the title compound as a yellow solid.

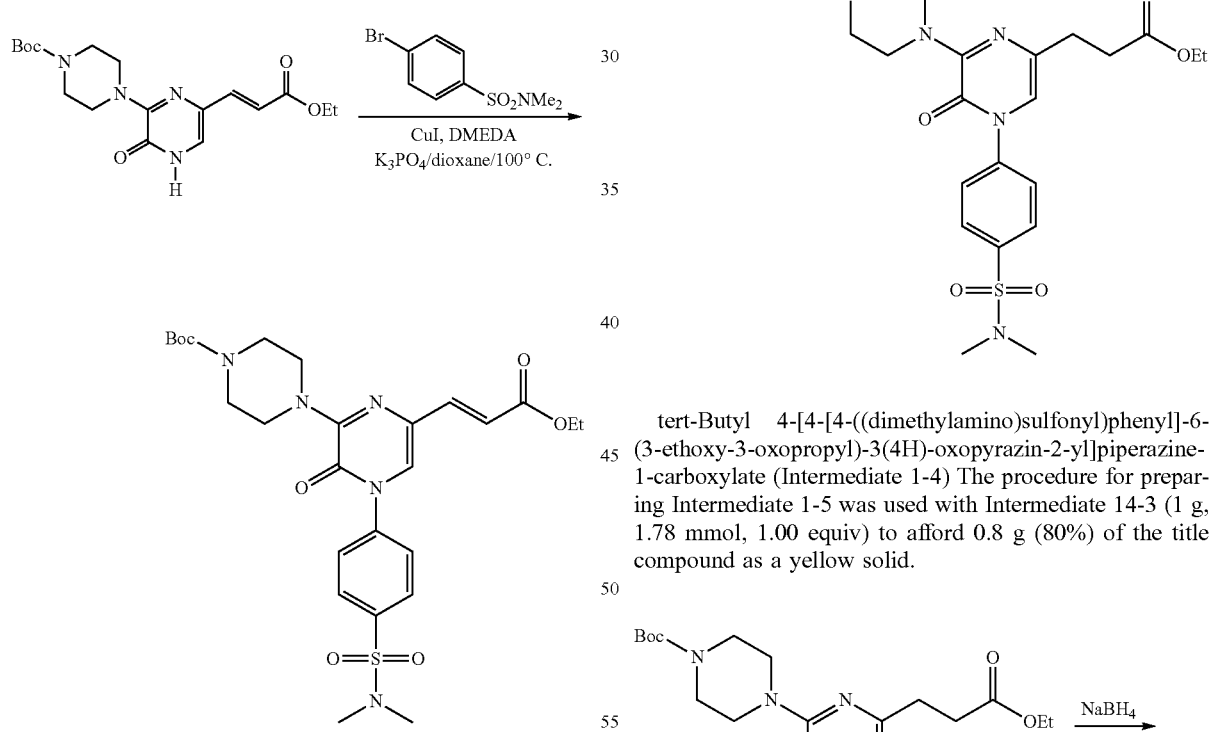

tert-Butyl 4-[4-[4-((dimethylamino)sulfonyl)phenyl]-6-[(E)-3-ethoxy-3-oxoprop-1-en-1-yl]-3(4H)-oxo-pyrazin-2-yl]piperazine-1-carboxylate (Intermediate 14-3) The procedure for preparing Intermediate 13-1 was used with Intermediate 14-2 (2 g, 5.29 mmol, 1.00 equiv) and 4-bromo-N,N-dimethylbenzene-1-sulfonamide (2.1 g, 7.95 mmol, 1.50 equiv). The crude product was purified with silica gel chromatography using EtOAc/petroleum ether (10:1) to afford 1 g (34%) of the title compound as a yellow solid.

tert-Butyl 4-[4-[4-((dimethylamino)sulfonyl)phenyl]-6-(3-ethoxy-3-oxopropyl)-3(4H)-oxopyrazin-2-yl]piperazine-1-carboxylate (Intermediate 1-4) The procedure for preparing Intermediate 1-5 was used with Intermediate 14-3 (1 g, 1.78 mmol, 1.00 equiv) to afford 0.8 g (80%) of the title compound as a yellow solid.

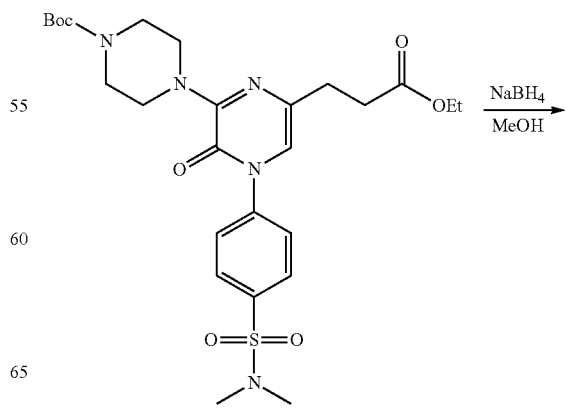

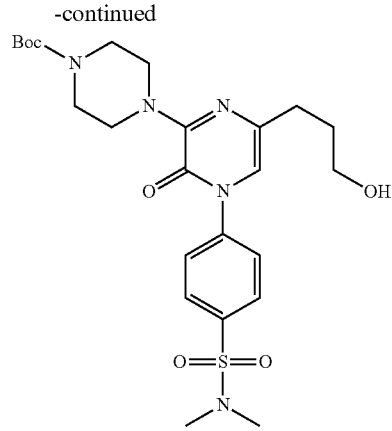

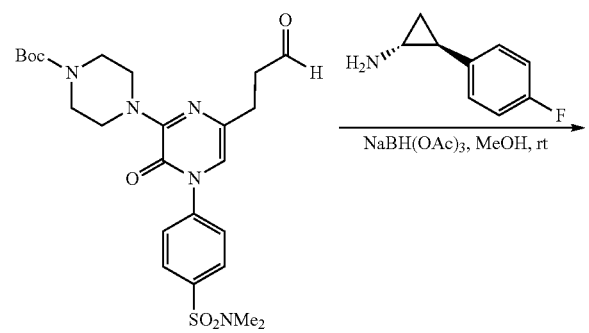

tert-Butyl 4-[4-[4-((dimethylamino)sulfonyl)phenyl]-6-(3-hydroxypropyl)-3(4H)-oxopyrazin-2-yl]piperazine-1-carboxylate (Intermediate 14-5) The procedure for preparing Intermediate 1-6 was used with Intermediate 14-4 (800 mg, 1.42 mmol, 1.00 equiv) to afford 520 mg (70%) of the title compound as a yellow solid.

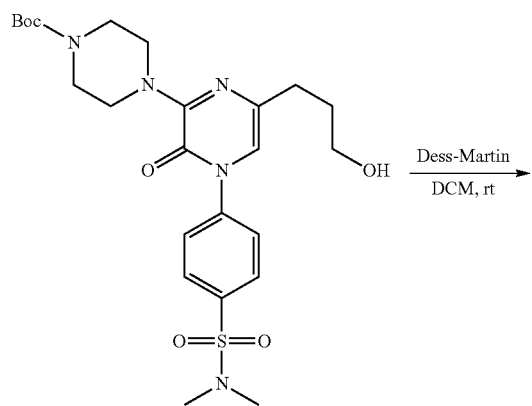

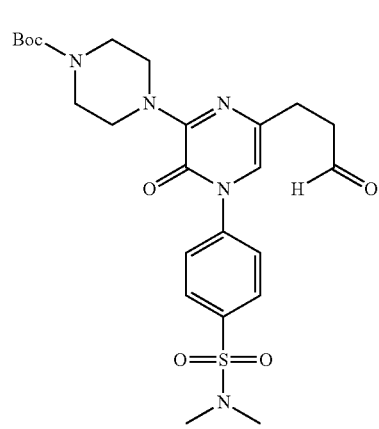

tert-Butyl 4-[4-[4-((dimethylamino)sulfonyl)phenyl]-3(4H)-oxo-6-(3-oxopropyl)-pyrazin-2-yl]piperazine-1-carboxylate (Intermediate 14-6) The procedure for preparing Intermediate 1-7 was used with Intermediate 14-5 (520 mg, 1.00 mmol, 1.00 equiv) to afford 370 mg (71%) of the title compound as a yellow solid.

tert-Butyl 4-[4-[4-((dimethylamino)sulfonyl)phenyl]-6-(3-[[(1R,2S)-2-(4-fluorophenyl)cyclopropyl]amino]propyl)-3(4H)-oxopyrazin-2-yl]piperazine-1-carboxylate (Intermediate 14-7) The reductive amination step for preparing Example 1 from Intermediate 1-7 was used with Intermediate 14-6 (370 mg, 0.71 mmol). The crude product was purified with silica gel chromatography using EtOAc, to afford 300 mg (64%) of the title compound as a yellow solid.

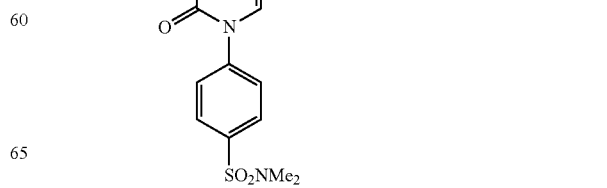

-continued

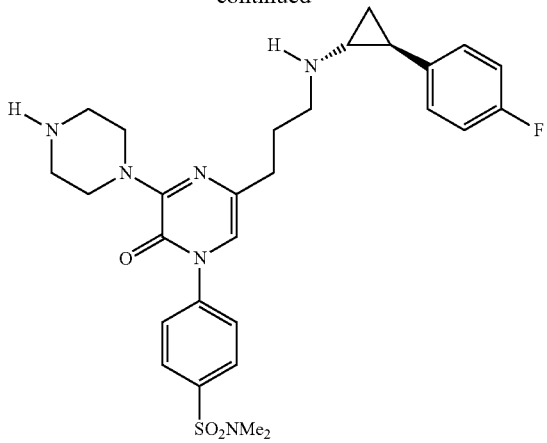

4-[5-(3-[([1R,2S]-2-[4-fluorophenyl]cyclopropyl)amino]propyl)-2-oxo-3-(piperazin-1-yl)pyrazin-1(2H)-yl]-N,N-dimethylbenzenesulfonamide (Example 14) A solution of Intermediate 14-7 (300 mg, 0.46 mmol, 1.00 equiv) and TFA (3 mL) in CH$_2$Cl$_2$ (15 mL) was stirred for 1 h at 25° C. The pH was adjusted to 7 with NaHCO$_3$ (5 mM). The resulting mixture was concentrated under vacuum. The crude product (2 mL) was purified by Prep-HPLC (2 #-AnalyseHPLC-SHIMADZU (HPLC-10), column: Atlantis HILIC OBD, particle size: 5 M, column size: 19×150 mm, mobile phase: H$_2$O (10 mM NH$_4$HCO$_3$+0.1% NH$_3$)/CH$_3$CN, 42.0% to 44.0% CH$_3$CN in 8 min, detector, UV 254/210 nm), to afford 56.9 mg (22%) of the title compound as a yellow solid.

LC-MS: (ES, m/z): 555 [M+H]$^+$. $^1$H NMR (400 MHz, MeOD-d$_4$) δ ppm: 7.96-7.89 (m, 2H), 7.72-7.64 (m, 2H), 7.06 (m, 2H), 7.00-6.90 (m, 2H), 6.85 (s, 1H), 3.77 (m, 4H), 2.91 (m, 4H), 2.81-2.71 (m, 8H), 2.47 (m, 2H), 2.29 (m, 1H), 1.90 (m, 3H), 1.10-0.92 (m, 2H).

Example 15

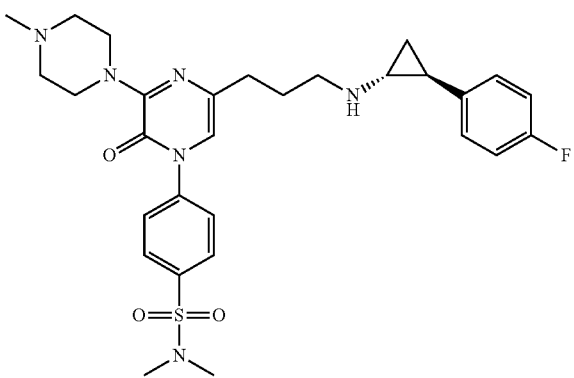 [SMILES: CN1CCN(c2nc(CCCN[C@@H]3C[C@H]3c3ccc(F)cc3)cn(-c3ccc(S(=O)(=O)N(C)C)cc3)c2=O)CC1]

4-[5-(3-[([1R,2S]-2-[4-fluorophenyl]cyclopropyl)amino]propyl)-3-(4-methylpiperazin-1-yl)-2-oxopyrazin-1(2H)-yl]-N,N-dimethylbenzenesulfonamide

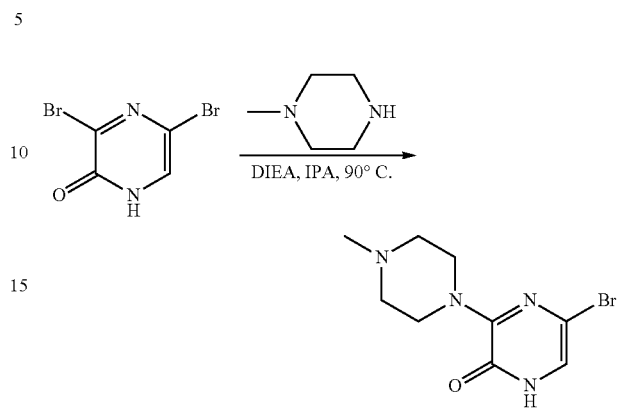

5-Bromo-3-(4-methylpiperazin-1-yl)-pyrazin-2(1H)-one (Intermediate 15-1)

The procedure for preparing Intermediate 2-1 was used with 3,5-dibromo-1,2-dihydropyrazin-2-one (10 g, 39.39 mmol, 1.00 equiv) and 1-methylpiperazine (4.78 g, 47.72 mmol, 1.21 equiv), to afford 10.2 g (95%) of the title compound as a tan solid.

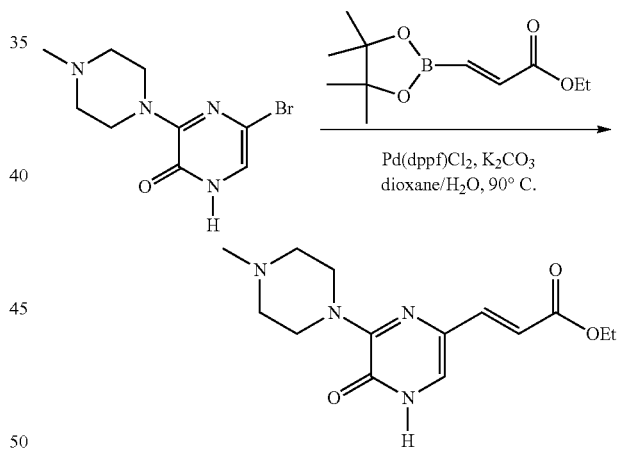

Ethyl (E)-3-[6-(4-methylpiperazin-1-yl)-5(4H)-oxopyrazin-2-yl]prop-2-enoate (Intermediate 15-2) The procedure for preparing Intermediate 1-4 was used with Intermediate 15-1 (5 g, 18.31 mmol, 1.00 equiv) to afford 2 g (37%) of the title compound as a light yellow solid.

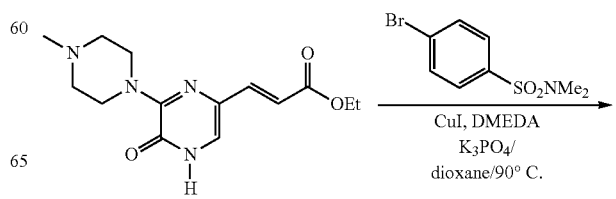

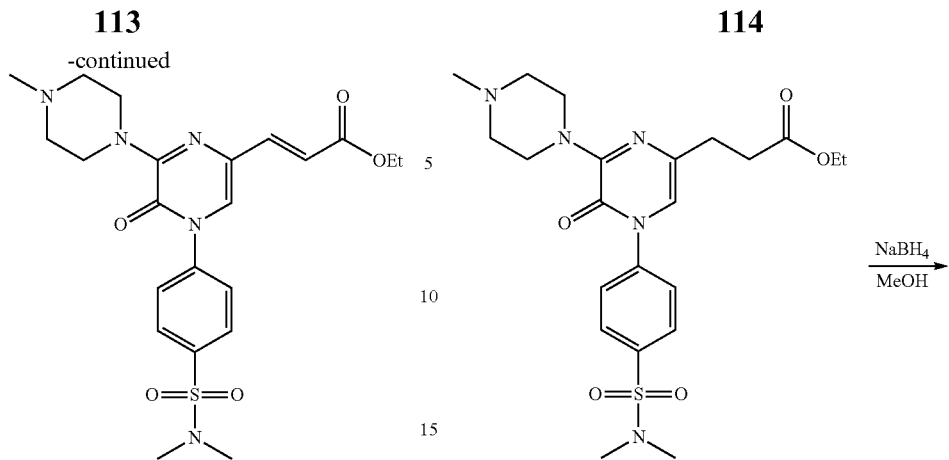

Ethyl (E)-3-[4-(4-[N,N-dimethylsulfamoyl]phenyl)-6-(4-methylpiperazin-1-yl)-5-oxo-4,5-dihydropyrazin-2-yl)prop-2-enoate (Intermediate 15-3) The procedure for preparing Intermediate 13-1 was used with Intermediate 15-2 (2.0 g, 6.84 mmol, 1.00 equiv) and 4-bromo-N,N-dimethylbenzene-1-sulfonamide and 4-bromo-N,N-dimethylbenzene-1-sulfonamide (2.7 g, 10.26 mmol, 1.50 equiv), using 16 h of reaction time at 90° C. The crude product was purified with silica gel chromatography using CH$_2$Cl$_2$/MeOH (10:1) to afford 1.25 g (38.4%) of the title compound as a light yellow solid.

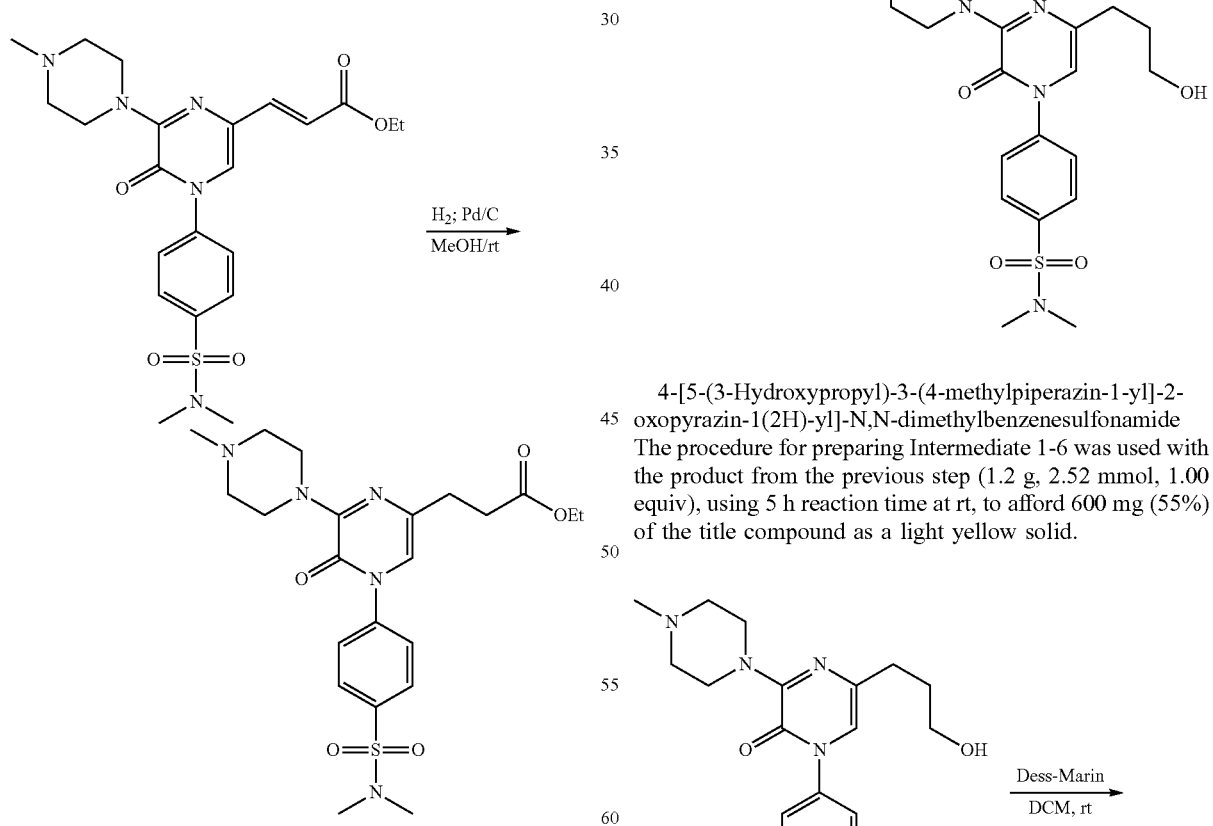

Ethyl 3-[4-(4-[N,N-dimethylsulfamoyl]phenyl)-6-(4-methylpiperazin-1-yl)-5-oxo-4,5-dihydropyrazin-2-yl]propanoate The procedure for preparing Intermediate 1-5 was used with Intermediate 15-3 (1.25 g, 2.63 mmol, 1.00 equiv) and Pd/C (125 mg), with 2 h reaction time, to afford 1.2 g (95%) of the title compound as a light yellow solid.

4-[5-(3-Hydroxypropyl)-3-(4-methylpiperazin-1-yl]-2-oxopyrazin-1(2H)-yl]-N,N-dimethylbenzenesulfonamide The procedure for preparing Intermediate 1-6 was used with the product from the previous step (1.2 g, 2.52 mmol, 1.00 equiv), using 5 h reaction time at rt, to afford 600 mg (55%) of the title compound as a light yellow solid.

115
-continued

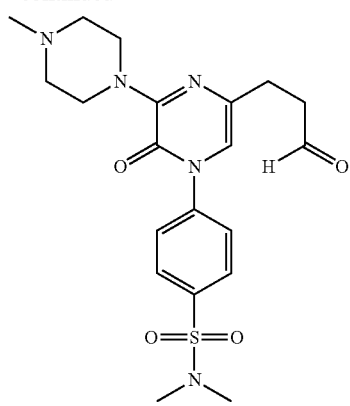

N,N-dimethyl-4-[3-(4-methylpiperazin-1-yl)-2-oxo-5-(3-oxopropyl)pyrazin-1(2H)-yl]benzenesulfonamide The procedure for preparing Intermediate 1-7 was used with the product from the previous step (600 mg, 1.38 mmol, 1.00 equiv) to afford 300 mg (78%) of the title compound as a light yellow solid.

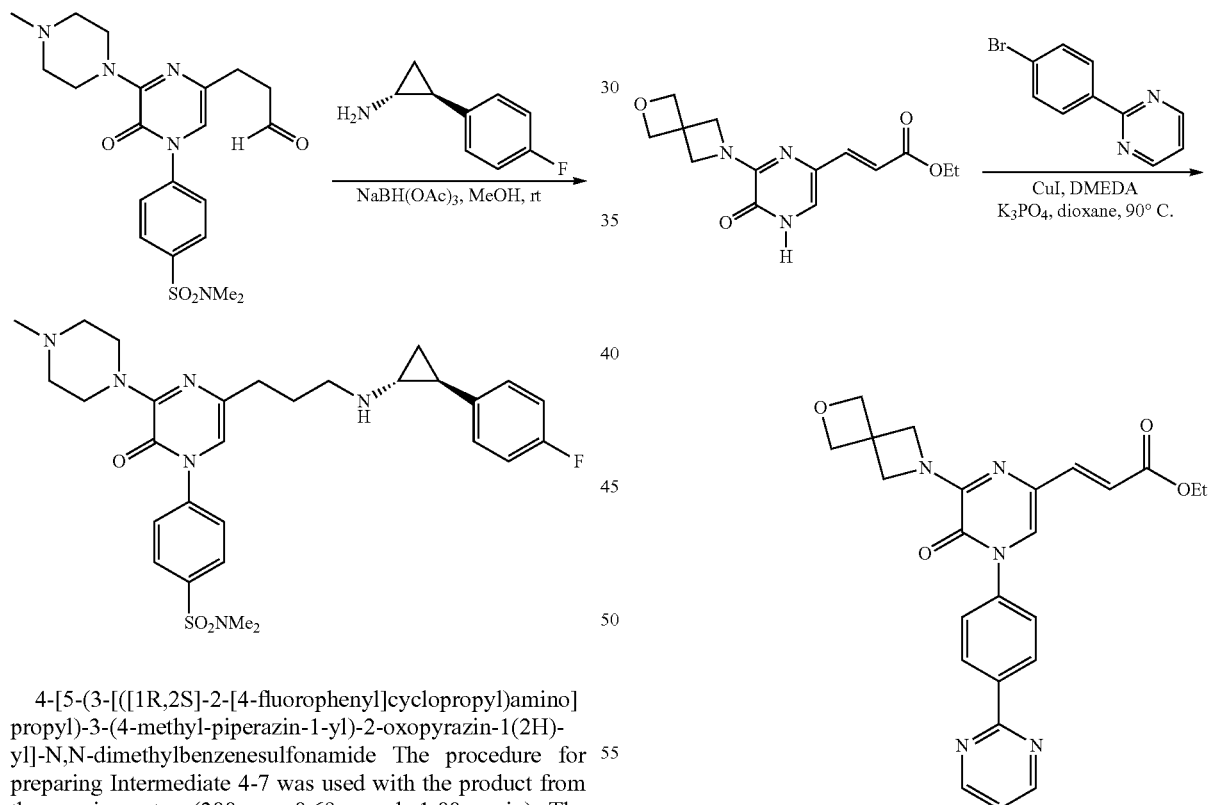

4-[5-(3-[([1R,2S]-2-[4-fluorophenyl]cyclopropyl)amino]propyl)-3-(4-methyl-piperazin-1-yl)-2-oxopyrazin-1(2H)-yl]-N,N-dimethylbenzenesulfonamide The procedure for preparing Intermediate 4-7 was used with the product from the previous step (300 mg, 0.69 mmol, 1.00 equiv). The crude product (5 mL) was purified using chromatographic Procedure B (10.0% to 29.0% $CH_3CN$ in 8 min), affording 15.1 mg (4%) of the title compound as an off-white solid.

LC-MS: (ES, m/z): 569 [M+H]$^+$. $^1$H NMR (400 MHz, Methanol-d$_4$) δ 7.95-7.92 (m, 2H), 7.71-7.67 (m, 2H), 7.23-7.16 (m, 2H), 7.08-6.99 (m, 2H), 4.95-4.80 (m, 2H), 3.65-3.45 (s, 2H), 3.35-3.15 (m, 6H), 3.00-2.90 (m, 4H), 2.76-2.71 (s, 6H), 2.62-2.54 (m, 2H), 2.54-2.45 (m, 1H), 2.15-2.05 (m, 2H), 1.55-1.47 (m, 1H), 1.41-1.32 (m, 1H).

116
Example 16

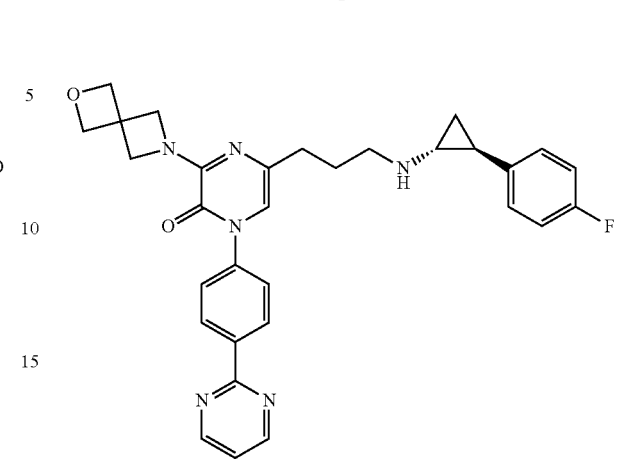

5-[3-([(1R,2S)-2-(4-fluorophenyl)cyclopropyl]amino)propyl]-1-[4-(pyrimidin-2-yl)phenyl]-3-[2-oxa-6-azaspiro[3.3]heptan-6-yl]pyrazin-2(1H)-one Ethyl (E)-3-(6-[2-oxa-6-azaspiro[3.3]heptan-6-yl]-5(4H)-oxo-4-[4-(pyrimidin-2-yl)phenyl]-pyrazin-2-yl)prop-2-enoate The procedure for preparing Intermediate 15-3 was used with Intermediate 13-1 and 2-(4-bromophenyl)pyrimidine with 6 h reaction time at 90° C. The crude product was purified with silica gel chromatography using EtOAc/petroleum ether (1:1) to afford 2.0 g (44%) of the title compound as a yellow solid.

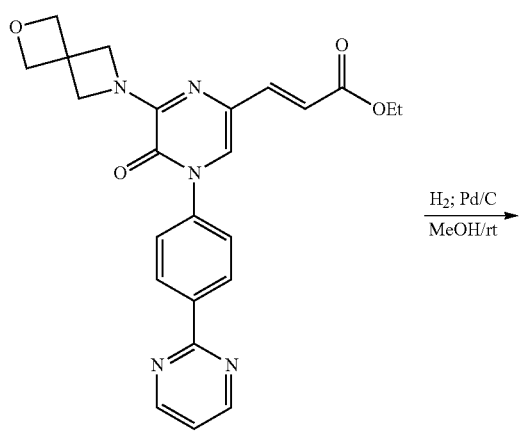

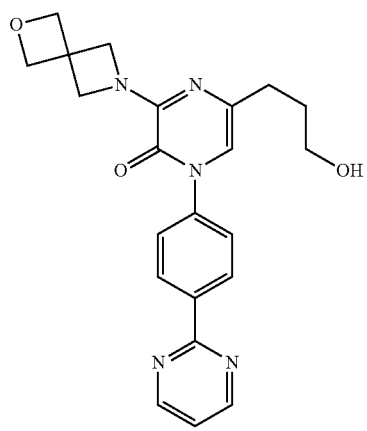

3-[4-(4-(Pyrimidin-2-yl)phenyl)-6-[2-oxa-6-azaspiro [3.3]heptan-6-yl]-5(4H)-oxopyrazin-2-yl]propan-1-ol The procedure for preparing Intermediate 1-6 was used with the product of the previous step (1.8 g, 4.02 mmol, 1.00 equiv) to afford 0.4 g (25%) of the title compound as an off-white solid.

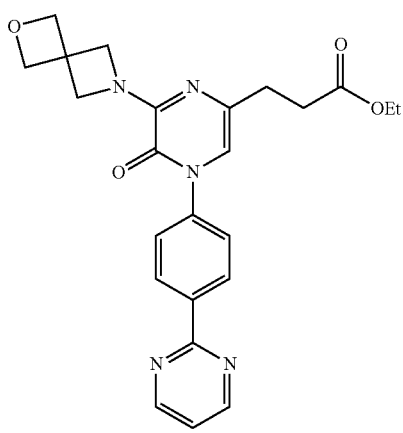

Ethyl 3-(6-[2-oxa-6-azaspiro[3.3]heptan-6-yl]-5(4H)-oxo-4-[4-(pyrimidin-2-yl)phenyl]-pyrazin-2-yl)propanoate The procedure for preparing Intermediate 1-5 was used with the product from the previous step (2 g, 4.49 mmol, 1.00 equiv) to afford 1.8 g (90%) of the title compound as a yellow solid.

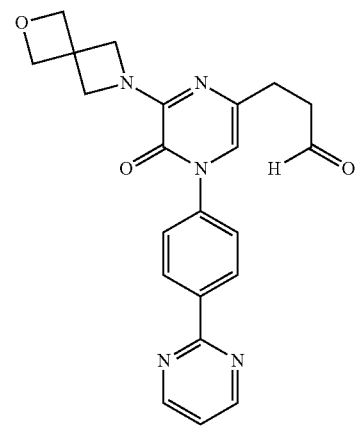

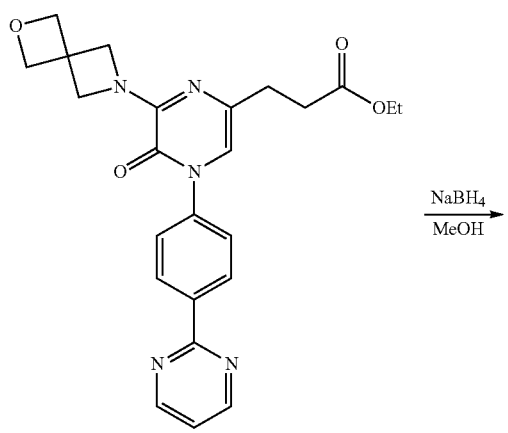

3-[4-(4-(Pyrimidin-2-yl)phenyl)-6-[2-oxa-6-azaspiro [3.3]heptan-6-yl]-5(4H)-oxopyrazin-2-yl]propanal The procedure for preparing Intermediate 1-7 was used with the product from the previous step (400 mg, 0.99 mmol, 1.00 equiv) to afford 0.12 g (30%) of the title compound as a light yellow oil.

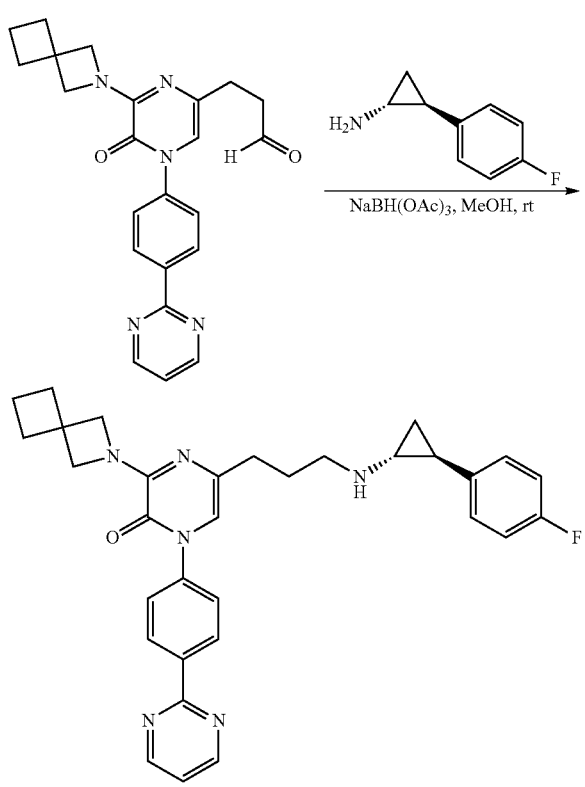

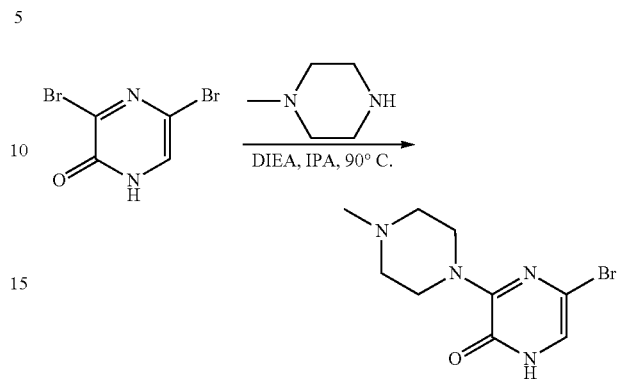

1-[4-(1H-1,2,3-triazol-1-yl)phenyl]-5-[3-([(1R,2S)-2-(4-fluorophenyl)-cyclopropyl]amino)propyl]-3-[4-methylpiperazin-1-yl]pyrazin-2(1H)-one 5-Bromo-3-(4-methylpiperazin-1-yl)-pyrazin-2(1H)-one (Intermediate 17-1) The procedure for preparing Intermediate 2-1 was used with 3,5-dibromo-1,2-dihydropyrazin-2-one (20 g, 78.78 mmol, 1.00 equiv) and 1-methylpiperazine (9.49 g, 94.90 mmol, 1.20 equiv). The crude product was purified using silica gel chromatography using EtOAc/petroleum ether (8:1) to afford 16.0 g (74.1%) of the title compound as a white solid.

1-(4-(Pyrimidin-2-yl)-phenyl)-3-(2-oxa-6-azaspiro[3.3]heptan-6-yl)-5-(3-[[(1R,2S)-2-(4-fluorophenyl)cyclopropyl]amino]propyl) pyrazin-2(1H)-one The reductive amination step for preparing Example 1 from Intermediate 1-7 was used with the product from the previous step (120 mg, 0.30 mmol). The crude product (4 mL) was purified using chromatographic Procedure E (50% to 55% CH$_3$CN in 7 min, Rt: 6.35 min), to afford 13.1 mg (8%) of the title compound as a light yellow solid.

LCMS: (ES, m/z): 539 [M+H]$^+$. $^1$H NMR (300 MHz, Methanol-d$_4$) δ ppm: 8.85 (d, J=4.8 Hz, 2H), 8.59-8.48 (m, 2H), 7.56-7.46 (m, 2H), 7.37 (m, 1H), 7.10-6.86 (m, 4H), 6.65 (s, 1H), 4.83 (s, 4H), 4.43 (s, 4H), 2.75 (t, J=7.2 Hz, 2H), 2.41 (t, J=7.2 Hz, 2H), 2.33-2.24 (m, 1H), 1.96-1.76 (m, 3H), 1.11-0.90 (m, 2H).

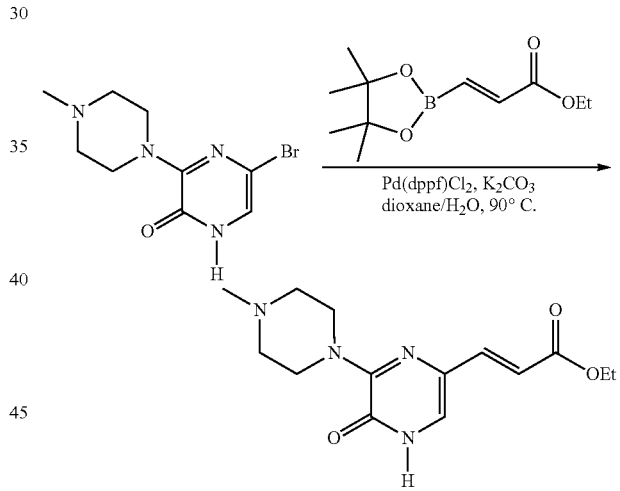

Example 17

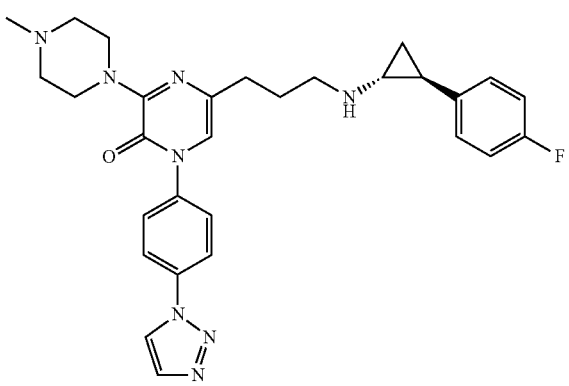 [SMILES: CN1CCN(c2nc(CCCN[C@@H]3C[C@H]3c3ccc(F)cc3)cn(-c3ccc(-n4ccnn4)cc3)c2=O)CC1]

Ethyl (E)-3-[6-(4-methylpiperazin-1-yl)-5(4H)-oxopyrazin-2-yl]prop-2-enoate (Intermediate 17-2) The procedure for preparing Intermediate 1-4 was used with Intermediate 17-1 (16.0 g, 58.61 mmol). The crude product was purified with silica gel chromatography using EtOAc/petroleum ether (6:1) to afford 9.0 g (52.4%) of the title compound as a yellow oil.

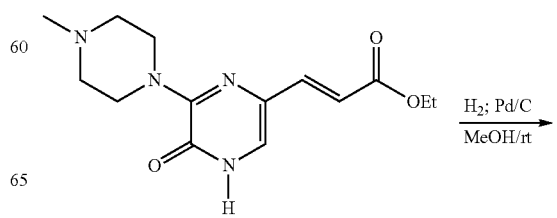

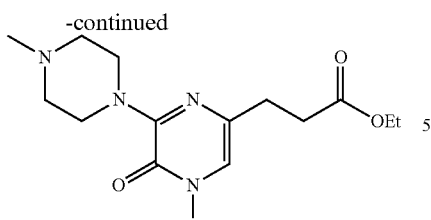

Ethyl 3-[6-(4-methylpiperazin-1-yl)-5(4H)-oxopyrazin-2-yl]propanoate (Intermediate 17-3) The procedure for preparing Intermediate 1-5 was used with Intermediate 17-2 (9.0 g, 30.72 mmol, 1.00 equiv) to afford 8.9 g (98.2%) of the title compound as a yellow oil.

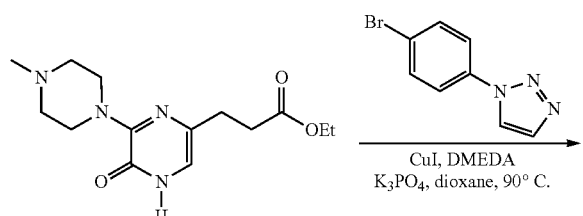

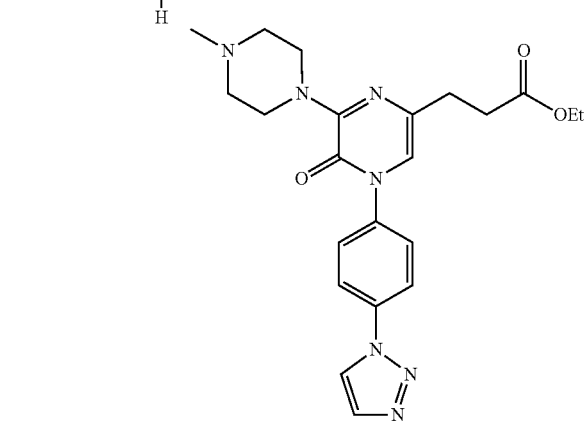

Ethyl 3-(4-(4-(1H-1,2,3-triazol-1-yl)phenyl)-6-(4-methylpiperazin-1-yl)-5(4H)-oxopyrazin-2-yl)propanoate The procedure for preparing Intermediate 13-1 was used with Intermediate 17-3 (2.9 g, 9.83 mmol, 1 equiv) and 1-(4-bromophenyl)-1H-1,2,3-triazole (3.3 g, 14.73 mmol, 1.5 equiv). The crude product was purified with silica gel chromatography using EtOAc/petroleum ether (1:1) to afford 1.2 g (27.9%) of the title compound as a yellow solid.

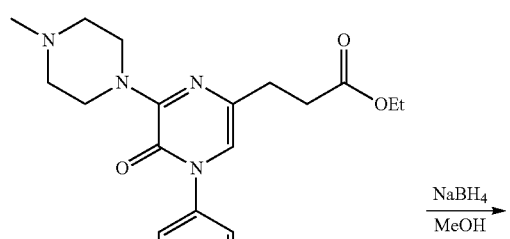

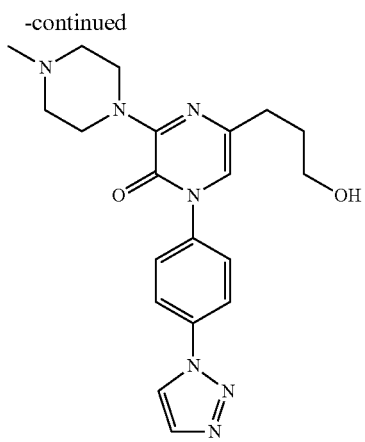

3-(4-(4-(1H-1,2,3-Triazol-1-yl)phenyl)-6-(4-methylpiperazin-1-yl)-5(4H)-oxopyrazin-2-yl)propan-1-ol The procedure for preparing Intermediate 1-6 was used with the product from the previous step (1.2 g, 2.74 mmol, 1 equiv) to afford 400 mg (36.9%) of the title compound as a yellow solid.

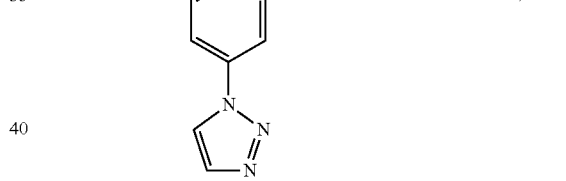

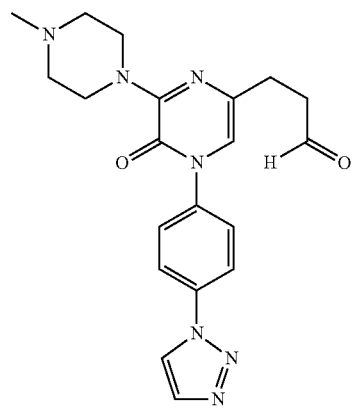

3-(4-(4-(1H-1,2,3-Triazol-1-yl)phenyl)-6-(4-methylpiperazin-1-yl)-5(4H)-oxopyrazin-2-yl)propanal The procedure for preparing Intermediate 1-7 was used with the product from the previous step (350 mg, 0.88 mmol, 1.00 equiv) to afford 160 mg (46. %) of the title compound as a yellow solid.

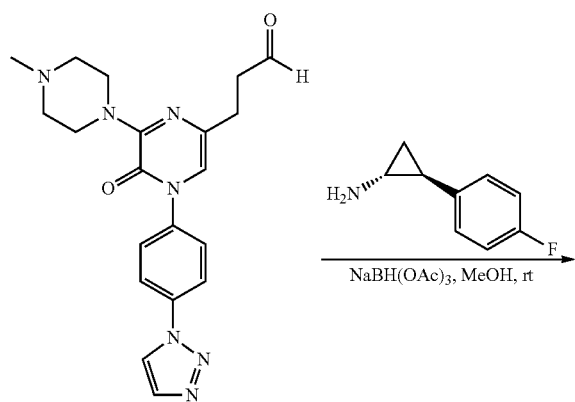

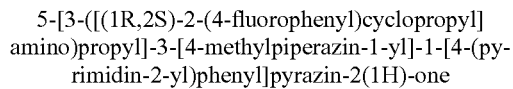

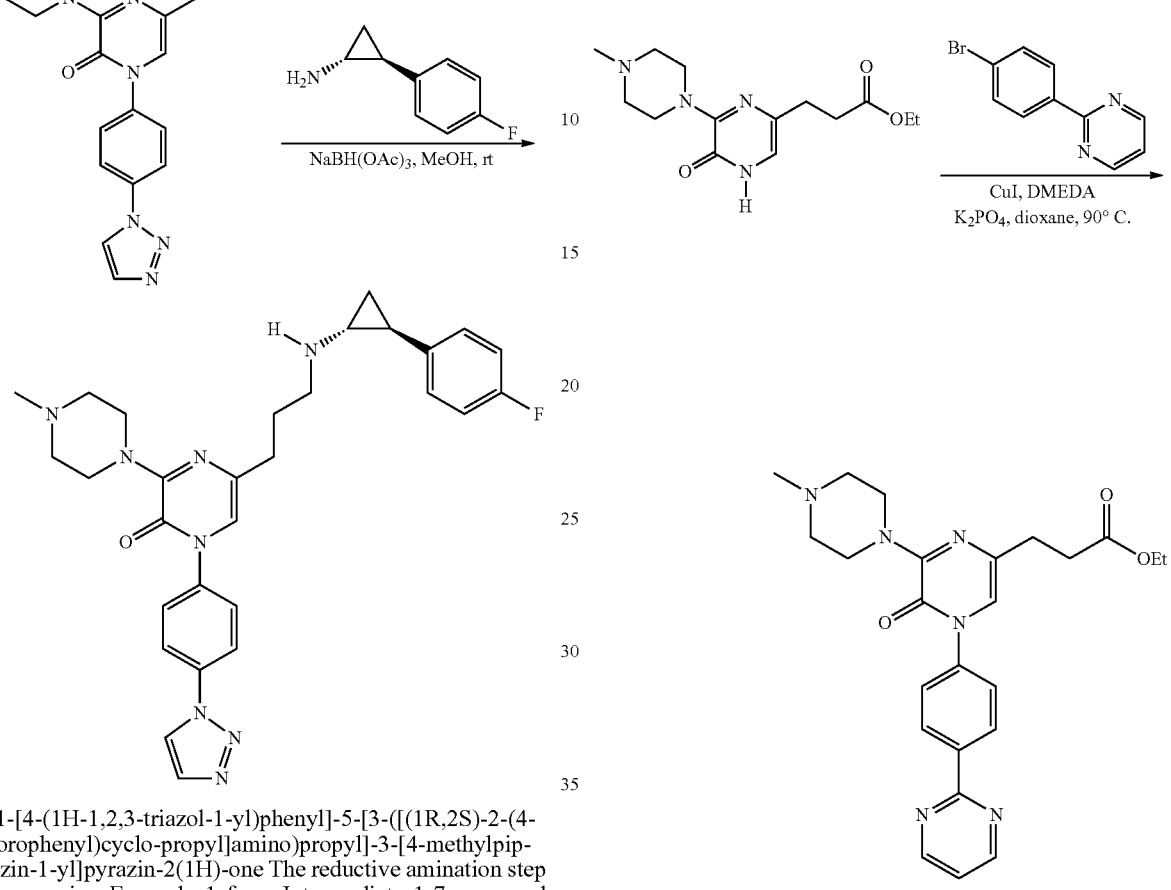

1-[4-(1H-1,2,3-triazol-1-yl)phenyl]-5-[3-([(1R,2S)-2-(4-fluorophenyl)cyclo-propyl]amino)propyl]-3-[4-methylpiperazin-1-yl]pyrazin-2(1H)-one The reductive amination step for preparing Example 1 from Intermediate 1-7 was used with the product from the previous step (150 mg, 0.41 mmol). The crude product (5 mL) was purified using chromatographic Procedure E (27% to 60% CH$_3$CN, Rt: 10.13 min), to afford 42.8 mg (21.25%) of the title compound as a white solid.

LC-MS: (ES, m/z): 529 [M+H]$^+$. $^1$H NMR (300 MHz, MeOD-d$_4$) δ ppm: 8.60 (s, 1H), 8.05-7.95 (m, 2H), 7.91 (s, 1H), 7.67-7.57 (m, 2H), 7.06-7.01 (m, 2H), 6.97-6.88 (m, 2H), 6.85 (s, 1H), 3.78 (m, 4H), 2.75 (t, J=7.4 Hz, 2H), 2.56-2.40 (m, 6H), 2.29 (s, 3H), 2.30-2.21 (m, 1H), 1.95-1.79 (m, 3H), 1.10-0.88 (m, 2H).

Example 18

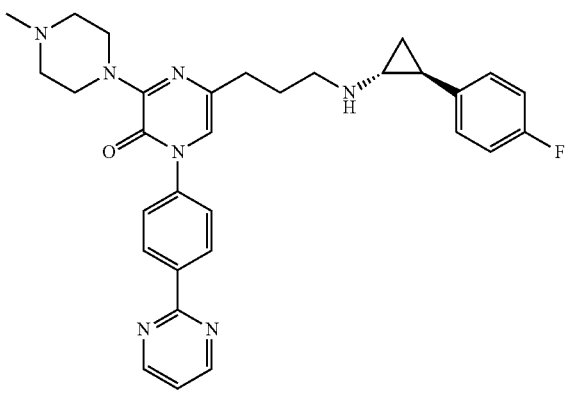 [SMILES: CN1CCN(c2nc(CCCN[C@@H]3C[C@H]3c3ccc(F)cc3)cn(-c3ccc(-c4ncccn4)cc3)c2=O)CC1]

5-[3-([(1R,2S)-2-(4-fluorophenyl)cyclopropyl]amino)propyl]-3-[4-methylpiperazin-1-yl]-1-[4-(pyrimidin-2-yl)phenyl]pyrazin-2(1H)-one

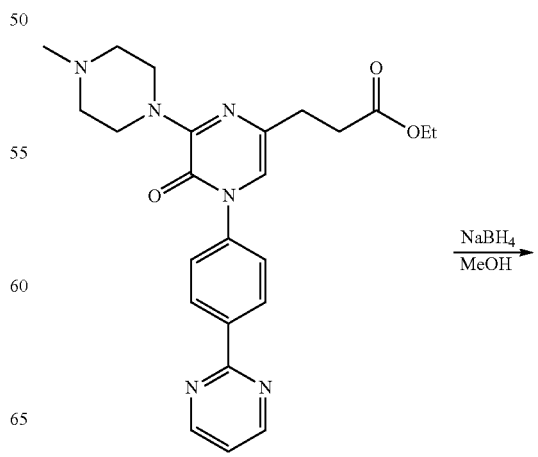

Ethyl 3-(4-(Pyrimidin-2-yl)phenyl)-6-(4-methylpiperazin-1-yl)-5(4H)-oxopyrazin-2-yl)propanoate The procedure for preparing Intermediate 13-1 was used with Intermediate 17-3 (2.2 g, 7.46 mmol, 1 equiv) and 2-(4-bromophenyl)pyrimidine (2.63 g, 11.12 mmol, 1.5 equiv). The crude product was purified with silica gel chromatography using EtOAc/petroleum ether (1:1) to afford 1.0 g (29.86%) of the title compound as a yellow solid.

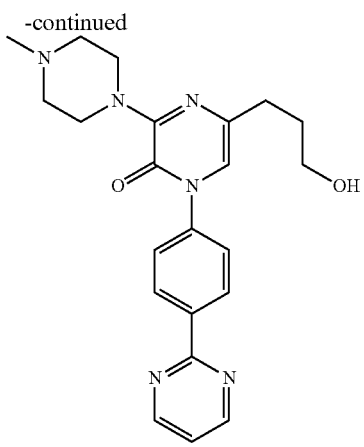
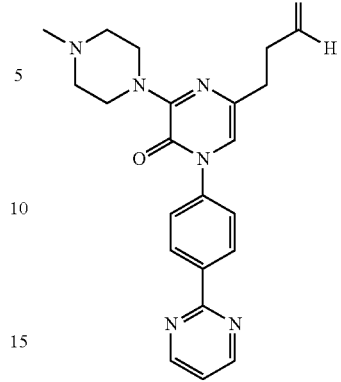

3-(4-(4-(Pyrimidin-2-yl)phenyl)-6-(4-methylpiperazin-1-yl)-5(4H)-oxopyrazin-2-yl)propan-1-ol The procedure for preparing Intermediate 1-6 was used with the product from the previous step (800 mg, 1.78 mmol, 1 equiv) to afford 300 mg (41.37%) of the title compound as a yellow solid.

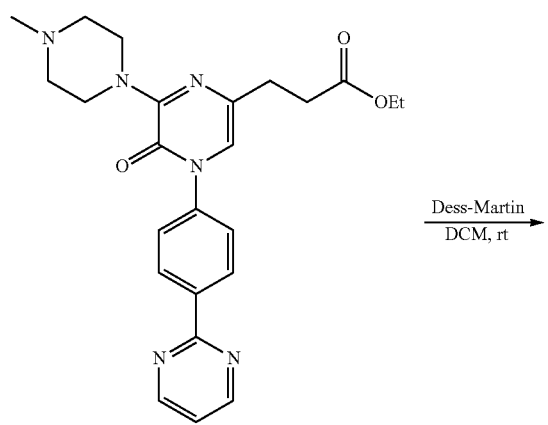
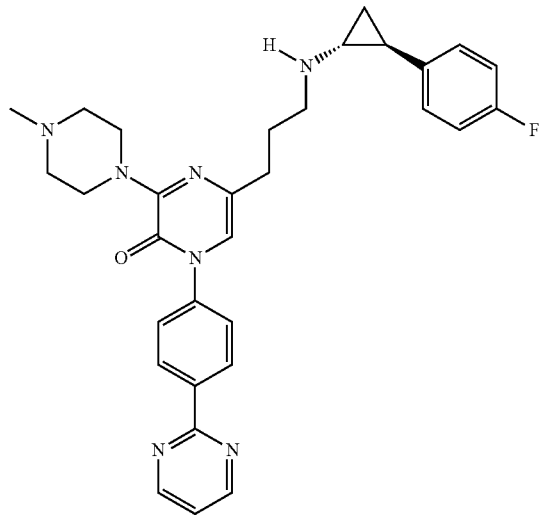

3-(4-(4-(Pyrimidin-2-yl)phenyl)-6-(4-methylpiperazin-1-yl)-5(4H)-oxopyrazin-2-yl)propanal The procedure for preparing Intermediate 1-7 was used with the product from the previous step (300 mg, 0.74 mmol, 1.00 equiv) to afford 150 mg (50.25%) of the title compound as a yellow solid.

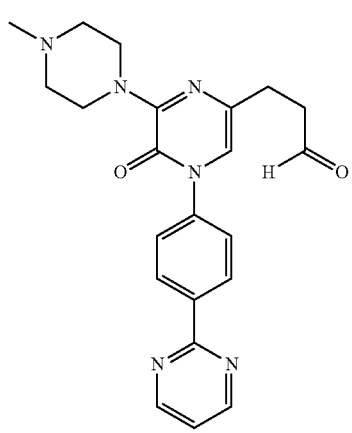

5-[3-([(1R,2S)-2-(4-fluorophenyl)cyclopropyl]amino)propyl]-3-[4-methyl-piperazin-1-yl]-1-[4-(pyrimidin-2-yl)phenyl]pyrazin-2(1H)-one The reductive amination step for preparing Example 1 from Intermediate 1-7 was used with the product from the previous step (150 mg, 0.37 mmol). The crude product (5 mL) was purified using chromatographic Procedure D (27% to 60% $CH_3CN$, Rt: 10.13 min), to afford 51.5 mg (25.75%) of the title compound as a white solid.

LC-MS: (ES, m/z): 540 [M+H]$^+$. $^1$H NMR (300 MHz, MeOD-d$_4$) δ ppm: 8.86 (d, J=4.9 Hz, 2H), 8.58-8.52 (m, 2H), 7.57-7.50 (m, 2H), 7.38 (t, J=4.9 Hz, 1H), 7.21-7.13 (m, 2H), 7.07-6.97 (m, 3H), 4.92-4.85 (m, 2H), 3.60-3.47 (m, 2H), 3.25-3.12 (m, 6H), 3.00-2.85 (m, 4H), 2.57 (t, J=7.3 Hz, 2H), 2.50-2.40 (m, 1H), 2.13-2.00 (m, 2H), 1.53-1.42 (m, 1H), 1.40-1.23 (m, 1H).

Example 19

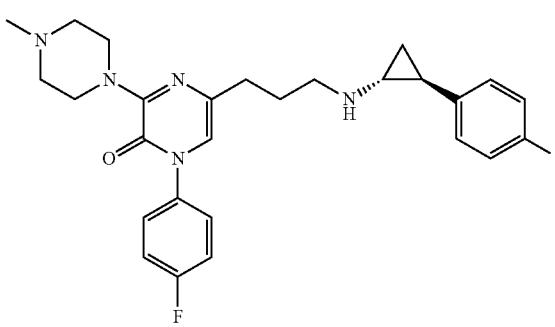

1-[4-Fluorophenyl]-5-[3-([(1R,2S)-2-(4-fluorophenyl)cyclopropyl]amino)propyl]-3-[4-methylpiperazin-1-yl]pyrazin-2(1H)-one

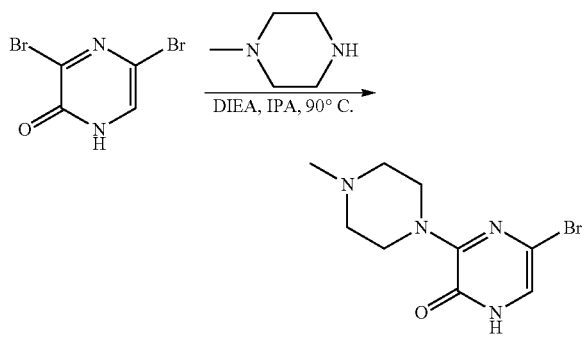

5-Bromo-3-(4-methylpiperazin-1-yl)-pyrazin-2(1H)-one The procedure for preparing Intermediate 2-1 was used with 3,5-dibromo-1,2-dihydropyrazin-2-one (10 g, 39.37 mmol, 1.00 equiv) and 1-methylpiperazine (4.72 g, 47.24 mmol, 1.20 equiv). The crude product was purified using silica gel chromatography using EtOAc/petroleum ether (8:1) to afford 10 g (93%) of the title compound as a off-white solid.

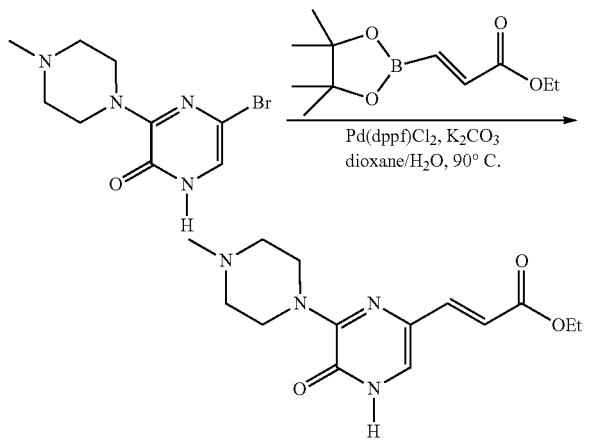

Ethyl (E)-3-[6-(4-methylpiperazin-1-yl)-5(4H)-oxopyrazin-2-yl]prop-2-enoate

The procedure for preparing Intermediate 1-4 was used with the product from the previous step (10 g, 36.63 mmol). The crude product was purified using silica gel chromatography using EtOAc/petroleum ether (6:1) to afford 5.6 g (52%) of the title compound as a yellow oil.

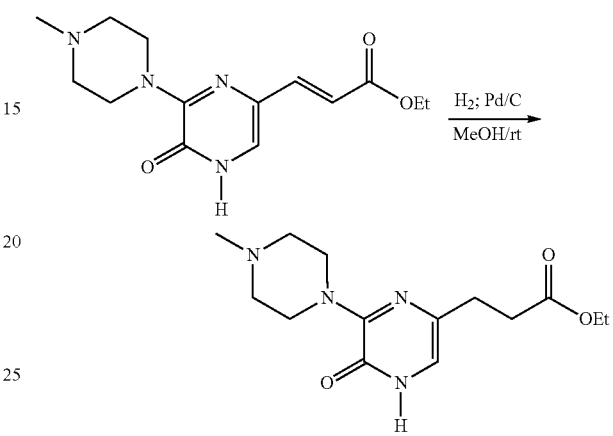

Ethyl 3-[6-(4-methylpiperazin-1-yl)-5(4H)-oxopyrazin-2-yl]propanoate The procedure for preparing Intermediate 1-5 was used with the product from the previous step (5.6 g, 19.18 mmol, 1.00 equiv) to afford 5.5 g (98%) of the title compound as a yellow oil.

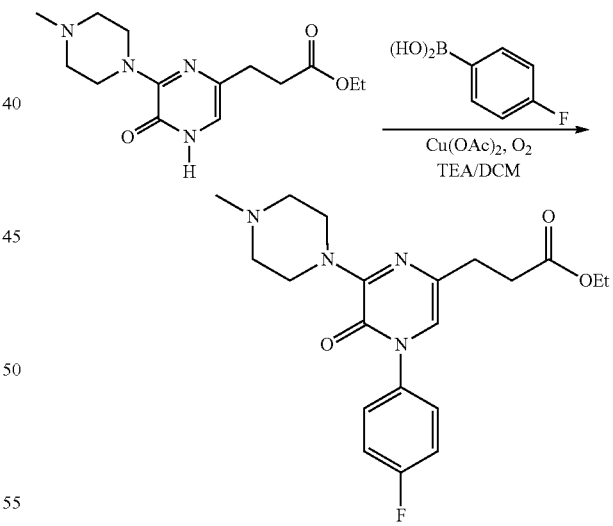

Ethyl 3-(4-(4-fluorophenyl)-6-(4-methylpiperazin-1-yl)-5 (4H)-oxopyrazin-2-yl)propanoate The procedure for preparing Intermediate 8-9 was used with the product from the previous step (1.5 g, 5.10 mmol, 1 equiv) and 4-fluorophenylboronic acid (1.07 g, 7.65 mmol, 1.5 equiv). The crude product was purified with silica gel chromatography using EtOAc/petroleum ether (1:1) to afford 1 g (51%) of the title compound as a yellow oil.

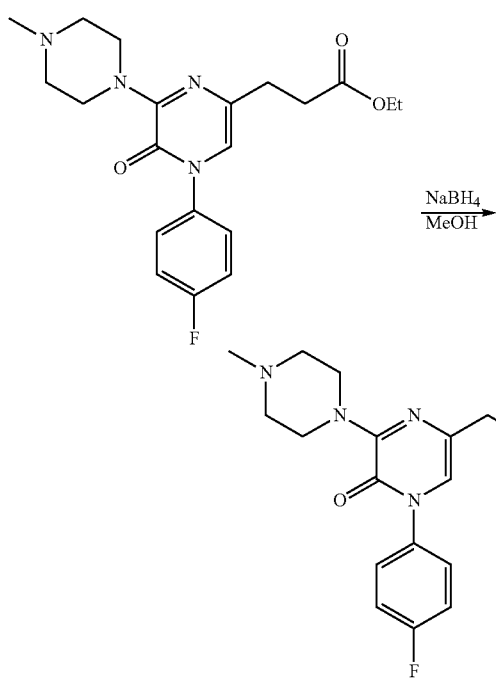

3-(4-(4-(4-Fluorophenyl)-6-(4-methylpiperazin-1-yl)-5 (4H)-oxopyrazin-2-yl)propan-1-ol The procedure for preparing Intermediate 1-6 was used with the product from the previous step (1 g, 2.58 mmol, 1 equiv) to afford 600 mg (67%) of the title compound as a yellow solid.

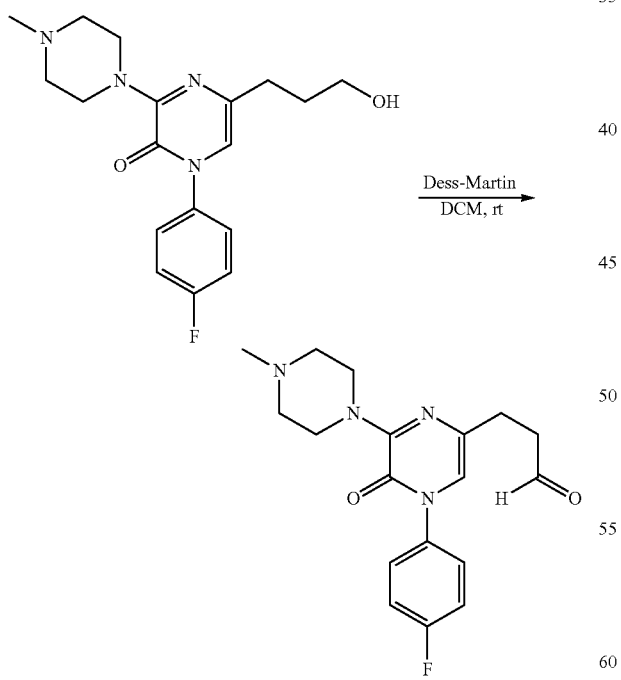

3-(4-(4-Fluorophenyl)-6-(4-methylpiperazin-1-yl)-5 (4H)-oxopyrazin-2-yl)propanal The procedure for preparing Intermediate 1-7 was used with the product from the previous step (600 mg, 1.73 mmol, 1.00 equiv) to afford 300 mg (50%) of the title compound as a yellow solid.

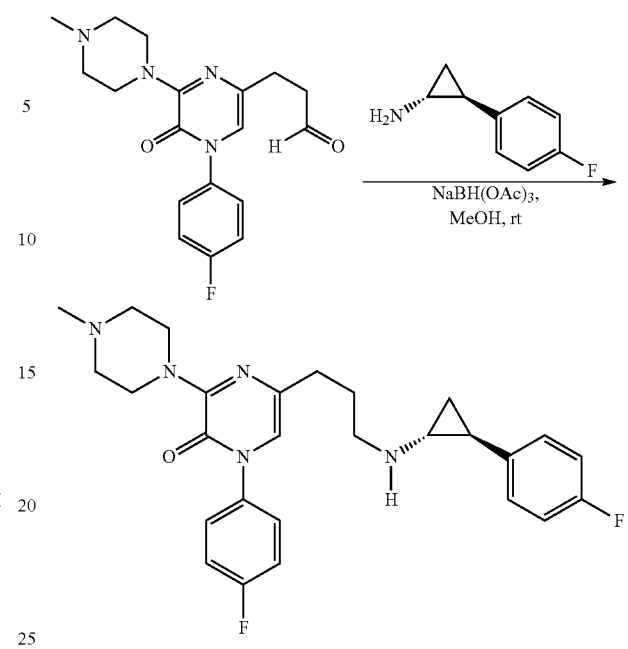

1-[4-Fluorophenyl]-5-[3-([(1R,2S)-2-(4-fluorophenyl)cyclopropyl]amino)propyl]-3-[4-methylpiperazin-1-yl]pyrazin-2(1H)-one The reductive amination step for preparing Example 1 from Intermediate 1-7 was used with the product from the previous step (300 mg, 0.87 mmol). The crude product was purified using chromatographic Procedure B (48% to 70% CH$_3$CN over 9 min), to afford 34 mg (8%) of the title compound as a yellow oil.

LC-MS: (ES, m/z): 480 [M+H]$^+$. $^1$H NMR (400 MHz, MeOD-d$_4$) δ ppm: 7.47-7.44 (s, 2H), 7.31-7.27 (t, J=17.2 Hz, 2H), 7.23-7.20 (m, 2H), 7.08-7.04 (t, J=17.6 Hz, 2H), 6.98 (s, 1H), 4.93-4.88 (m, 2H), 3.59-3.54 (s, 2H), 3.33-3.24 (m, 6H), 3.00-2.96 (m, 4H), 2.61-2.57 (m, 2H), 2.53-2.48 (m, 1H), 2.15-2.07 (m, 2H), 1.52-1.49 (m, 1H), 1.41-1.37 (m, 1H).

Example 20

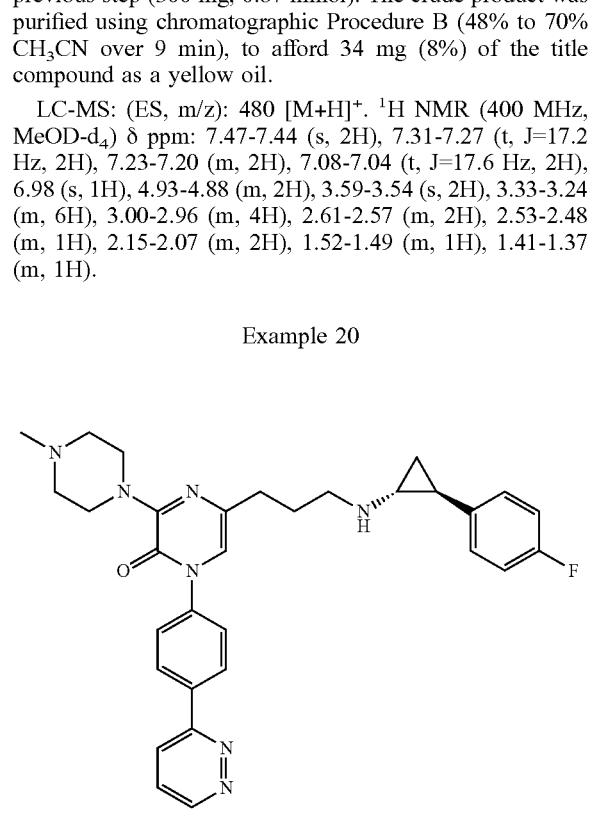

5-[3-([(1R,2S)-2-(4-fluorophenyl)cyclopropyl]
amino)propyl]-3-[4-methylpiperazin-1-yl]-1-[4-
(pyridazin-3-yl)phenyl]pyrazin-2(1H)-one preparing Intermediate 13-1 was used with the product from the previous step (600 mg, 2.37 mmol, 1 equiv) and 3-(4-bromophenyl)pyridazine (836 mg, 3.56 mmol, 1.5 equiv), using an overnight reaction time at 90° C. The crude product was purified with silica gel chromatography using $CH_2Cl_2$/MeOH (10:1) to afford 600 mg (61.2%) of the title compound as a yellow solid.

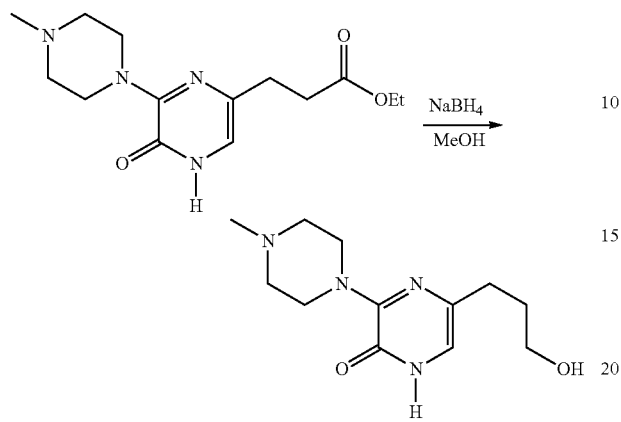

5-(3-Hydroxypropyl)-3-(4-methylpiperazin-1-yl)pyrazin-2(1H)-one The procedure for preparing Intermediate 1-6 was used with Intermediate 17-3 (1.0 g, 3.34 mmol, 1 equiv) with 1 hr reaction time, to afford 600 mg (69.96%) of the title compound as a yellow oil.

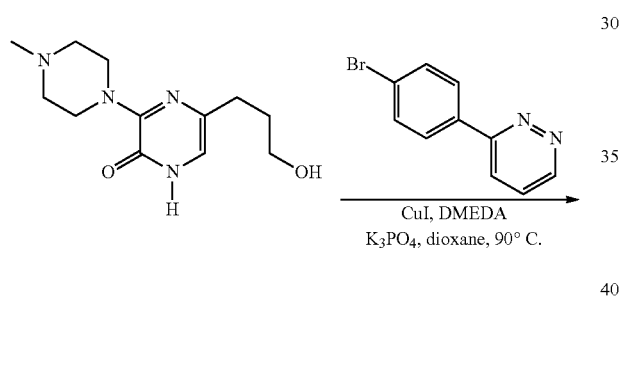

3-(4-(4-(Pyridazin-3-yl)phenyl)-6-(4-methylpiperazin-1-yl)-5(4H)-oxopyrazin-2-yl)propanal The procedure for preparing Intermediate 1-7 was used with the product from the previous step (300 mg, 0.74 mmol, 1.00 equiv) to afford 150 mg (50.3%) of the title compound as a yellow solid.

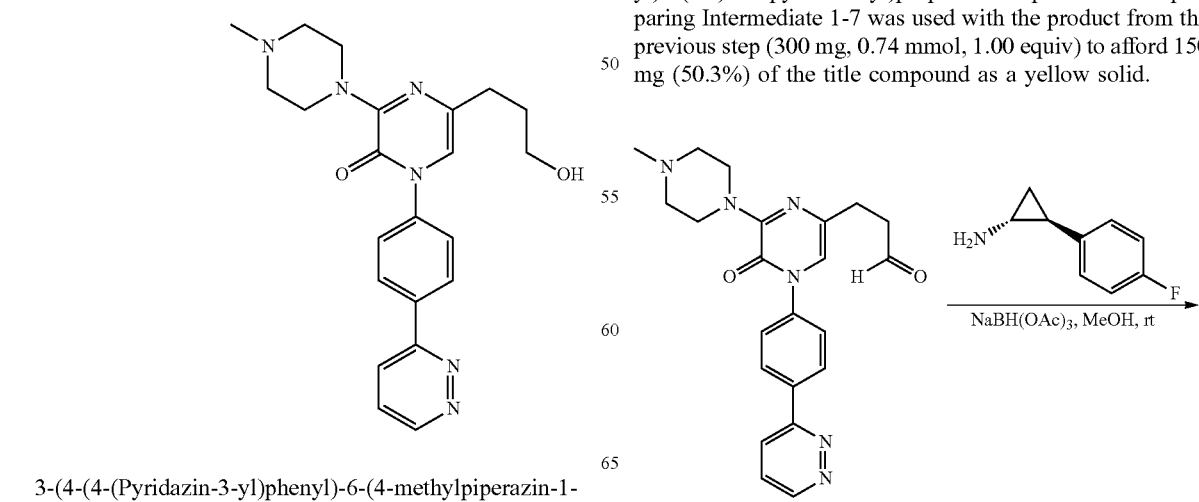

3-(4-(4-(Pyridazin-3-yl)phenyl)-6-(4-methylpiperazin-1-yl)-5(4H)-oxopyrazin-2-yl)propan-1-ol The procedure for

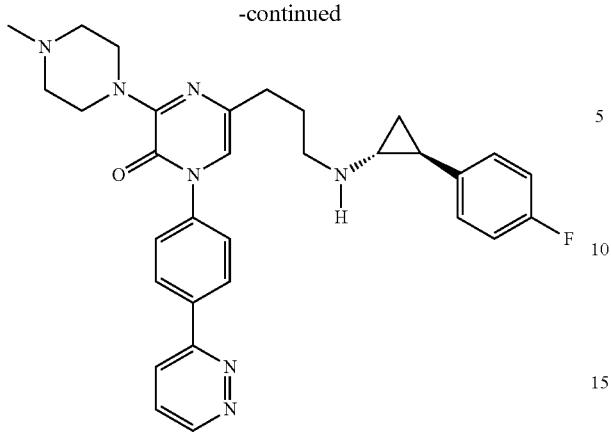

5-[3-([(1R,2S)-2-(4-fluorophenyl)cyclopropyl]amino)propyl]-3-[4-methyl-piperazin-1-yl]-1-[4-(pyridazin-3-yl)phenyl]pyrazin-2(1H)-one The reductive amination step for preparing Example 1 from Intermediate 1-7 was used with the product from the previous step (150 mg, 0.37 mmol). The crude product (5 mL) was purified using chromatographic Procedure E (31% to 68% $CH_3CN$ in 8 min, Rt: 7.13 min), to afford 29.7 mg (14.85%) of the title compound as a white solid.

LC-MS: (ES, m/z): 540 [M+H]$^+$. $^1$H NMR (300 MHz, MeOD-d$_4$) δ ppm: 9.16 (dd, J=4.9, 1.5 Hz, 1H), 8.28-8.18 (m, 3H), 7.85-7.77 (m, 1H), 7.62-7.54 (m, 2H), 7.09-6.98 (m, 2H), 6.96-6.84 (m, 3H), 3.85-3.73 (m, 4H), 2.76 (t, J=7.4 Hz, 2H), 2.57-2.41 (m, 6H), 2.34-2.24 (m, 4H), 1.95-1.82 (m, 3H), 1.10-0.89 (m, 2H).

Example 21

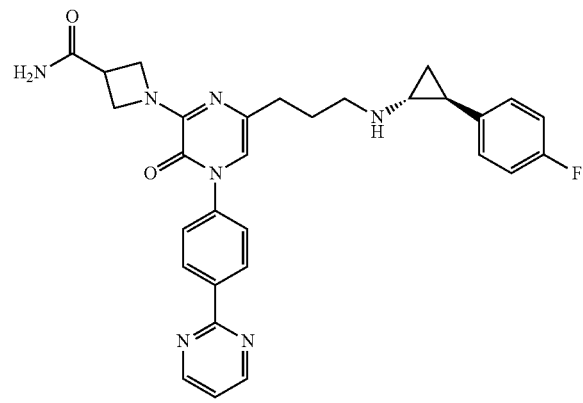 [SMILES: NC(=O)C1CN(c2nc(CCCN[C@@H]3C[C@H]3c3ccc(F)cc3)cn(-c3ccc(-c4ncccn4)cc3)c2=O)C1]

1-[6-(3-[([1R,2S]-2-[4-fluorophenyl]cyclopropyl)amino]propyl)-3-oxo-4-(4-[pyrimidin-2-yl]phenyl)-3,4-dihydropyrazin-2-yl]azetidine-3-carboxamide

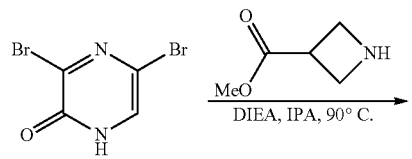

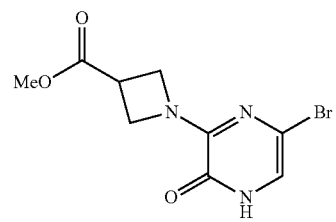

Methyl 1-(6-bromo-3(4H)-oxopyrazin-2-yl)azetidine-3-carboxylate The procedure for preparing Intermediate 2-1 was used with 3,5-dibromo-1,2-dihydropyrazin-2-one (10 g, 39.39 mmol, 1.00 equiv) and methyl azetidine-3-carboxylate (6.8 g, 59.36 mmol, 1.50 equiv), using 2 hr reaction time at 90° C., affording 8 g (67%) of the title compound as a light yellow solid.

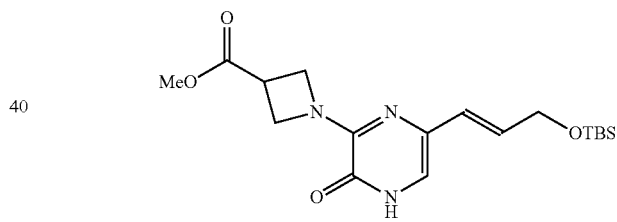

(E)-Methyl 1-(6-(3-(tert-butyldimethylsilyloxy)prop-1-enyl)-3(4H)-oxopyrazin-2-yl)azetidine-3-carboxylate The procedure for preparing Intermediate 3-3 was used with the product from the previous step (8 g, 31.63 mmol), using a 2 hr reaction time at 90° C. The crude product was purified with silica gel chromatography using EtOAc/petroleum ether (1:20) to afford 3 g (28.4%) of the title compound as a light yellow oil.

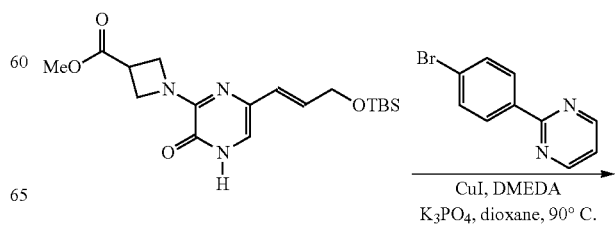

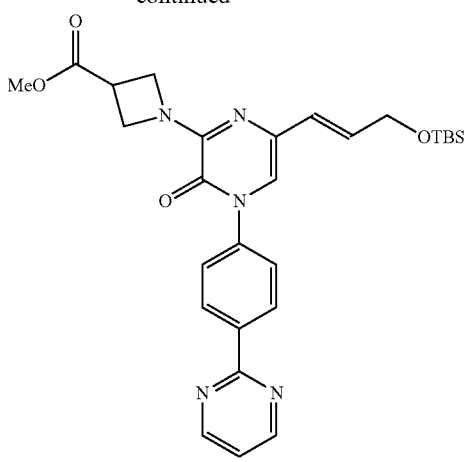

(E)-Methyl 1-(6-(3-(tert-butyldimethylsilyloxy)prop-1-enyl)-3(4H)-oxo-4-(4-(pyrimidin-2-yl)phenyl)-pyrazin-2-yl)azetidine-3-carboxylate The procedure for preparing Intermediate 13-1 was used with the product from the previous step (3 g, 9.81 mmol, 1.00 equiv), and 2-(4-bromophenyl)pyrimidine (3.1 g, 14.89 mmol, 1.50 equiv). The crude product was purified with silica gel chromatography using EtOAc/petroleum ether to afford 2.3 g (53%) of the title compound as a yellow oil.

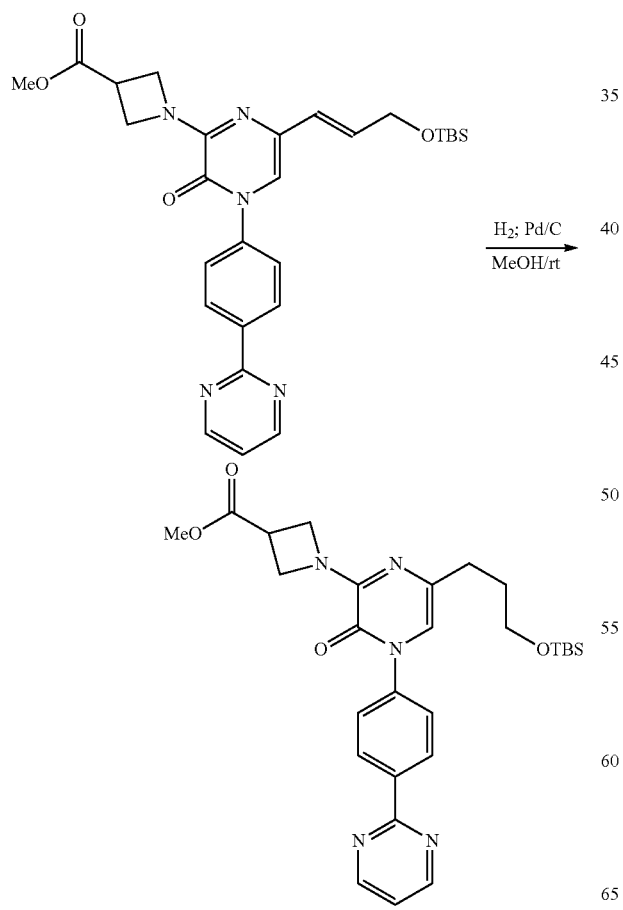

Methyl 1-(6-(3-(tert-butyldimethylsilyloxy)propyl)-3(4H)-oxo-4-(4-(pyrimidin-2-yl)phenyl)-pyrazin-2-yl)azetidine-3-carboxylate The procedure for preparing Intermediate 1-5 was used with the product from the previous step (2.3 g, 3.38 mmol, 1.00 equiv) to afford 2.1 g (89%) of the title compound as a light yellow oil.

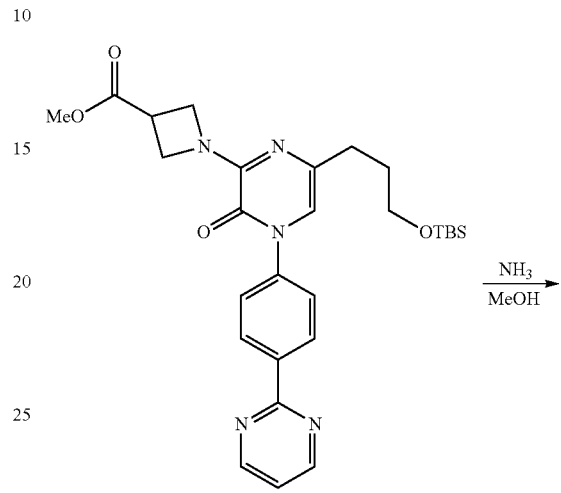

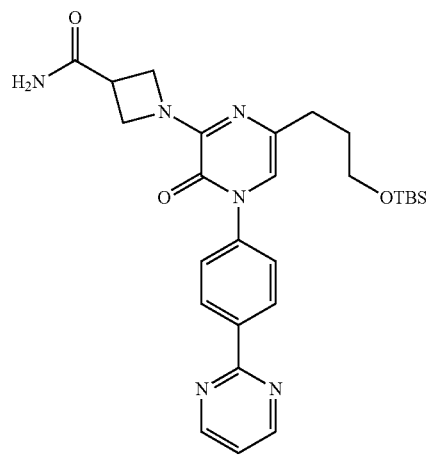

1-(6-(3-(tert-butyldimethylsilyloxy)propyl)-3(4H)-oxo-4-(4-(pyrimidin-2-yl)phenyl)-pyrazin-2-yl)azetidine-3-carboxamide A solution of the product from the previous step (2.1 g, 3.02 mmol, 1.00 equiv) in MeOH (10 mL) was combined with a solution of NH$_3$ (4 g, 5.00 equiv) in MeOH (5 mL). The resulting solution was stirred for 16 h at 90° C., then cooled and concentrated under vacuum, to afford 1.5 g (70%) of the title compound as a light yellow oil.

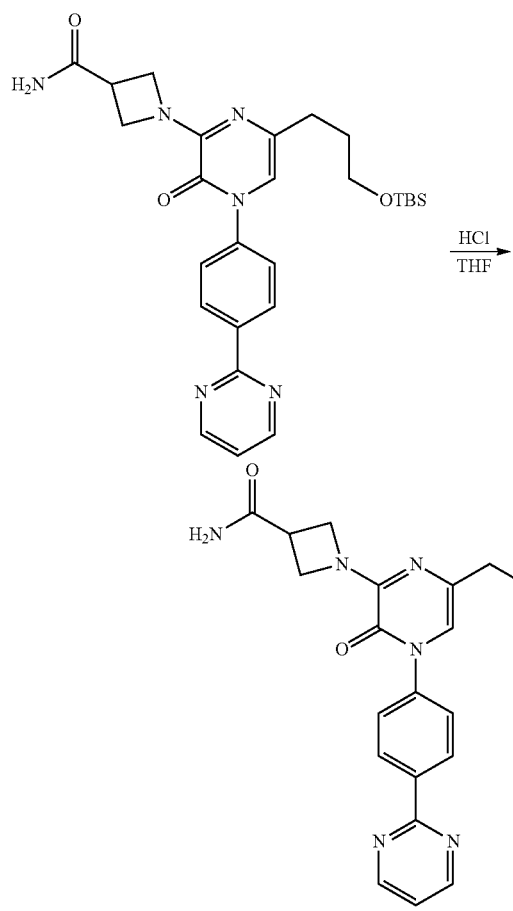

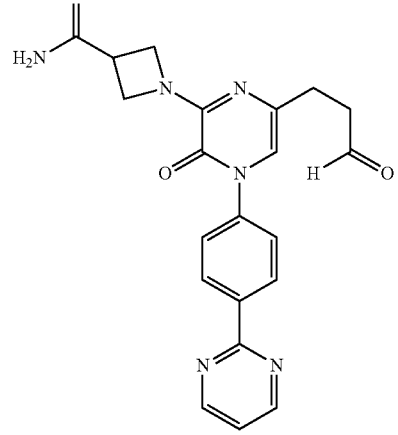

1-(3(4H)-oxo-6-(3-oxopropyl)-4-(4-(pyrimidin-2-yl)phenyl)-pyrazin-2-yl)-azetidine-3-carboxamide The procedure for preparing Intermediate 1-7 was used with the product from the previous step (760 mg, 1.15 mmol), affording 360 mg (47%) of the title compound as a light yellow solid.

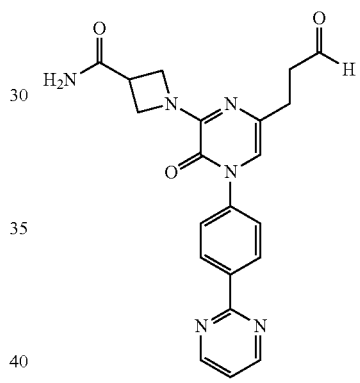

1-(6-(3-Hydroxypropyl)-3(4H)-oxo-4-(4-(pyrimidin-2-yl)phenyl)-pyrazin-2-yl)azetidine-3-carboxamide A solution of the product from the previous step (1.5 g, 2.00 mmol, 1.00 equiv) in THF (20 mL) was combined with a solution of HCl (3 mL, 2.00 equiv) in $H_2O$ (1 mL). The resulting solution was stirred for 1 h at 25° C. The pH value of the solution was adjusted to 7 with 1 M $Na_2CO_3$, and the residue was then purified with silica gel chromatography using $H_2O/CH_3CN$ (5:1) to afford 760 mg (64%) of the title compound as a light yellow solid.

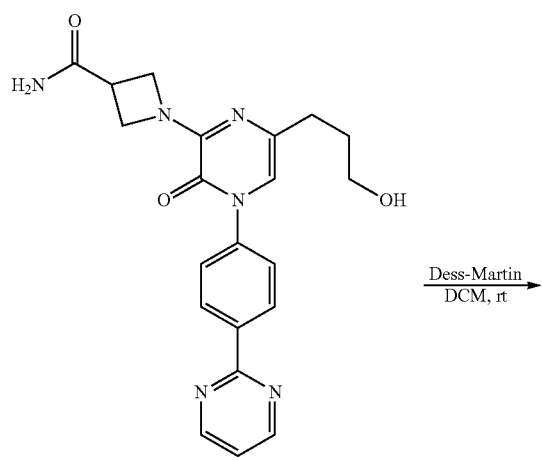

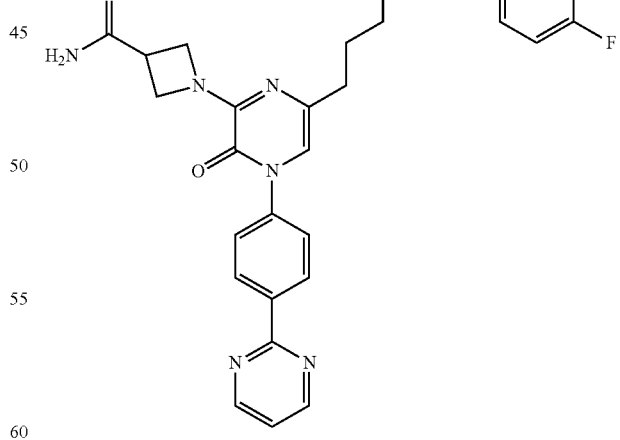

1-[6-(3-[([1R,2S]-2-[4-fluorophenyl]cyclopropyl)amino]propyl)-3-oxo-4-(4-[pyrimidin-2-yl]phenyl)-3,4-dihydropyrazin-2-yl]azetidine-3-carboxamide The procedure for preparing Intermediate 4-7 was used with the product from the previous step (126 mg, 0.83 mmol, 1.20 equiv). The crude product (3 mL) was purified using chromatographic Procedure C (38.0% to 50.0% CH₃CN in 8 min), to afford 47.7 mg (10%) of the title compound as a light yellow solid.

LC-MS: (ES, m/z): 540 [M+H]⁺. ¹H NMR (300 MHz, MeOD-d₄) δ ppm: 8.95-8.61 (m, 2H), 8.65-8.45 (m, 2H), 7.62-7.48 (m, 2H), 7.48-7.31 (m, 1H), 7.11-6.89 (m, 4H), 6.82 (s, 1H), 4.66-4.19 (s, 4H), 3.59-3.40 (m, 1H), 2.85-2.65 (m, 2H), 2.62-2.36 (m, 2H), 2.36-2.17 (m, 1H), 2.00-1.61 (m, 3H), 1.12-0.89 (m, 2H).

Example 22

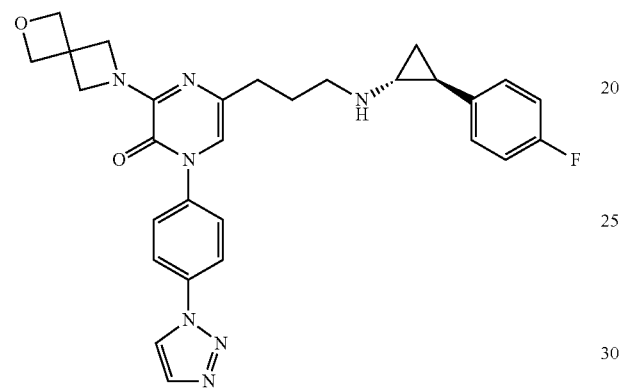

1-[4-(1H-1,2,3-triazol-1-yl)phenyl]-5-[3-([(1R,2S)-2-(4-fluorophenyl)-cyclopropyl)amino]propyl)-3-(2-oxa-6-azaspiro[3.3]heptan-6-yl)pyrazin-2(1H)-one

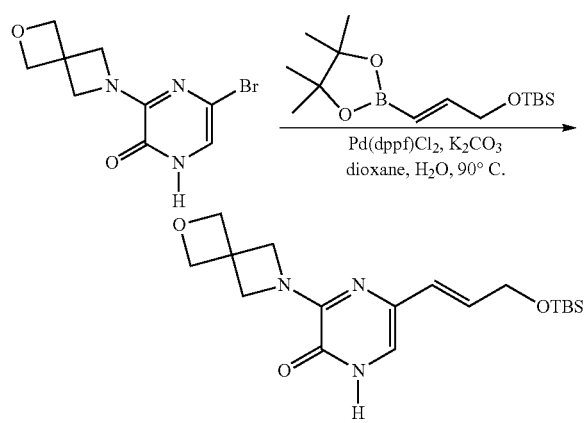

5-(E)-[3-[(tert-Butyldimethylsilyl)oxy]propyl]-3-[2-oxa-6-azaspiro[3.3]heptan-6-yl]-pyrazin-2(1H)one (Intermediate 22-1) The procedure for preparing Intermediate 3-3 was used with Intermediate 7-1 (4 g, 14.70 mmol). The crude product was purified with silica gel chromatography using EtOAc/petroleum ether (1:15) to afford 1 g (19%) of the title compound as a light yellow oil.

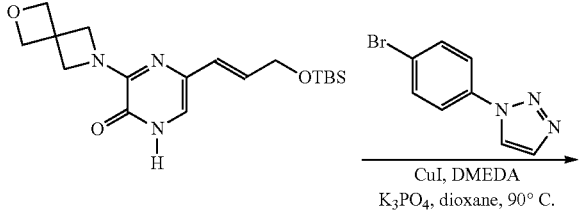

5-(E)[3-[(tert-Butyldimethylsilyl)oxy]prop-1-en-1-yl]-3-[2-oxa-6-azaspiro[3.3]-heptan-6-yl]-1-[4-(1H-1,2,3-triazol-1-yl)phenyl]-pyrazin-2(1H)one (Intermediate 22-2) The procedure for preparing Intermediate 13-1 was used with Intermediate 22-1 (1 g, 2.75 mmol, 1.00 equiv) and 1-(4-bromophenyl)-1H-1,2,3-triazole (950 mg, 4.24 mmol, 1.50 equiv), using 16 hr of reaction time at 90° C. The crude product was purified with silica gel chromatography using EtOAc/petroleum ether (1:20) to afford 1 g (72%) of the title compound as a light yellow oil.

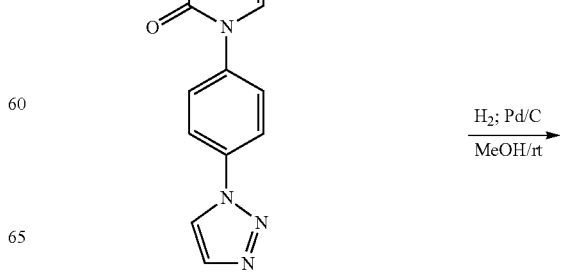

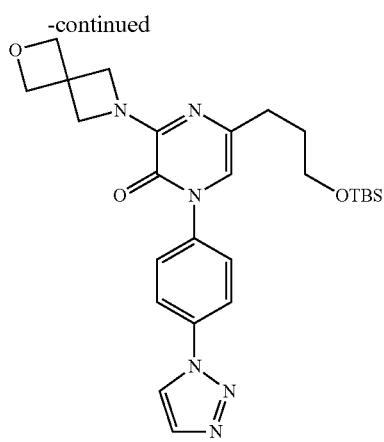

5-[3-[(tert-Butyldimethylsilyl)oxy]propyl]-3-[2-oxa-6-azaspiro[3.3]heptan-6-yl]-1-[4-(1H-1,2,3-triazol-1-yl)phenyl]-pyrazin-2(1H)-one (Intermediate 22-3) The procedure for preparing Intermediate 1-5 was used with Intermediate 22-2 (1 g, 1.97 mmol, 1.00 equiv) to afford 0.9 g (90%) of the title compound as a light yellow oil.

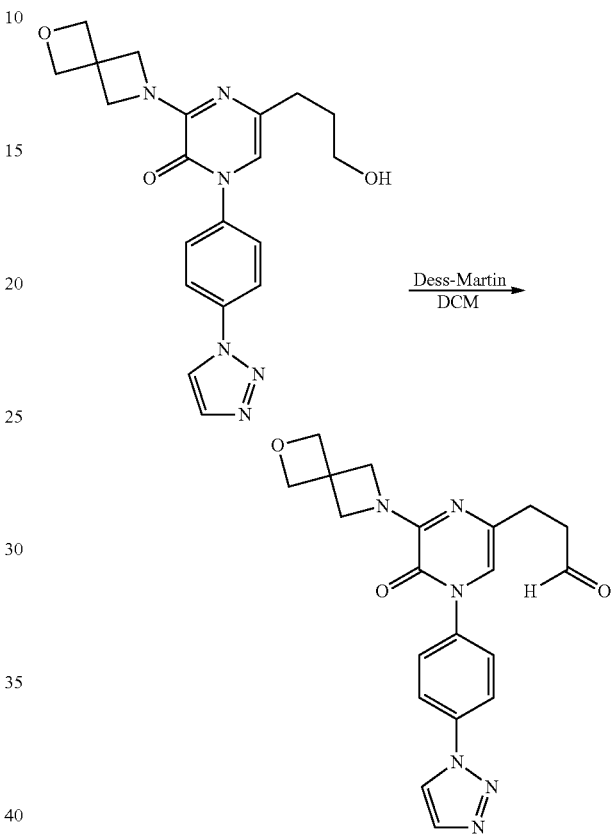

3-(6-[2-Oxa-6-azaspiro[3.3]heptan-6-yl]-5(4H)-oxo-4-[4-(1H-1,2,3-triazol-1-yl)phenyl]-pyrazin-2-yl)propan-1-ol (Intermediate 22-4) A solution of Intermediate 22-3 (900 mg, 1.77 mmol, 1.00 equiv) and Bu$_4$NF (700 mg, 2.68 mmol, 1.50 equiv) in THF (20 mL). was stirred for 1 h at 25° C., then purified with silica gel chromatography using with H$_2$O/MeCN (5:1), to afford 0.52 g (75%) of the title compound as a light yellow solid.

3-(6-[2-Oxa-6-azaspiro[3.3]heptan-6-yl]-5(4H)-oxo-4-[4-(1H-1,2,3-triazol-1-yl)phenyl]-pyrazin-2-yl)propanal
The procedure for preparing Intermediate 1-7 was used with the product from the previous step (520 mg, 1.32 mmol, 1.00 equiv) to afford 300 mg (58%) of the title compound as a light yellow solid.

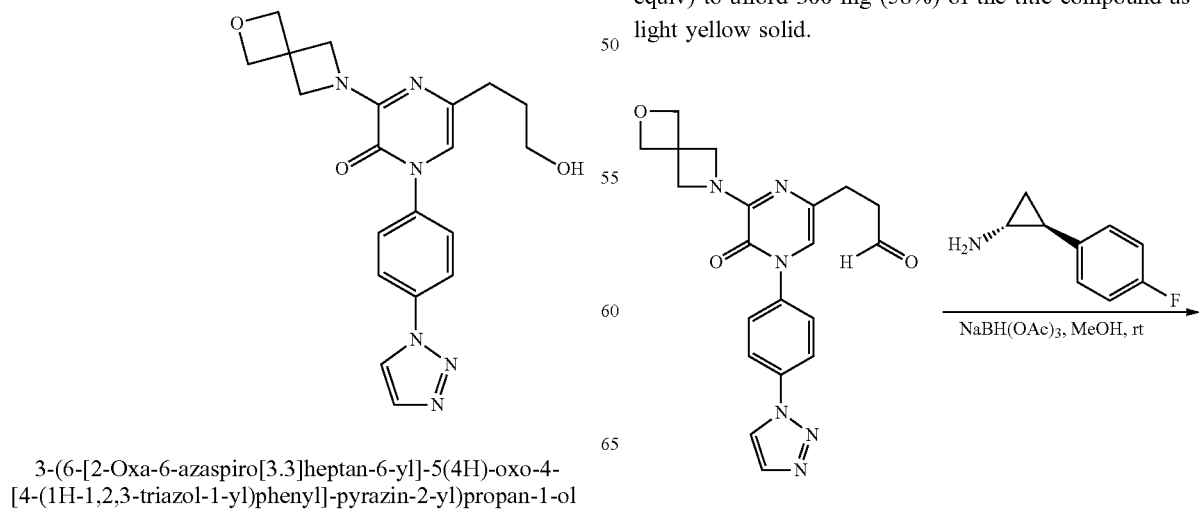

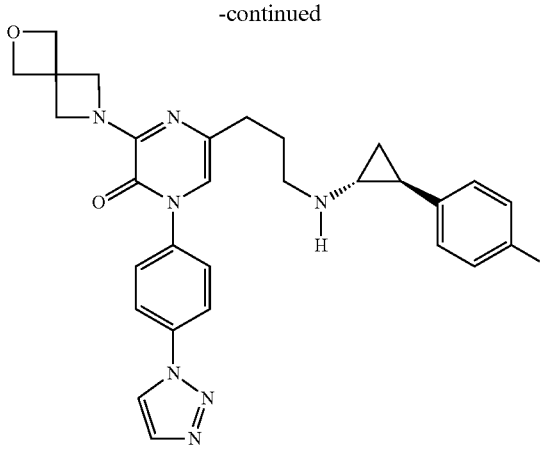

1-[4-(1H-1,2,3-triazol-1-yl)phenyl]-5-[3-([(1R,2S)-2-(4-fluorophenyl)cyclo-propyl)amino]propyl)-3-(2-oxa-6-azaspiro[3.3]heptan-6-yl)pyrazin-2(1H)-one The procedure for preparing Intermediate 4-7 was used with the product from the previous step (300 mg, 0.76 mmol). The crude product (2 mL) was purified using chromatographic Procedure C (38.0% to 50.0% $CH_3CN$ in 8 min), to afford 11.8 mg (3%) of the title compound as a white solid.

LC-MS: (ES, m/z): 528 [M+H]$^+$. $^1$H NMR (300 MHz, MeOD-d$_4$) δ ppm: 8.70-8.51 (m, 1H), 8.11-7.99 (m, 2H), 7.99-7.80 (m, 1H), 7.79-7.47 (m, 2H), 7.13-6.80 (m, 4H), 6.64 (s, 1H), 4.82 (s, 4H), 4.43 (s, 4H), 2.88-2.58 (m, 2H), 2.52-2.35 (m, 2H), 2.35-2.20 (s, 1H), 2.09-1.71 (m, 3H), 1.12-0.82 (m, 2H).

Example 23

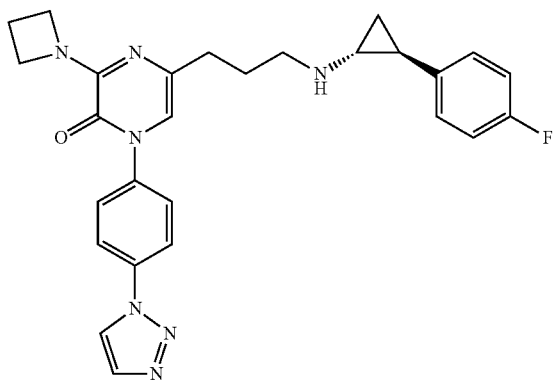 [SMILES: O=c1c(N2CCC2)nc(CCCN[C@@H]2C[C@H]2c2ccc(F)cc2)cn1-c1ccc(-n2ccnn2)cc1]

1-[4-(1H-1,2,3-triazol-1-yl)phenyl]-3-[azetidin-1-yl]-5-[3-([(1R,2S)-2-(4-fluorophenyl)cyclopropyl]amino)propyl]pyrazin-2(1H)-one

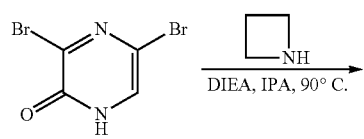

5-Bromo-3-(azetidin-1-yl)-pyrazin-2(1H)-one The procedure for preparing Intermediate 2-1 was used with 3,5-dibromo-1,2-dihydropyrazin-2-one (5.0 g, 19.76 mmol, 1 equiv) and azetidine (1.46 g, 25.61 mmol, 1.3 equiv), to afford 4.0 g (88%) of the title compound as a light yellow solid.

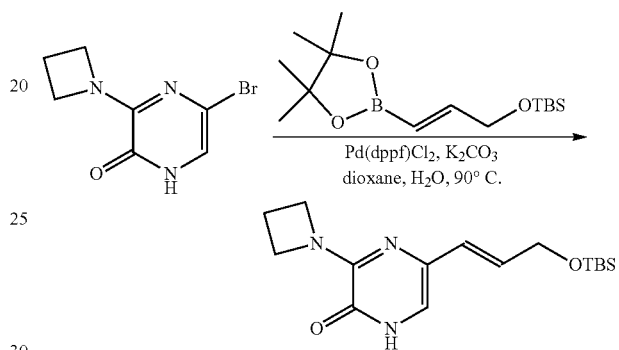

5-(E)-[3-[(tert-Butyldimethylsilyl)oxy]propyl]-3-(azetidin-1-yl)-pyrazin-2(1H)one The procedure for preparing Intermediate 3-3 was used with the product from the previous step (4 g, 17.39 mmol), with 16 hr of reaction time at 90° C. The crude product was purified with silica gel chromatography using EtOAc/petroleum ether (1:4) to afford 1.4 g (25.04%) of the title compound as a brown oil.

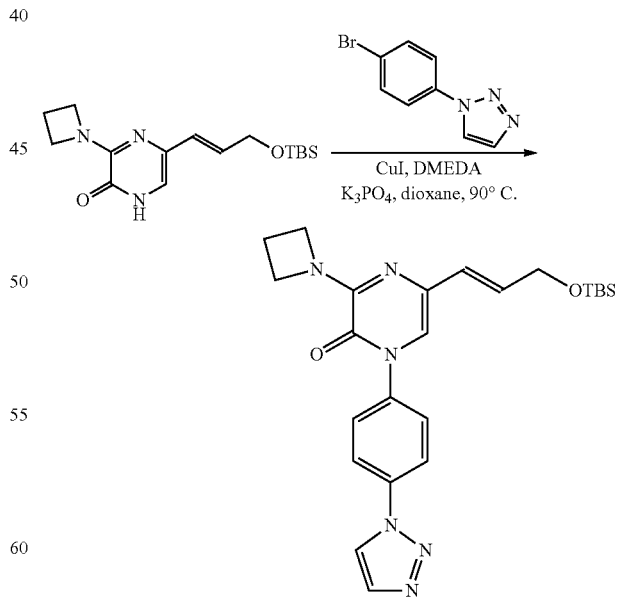

5-(E)[3-[(tert-Butyldimethylsilyl)oxy]prop-1-en-1-yl]-3-(azetidin-1-yl)-1-[4-(1H-1,2,3-triazol-1-yl)phenyl]-pyrazin-2(1H)one The procedure for preparing Intermediate 13-1 was used with the product from the previous step (1.4 g, 4.35 mmol, 1 equiv) and 1-(4-bromophenyl)-1H-1,2,3-triazole (1.46 g, 6.53 mmol, 1.5 equiv), using 16 hr of reaction time at 90° C. The crude product was purified with silica gel chromatography using EtOAc/petroleum ether to afford 1.1 g (54.37%) of the title compound as a yellow solid.

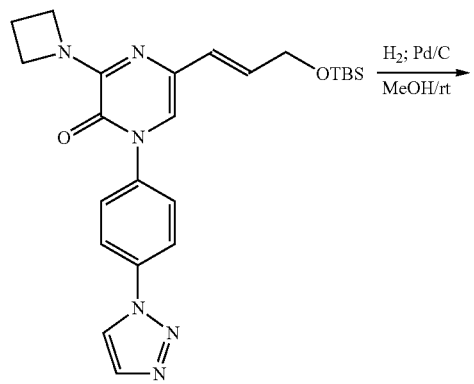

5-[3-[(tert-Butyldimethylsilyl)oxy]propyl]-3-(azetidin-1-yl)-2(1H)-oxo-1-[4-(1H-1,2,3-triazol-1-yl)phenyl]-pyrazine The procedure for preparing Intermediate 1-5 was used with the product from the previous step (1.0 g, 2.15 mmol, 1 equiv) to afford 1.0 g (99.57%) of the title compound as a yellow oil.

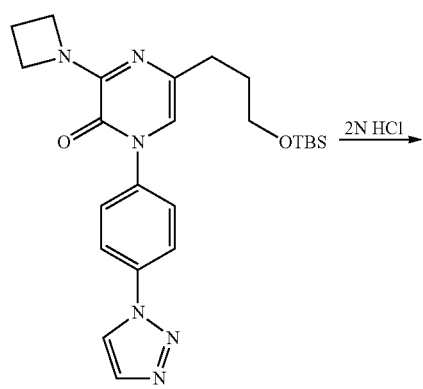

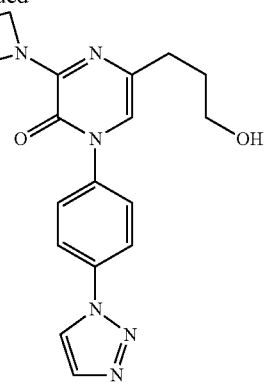

3-(6-(azetidin-1-yl)-5(4H)-oxo-4-[4-(1H-1,2,3-triazol-1-yl)phenyl]-pyrazin-2-yl)propan-1-ol A solution of the product from the previous step (900 mg, 1.93 mmol, 1 equiv) and 2 N aq HCl (3 mL) in THF (30 mL) was stirred for 15 min at rt. The pH value of the solution was adjusted to 8 with Na$_2$CO$_3$. The resulting solution was extracted with 3×30 mL of CH$_2$Cl$_2$, and the combined organic layers were purified with silica gel chromatography using CH$_2$Cl$_2$/MeOH (8:1) to afford 400 mg (58.84%) of the title compound as a light yellow solid.

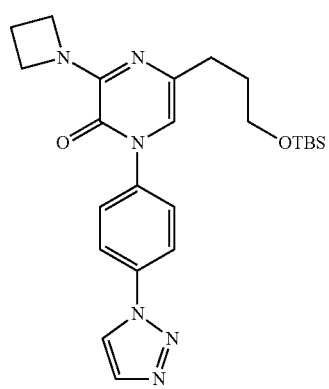

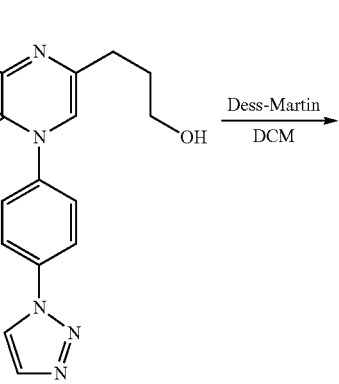

3-(6-(azetidin-1-yl)-5(4H)-oxo-4-[4-(1H-1,2,3-triazol-1-yl)phenyl]-pyrazin-2-yl)propanal The procedure for preparing Intermediate 1-7 was used with the product from the previous step (380 mg, 1.08 mmol, 1.00 equiv) to afford 200 mg (52.9%) of the title compound as a yellow solid.

147 148

5-[3-([(1R,2S)-2-(4-fluorophenyl)cyclopropyl]
amino)propyl]-1-[pyrimidin-5-yl]-3-[2-oxa-6-
azaspiro[3.3]heptan-6-yl]pyrazin-2(1H)-one

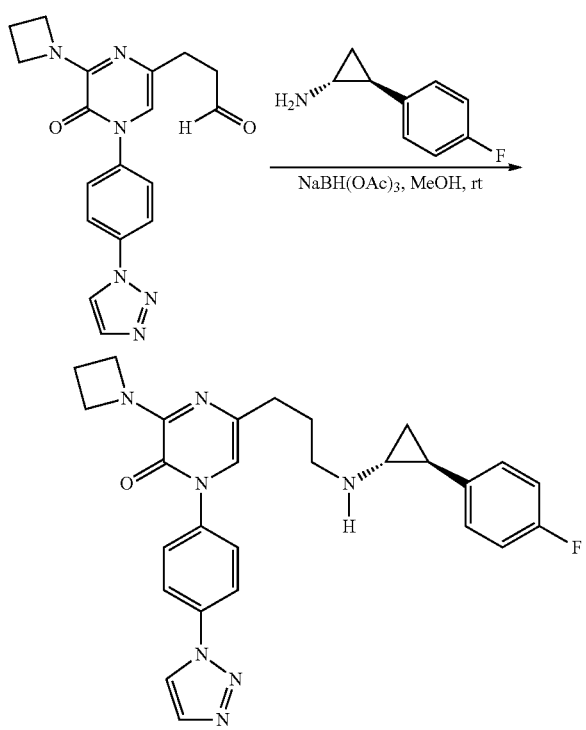

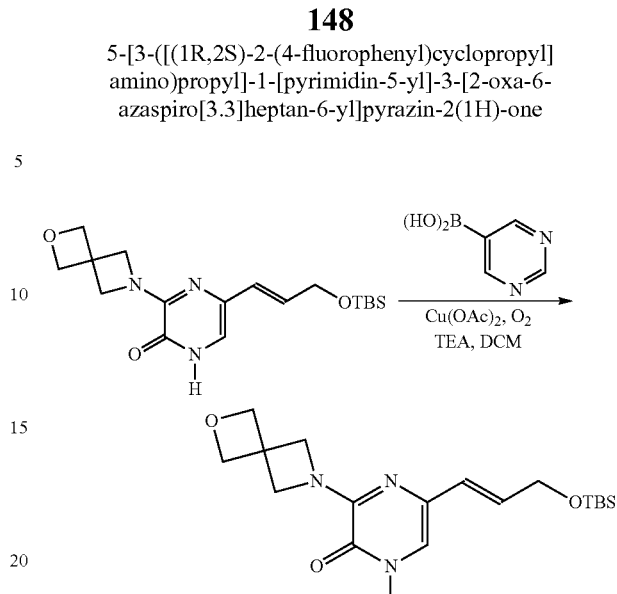

1-[4-(1H-1,2,3-triazol-1-yl)phenyl]-3-[azetidin-1-yl]-5-[3-([(1R,2S)-2-(4-fluorophenyl)cyclopropyl]amino)propyl]pyrazin-2(1H)-one The reductive amination step for preparing Example 1 from Intermediate 1-7 was used with the product from the previous step (200 mg, 0.57 mmol). The crude product was purified using chromatographic Procedure E (30.0% to 65.0% CH$_3$CN in 8.1 min), to afford 7.9 mg (2.85%) of the title compound as a white solid.

LC-MS: (ES, m/z): 486 [M+H]$^+$. $^1$H NMR (400 MHz, MeOD-d$_4$) δ ppm: 8.62 (s, 1H), 8.03 (d, J=8.8 Hz, 2H), 7.93 (s, 1H), 7.64 (d, J=8.8 Hz, 2H), 7.15-7.10 (m, 2H), 6.99 (t, J=8.8 Hz, 2H), 6.65 (s, 1H), 4.42-4.27 (m, 4H), 3.04-2.96 (m, 2H), 2.65-2.56 (m, 1H), 2.47 (t, J=6.8 Hz, 2H), 2.41-2.30 (m, 2H), 2.20-2.10 (m, 1H), 2.00-1.92 (m, 2H), 1.20-1.10 (m, 2H).

5-(E)[3-[(tert-Butyldimethylsilyl)oxy]prop-1-en-1-yl]-3-[2-oxa-6-azaspiro[3.3]-heptan-6-yl]-1-(pyrimidin-5-yl)-pyrazin-2(1H)one The procedure for preparing Intermediate 8-9 was used with Intermediate 22-1 (2 g, 5.51 mmol, 1 equiv) and (pyrimidin-5-yl)boronic acid (1.1 g, 8.26 mmol, 1.5 equiv). The crude product was purified using silica gel chromatography using CH$_2$Cl$_2$/MeOH (1:10) to afford 1 g (41.1%) of the title compound as a solid.

Example 24

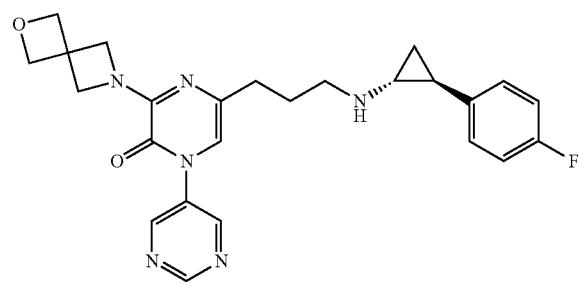 [SMILES: O=c1c(N2CC3(COC3)C2)nc(CCCN[C@@H]2C[C@H]2c2ccc(F)cc2)cn1-c1cncnc1]

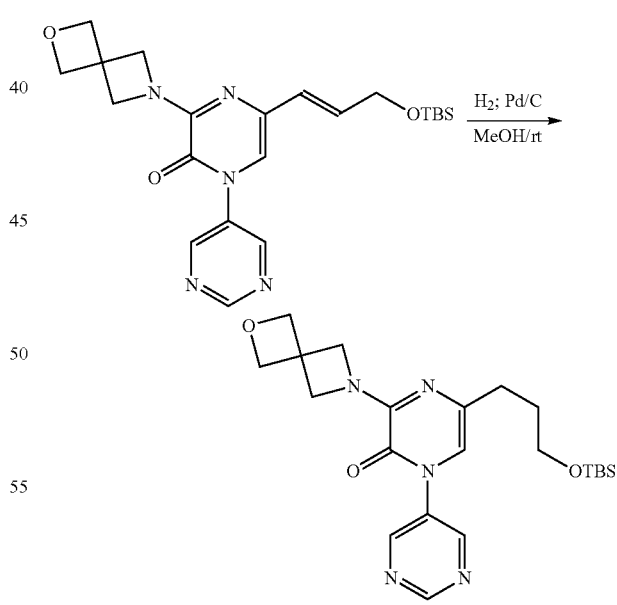

5-[3-[(ter-Butyldimethylsilyl)oxy]propyl]-3-[2-oxa-6-azaspiro[3.3]heptan-6-yl]-1-(pyrimidin-5-yl)-pyrazin-2(1H)-one The procedure for preparing Intermediate 1-5 was used with the product from the previous step (g, 2.27 mmol, 1 equiv) to afford 900 mg (89.6%) of the title compound as a yellow solid.

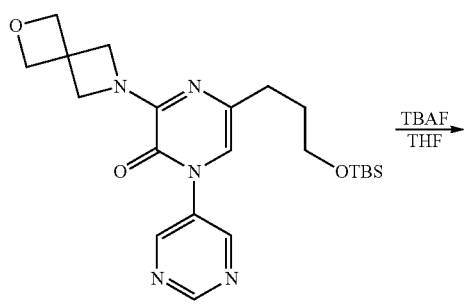

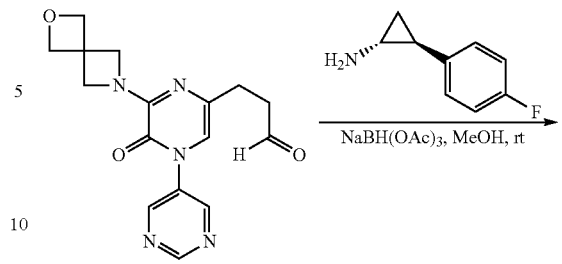

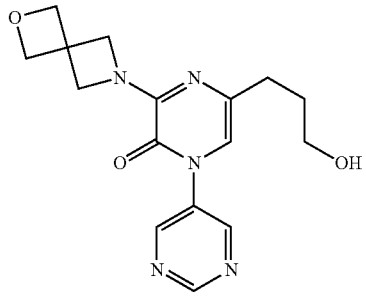

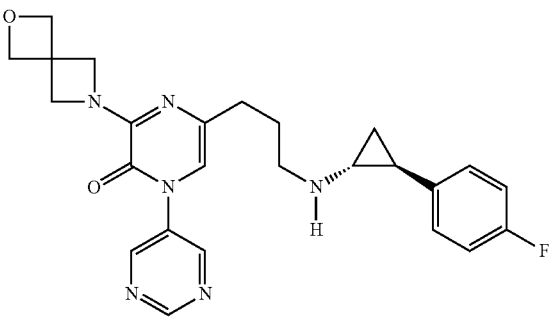

3-(6-[2-Oxa-6-azaspiro[3.3]heptan-6-yl]-5(4H)-oxo-4-(pyrimidin-5-yl)-pyrazin-2-yl)propan-1-ol The procedure for preparing Intermediate 22-4 was used with the product from the previous step (900 mg, 2.03 mmol). The crude product (10 mL) was purified by Flash-Prep-HPLC (Intel Flash-1: MeCN/$H_2O$=1:10 increasing to MeCN/$H_2O$=5:10 within 40 min; Detector, 220 nm), affording 400 mg (59.86%) of the title compound as a yellow solid.

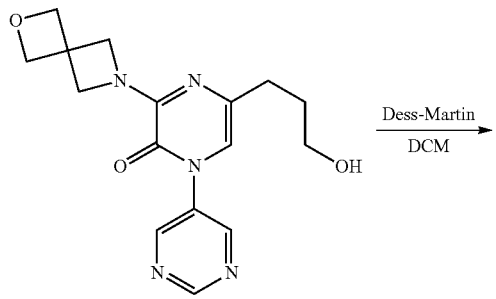

3-(6-[2-Oxa-6-azaspiro[33]heptan-6-yl]-5(4H)-oxo-4-(pyrimidin-5-yl)-pyrazin-2-yl)propanal The procedure for preparing Intermediate 1-7 was used with the product from the previous step (400 mg, 1.21 mmol, 1 equiv) to afford 200 mg (50.31%) of the title compound as a light yellow solid.

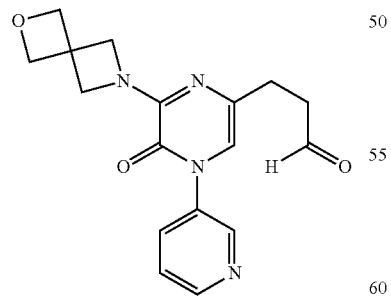

5-[3-([(1R,2S)-2-(4-fluorophenyl)cyclopropyl]amino)propyl]-1-[pyrimidin-5-yl]-3-[2-oxa-6-azaspiro[3.3]heptan-6-yl]pyrazin-2(1H)-one The reductive amination step for preparing Example 1 from Intermediate 1-7 was used with the product from the previous step (200 mg, 0.61 mmol). The crude product (5 mL) was purified using chromatographic Procedure C (38.0% to 52.0% $CH_3CN$ in 7 min), to afford 24.8 mg (8.78%) of the title compound as a light yellow solid.

LC-MS: (ES, m/z): 463 [M+H]$^+$. $^1$H NMR (400 MHz, MeOD-$d_4$) δ ppm: 9.20 (s, 1H), 8.97 (s, 2H), 7.11-7.055 (m, 2H) 7.01-6.94 (m, 2H), 6.73 (s, 1H), 4.83 (s, 4H), 4.09 (brs, 4H), 2.82-2.73 (m, 2H), 2.48-2.39 (m, 2H), 2.35-2.27 (m, 1H), 1.98-1.82 (m, 3H), 1.12-1.04 (m, 1H), 1.03-0.96 (m, 1H).

Example 25

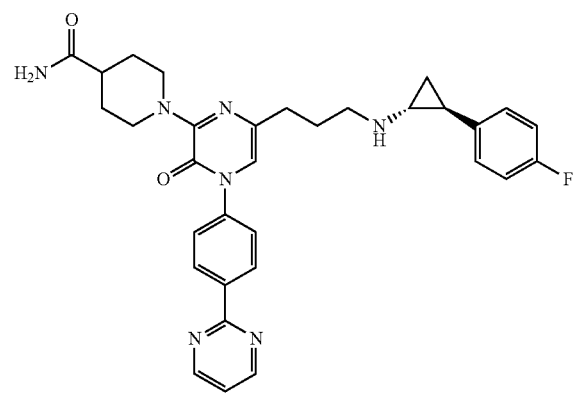 [SMILES: NC(=O)C1CCN(c2nc(CCCN[C@@H]3C[C@H]3c3ccc(F)cc3)cn(-c3ccc(-c4ncccn4)cc3)c2=O)CC1]

151

1-[6-(3-[[(1R,2S)-2-(4-Fluorophenyl)cyclopropyl]amino]propyl)-3-oxo-4-[4-(pyrimidin-2-yl)phenyl]-3,4-dihydropyrazin-2-yl]piperidine-4-carboxamide

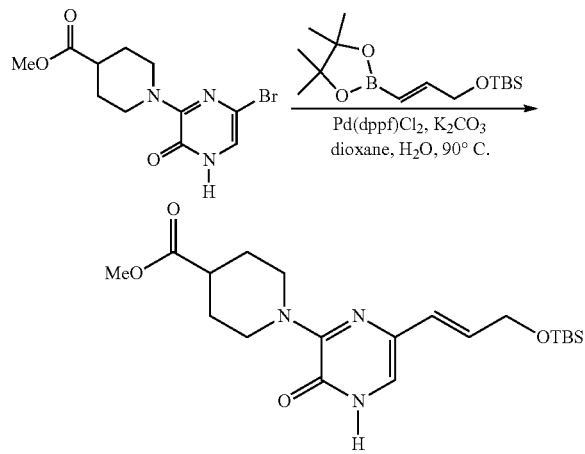

Methyl 1-[6-[(E)-3-[(tert-butyldimethylsilyl)oxy]prop-1-en-1-yl]-3(4H)-oxopyrazin-2-yl]piperidine-4-carboxylate
The procedure for preparing Intermediate 3-3 was used with Intermediate 10-1 (10 g, 31.63 mmol), using 3 hr of reaction time at 90° C. The crude product was purified with silica gel chromatography using EtOAc/petroleum ether (1:20) to afford 4 g (31%) of the title compound as a light yellow oil.

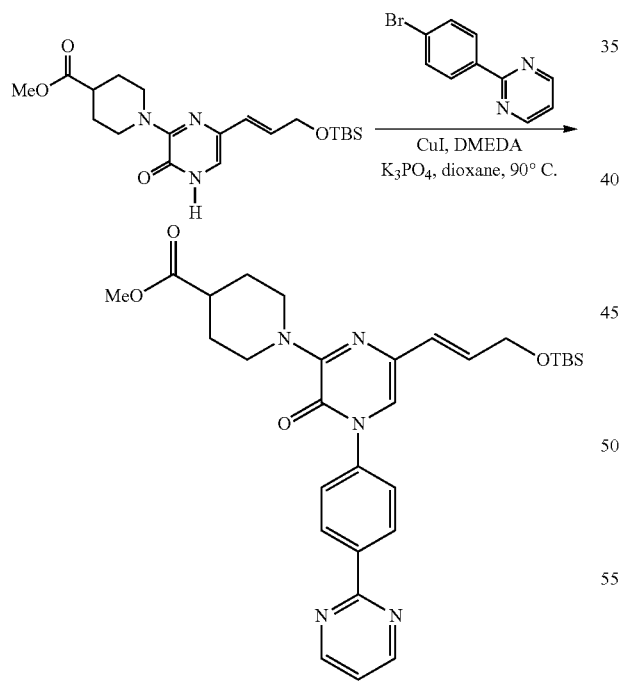

Methyl 1-[6-[(E)-3-[(tert-butyldimethylsilyl)oxy]prop-1-en-1-yl]-3(4H)-oxo-4-[4-(pyrimidin-2-yl)phenyl]-pyrazin-2-yl]piperidine-4-carboxylate The procedure for preparing Intermediate 13-1 was used with the product from the previous step (4 g, 9.81 mmol, 1.00 equiv) and 2-(4-bromophenyl)pyrimidine (3.5 g, 14.89 mmol, 1.50 equiv), using 16 hr of reaction time at 90° C. The crude product was purified with silica gel chromatography using EtOAc/petroleum ether to afford 1.9 g (34%) of the title compound as a yellow oil.

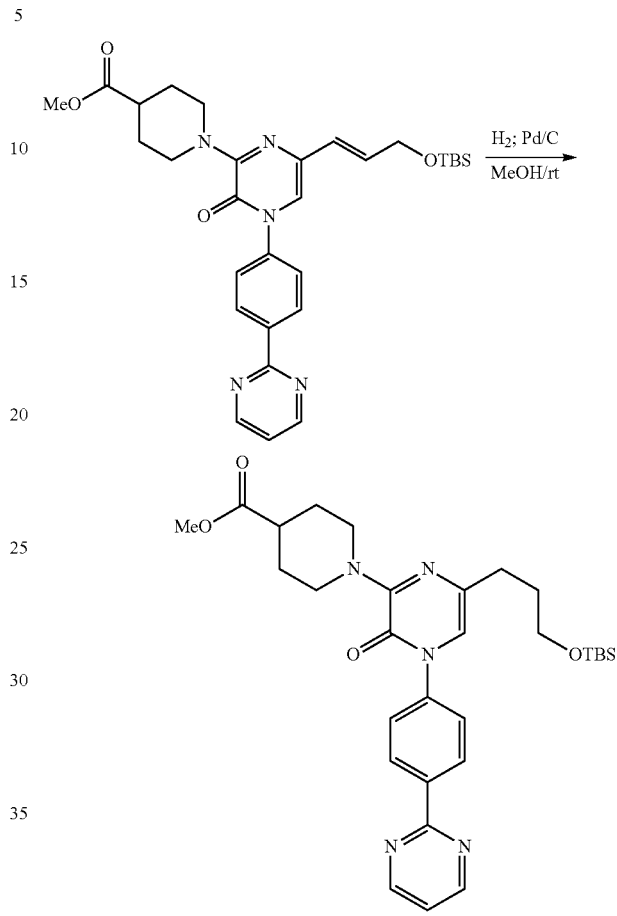

Methyl 1-(6-[3-[(tert-butyldimethylsilyl)oxy]propyl]-3(4H)-oxo-4-[4-(pyrimidin-2-yl)phenyl]-pyrazin-2-yl)piperidine-4-carboxylate The procedure for preparing of Intermediate 1-5 was used with the product from the previous step (1.9 g, 3.38 mmol, 1.00 equiv) to afford 1.7 g (89%) of the title compound as a light yellow oil.

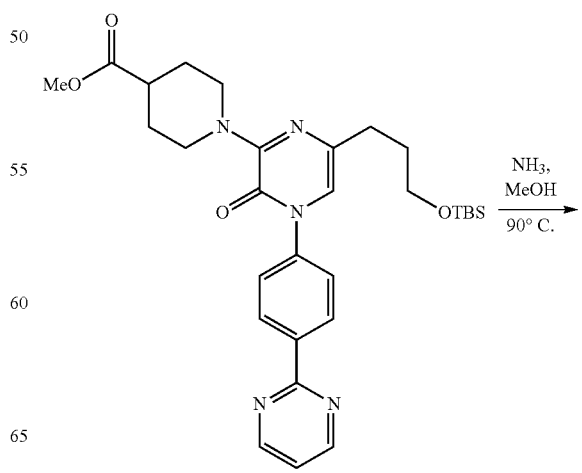

-continued

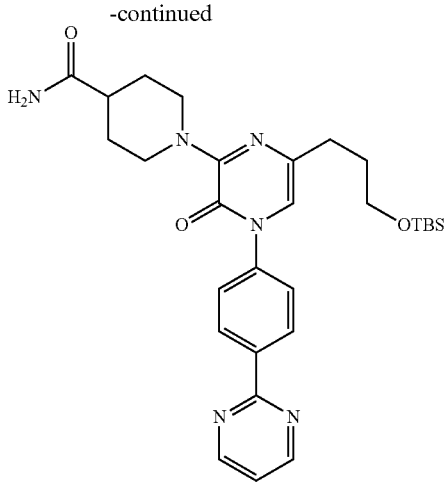

1-(6-[3-[(tert-Butyldimethylsilyl)oxy]propyl]-3(4H)-oxo-4-[4-(pyrimidin-2-yl)phenyl]-pyrazin-2-yl)piperidine-4-carboxamide A solution of the product from the previous step (1.7 g, 3.02 mmol, 1.00 equiv) in MeOH (10 mL) was combined with a solution of NH₃ (4 g, 5.00 equiv) in MeOH (5 mL). The resulting solution was stirred for 96 h at 90° C., then cooled and concentrated under vacuum to afford 1.1 g (66%) of the title compound as a light yellow oil.

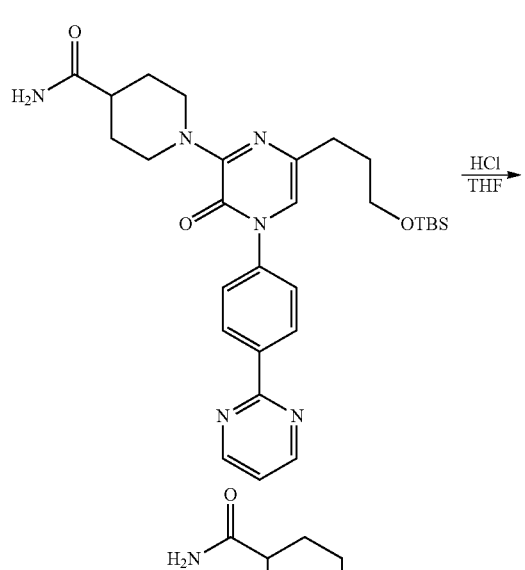

1-[6-(3-Hydroxypropyl)-3(4H)-oxo-4-[4-(pyrimidin-2-yl)phenyl]-pyrazin-2-yl]piperidine-4-carboxamide A solution of the product from the previous step (1.1 g, 2.00 mmol, 1.00 equiv), HCl (3 mL, 2.00 equiv) in H₂O (1 mL) and THF (20 mL), was stirred for 1 h at 25° C. The pH adjusted to 7 with Na₂CO₃ (1 M). The crude product was purified with silica gel chromatography with H₂O/MeCN (5:1) to afford 500 mg (57%) of the title compound as a light yellow solid.

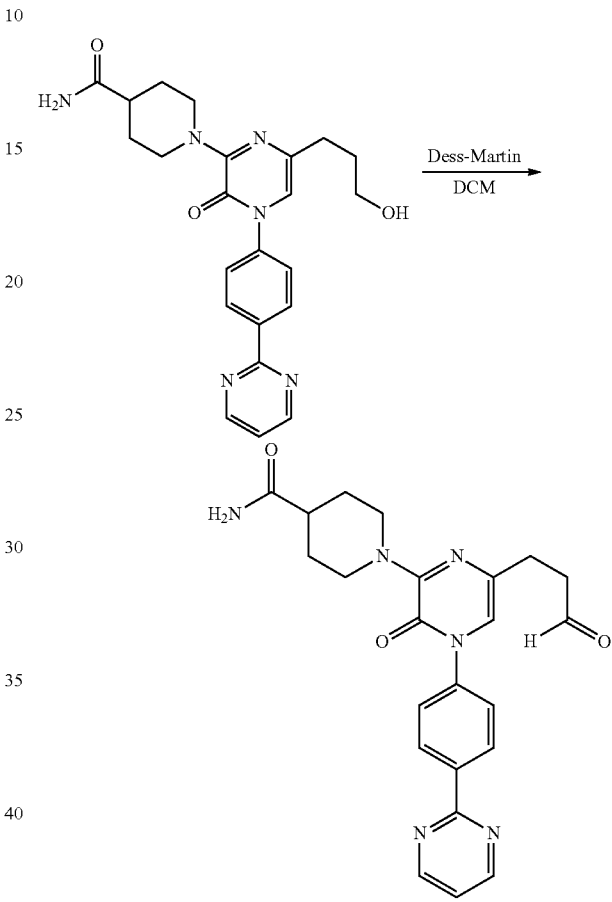

1-[3(4H)-Oxo-6-(3-oxopropyl)-4-[4-(pyrimidin-2-yl)phenyl]-pyrazin-2-yl]-piperidine-4-carboxamide The procedure for preparing Intermediate 1-7 was used with the product from the previous step (500 mg, 1.15 mmol, 1.00 equiv) to afford 300 mg (60%) of the title compound as a light yellow solid.

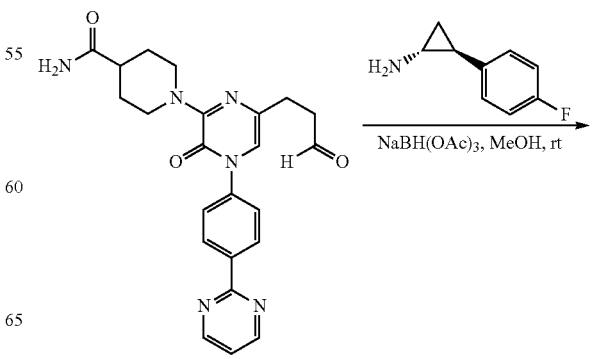

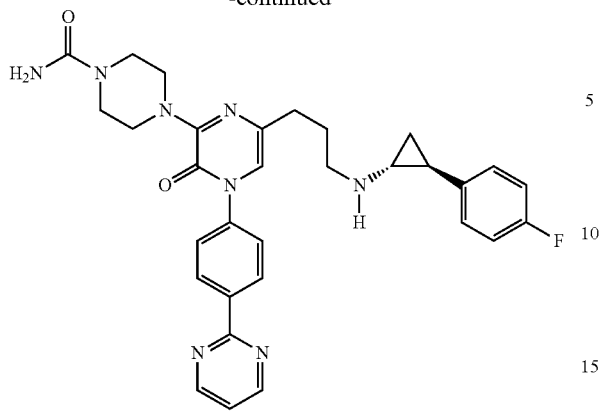

1-[6-(3-[[(1R,2S)-2-(4-Fluorophenyl)cyclopropyl]amino]propyl)-3-oxo-4-[4-(pyrimidin-2-yl)phenyl]-3,4-dihydropyrazin-2-yl]piperidine-4-carboxamide The procedure for preparing Intermediate 4-7 was used with the product from the previous step (300 mg, 0.69 mmol). The crude product (3 mL) was purified using chromatographic Procedure C (38.0% to 50.0% $CH_3CN$ in 8 min), to afford 73.9 mg (19%) of the title compound as a light yellow solid.

LC-MS: (ES, m/z): 568 [M+H]$^+$. $^1$H NMR (300 MHz, MeOD-d$_4$) δ ppm: 8.95-8.61 (d, J=4.8 Hz, 2H), 8.65-8.45 (m, 2H), 7.62-7.48 (m, 2H), 7.48-7.31 (m, 1H), 7.11-6.89 (m, 4H), 6.82 (s, 1H), 4.82-4.66 (m, 2H), 2.95-2.85 (m, 2H), 2.85-2.69 (m, 2H), 2.62-2.45 (m, 3H), 2.29 (s, 1H), 2.01-1.61 (m, 7H), 1.12-0.92 (m, 2H).

Example 26

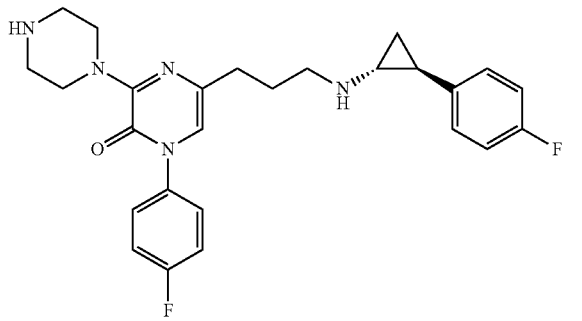 [SMILES: O=c1c(N2CCNCC2)nc(CCCN[C@@H]2C[C@H]2c2ccc(F)cc2)cn1-c1ccc(F)cc1]

1-[4-Fluorophenyl]-5-[3-([(1R,2S)-2-(4-fluorophenyl)cyclopropyl]amino)propyl]-3-(piperazin-1-yl)pyrazin-2(1H)-one

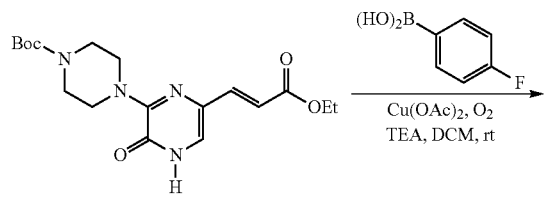

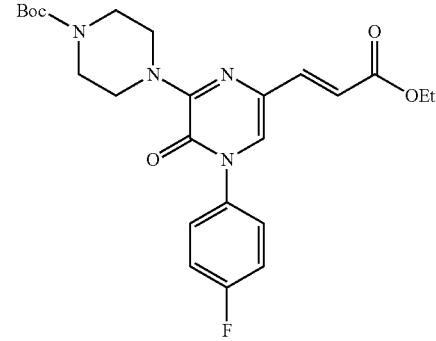

tert-Butyl 4-[6-[(E)-3-ethoxy-3-oxoprop-1-en-1-yl]-4-(4-fluorophenyl)-3(4H)-oxo-pyrazin-2-yl]piperazine-1-carboxylate The procedure for preparing Intermediate 8-9 was used with Intermediate 14-2 (2.5 g, 6.61 mmol, 1.00 equiv) and (4-fluorophenyl)boronic acid (1.65 g, 11.79 mmol, 1.50 equiv). The crude product was purified using silica gel chromatography using EtOAc/petroleum ether (1:1) to afford 1.6 g (51%) of the title compound as a yellow oil.

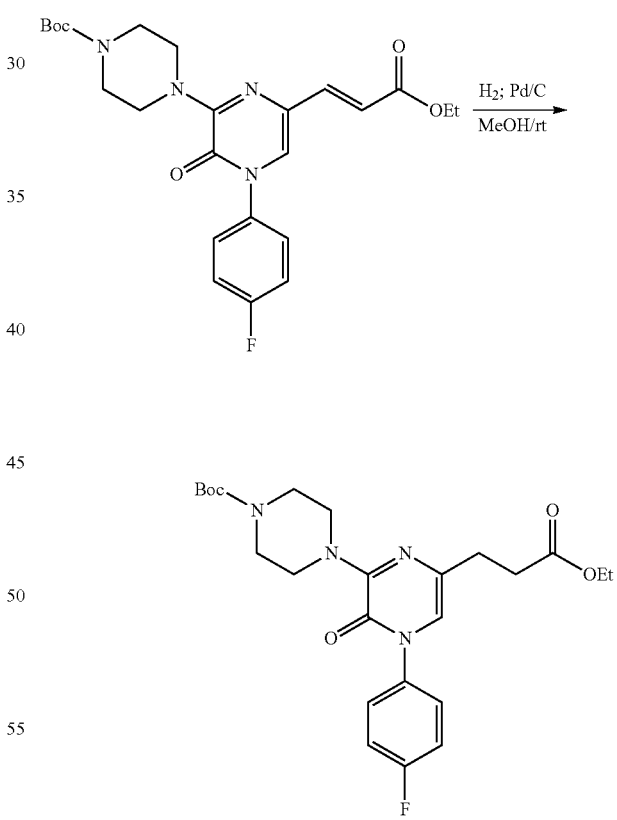

tert-Butyl 4-[6-(3-ethoxy-3-oxopropyl)-4-(4-fluorophenyl)-3(4H)-oxopyrazin-2-yl]piperazine-1-carboxylate (Intermediate 26-2) The procedure for preparing Intermediate 1-5 was used with the product from the previous step (1.6 g, 3.39 mmol, 1.00 equiv) to afford 1.5 g (93%) of the title compound as a yellow solid.

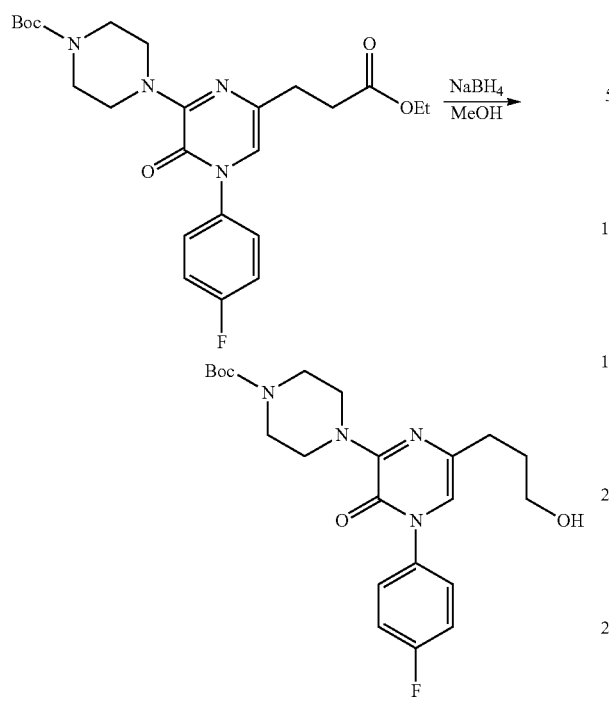

tert-Butyl 4-[4-(4-fluorophenyl)-6-(3-hydroxypropyl)-3(4H)-oxopyrazin-2-yl]piperazine-1-carboxylate The procedure for preparing Intermediate 1-6 was used with the product of the previous step (1.5 g, 3.16 mmol, 1.00 equiv) to afford 1.1 g (80%) of the title compound as a yellow oil.

tert-Butyl 4-[4-(4-fluorophenyl)-3(4H)-oxo-6-(3-oxopropyl)-pyrazin-2-yl]-piperazine-1-carboxylate The procedure for preparing Intermediate 1-7 was used with the product from the previous step (600 mg, 1.39 mmol, 1.00 equiv) to afford 400 mg (66.98%) of the title compound as a yellow oil.

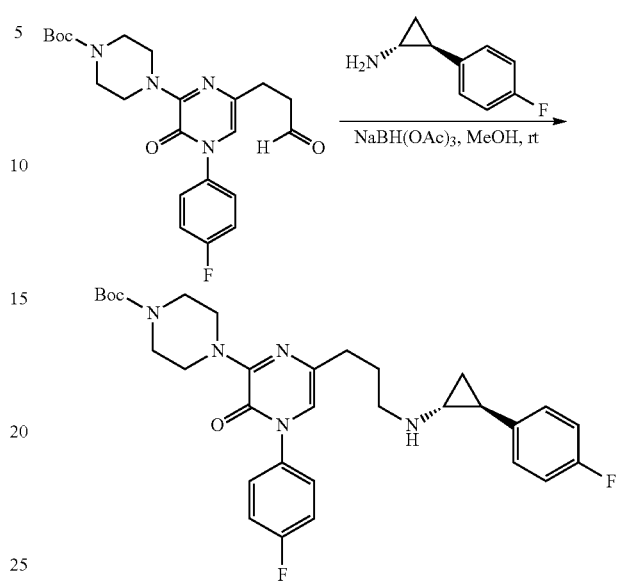

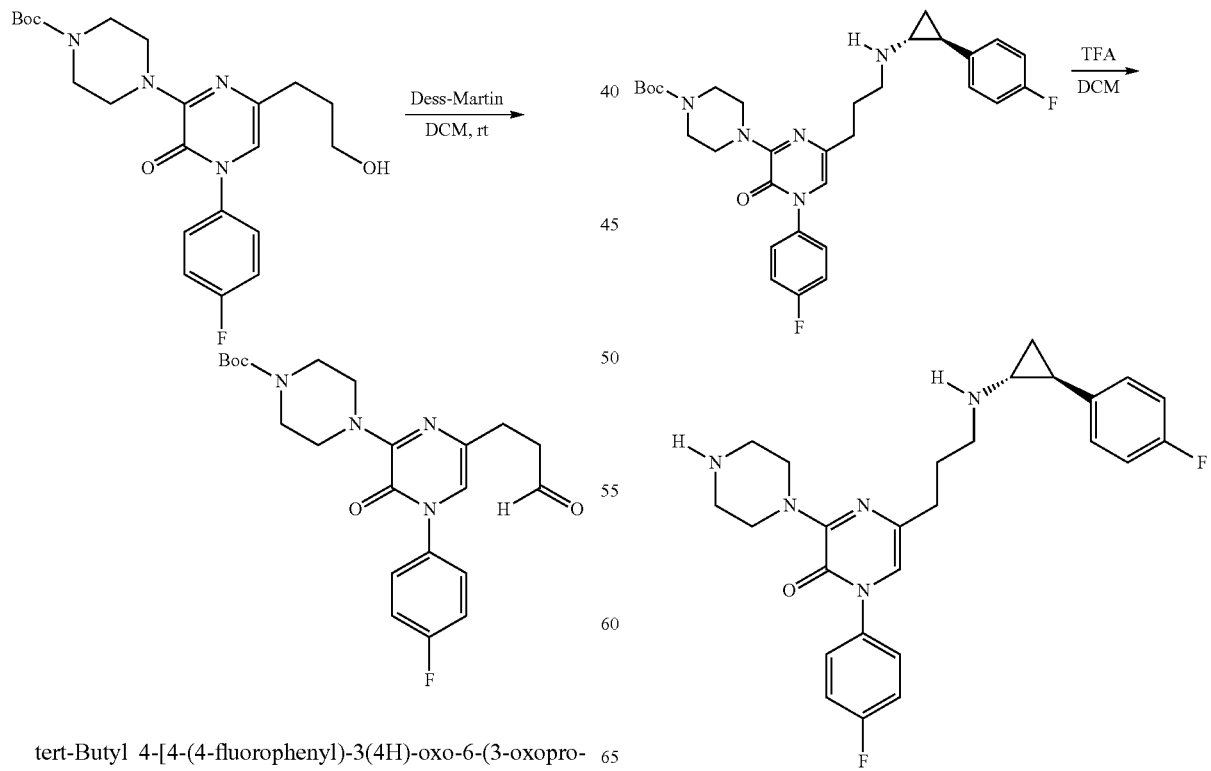

tert-Butyl 4-[4-(4-fluorophenyl)-6-(3-[[(1R,2S)-2-(4-fluorophenyl)-cyclopropyl]amino]propyl)-3(4H)-oxopyrazin-2-yl]piperazine-1-carboxylate The reductive amination step for preparing Example 1 from Intermediate 1-7 was used with the product from the previous step (400 mg, 0.93 mmol), affording 300 mg (57%) of the title compound as a yellow oil, which was carried forward without further purification.

1-[4-Fluorophenyl]-5-[3-([[(1R,2S)-2-(4-fluorophenyl)cyclopropyl]amino)-propyl]-3-(piperazin-1-yl)pyrazin-2(1H)-one The deprotection step for preparing Example 14 from Intermediate 14-7 was used with the product from the previous step (300 mg, 0.53 mmol, 1.00 equiv). The crude product (3 mL) was purified using chromatographic Procedure D (15% to 60% CH$_3$CN in 6.5 min, Rt: 6.88 min), to afford 113.4 mg (46%) of the title compound as a light yellow solid.

LCMS: (ES, m/z): 466 [M+H]$^+$. $^1$H NMR (300 MHz, Methanol-d$_4$) δ ppm: 7.51-7.41 (m, 2H), 7.30-7.27 (m, 2H), 7.27-7.17 (m, 2H), 7.07-7.0 (m, 2H), 6.98 (s, 1H), 4.10-4.0 (m, 4H), 3.40-3.20 (m, 6H), 3.04-2.94 (m, 1H), 2.60-2.50 (m, 2H), 2.56-2.46 (m, 1H), 2.11-2.0 (m, 2H), 1.58-1.47 (m, 1H), 1.44-1.29 (m, 1H).

Example 27

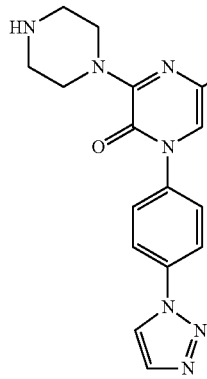

1-[4-(1H-1,2,3-triazol-1-yl)phenyl]-5-[3-([[(1R,2S)-2-(4-fluorophenyl)-cyclopropyl]amino)propyl]-3-[piperazin-1-yl]pyrazin-2(1H)-one tert-Butyl 4-(4-(4-(1H-1,2,3-triazol-1-yl)phenyl)-6-(3-ethoxy-3-oxopropyl)-3(4H)-oxopyrazin-2-yl)piperazine-1-carboxylate (Intermediate 27-1) The procedure for preparing Intermediate 13-1 was used with Intermediate 26-2 (1.5 g, 3.95 mmol, 1 equiv) and 1-(4-bromophenyl)-1H-1,2,3-triazole (1.34 g, 5.92 mmol, 1.5 equiv). The crude product was purified with silica gel chromatography using EtOAc/petroleum ether (1:1) to afford 0.7 g (33.98%) of the title compound as a yellow solid.

tert-Butyl 4-(4-(4-(1H-1,2,3-triazol-1-yl)phenyl)-6-(3-hydroxypropyl)-3(4H)-oxopyrazin-2-yl)piperazine-1-carboxylate The procedure for preparing Intermediate 1-6 was used with the product from the previous step (0.7 g, 1.34 mmol, 1 equiv) with 1 hr reaction time, to afford 400 mg (62.21%) of the title compound as a yellow solid.

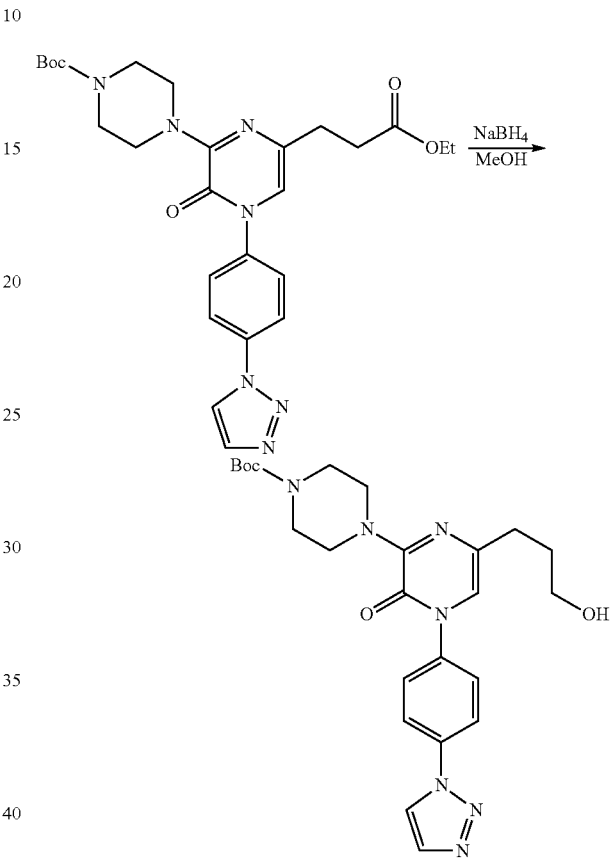

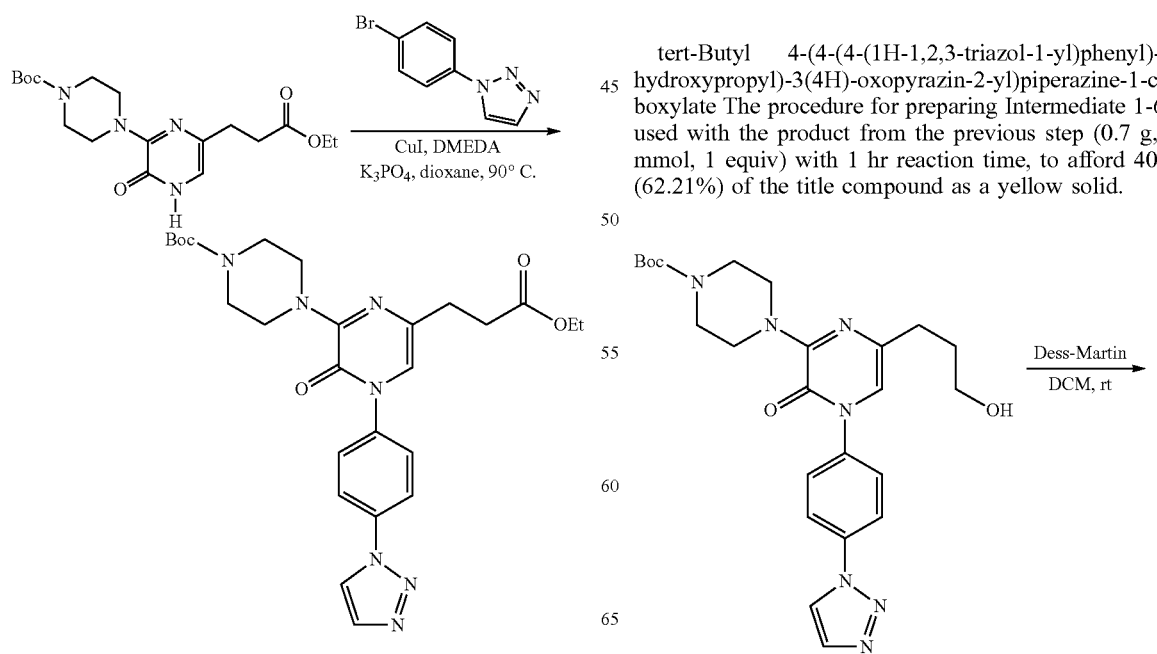

-continued

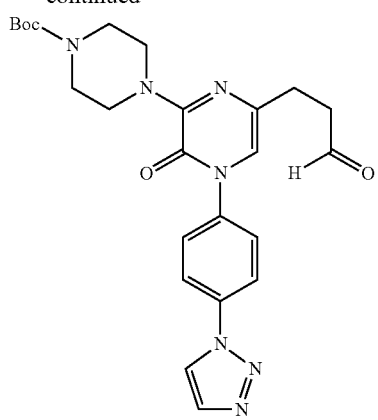

tert-Butyl 4-(4-(4-(1H-1,2,3-triazol-1-yl)phenyl)-3(4H)-oxo-6-(3-oxopropyl)-pyrazin-2-yl)piperazine-1-carboxylate The procedure for preparing Intermediate 1-7 was used with the product from the previous step (400 mg, 0.83 mmol, 1.00 equiv) to afford 300 mg (75.37%) of the title compound as a yellow solid.

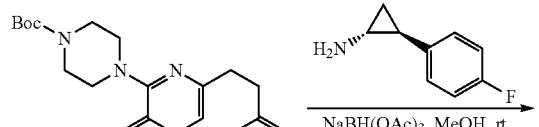

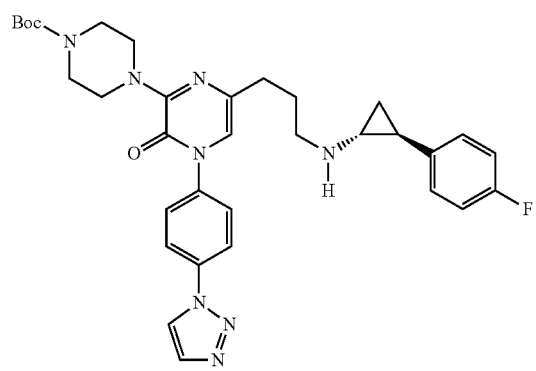

tert-Butyl 4-[4-(4-[1H-1,2,3-triazol-1-yl]phenyl)-6-(3-[(1R,2S)-2-(4-fluoro-phenyl)cyclopropylamino]propyl)-3(4H)-oxopyrazin-2-yl]piperazine-1-carboxylate The reductive amination step for preparing Example 1 from Intermediate 1-7 was used with the product from the previous step (300 mg, 0.63 mmol). The crude product was purified with silica gel chromatography using CH$_2$Cl$_2$/MeOH (10:1) to afford 220 mg (57%) of the title compound as a white solid.

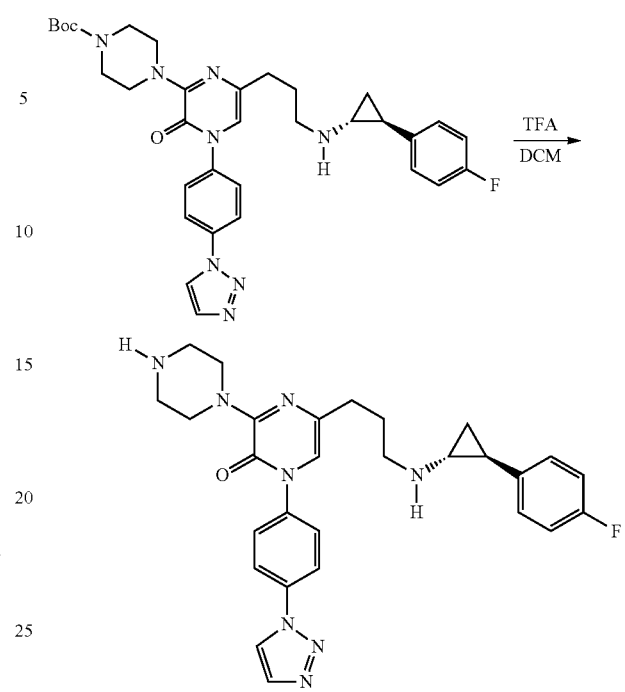

1-[4-(1H-1,2,3-triazol-1-yl)phenyl]-5-[3-([(1R,2S)-2-(4-fluorophenyl)cyclo-propyl]amino)propyl]-3-[piperazin-1-yl]pyrazin-2(1H)-one The deprotection step for preparing Example 14 from Intermediate 14-7 was used with the product from the previous step (220 mg, 0.41 mmol, 1 equiv). The crude product (5 mL) was purified using chromatographic Procedure E (27% to 60% CH$_3$CN, Rt: 10.13 min), to afford 52 mg (18.44%) of the title compound as a white solid.

LC-MS: (ES, m/z): 515 [M+H]$^+$. $^1$H NMR (300 MHz, MeOD-d$_4$) δ ppm: 8.59 (s, 1H), 8.03-8.01 (d, J=8.7 Hz, 2H), 7.90 (s, 1H) 7.63-7.60 (d, J=8.7 Hz, 2H), 7.08-6.89 (m, 2H), 6.97-6.87 (m, 2H), 6.86-6.83 (s, 1H), 3.78-3.68 (m, 4H), 2.92-2.84 (m, 4H), 2.79-2.71 (m, 2H), 2.50-2.41 (m, 2H), 2.31-2.23 (m, 1H), 1.95-1.80 (m, 3H), 1.10-0.95 (m, 2H).

Example 28

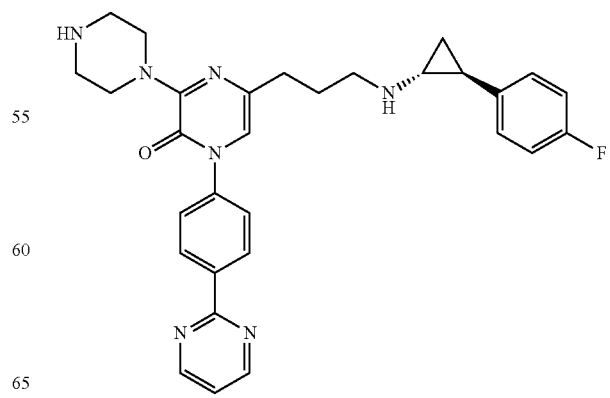

5-[3-([(1R,2S)-2-(4-fluorophenyl)cyclopropyl]amino)propyl]-3-[piperazin-1-yl]-1-[4-(pyrimidin-2-yl)phenyl]pyrazin-2(1H)-one

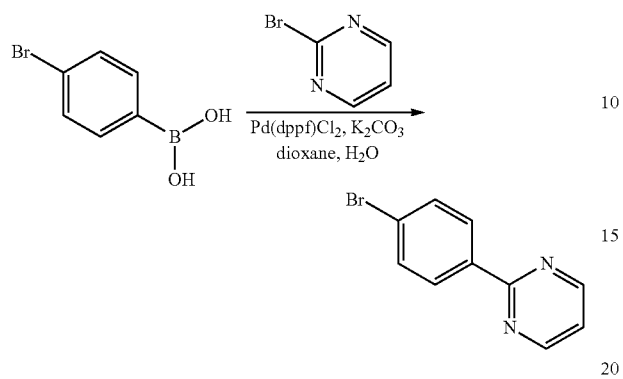

2-(4-Bromophenyl)pyrimidine A solution of 4-bromophenylboronic acid (5.0 g, 25.12 mmol, 1 equiv), 2-bromopyrimidine (5.92 g, 37.68 mmol, 1.5 equiv), $K_2CO_3$ (10.40 g, 75.37 mmol, 3 equiv), and $Pd(dppf)Cl_2$ (1.84 g, 2.51 mmol, 0.1 equiv) in dioxane (450 mL)/$H_2O$ (100 mL) was stirred overnight at 90° C. under $N_2$. The residue was purified using silica gel chromatography using EtOAc/petroleum ether (6:1) to afford 2.0 g (34%) of the title compound as a yellow oil.

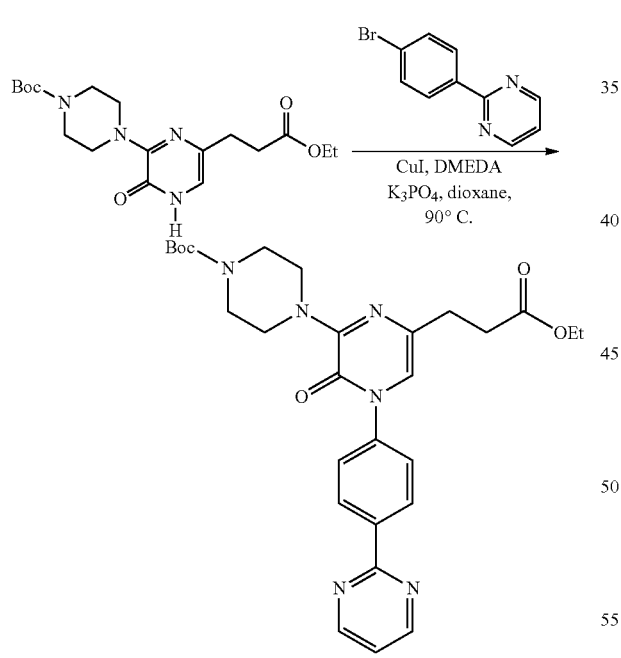

tert-Butyl 4-(6-(3-ethoxy-3-oxopropyl)-3(4H)-oxo-4-(4-(pyrimidin-2-yl)phenyl)-pyrazin-2-yl)piperazine-1-carboxylate The procedure for preparing Intermediate 13-1 was used with Intermediate 27-1 (1.79 g, 4.72 mmol, 1.1 equiv) and 2-(4-bromophenyl)pyrimidine (1.0 g, 4.29 mmol, 1 equiv). The crude product was purified with silica gel chromatography using EtOAc/petroleum ether (1:1) to afford 0.6 g (27.87%) of the title compound as a yellow solid.

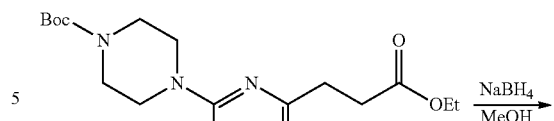

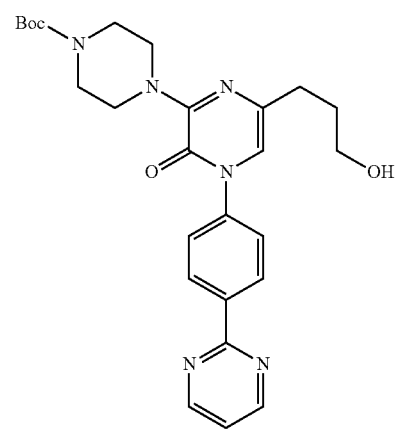

tert-Butyl 4-(6-(3-hydroxypropyl)-3(4H)-oxo-4-(4-(pyrimidin-2-yl)phenyl)-pyrazin-2-yl)piperazine-1-carboxylate The procedure for preparing Intermediate 1-6 was used with the product from the previous step (0.6 g, 2.74 mmol, 1 equiv), with 1 hr reaction time, to afford 350 mg (39.8%) of the title compound as a yellow solid.

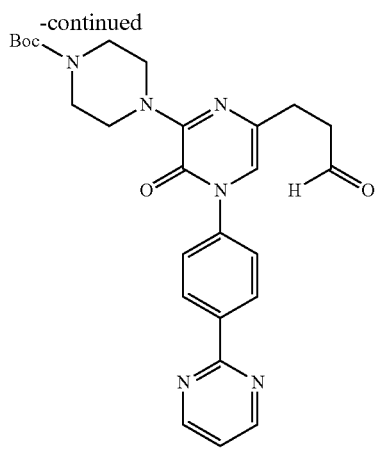

tert-Butyl 4-(3(4H)-oxo-6-(3-oxopropyl)-4-(4-(pyrimidin-2-yl)phenyl)-pyrazin-2-yl)piperazine-1-carboxylate The procedure for preparing Intermediate 1-7 was used with the product from the previous step (350 mg, 0.71 mmol, 1.00 equiv) to afford 210 mg (60%) of the title compound as a yellow solid.

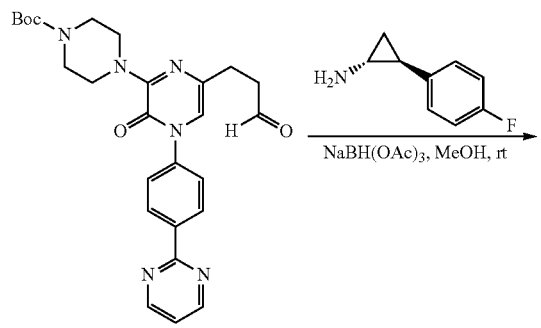

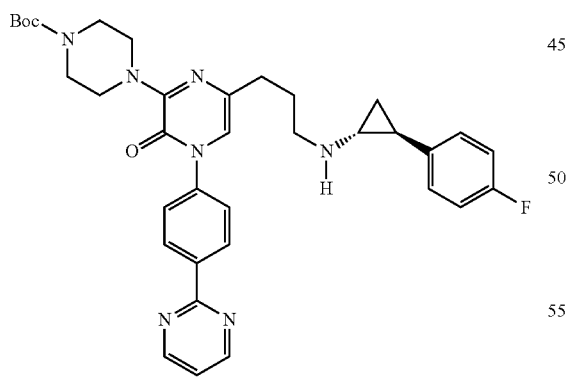

tert-Butyl 4-(6-(3-((1R,2S)-2-(4-fluorophenyl)cyclopropylamino)propyl)-3(4H)-oxo-4-(4-(pyrimidin-2-yl)phenyl)-pyrazin-2-yl)piperazine-1-carboxylate The reductive amination step for preparing Example 1 from Intermediate 1-7 was used with the product from the previous step (210 mg, 0.41 mmol), affording 190 mg (52%) of the title compound as a white solid, which was carried forward without further purification.

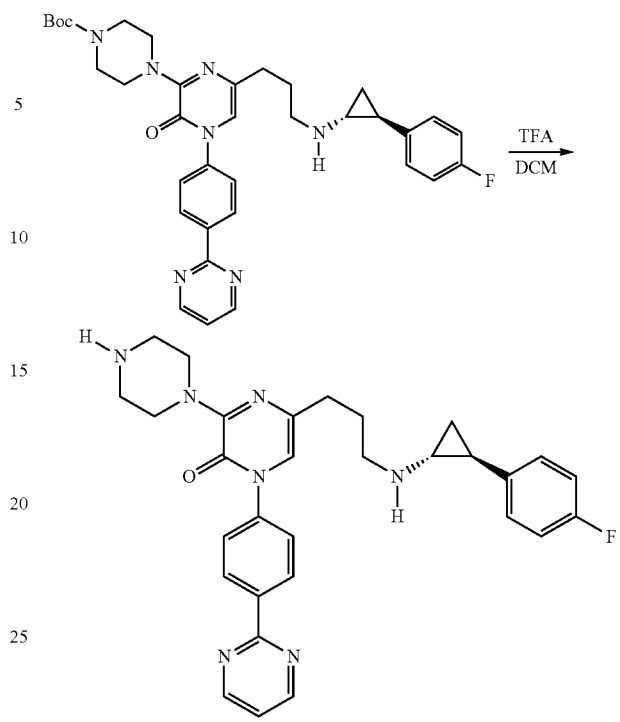

5-[3-([(1R,2S)-2-(4-fluorophenyl)cyclopropyl]amino)propyl]-3-[piperazin-1-yl]-1-[4-(pyrimidin-2-yl)phenyl]pyrazin-2(1H)-one The deprotection step for preparing Example 14 from Intermediate 14-7 was used with the product from the previous step (190 mg, 0.30 mmol, 1 equiv). The crude product (5 mL) was purified using chromatographic Procedure D (27% to 60% $CH_3CN$, Rt: 8.3 min), to afford 23.8 mg (14.96%) of the title compound as a white solid.

LC-MS: (ES, m/z): 526 [M+H]$^+$. $^1$H NMR (300 MHz, MeOD-d$_4$) δ ppm: 8.95-8.90 (m, 2H), 8.62-8.56 (m, 2H), 7.64-7.56 (m, 2H), 7.49-7.43 (m, 1H), 7.27-7.17 (m, 2H), 7.10-7.01 (m, 3H), 4.14-4.04 (m, 4H), 3.43-3.32 (m, 4H), 3.31-3.23 (m, 2H), 3.05-2.95 (m, 1H), 2.68-2.52 (m, 3H), 2.23-2.09 (m, 2H), 1.62-1.52 (m, 1H), 1.42-1.32 (m, 1H).

Example 29

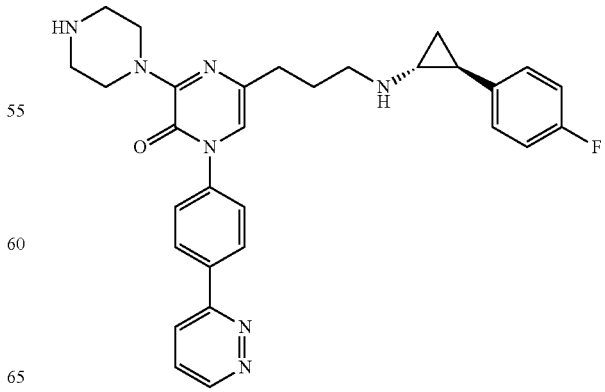

167

5-[3-([(1R,2S)-2-(4-fluorophenyl)cyclopropyl]amino)propyl]-3-[piperazin-1-yl]-1-[4-(pyridazin-3-yl)phenyl]pyrazin-2(1H)-one

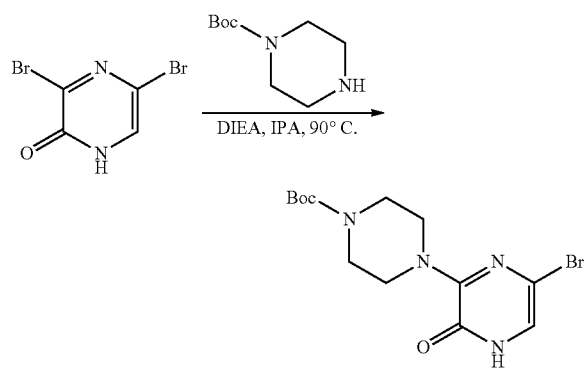

tert-Butyl 4-(6-bromo-3(4H)-oxopyrazin-2-yl)piperazine-1-carboxylate The procedure for preparing Intermediate 2-1 was used with 3,5-dibromo-1,2-dihydropyrazin-2-one (5 g, 19.84 mmol, 1.00 equiv) and tert-butyl piperazine-1-carboxylate (4.06 g, 21.82 mmol, 1.1 equiv). The crude product was purified with silica gel chromatography using EtOAc/petroleum ether (4:1) to afford 5 g (70%) of the title compound as a white solid.

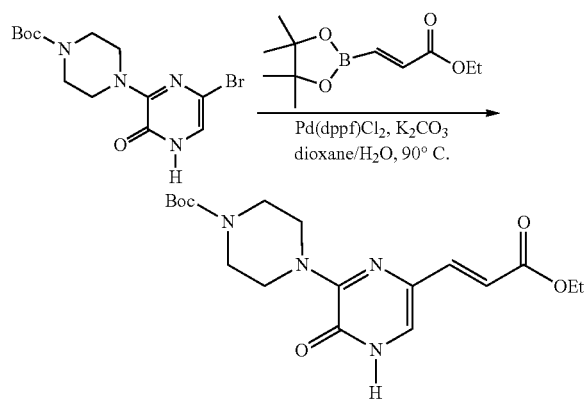

tert-Butyl 4-[6-[(E)-3-ethoxy-3-oxoprop-1-en-1-yl]-3(4H)-oxopyrazin-2-yl]-piperazine-1-carboxylate The procedure for preparing Intermediate 1-4 was used with the product from the previous step (5.0 g, 13.96 mmol, 1 equiv). The crude product was purified with silica gel chromatography using EtOAc/petroleum ether (1:2) to afford 2.20 g (41%) of the title compound as an orange oil.

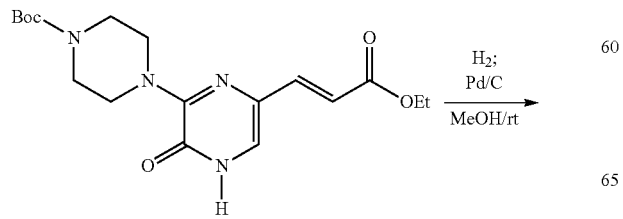

168

-continued

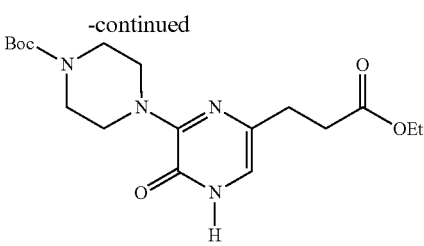

tert-Butyl 4-(6-(3-ethoxy-3-oxopropyl)-3(4H)-oxopyrazin-2-yl)piperazine-1-carboxylate The procedure for preparing Intermediate 1-5 was used with the product from the previous step (2.20 g, 5.82 mmol, 1.00 equiv) to afford 2.1 g (95%) of the title compound as an orange oil.

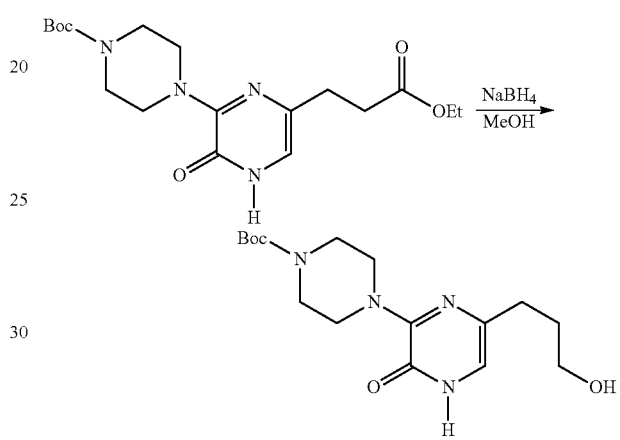

tert-Butyl 4-[6-(3-hydroxypropyl)-3(4H)-oxopyrazin-2-yl]piperazine-1-carboxylate The procedure for preparing Intermediate 1-6 was used with the product of the previous step (1.5 g, 3.94 mmol, 1.00 equiv) to afford 700 mg (52%) of the title compound as a light yellow solid.

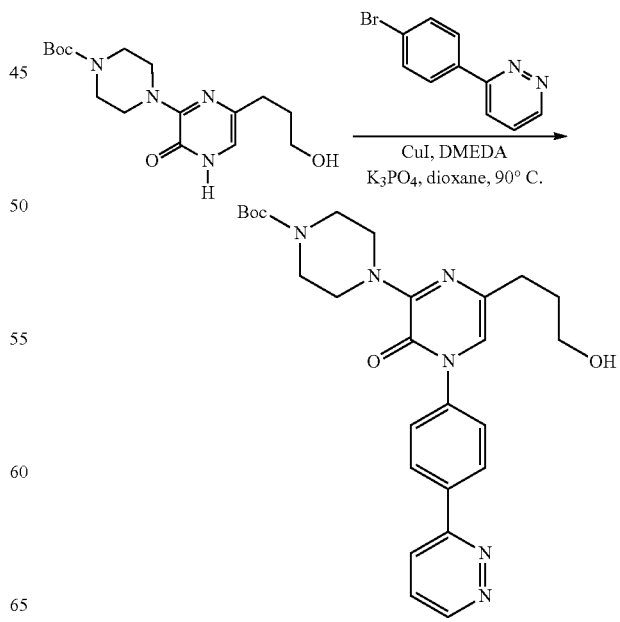

169 tert-Butyl 4-[6-(3-hydroxypropyl)-3(4H)-oxo-4-[4-(pyridazin-3-yl)phenyl]-pyrazin-2-yl]piperazine-1-carboxylate The procedure for preparing Intermediate 13-1 was used with the product from the previous step (700 mg, 2.07 mmol, 1.00 equiv) and 3-(4-bromophenyl)pyridazine (723 mg, 3.08 mmol, 1.49 equiv). The crude product was purified with silica gel chromatography using EtOAc/petroleum ether (1:3) to afford 400 mg (39%) of the title compound as a light yellow solid.

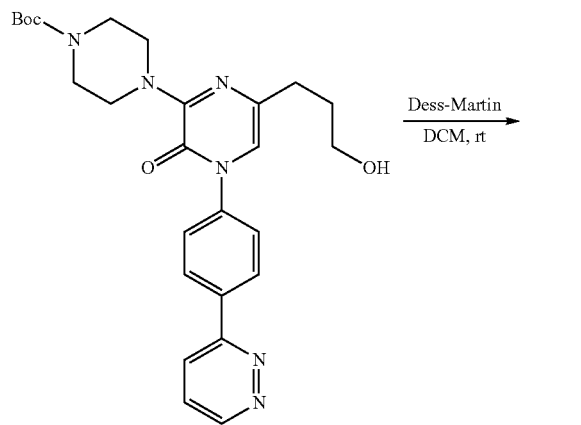

tert-Butyl 4-[3(4H)-oxo-6-(3-oxopropyl)-4-[4-(pyridazin-3-yl)phenyl]-pyrazin-2-yl]piperazine-1-carboxylate The procedure for preparing Intermediate 1-7 was used with the product from the previous step (400 mg, 0.81 mmol, 1.00 equiv) to afford 350 mg (88%) of the title compound as a light yellow solid.

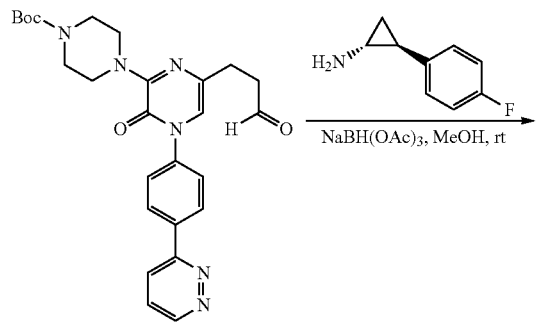

170

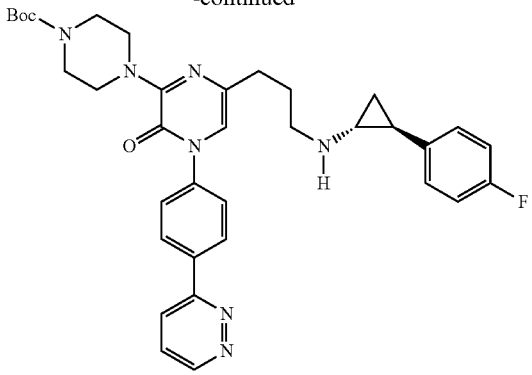

tert-Butyl 4-[6-(3-[[(1R,2S)-2-(4-fluorophenyl)cyclopropyl]amino]propyl)-3(4H)-oxo-4-[4-(pyridazin-3-yl)phenyl]-pyrazin-2-yl]piperazine-1-carboxylate The reductive amination step for preparing Example 1 from Intermediate 1-7 was used with the product from the previous step (350 mg, 0.71 mmol). The crude product was purified using silica gel chromatography using $CH_2Cl_2$/MeOH (1:10) to afford 300 mg (67%) of the title compound as a light yellow solid.

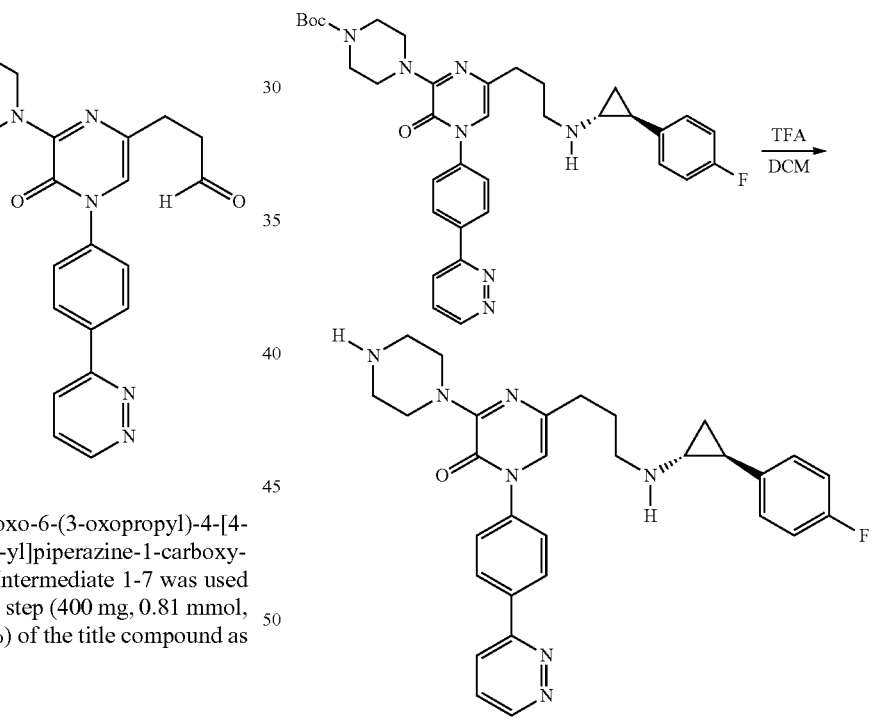

5-[3-([(1R,2S)-2-(4-fluorophenyl)cyclopropyl]amino)propyl]-3-[piperazin-1-yl]-1-[4-(pyridazin-3-yl)phenyl]pyrazin-2(1H)-one The deprotection step for preparing Example 14 from Intermediate 14-7 was used with the product from the previous step (400 mg, 0.64 mmol, 1.00 equiv). The crude product (2 mL) was purified by Flash-Prep-HPLC (IntelFlash-1, column: silica gel, detector, UV 254 nm) to afford 57.4 mg (17%) of the title compound as a light yellow solid.

LC-MS: (ES, m/z): 526 [M+H]$^+$. $^1$H NMR (400 MHz, Methanol-$d_4$) δ 9.25-9.22 (s, 1H), 8.34-8.28 (m, 3H), 7.92-7.86 (m, 1H), 7.68-7.64 (m, 2H), 7.25-7.19 (m, 2H), 7.11-

7.04 (m, 3H), 4.11-4.03 (m, 4H), 3.41-3.33 (m, 4H), 3.32-3.27 (m, 2H), 3.03-2.97 (m, 1H), 2.67-2.59 (m, 2H), 2.56-2.48 (m, 1H), 2.20-2.09 (m, 2H), 1.58-1.49 (m, 1H), 1.44-1.36 (m, 1H)

Example 30

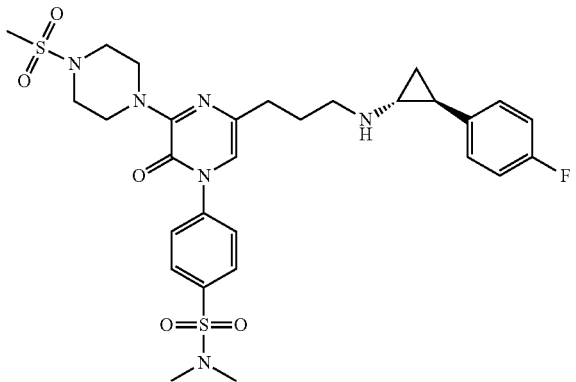 [SMILES: CN(C)S(=O)(=O)c1ccc(-n2cc(CCCN[C@@H]3C[C@H]3c3ccc(F)cc3)nc(N3CCN(S(C)(=O)=O)CC3)c2=O)cc1]

4-[5-(3-[[(1R,2S)-2-(4-Fluorophenyl)cyclopropyl]amino]propyl)-3-(4-methanesulfonylpiperazin-1-yl)-2(1H)-oxopyrazin-1-yl]-N,N-dimethylbenzene-1-sulfonamide

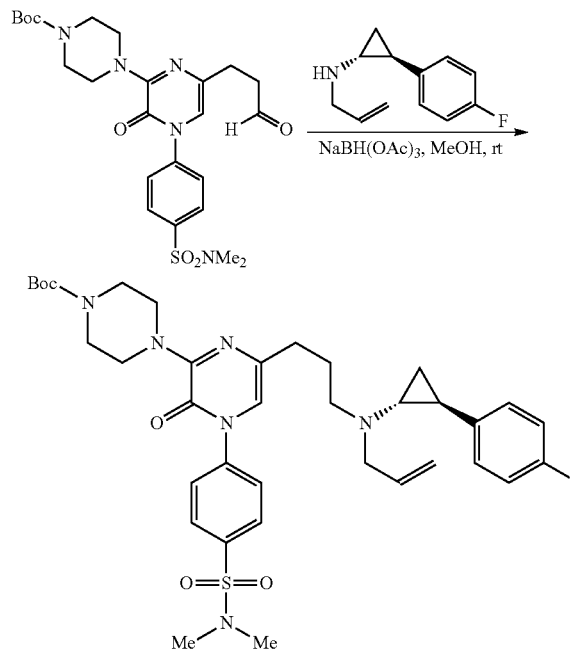

tert-Butyl 4-[4-[4-((dimethylamino)sulfonyl)phenyl]-6-(3-[[(1R,2S)-2-(4-fluorophenyl)cyclopropyl](prop-2-en-1-yl)amino]propyl)-3(4H)-oxopyrazin-2-yl]-piperazine-1-carboxylate The reductive amination step for preparing Example 1 from Intermediate 1-7 was used with Intermediate 14-6 (760 mg, 1.46 mmol, 1.00 equiv) and (1R,2S)-2-(4-fluorophenyl)-N-(prop-2-en-1-yl)cyclopropan-1-amine (560 mg, 2.93 mmol, 2.00 equiv). The crude product was purified with silica gel chromatography using EtOAc/petroleum ether (1:1), to afford 0.8 g (79%) of the title compound as a light yellow oil.

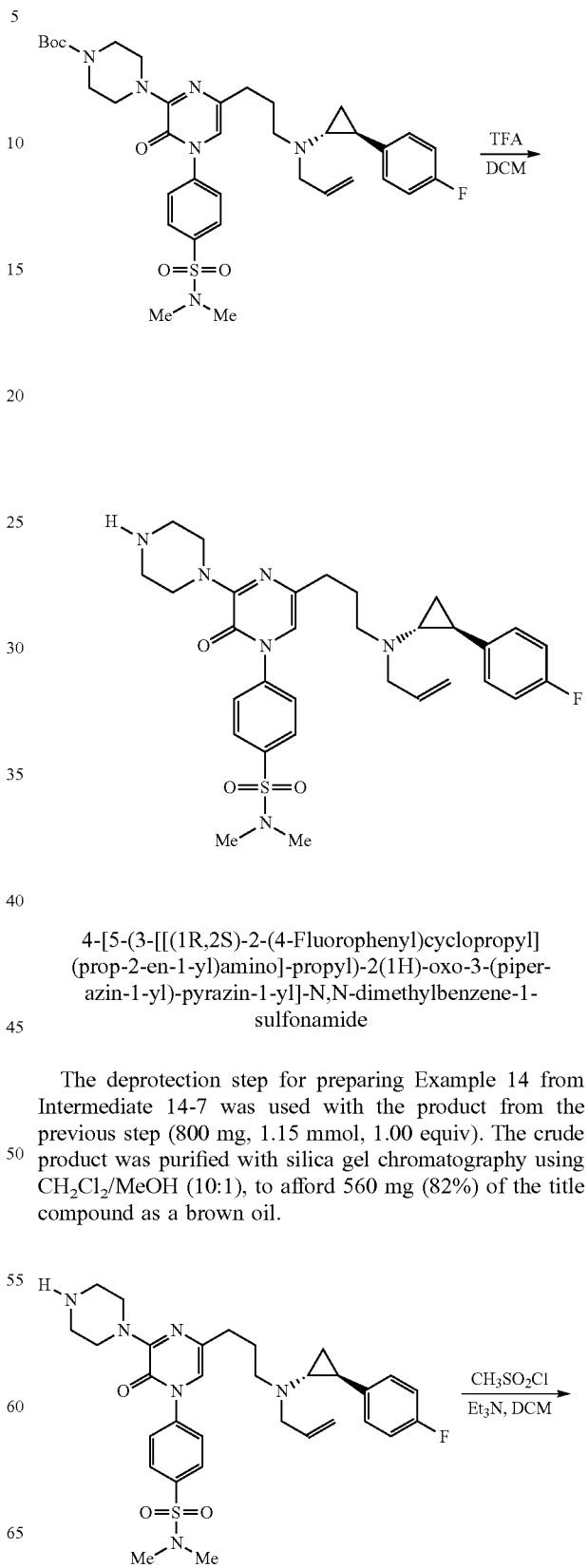

4-[5-(3-[[(1R,2S)-2-(4-Fluorophenyl)cyclopropyl](prop-2-en-1-yl)amino]-propyl)-2(1H)-oxo-3-(piperazin-1-yl)-pyrazin-1-yl]-N,N-dimethylbenzene-1-sulfonamide The deprotection step for preparing Example 14 from Intermediate 14-7 was used with the product from the previous step (800 mg, 1.15 mmol, 1.00 equiv). The crude product was purified with silica gel chromatography using $CH_2Cl_2$/MeOH (10:1), to afford 560 mg (82%) of the title compound as a brown oil.

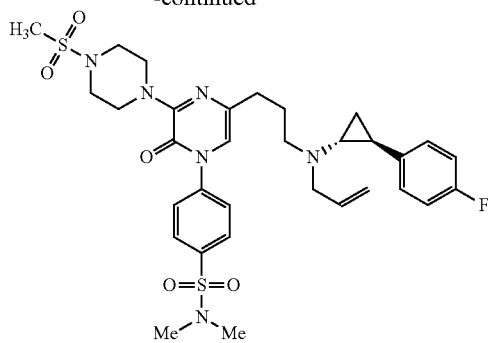

4-[5-(3-[[(1R,2S)-2-(4-Fluorophenyl)cyclopropyl](prop-2-en-1-yl)amino]propyl)-3-(4-methanesulfonylpiperazin-1-yl)-2(1H)-oxopyrazin-1-yl]-N,N-dimethylbenzene-1-sulfonamide A solution of the compound from the previous step (560 mg, 0.94 mmol, 1.00 equiv) and Et$_3$N (286 mg, 2.83 mmol, 3.00 equiv) in CH$_2$Cl$_2$ (10 mL) was stirred for 30 min at 0° C., then CH$_3$SO$_2$Cl (161 mg, 1.41 mmol, 1.50 equiv) was added. The resulting solution was stirred for 60 min at rt and extracted with 3×30 mL of CH$_2$Cl$_2$. The combined organic layers were dried over Na$_2$SO$_4$ and purified with silica gel chromatography using EtOAc/petroleum ether (1:10), to afford 0.5 g (79%) of the title compound as a light yellow oil.

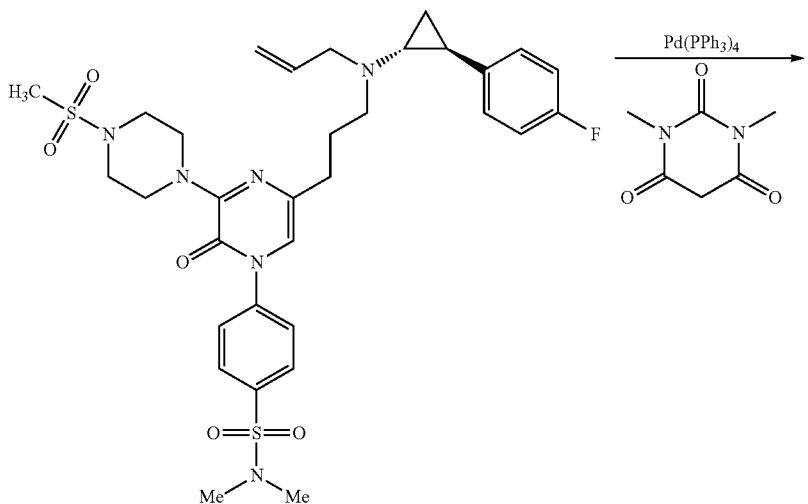

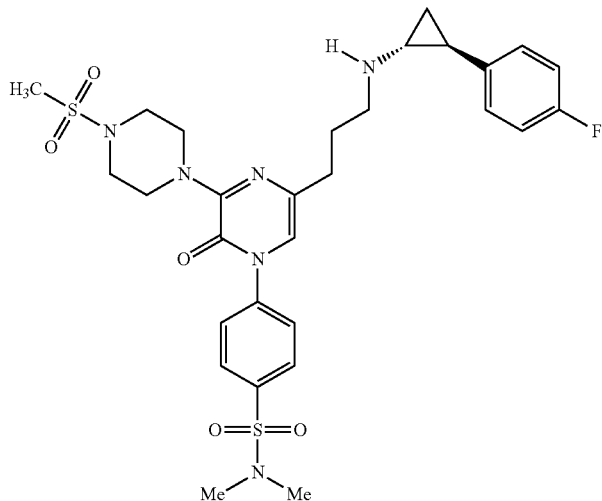

4-[5-(3-[[(1R,2S)-2-(4-Fluorophenyl)cyclopropyl]amino] propyl)-3-(4-methanesulfonylpiperazin-1-yl)-2(1H)-oxopyrazin-1-yl]-N,N-dimethylbenzene-1-sulfonamide A solution of the product from the previous step (500 mg, 0.74 mmol, 1.00 equiv), Pd(PPh₃)₄ (172 mg, 0.15 mmol, 0.20 equiv), and 1,3-dimethyl-1,3-diazinane-2,4,6-trione (348 mg, 2.23 mmol, 3.00 equiv) in THF (15 mL) was stirred for 2 h at 50° C. under N₂. The crude product was purified first with silica gel chromatography using CH₂Cl₂/MeOH (50:1), and then with chromatographic Procedure E (28% to 80% CH₃CN, Rt: 7.75 min), to afford 182 mg (39%) of the title compound as a white solid.

LCMS: (ES, m/z): 633 [M+H]⁺. ¹H NMR (300 MHz, Methanol-d₄) δ ppm: 7.96-7.85 (d, J=8.4 Hz, 2H), 7.71-7.60 (d, J=8.4 Hz, 2H), 7.09-6.84 (m, 5H), 3.85 (m, 4H), 3.26 (m, 4H), 2.85-2.65 (m, 11H), 2.45-2.31 (m, 2H), 2.29-2.21 (m, 1H), 1.95-1.78 (m, 3H), 1.10-0.88 (m, 2H).

Example 31

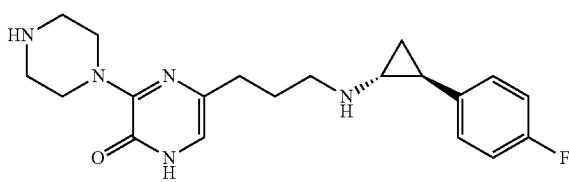 [SMILES: O=c1[nH]cc(CCCN[C@@H]2C[C@H]2c2ccc(F)cc2)nc1N1CCNCC1]

5-[3-([(1R,2S)-2-(4-fluorophenyl)cyclopropyl] amino)propyl]-3-[piperazin-1-yl]pyrazin-2(1H)-one

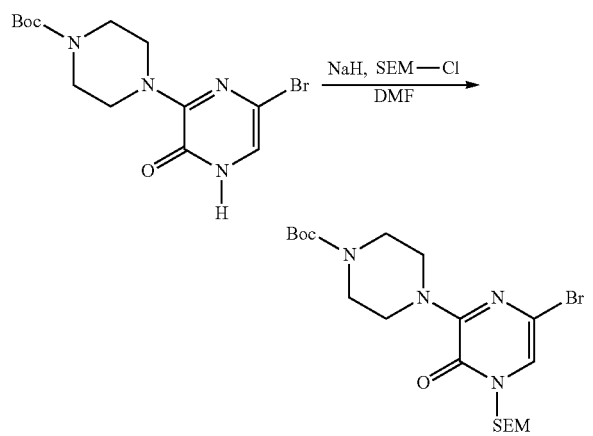

tert-Butyl 4-(6-bromo-3(4H)-oxo-4-[[2-(trimethylsilyl) ethoxy]methyl]-pyrazin-2-yl)piperazine-1-carboxylate The procedure for preparing Intermediate 2-2 was used with Intermediate 14-1 (10 g, 27.84 mmol, 1.00 equiv) and [2-(chloromethoxy)-ethyl]trimethylsilane (6.8 g, 40.79 mmol, 1.50 equiv). The crude product was purified with silica gel chromatography using EtOAc/petroleum ether (1:30) to afford 10.5 g (77%) of the title compound as an off-white oil.

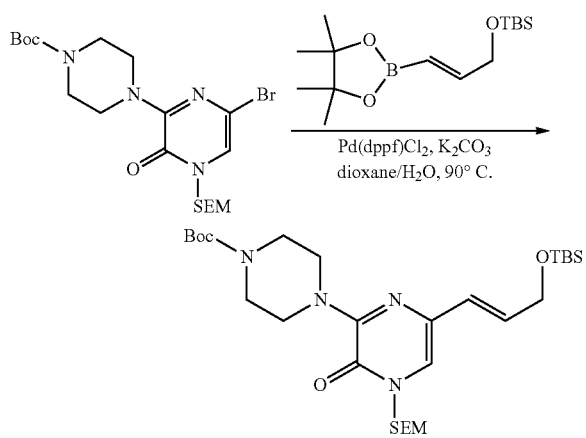

tert-Butyl 4-[6-[(1E)-3-[(tert-butyldimethylsilyl)oxy] prop-1-en-1-yl]-3(4H)-oxo-4-[[2-(trimethylsilyl)ethoxy] methyl]-pyrazin-2-yl]piperazine-1-carboxylate The procedure for preparing Intermediate 3-3 was used with the product from the previous step (4 g, 8.17 mmol). The crude product was purified with silica gel chromatography using EtOAc/petroleum ether (1:50) to afford 1.5 g (32%) of the title compound as a light yellow oil.

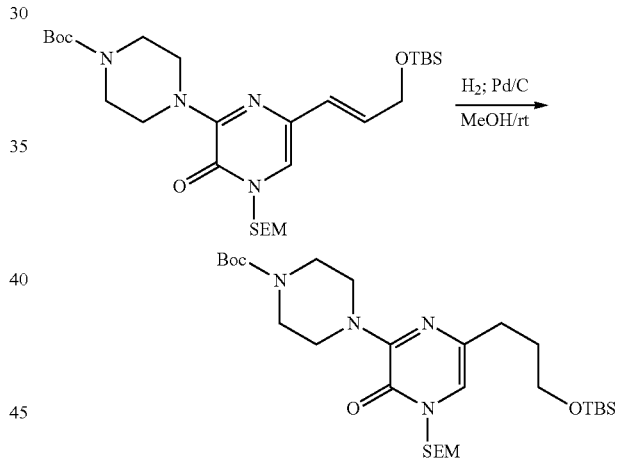

tert-butyl 4-(6-[3-[(tert-butyldimethylsilyl)oxy]propyl]-3 (4H)-oxo-4-[[2-(trimethylsilyl)ethoxy]methyl]-pyrazin-2-yl)piperazine-1-carboxylate The procedure for preparing of Intermediate 3-4 was used with the product from the previous step (1.5 g, 2.58 mmol, 1.00 equiv) to afford 1.0 g (66%) of the title compound as a light yellow oil.

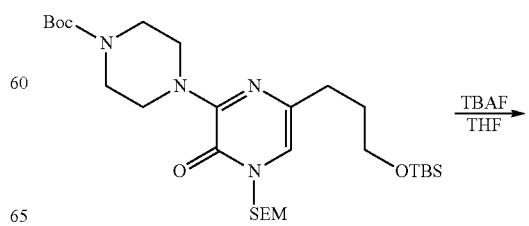

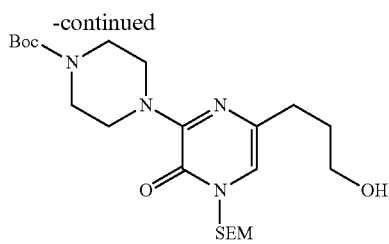

tert-Butyl 4-[6-(3-hydroxypropyl)-3(4H)-oxo-4-[[2-(trimethylsilyl)ethoxy]-methyl]-pyrazin-2-yl]piperazine-1-carboxylate The procedure for preparing Intermediate 22-4 was used with the product from the previous step (1 g, 1.72 mmol, 1.00 equiv) to afford 0.6 g (75%) of the title compound as a light yellow oil.

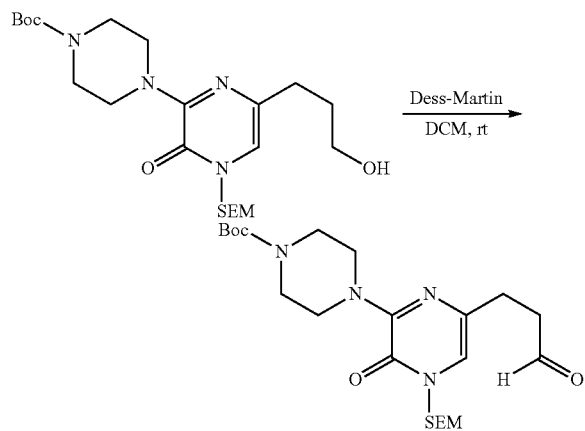

tert-Butyl 4-[3(4H)-oxo-6-(3-oxopropyl)-4-[[2-(trimethylsilyl)ethoxy]methyl]-pyrazin-2-yl]piperazine-1-carboxylate The procedure for preparing Intermediate 1-7 was used with the product from the previous step (600 mg, 1.28 mmol, 1.00 equiv) to afford 0.3 g (50%) of the title compound as a light yellow solid.

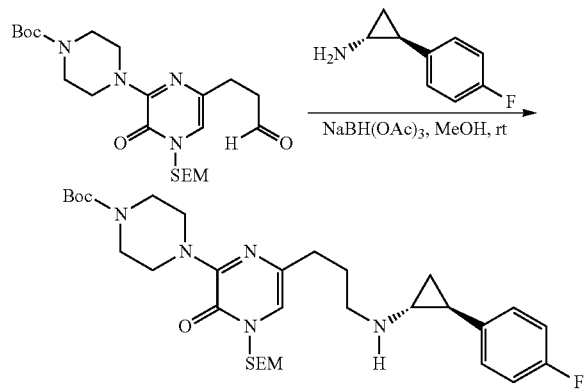

tert-Butyl 4-[6-(3-[[(1R,2S)-2-(4-fluorophenyl)cyclopropyl]amino]propyl)-3(4H)-oxo-4-[[2-(trimethylsilyl)ethoxy]methyl]-pyrazin-2-yl]piperazine-1-carboxylate The procedure for preparing Intermediate 4-7 was used with the product from the previous step (300 mg, 0.64 mmol), affording 0.2 g (52%) of the title compound as a light yellow oil. The product was carried forward without further purification.

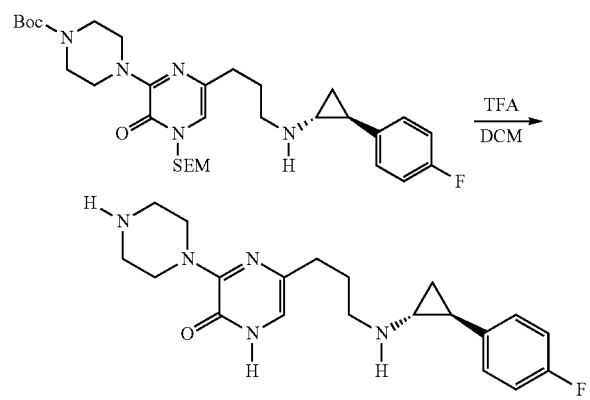

5-[3-([(1R,2S)-2-(4-fluorophenyl)cyclopropyl]amino)propyl]-3-[piperazin-1-yl]pyrazin-2(1H)-one The deprotection step for preparing Example 14 from Intermediate 14-7 was used with the product from the previous step (200 mg, 0.17 mmol, 1.00 equiv). The crude product (5 mL) was purified using chromatographic Procedure B (30.0% to 50.0% CH$_3$CN in 8 min), to afford 114.6 mg (45%) of the title compound as a light yellow oil.

LC-MS: (ES, m/z): 372 [M+H]$^+$. $^1$H NMR (300 MHz, MeOD-d$_4$) δ ppm: 7.23-7.07 (m, 2H), 7.07-6.93 (m, 2H), 6.82-6.69 (s, 1H), 4.02-3.89 (m, 4H), 3.28-3.14 (m, 6H), 2.99-2.81 (m, 1H), 2.66-2.31 (m, 3H), 2.13-1.89 (m, 2H), 1.60-1.41 (m, 1H), 1.41-1.22 (m, 1H).

Example 32

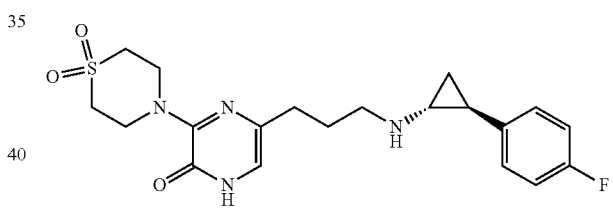

3-[1,1-Dioxidothiomorpholino]-5-[3-([(1R,2S)-2-(4-fluorophenyl)cyclopropyl]amino)propyl]pyrazin-2(1H)-one

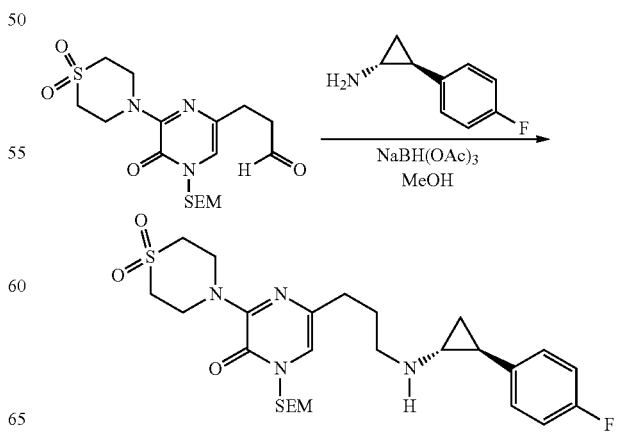

5-(3-[[(1R,2S)-2-(4-Fluorophenyl)cyclopropyl]amino]propyl)-3-(1,1-dioxothiomorpholin-4-yl)-1-[[2-(trimethylsilyl)ethoxy]methyl]-pyrazin-2(1H)-one The reductive amination step for preparing Example 1 from Intermediate 1-7 was used with Intermediate 8-6 (150 mg, 0.36 mmol, 1 equiv) and (1R,2S)-2-(4-fluorophenyl)-cyclopropan-1-amine (109 mg, 0.72 mmol). The crude product was purified with silica gel chromatography using EtOAc/petroleum ether (3:2) to afford 140 mg (70.46%) of the title compound as an orange oil.

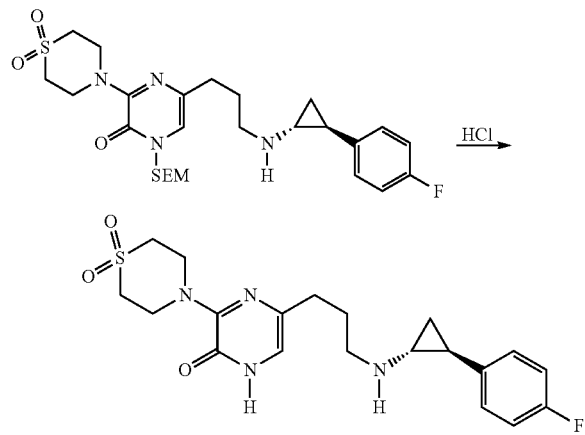

3-[1,1-Dioxidothiomorpholino]-5-[3-([(1R,2S)-2-(4-fluorophenyl)cyclopropyl]-amino)propyl]pyrazin-2(1H)-one
The deprotection step for preparing Example 2 from Intermediate 2-7 was used with the product from the previous step (140 mg, 0.25 mmol, 1 equiv). The crude product (5 mL) was purified using chromatographic Procedure C (20.0% to 50.0% CH₃CN in 8 min), to afford 61 mg (28%) of the title compound as a white solid.

LC-MS: (ES, m/z): 421 [M+H]⁺. ¹H NMR (300 MHz, MeOD-d₄) δ ppm: 7.04-6.95 (m, 2H), 6.93-6.89 (m, 2H), 6.66 (s, 1H), 4.29-4.25 (m, 4H), 3.13-3.09 (m, 4H), 2.74-2.68 (m, 2H), 2.46-2.41 (m, 2H), 2.29-2.24 (m, 1H), 1.92-1.80 (m, 3H), 1.06-0.92 (m, 2H).

Example 33

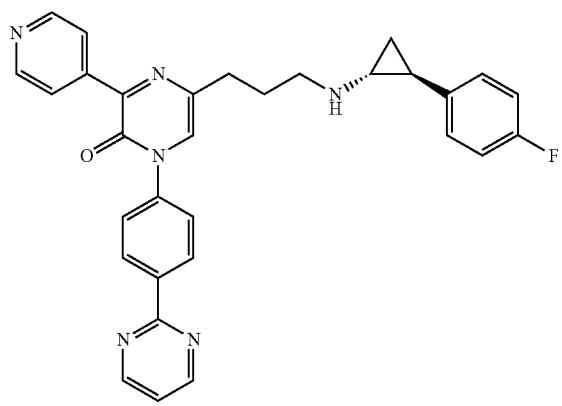 [SMILES: O=c1c(-c2ccncc2)nc(CCCN[C@@H]2C[C@H]2c2ccc(F)cc2)cn1-c1ccc(-c2ncccn2)cc1]

5-[3-([(1R,2S)-2-(4-Fluorophenyl)cyclopropyl]amino)propyl]-3-(pyridin-4-yl)-1-[4-(pyrimidin-2-yl)phenyl]pyrazin-2(1H)-one

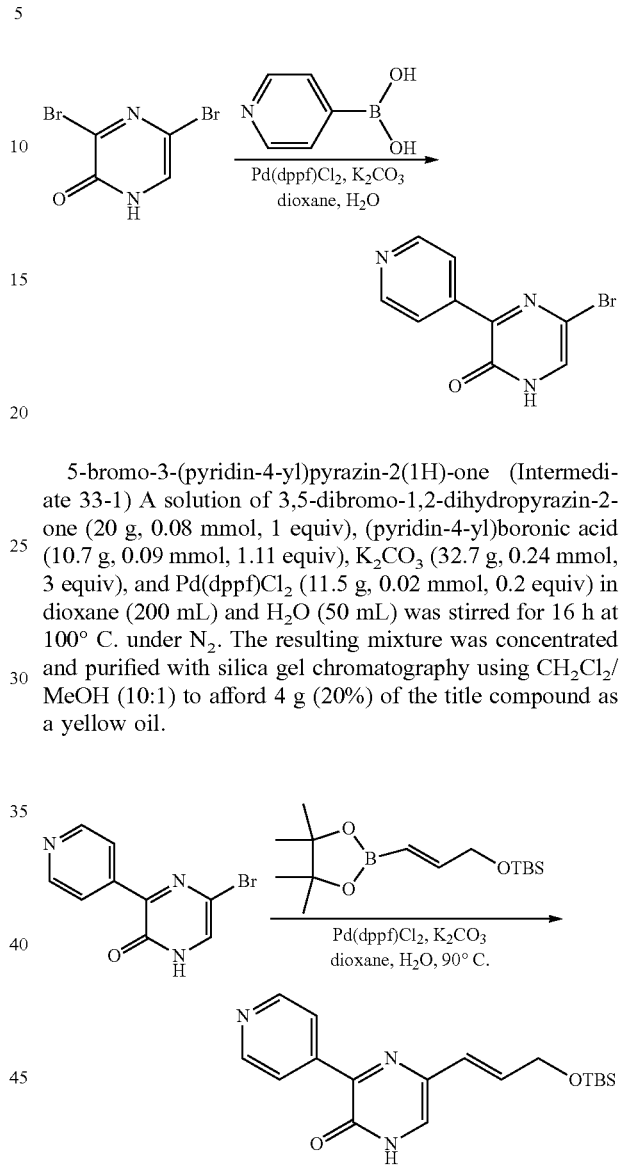

5-bromo-3-(pyridin-4-yl)pyrazin-2(1H)-one (Intermediate 33-1) A solution of 3,5-dibromo-1,2-dihydropyrazin-2-one (20 g, 0.08 mmol, 1 equiv), (pyridin-4-yl)boronic acid (10.7 g, 0.09 mmol, 1.11 equiv), K₂CO₃ (32.7 g, 0.24 mmol, 3 equiv), and Pd(dppf)Cl₂ (11.5 g, 0.02 mmol, 0.2 equiv) in dioxane (200 mL) and H₂O (50 mL) was stirred for 16 h at 100° C. under N₂. The resulting mixture was concentrated and purified with silica gel chromatography using CH₂Cl₂/MeOH (10:1) to afford 4 g (20%) of the title compound as a yellow oil.

(E)-5-(3-((tert-butyldimethylsilyl)oxy)prop-1-en-1-yl)-3-(pyridin-4-yl)pyrazin-2(1H)-one (Intermediate 33-2) The procedure for preparing Intermediate 3-3 was used with Intermediate 33-1 (4 g, 15.87 mmol). The crude product was purified with silica gel chromatography using CH₂Cl₂/MeOH (10:1) to afford 1.5 g (28%) of the title compound as a yellow solid.

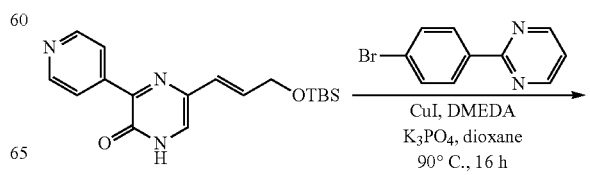

-continued

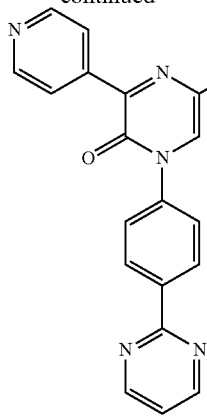

(E)-5-(3-((tert-butyldimethylsilyl)oxy)prop-1-en-1-yl)-3-(pyridin-4-yl)-1-(4-(pyrimidin-2-yl)phenyl)pyrazin-2(1H)-one (Intermediate 33-3) The procedure for preparing Intermediate 13-1 was used with Intermediate 33-2 (1.5 g, 4.37 mmol, 1 equiv) and 2-(4-bromophenyl)pyrimidine (1.23 g, 5.24 mmol, 1.200 equiv). The crude product was purified with silica gel chromatography using EtOAc/petroleum ether (1:1) to afford 800 mg (37%) of the title compound as a yellow solid.

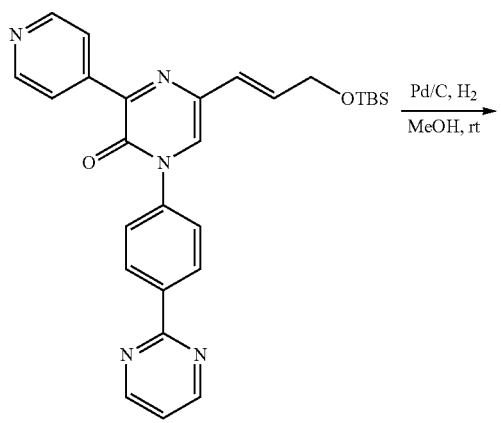

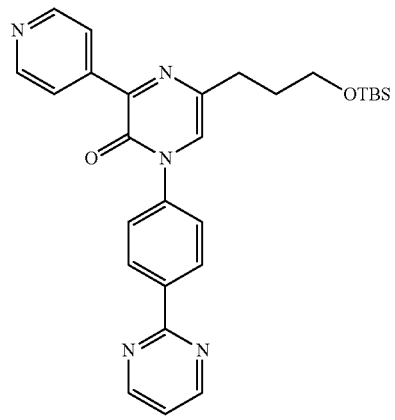

5-(3-((tert-Butyldimethylsilyl)oxy)propyl)-3-(pyridin-4-yl)-1-(4-(pyrimidin-2-yl)phenyl)pyrazin-2(1H)-one (Intermediate 33-4) A solution of Intermediate 33-3 (600 mg, 1.15 mmol, 1 equiv) in MeOH (20 mL) was stirred over Pd/C (59.7 mg, 0.56 mmol, 0.49 equiv) under an H₂ atmosphere for 60 min at rt. The product was filtered, and the filtrate was concentrated to afford 400 mg (70%) of the title compound as a yellow solid.

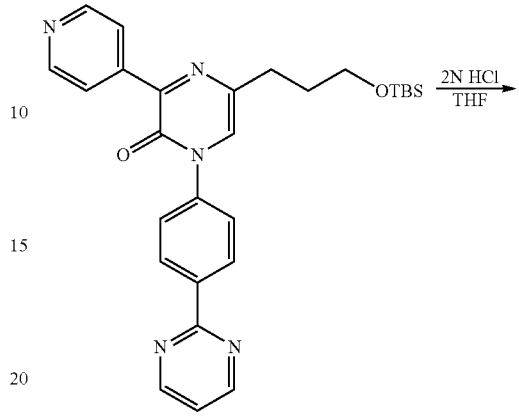

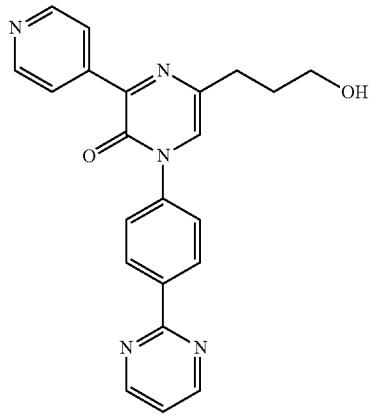

5-(3-Hydroxypropyl)-3-(pyridin-4-yl)-1-(4-(pyrimidin-2-yl)phenyl)pyrazin-2(1H)-one (Intermediate 33-5) A solution of Intermediate 33-4 (400 mg, 0.18 mmol), in HCl (2N, 4 mL) and THF (8 mL) was stirred for 60 min at rt. The pH was adjusted to 7 with Na₂CO₃. The resulting solution was extracted with 3×30 mL of CH₂Cl₂. The combined organic layers were concentrated to afford 210 mg (88%) of the title compound as a yellow oil.

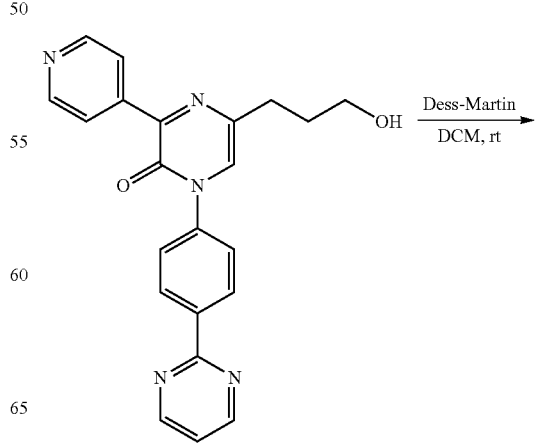

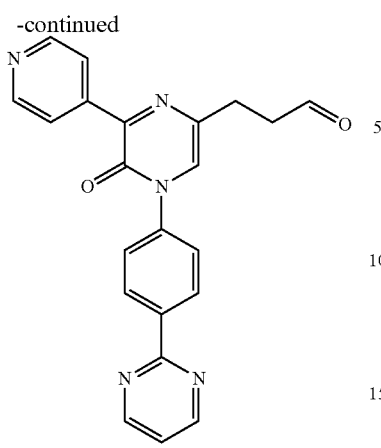

3-(5-Oxo-6-(pyridin-4-yl)-4-(4-(pyrimidin-2-yl)phenyl)-4,5-dihydropyrazin-2-yl)propanal The procedure for preparing Intermediate 1-7 was used with Intermediate 33-5 (210 mg, 0.54 mmol, 1 equiv) and Dess-Martin reagent (346.6 mg, 0.82 mmol, 1.5 equiv). The crude product was purified with silica gel chromatography using EtOAc/petroleum ether (1:1) to afford 140 mg (67%) of the title compound as a yellow solid.

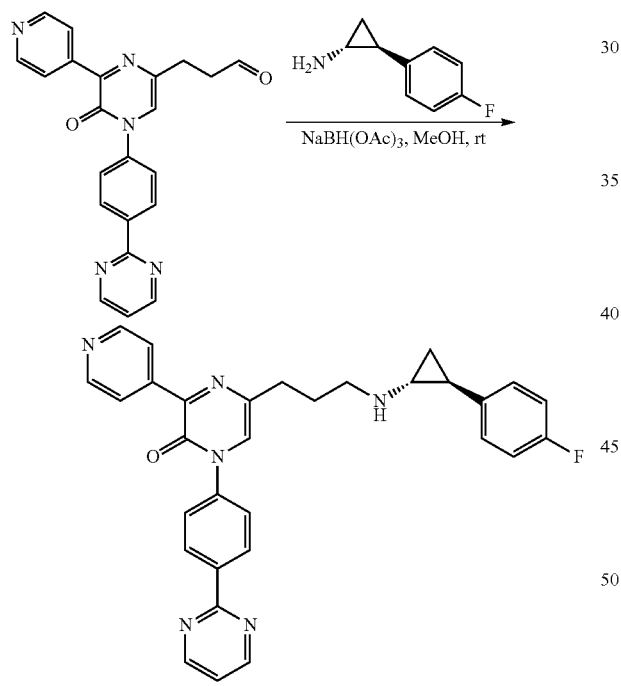

5-[3-([(1R,2S)-2-(4-fluorophenyl)cyclopropyl]amino)propyl]-3-(pyridin-4-yl)-1-[4-(pyrimidin-2-yl)phenyl]pyrazin-2(1H)-one The reductive amination step for preparing Example 1 from Intermediate 1-7 was used with the product from the previous step (140 mg, 0.37 mmol, 1 equiv) and (1R,2S)-2-(4-fluorophenyl)cyclopropan-1-amine (99.4 mg, 0.66 mmol, 1.8 equiv). The crude product was purified using chromatographic Procedure E (42% to 45% CH₃CN in 7 min), to afford 49.2 mg (25.98%) of the title compound as a yellow solid.

LCMS: (ES, m/z): 519 [M+H]⁺. ¹H NMR (300 MHz, Methanol-d₄) δ ppm: 8.92-8.90 (d, J=4.8 Hz, 2H), 8.75-8.64 (m, 5H), 8.77-8.33 (m, 2H), 7.74-7.61 (t, J=8.7 Hz, 3H), 7.49-7.34 (t, J=4.8 Hz, 1H), 7.11-6.68 (m, 4H), 2.90-2.81 (t, J=7.35 Hz, 2H), 2.81-2.71 (t, J=7.35 Hz, 2H), 2.39-2.29 (m, 1H), 2.1-1.88 (m, 3H), 1.16-0.94 (m, 2H).

Example 34

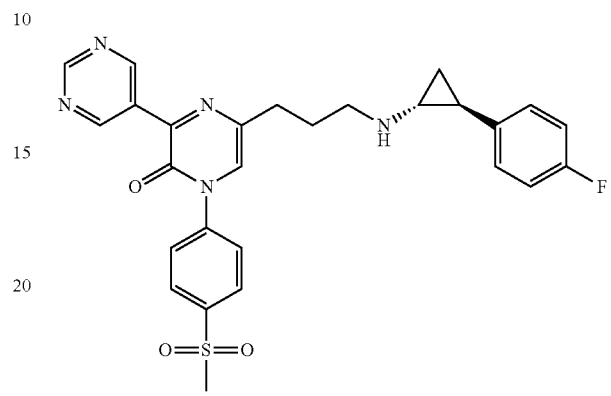

5-[3-([(1R,2S)-2-(4-fluorophenyl)cyclopropyl]amino)propyl]-1-[4-(methylsulfonyl)phenyl]-3-(pyrimidin-5-yl)pyrazin-2(1H)-one

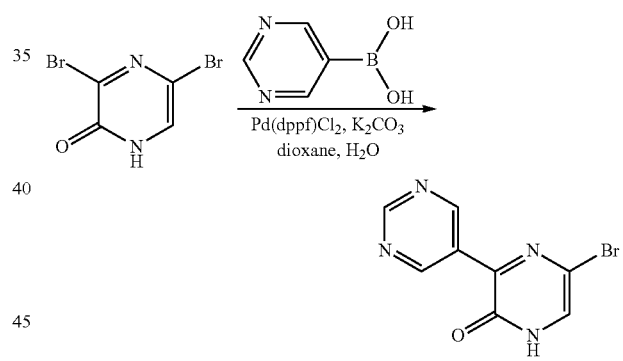

5-bromo-3-(pyrimidin-5-yl)pyrazin-2(1H)-one (Intermediate 34-1) A solution of 3,5-dibromo-1,2-dihydropyrazin-2-one (20 g, 78.78 mmol, 1 equiv), K₂CO₃ (32.7 g, 236.60 mmol, 3.003 equiv), (pyrimidin-5-yl)boronic acid (14.6 g, 117.83 mmol, 1.496 equiv), and Pd(dppf)Cl₂ (5.8 g, 7.93 mmol, 0.101 equiv) in dioxane (200 mL) and H₂O (20 mL) was stirred for 2 hr at 90° C., then concentrated to afford 8 g (40%) of the title compound as a light yellow oil.

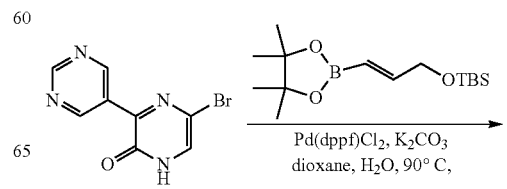

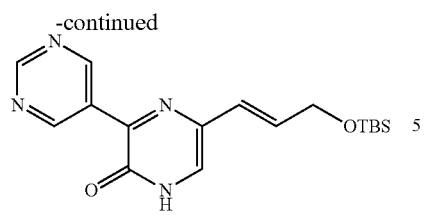

(E)-5-(3-((tert-butyldimethylsilyl)oxy)prop-1-en-1-yl)-3-(pyrimidin-5-yl)pyrazin-2(1H)-one (Intermediate 32-2) The procedure for preparing Intermediate 3-3 was used with the product from the previous step (4.5 g, 17.78 mmol). The Crude product was purified with silica gel chromatography using EtOAc/petroleum ether (4:1) to afford 3.8 g (61.99%) of the title compound as a yellow oil.

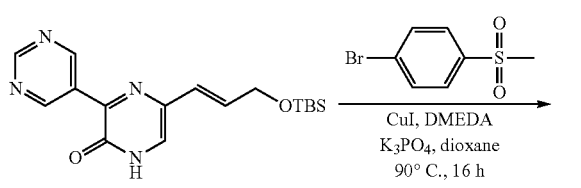

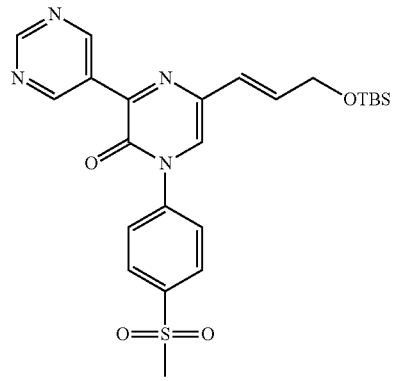

(E)-5-(3-((tert-butyidimethylsilyl)oxy)prop-1-en-1-yl)-1-(4-(methylsulfonyl)-phenyl)-3-(pyrimidin-5-yl)pyrazin-2(1H)-one A solution of product from the previous step (3.8 g, 11.03 mmol 1 equiv), 1-bromo-4-methanesulfonylbenzene (3.9 g, 16.55 mmol, 1.5 equiv). CuI (2.1 g, 11.03 mmol, 1 equiv), DMEDA (0.9 g, 22.06 mmol, 2 equiv), and $K_3PO_4$ (7.0 g, 33.09 mmol, 3 equiv) in dioxane (50 mL) was stirred for 16 hr at 90° C., then concentrated and purified with silica gel chromatography using $CH_2Cl_2$/MeOH (1:10). A second batch was submitted to the same reaction and purification conditions to afford an overall yield of 800 mg (7.3%) of the title compound as a light yellow solid.

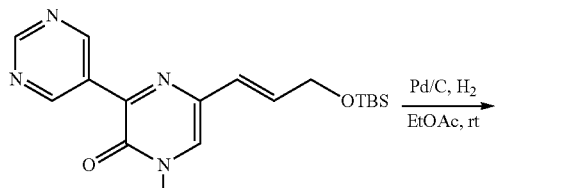

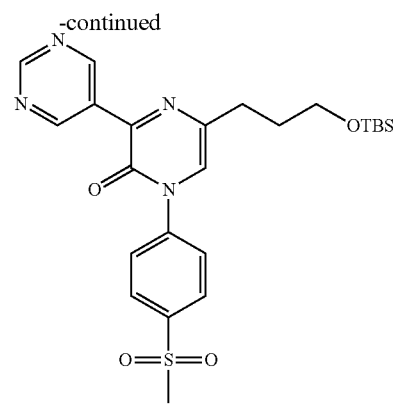

5-(3-((tert-Butyldimethylsilyl)oxy)propyl)-1-(4-(methylsulfonyl)phenyl)-3-(pyrimidin-5-yl)pyrazin-2(1H)-one The procedure for preparing Intermediate 3-4 was used with the product from the previous step (800 mg, 0.40 mmol, 1 equiv) to afford 600 mg (79.6%) of the title compound as a light yellow solid.

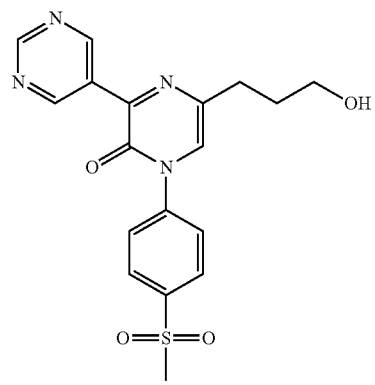

5-(3-Hydroxypropyl)-1-(4-(methylsulfonyl)phenyl)-3-(pyrimidin-5-yl)pyrazin-2(1H)-one The procedure for preparing Intermediate 33-5 was used with the product from the previous step (600 mg). The crude product was purified with silica gel chromatography using $CH_2Cl_2$/MeOH (1:10) to afford 300 mg (64.7%) of the title compound as a light yellow solid.

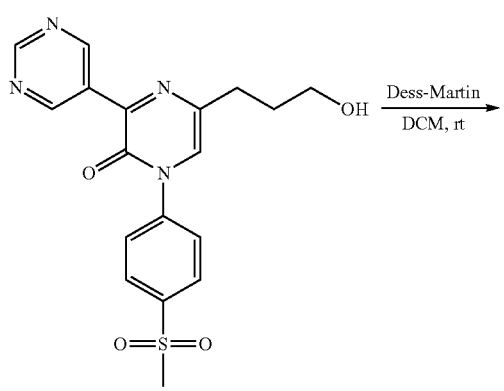

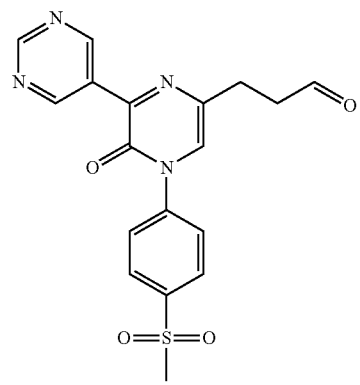

3-(4-(4-(Methylsulfonyl)phenyl)-5-oxo-6-(pyrimidin-5-yl)-4,5-dihydropyrazin-2-yl)propanal The procedure for preparing Intermediate 1-7 was used with the product from the previous step (300 mg, 0.77 mmol, 1 equiv) and Dess-Martin reagent (394.4 mg, 0.93 mmol, 1.2 equiv). The crude product was purified with silica gel chromatography using CH$_2$Cl$_2$/MeOH (1:10) to afford 200 mg (67.45%) of the title compound as a light yellow solid.

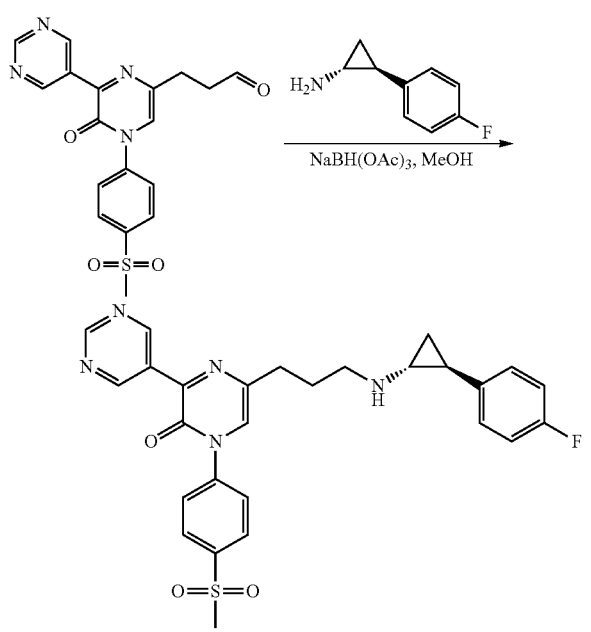

5-[3-([(1R,2S)-2-(4-fluorophenyl)cyclopropyl]amino) propyl]-1-[4-(methyl-sulfonyl)phenyl]-3-(pyrimidin-5-yl) pyrazin-2(1H)-one The procedure for preparing Intermediate 4-7 was used with the product from the previous step (200 mg, 0.52 mmol, 1 equiv) and (1R,2S)-2-(4-fluorophenyl)cyclopropan-1-amine (1180 mg, 0.78 mmol, 1.5 equiv). The crude product was purified using chromatographic Procedure F (18% to 28% CH$_3$CN in 7 min), to afford 20.9 mg (7.7%) of the title compound as a light yellow solid.

LC-MS: (ES, m/z): 520 [M+H]$^+$ $^1$H NMR (300 MHz, MeOD-d$_4$) δ ppm: 9.67 (s, 2H), 9.21 (s, 1H), 8.19-8.16 (d, J=9.0 Hz, 2H), 7.84-7.81 (d, J=9.0 Hz, 2H), 7.63 (s, 1H), 7.20-7.16 (m, 2H), 7.04-6.99 (m, 2H), 3.36-3.30 (m, 2H), 3.20 (s, 3H), 3.17-2.98 (m, 1H), 2.85-2.80 (m, 2H), 2.49-2.44 (m, 1H), 2.24-2.19 (m, 2H), 1.50-1.37 (m, 2H).

Example 35

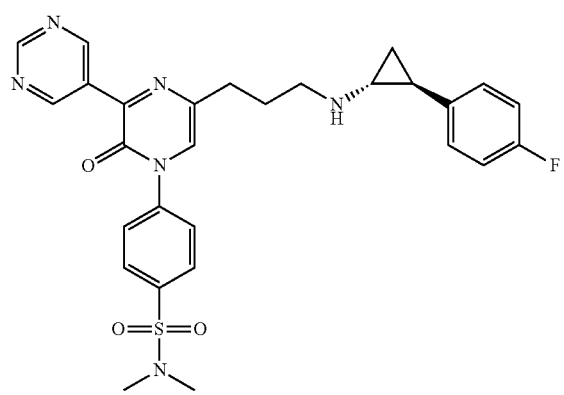 [SMILES: CN(C)S(=O)(=O)c1ccc(-n2cc(CCCN[C@@H]3C[C@H]3c3ccc(F)cc3)nc(-c3cncnc3)c2=O)cc1]

4-[5-(3-[[(1R,2S)-2-[4-fluorophenyl]cyclopropyl) amino]propyl)-2-oxo-3-(pyrimidin-5-yl)pyrazin-1 (2H)-yl]-N,N-dimethylbenzenesulfonamide

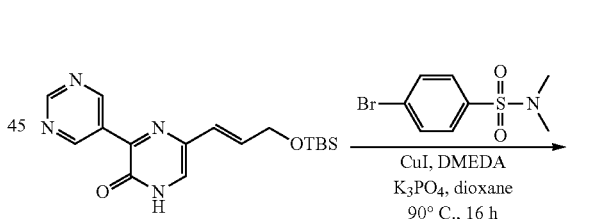

(E)-4-(5-(3-((tert-butyldimethylsilyl)oxy)prop-1-en-1-yl)-2-oxo-3-(pyrimidin-5-yl)pyrazin-1(2H)-yl)-N,N-dimethylbenzenesulfonamide The procedure for preparing Intermediate 13-1 was used with Intermediate 34-2 (2.6 g, 7.55 mmol, 1 equiv) and 4-bromo-N,N-dimethylbenzene-1-sulfonamide (3.0 g, 11.32 mmol, 1.5 equiv). The crude product was purified with silica gel chromatography using EtOAc/petroleum ether (2:1) to afford 550 mg (10.13%) of the title compound as a light yellow oil.

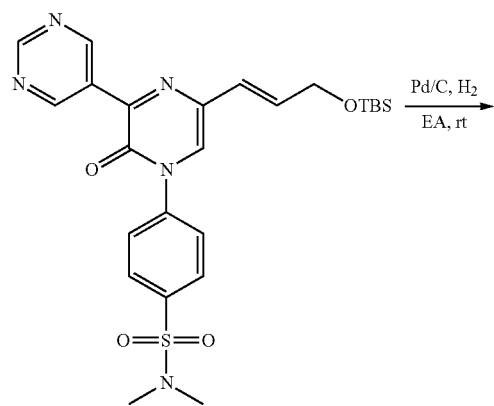

4-(5-(3-((tert-Butyldimethylsilyl)oxy)propyl)-2-oxo-3-(pyrimidin-5-yl)pyrazin-1(2H)-yl)-N,N-dimethylbenzenesulfonamide The procedure for preparing Intermediate 3-4 was used with the product from the previous step (550 mg, 1.04 mmol, 1 equiv) to afford 420 mg (76.07%) of the title compound as a light yellow oil.

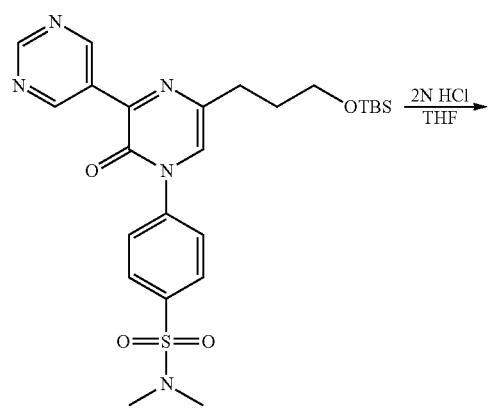

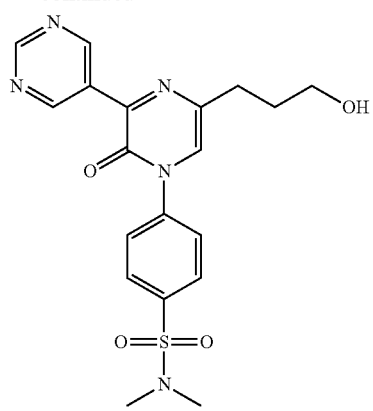

4-(5-(3-Hydroxypropyl)-2-oxo-3-(pyrimidin-5-yl)pyrazin-1(2H)-yl)-N,N-dimethylbenzenesulfonamide The procedure for preparing Intermediate 33-5 was used with the product from the previous step (420 mg, 0.79 mmol, 1 equiv) to afford 180 mg (55%) of the title compound as a light yellow oil.

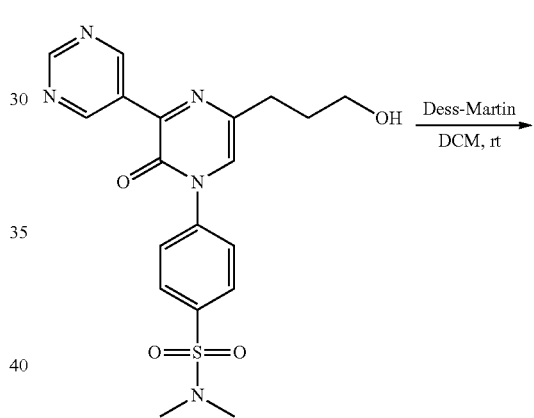

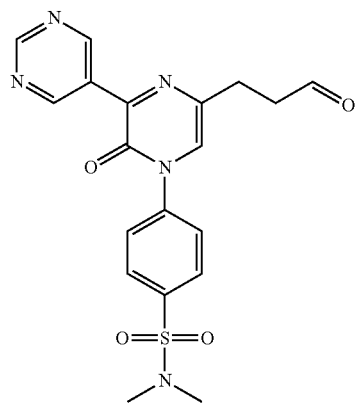

N,N-Dimethyl-4-(2-oxo-5-(3-oxopropyl)-3-(pyrimidin-5-yl)pyrazin-1(2H)-yl)benzenesulfonamide The procedure for preparing Intermediate 1-7 was used with the product from the previous step (180 mg, 0.43 mmol, 1 equiv) and Dess-Martin reagent (220.5 mg, 0.52 mmol, 1.20 equiv). The crude product was purified with silica gel chromatography using CH$_2$Cl$_2$/MeOH (40:1) to afford 120 mg (67%) of the title compound as a light yellow oil.

191

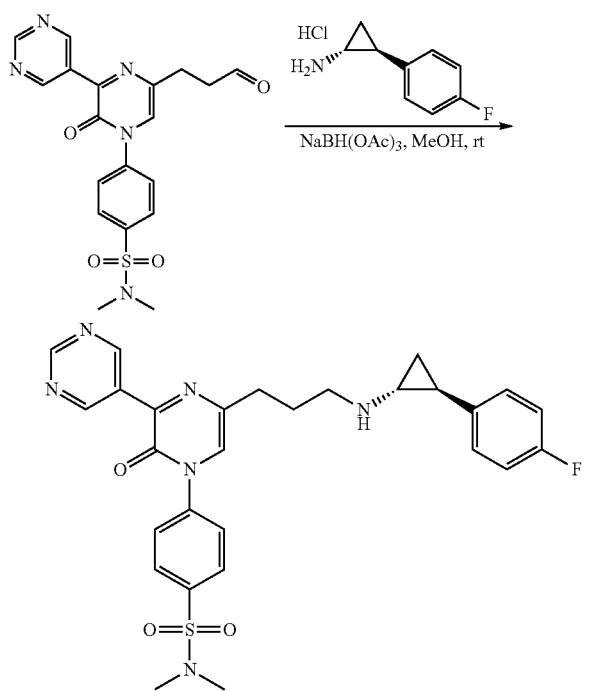

4-(5-(3-(((1R,2S)-2-(4-fluorophenyl)cyclopropyl)amino) propyl)-2-oxo-3-(pyrimidin-5-yl)pyrazin-1(2H)-yl)-N,N-dimethylbenzenesulfonamide The procedure for preparing Intermediate 4-7 was used with the product from the previous step (120 mg, 0.29 mmol, 1 equiv) and (1R,2S)-2-(4-fluorophenyl)cyclopropan-1-amine (52.9 mg, 0.35 mmol, 1.2 equiv). The crude product was purified using chromatographic Procedure A (15% to 45% $CH_3CN$), to afford 13.3 mg (5.57%) of the title compound as a colorless solid.

LC-MS: (ES, m/z): 549 [M+H]$^+$. $^1$H NMR (300 MHz, MeOD-d$_4$) δ ppm: 9.67 (s, 2H), 9.21 (s, 1H), 8.19-8.16 (d, J=9.0 Hz, 2H), 7.84-7.81 (d, J=9.0 Hz, 2H), 7.63 (s, 1H), 7.20-7.16 (m, 2H), 7.04-6.99 (m, 2H), 3.36-3.30 (m, 2H), 3.29-3.21 (m, 3H), 3.17-2.98 (m, 1H), 2.85-2.80 (m, 2H), 2.78 (s, 6H), 2.49-2.44 (m, 1H), 2.24-2.19 (m, 2H), 1.50-1.37 (m, 2H).

Example 36

192

1-[4-fluorophenyl]-5-[3-([(1R,2S)-2-(4-fluorophenyl)cyclopropyl]amino)propyl]-3-[1H-pyrazol-4-yl] pyrazin-2(1H)-one 5-Bromo-3-(1-(4-methoxybenzyl)-1H-pyrazol-4-yl) pyrazin-2(1H)-one A solution of 3,5-dibromo-1,2-dihydropyrazin-2-one (4.8 g, 19.10 mmol, 1 equiv), 1-[(4-methoxyphenyl)methyl]-4-(4,4,5,5-tetramethyl-1,3,2-dioxaborolan-2-yl)-1H-pyrazole (6 g, 19.10 mmol, 1 equiv), $K_2CO_3$ (7.9 g, 57.29 mmol, 3 equiv), and Pd(dppf)Cl$_2$ (1.4 g, 1.91 mmol, 0.1 equiv) in dioxane (100 mL) and $H_2O$ (10 mL) was stirred for 4 hr under $N_2$ at 90° C. The resulting mixture was concentrated under vacuum and purified with silica gel chromatography using $CH_2Cl_2$/MeOH (30:1) to afford 2.4 g (34.8%) of the title compound as a yellow oil.

5-Bromo-1-(4-fluorophenyl)-3-(1-(4-methoxybenzyl)-1H-pyrazol-4-yl)pyrazin-2(1H)-one A solution of the product from the previous step (2.4 g, 6.64 mmol, 1 equiv), (4-fluorophenyl)boronic acid (1.9 g, 13.29 mmol, 2.00 equiv), TEA (1.3 g, 13.29 mmol, 2 equiv), and Cu(OAc)$_2$ (1.8 g, 9.97 mmol, 1.5 equiv) in $CH_2Cl_2$ (50 mL) was stirred for 16 hr at rt, then concentrated under vacuum and purified with silica gel chromatography using $CH_2Cl_2$/MeOH (50:1) to afford 1.4 g (46.3%) of the title compound as a yellow oil.

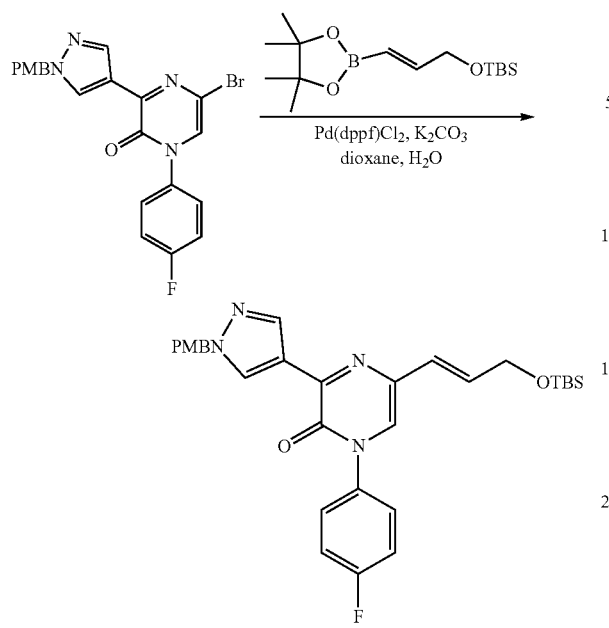

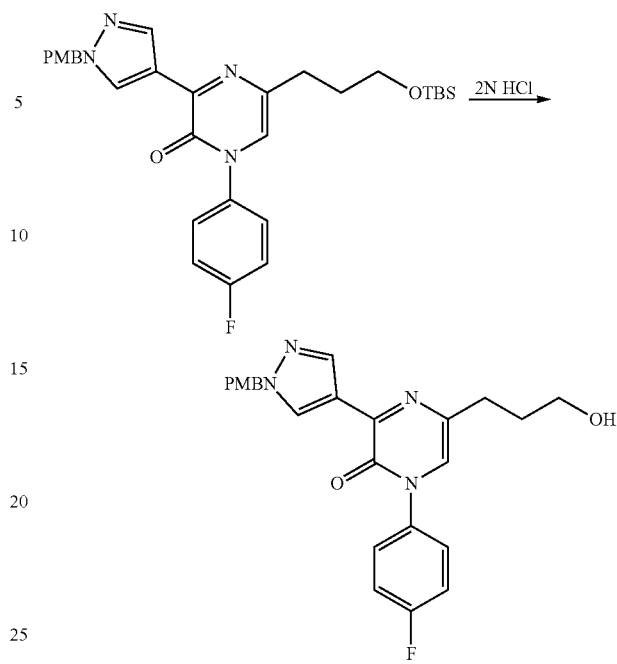

(E)-5-(3-((tert-butyldimethylsilyl)oxy)prop-1-en-1-yl)-1-(4-fluorophenyl)-3-(1-(4-methoxybenzyl)-1H-pyrazol-4-yl)pyrazin-2(1H)-one The procedure for preparing Intermediate 3-3 was used with the product from the previous step (1.3 g, 2.86 mmol). The crude product was purified with silica gel chromatography using CH$_2$Cl$_2$/MeOH (20:1) to afford 1 g (64%) of the title compound as a yellow oil.

1-(4-Fluorophenyl)-5-(3-hydroxypropyl)-3-(1-(4-methoxybenzyl)-1H-pyrazol-4-yl)pyrazin-2(1H)-one A solution of the product from the previous step (800 mg, 1.46 mmol, 1 equiv) and HCl (2 mL, 4 M in dioxane) in dioxane (2 mL) was stirred for 2 hr at rt, then concentrated under vacuum to afford 400 mg (63.2%) of the title compound as a yellow oil.

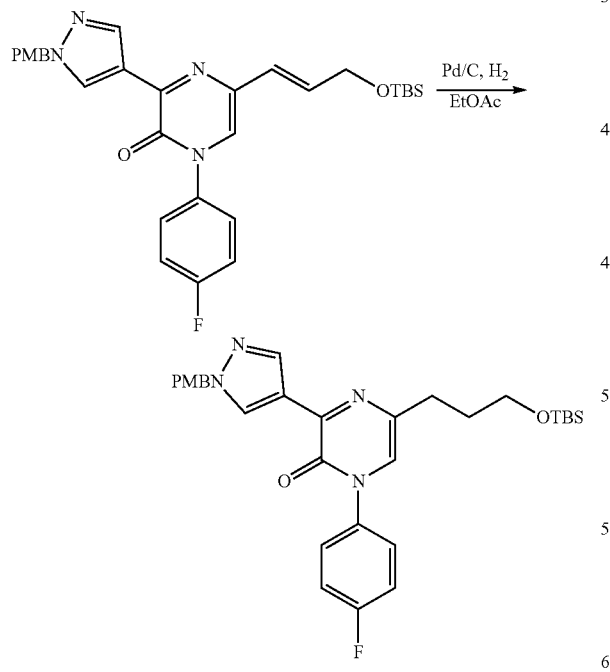

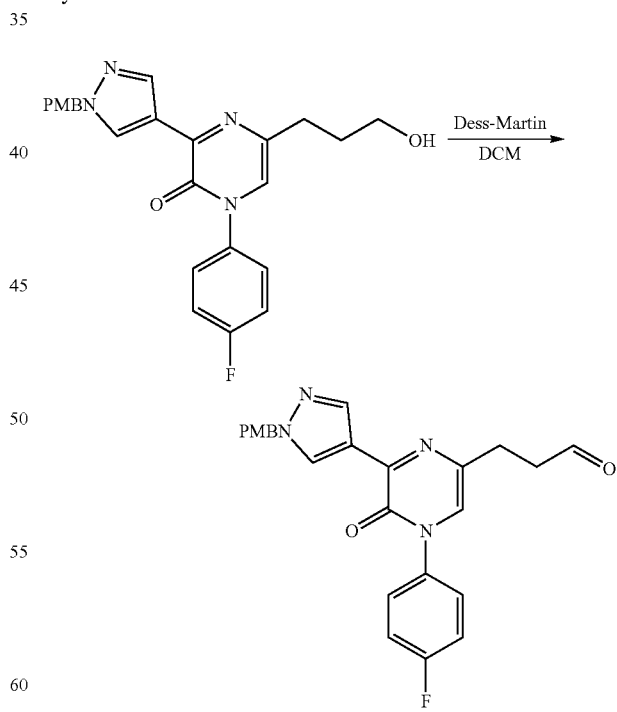

5-(3-((tert-Butyldimethylsilyl)oxy)propyl)-1-(4-fluorophenyl)-3-(1-(4-methoxybenzyl)-1H-pyrazol-4-yl)pyrazin-2(1H)-one The procedure for preparing Intermediate 3-4 was used with the product from the previous step (1 g, 1.83 mmol, 1 equiv) to afford 900 mg (90%) of the title compound as a yellow oil.

3-(4-(4-Fluorophenyl)-6-(1-(4-methoxybenzyl)-1H-pyrazol-4-yl)-5-oxo-4,5-dihydropyrazin-2-yl)propanal The procedure for preparing Intermediate 1-7 was used with the product from the previous step (350 mg, 0.81 mmol, 1 equiv) and Dess-Martin reagent (410.0 mg, 0.97 mmol, 1.2 equiv), with 4 hr reaction time. The crude product was purified with silica gel chromatography using CH$_2$Cl$_2$/MeOH (10:1) to afford 250 mg (71.8%) of the title compound as a yellow oil.

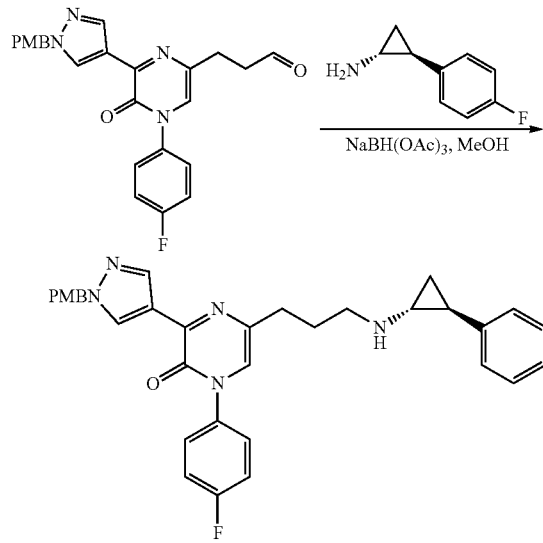

1-(4-Fluorophenyl)-5-(3-(((1R,2S)-2-(4-fluorophenyl)cyclopropyl)amino)propyl)-3-(1-(4-methoxybenzyl)-1H-pyrazol-4-yl)pyrazin-2(1H)-one The procedure for preparing Intermediate 4-7 was used with the product from the previous step (250 mg, 0.58 mmol, 1 equiv) and (1R,2S)-2-(4-fluorophenyl)cyclopropan-1-amine (104.9 mg, 0.69 mmol, 1.2 equiv), with 16 hr of reaction time. The crude product was purified with silica gel chromatography using CH$_2$Cl$_2$/MeOH (5:1) to afford 200 mg (61%) of the title compound as a yellow oil.

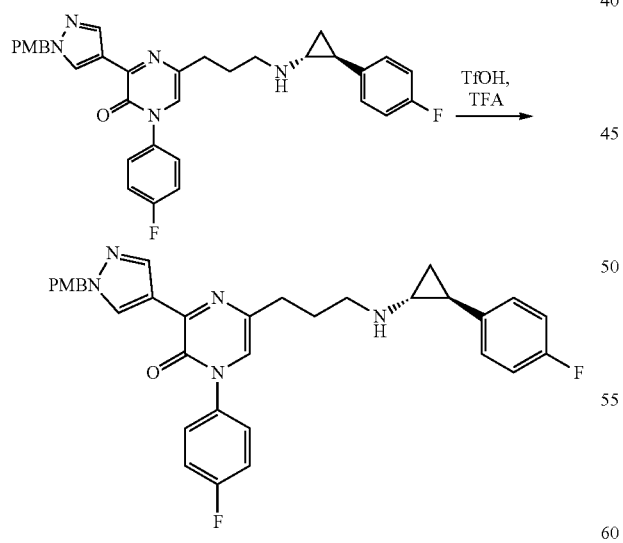

1-(4-Fluorophenyl)-5-(3-(((1R,2S)-2-(4-fluorophenyl)cyclopropyl)amino)propyl)-3-(1H-pyrazol-4-yl)pyrazin-2 (1H)-one A solution of the product from the previous step (200 mg, 0.35 mmol, 1 equiv) in a mixture of TFA (1 mL), TfOH (1 mL), and CH$_2$Cl$_2$ (5 mL) was stirred for 6 hr at rt. The resulting mixture was concentrated under vacuum. The crude product (200 mg) was purified using chromatographic Procedure F (25% to 35% CH$_3$CN in 7 min), to afford 18.6 mg (9.4%) of the title compound as a yellow solid.

LC-MS: (ES, m/z): 448 [M+H]$^+$ $^1$H NMR (300 MHz, MeOD-d$_4$) δ ppm: 8.47 (s, 2H), 7.57-7.52 (m, 2H), 7.36-7.30 (m, 3H), 7.22-7.17 (m, 2H), 7.06-7.01 (t, J=8.7 Hz, 2H), 3.37-3.34 (m, 2H), 3.03-2.98 (m, 1H), 2.79-2.71 (t, J=7.2 Hz, 2H), 2.51-2.44 (m, 1H), 2.36-2.18 (m, 2H), 1.54-1.47 (m, 1H), 1.43-1.31 (m, 1H).

Example 37

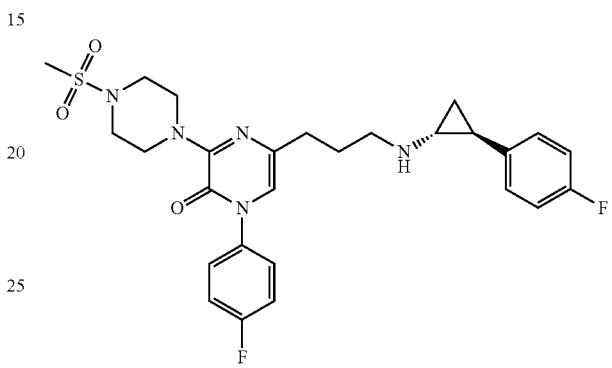

1-(4-Fluorophenyl)-5-(3-(((1R,2S)-2-(4-fluorophenyl)cyclopropyl)amino)propyl)-3-(4-(methylsulfonyl)piperazin-1-yl)pyrazin-2(1H)-one

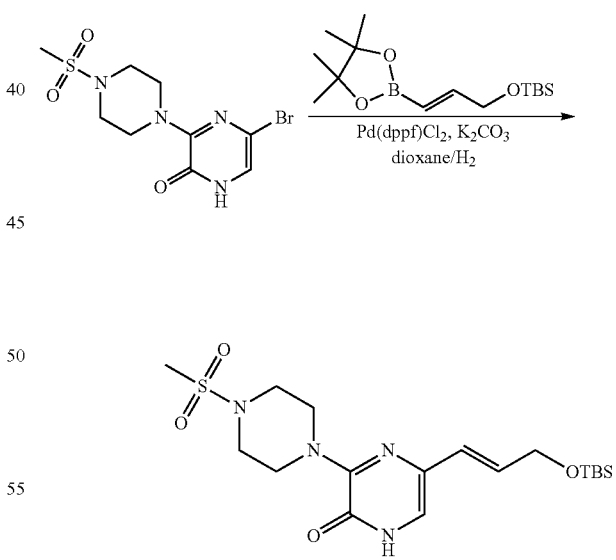

(E)-5-(3-((tert-butyldimethylsilyl)oxy)prop-1-en-1-yl)-3-(4-(methylsulfonyl)-piperazin-1-yl)pyrazin-2(1H)-one (Intermediate 37-1) The procedure for preparing Intermediate 3-3 was used with Intermediate 3-1 (10 g, 29.66 mmol) with 3 h reaction time at 90° C. The crude product was purified with silica gel chromatography using EtOAc/petroleum ether (1:1) to afford 2.8 g (22%) of the title compound as a yellow oil.

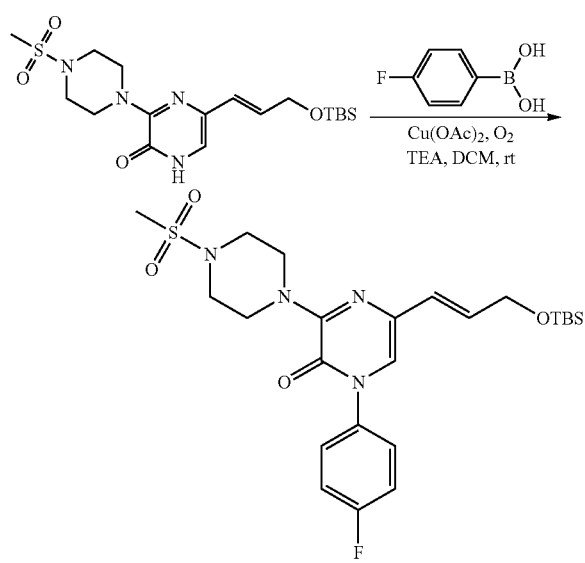

(E)-5-(3-((tert-butyldimethylsilyl)oxy)prop-1-en-1-yl)-1-(4-fluorophenyl)-3-(4-(methylsulfonyl)piperazin-1-yl)pyrazin-2(1H)-one The procedure for preparing Intermediate 8-9 was used with the product from the previous step and 4-fluorophenylboronic acid (1.1 g, 1.5 equiv). The crude product was purified with silica gel chromatography using EtOAc/petroleum ether (1:3) to afford 1.6 g (58%) of the title compound as a yellow oil.

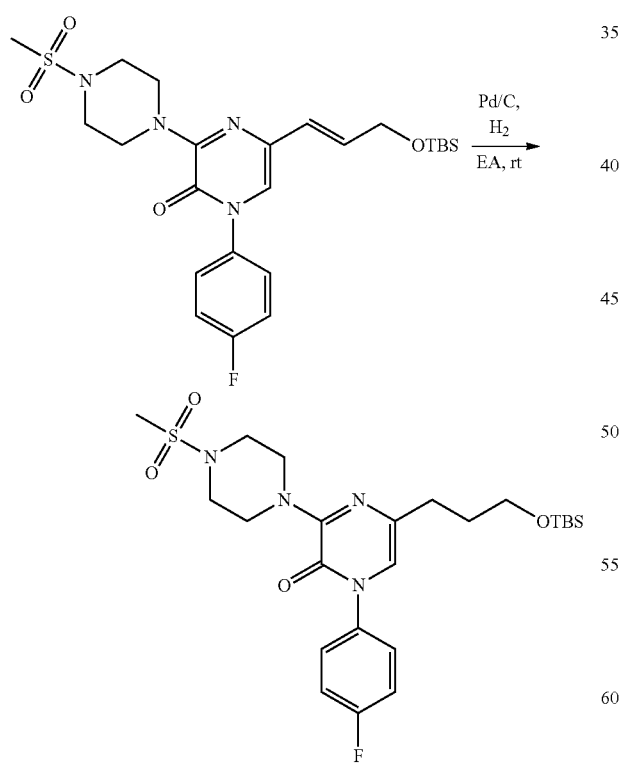

5-(3-((tert-Butyldimethylsilyl)oxy)propyl)-1-(4-fluorophenyl)-3-(4-(methyl-sulfonyl)piperazin-1-yl)pyrazin-2(1H)-one The procedure for preparing Intermediate 3-4 was used with the product from the previous step (1.6 g, 1.0 equiv) to afford 1 g (60%) of the title compound as a yellow oil.

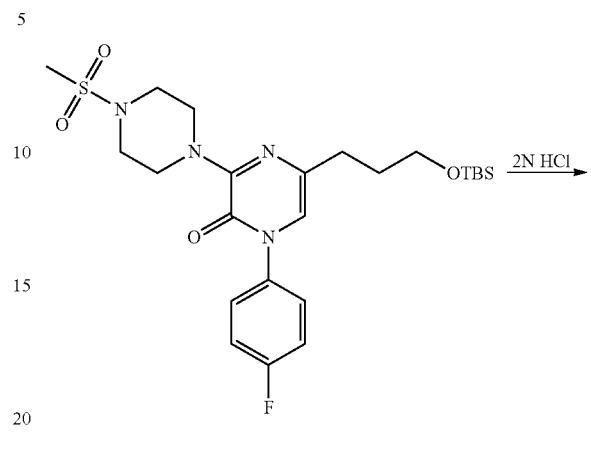

1-(4-Fluorophenyl)-5-(3-hydroxypropyl)-3-(4-(methyl-sulfonyl)piperazin-1-yl)pyrazin-2(1H)-one The procedure for preparing Intermediate 33-5 was used with the product from the previous step (1 g, 1.0 equiv). The crude product was purified with silica gel chromatography using EtOAc/petroleum ether (1:1) to afford 390 mg of the title compound as a yellow solid.

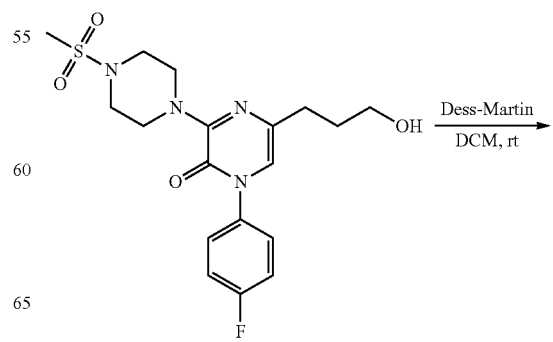

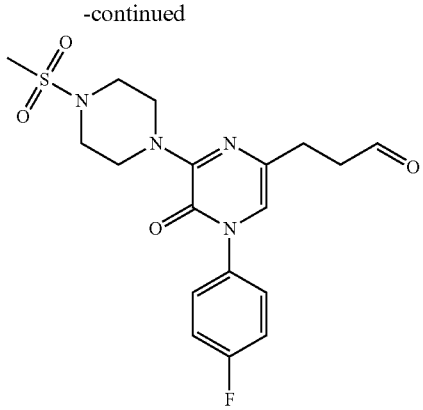

3.30 (m, 4H), 2.87 (s, 3H), 2.84-2.73 (t, J=7.5 Hz, 2H), 2.50 (t, J=7.3 Hz, 2H), 2.36-2.26 (m, 1H), 1.95-1.85 (m, 3H), 1.14-0.93 (m, 2H).

Example 38

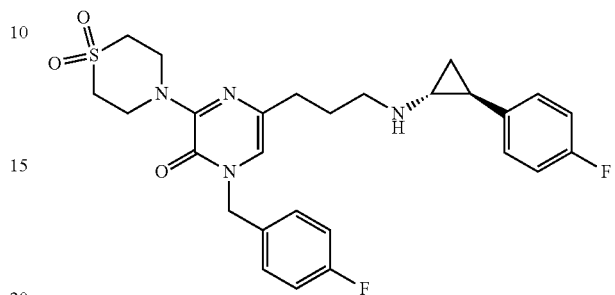

3-(4-(4-Fluorophenyl)-6-(4-(methylsulfonyl)piperazin-1-yl)-5-oxo-4,5-dihydropyrazin-2-yl)propanal The procedure for preparing Intermediate 1-7 was used with the product from the previous step (380 mg, 0.93 mmol, 1 equiv) and Dess-Martin reagent (589.0 mg, 1.39 mmol, 1.500 equiv). The crude product was purified with silica gel chromatography using EtOAc/petroleum ether (1:1) to afford 340 mg (89.9%) of the title compound as a yellow oil.

3-(1,1-dioxidothiomorpholino)-1-(4-fluorobenzyl)-5-[3-([(1R,2S)-2-(4-fluorophenyl)cyclopropyl]amino)propyl]pyrazin-2(1H)-one

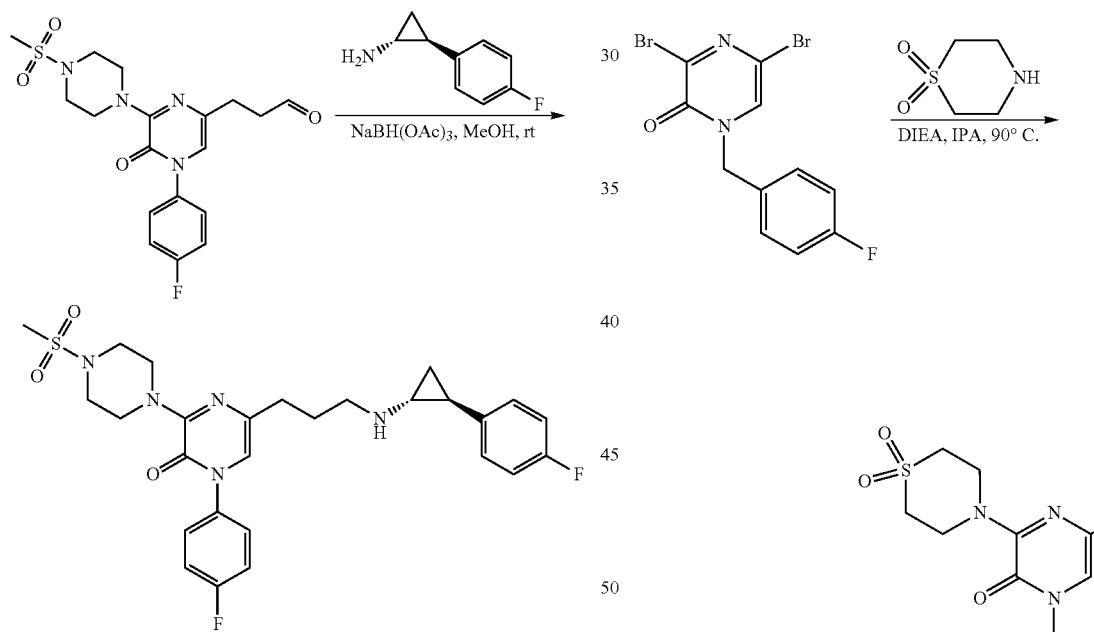

1-(4-Fluorophenyl)-5-(3-(((1R,2S)-2-(4-fluorophenyl)cyclopropyl)amino)-propyl)-3-(4-(methylsulfonyl)piperazin-1-yl)pyrazin-2(1H)-one The reductive amination step for preparing Example 1 from Intermediate 1-7 was used with the product from the previous step (340 mg, 0.83 mmol, 1 equiv) and (1R,2S)-2-(4-fluorophenyl)-cyclopropan-1-amine (226.5 mg, 1.50 mmol, 1.8 equiv). The crude product was purified using chromatographic Procedure C (40% to 56% CH$_3$CN in 16.5 min), to afford 67.1 mg (14.9%) of the title compound as a white solid.

LCMS: (ES, m/z): 544 [M+H]$^+$. $^1$H NMR (300 MHz, Methanol-d$_4$) δ ppm: 7.50-7.39 (m, 2H), 7.35-7.22 (m, 2H), 7.13-6.91 (m, 4H), 6.86 (s, 1H), 3.91-3.81 (m, 4H), 3.32-

5-bromo-3-(1,1-dioxidothiomorpholino)-1-(4-fluorobenzyl)pyrazin-2(1H)-one A solution of thiomorpholine-1,1-dioxide (2.8 g, 20.72 mmol, 1.5 equiv), 3,5-dibromo-1-[(4-fluorophenyl)methyl]-1,2-dihydropyrazin-2-one (5 g, 13.81 mmol, 1 equiv), IPA (30 mL), DIEA (5.4 g, 41.44 mmol, 3 equiv). The resulting solution was stirred for 2 hr at 90° C. The resulting mixture was concentrated. The solid that formed was washed with 100 ml CH$_2$Cl$_2$. The solids were collected by filtration to afford 4 g (70%) of the title compound as a light yellow solid.

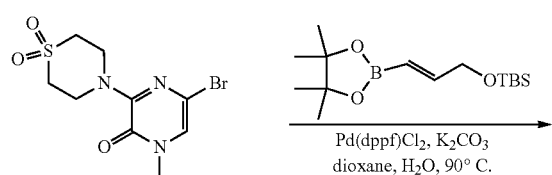

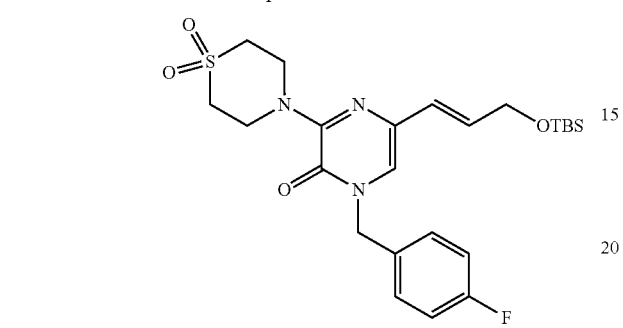

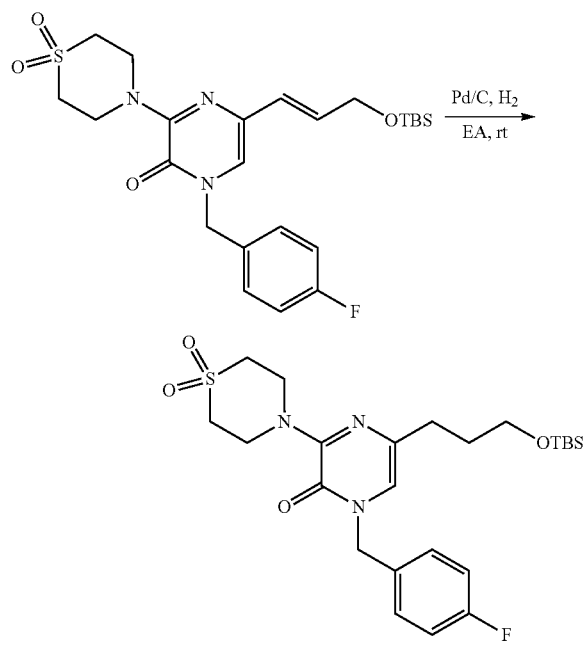

(E)-5-(3-((tert-butyldimethylsilyl)oxy)prop-1-en-1-yl)-3-(1,1-dioxido-thiomorpholino)-1-(4-fluorobenzyl)pyrazin-2(1H)-one The procedure for preparing Intermediate 3-3 was used with the product from the previous step (4 g, 9.61 mmol), using 2 hr reaction time at 90° C. The crude product was purified with silica gel chromatography using EtOAc/petroleum ether (1:4) to afford 3 g (61%) of the title compound as a light yellow oil.

5-(3-((tert-Butyldimethylsilyl)oxy)propyl)-3-(1,1-dioxidothiomorpholino)-1-(4-fluorobenzyl)pyrazin-2(1H)-one The procedure for preparing Intermediate 3-4 was used with the product from the previous step (3 g, 5.91 mmol, 1 equiv) to afford 2.5 g (83%) of the title compound as a light yellow oil.

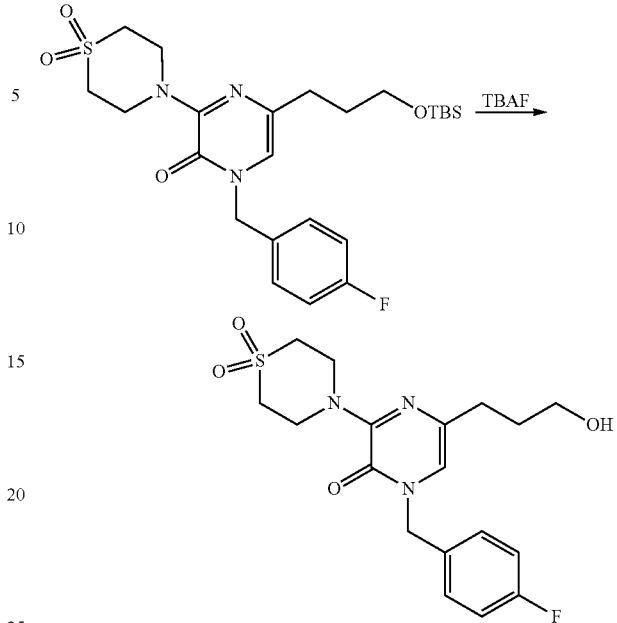

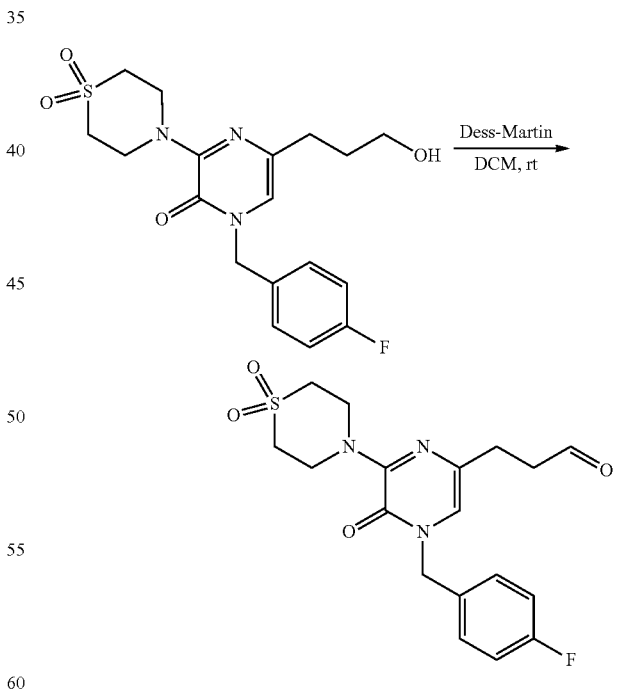

3-(1,1-Dioxidothiomorpholino)-1-(4-fluor benzyl)-5-(3-hydroxypropyl)pyrazin-2(1H)-one The procedure for preparing Intermediate 22-4 was used with the product from the previous step (2.5 g, 490 mmol), using 2 hr reaction time. The crude product was purified using $C_{18}$ reverse phase chromatography using $H_2O$/MeCN (3:1) to afford 1.2 g (61.9%) of the title compound as a light yellow oil.

3-(6-(1,1-Dioxidothiomorpholino)-4-(4-fluorobenzyl)-5-oxo-4,5-dihydropyrazin-2-yl)propanal The procedure for preparing Intermediate 1-7 was used with the product from the previous step (600 mg, 1.52 mmol, 1 equiv) and Dess-Martin reagent (772.2 mg, 1.82 mmol, 1.200 equiv), using 2 hr of reaction time. The crude product was purified with silica gel chromatography using EtOAc/petroleum ether (1:2) to afford 400 mg (67%) of the title compound as a light yellow oil.

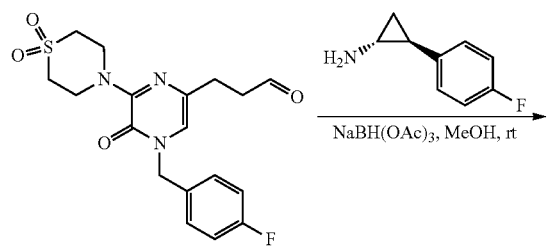

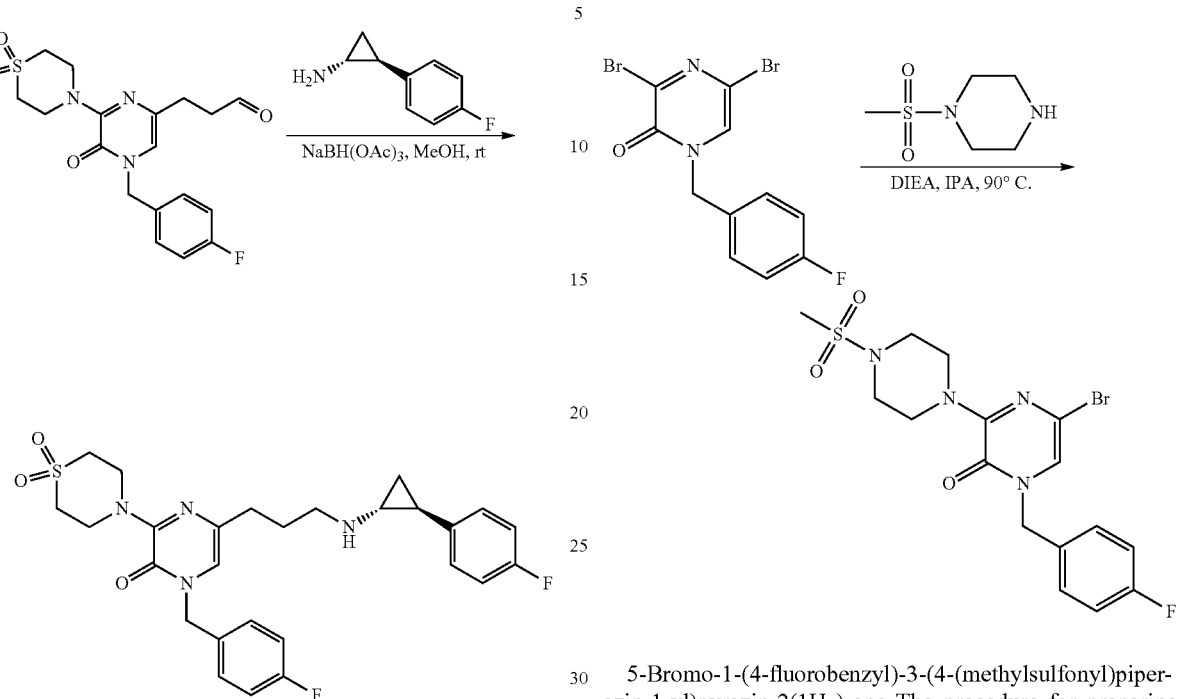

3-(1,1-Dioxidothiomorpholino)-1-(4-fluorobenzyl)-5-(3-(((1R,2S)-2-(4-fluoro-phenyl)cyclopropyl)amino)propyl) pyrazin-2(1H)-one The procedure for preparing Intermediate 4-7 was used with the product from the previous step (400 mg, 1.02 mmol, 1 equiv) and (1R,2S)-2-(4-fluorophenyl)cyclopropan-1-amine (184.4 mg, 1.22 mmol, 1.2 equiv). The crude product was purified using chromatographic Procedure E (44% to 74% CH$_3$CN), to afford 69.3 mg (12.9%) of the title compound as an off-white semi-solid.

LC-MS: (ES, m/z): 529 [M+H]$^+$. $^1$H NMR (300 MHz, MeOD-d$_4$) δ ppm: 7.41-7.36 (m, 2H), 7.09-7.02 (m, 4H), 7.02-6.93 (m, 3H), 5.12-5.00 (s, 2H), 4.31-4.28 (m, 4H), 3.20-3.10 (m, 4H), 2.73-2.66 (t, J=7.2 Hz, 2H), 2.48-2.43 (t, J=7.2 Hz, 2H), 2.29-2.24 (m, 1H), 2.09-1.82 (m, 3H), 1.06-0.95 (m, 2H).

Example 39

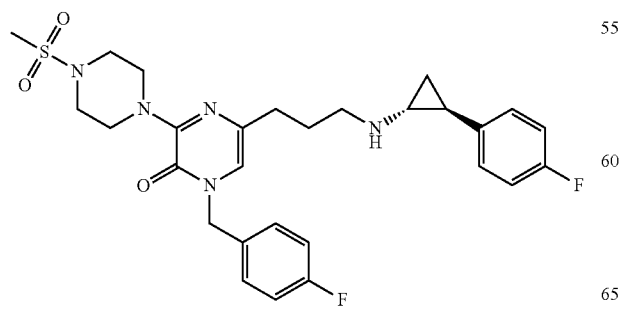

1-(4-fluorobenzyl)-5-[3-([(1R,2S)-2-(4-fluorophenyl)cyclopropyl]amino)propyl]-3-[4-(methylsulfonyl)piperazin-1-yl]pyrazin-2(1H)-one

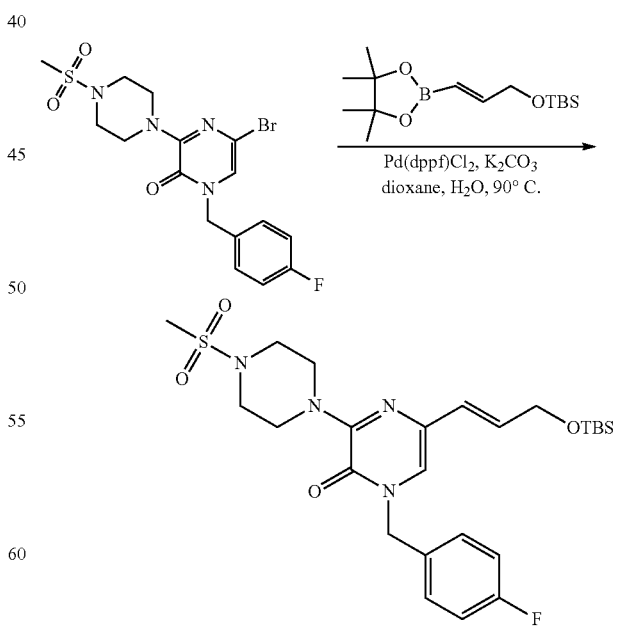

5-Bromo-1-(4-fluorobenzyl)-3-(4-(methylsulfonyl)piperazin-1-yl)pyrazin-2(1H$_1$)-one The procedure for preparing Intermediate 2-1 was used with 3,5-dibromo-1-[(4-fluorophenyl)methyl]-1,2-dihydropyrazin-2-one (5 g, 13.81 mmol, 1 equiv) and 1-methanesulfonylpiperazine (3.4 g, 0.02 mmol, 1.5 equiv). The crude product was purified with silica gel chromatography using EtOAc/petroleum ether (1:1) to afford 4.8 g (78%) of the title compound as a yellow oil.

(E)-5-(3-((tert-butyldimethylsilyl)oxy)prop-1-en-1-yl)-1-(4-fluorobenzyl)-3-(4-(methylsulfonyl)piperazin-1-yl) pyrazin-2(1H)-one The procedure for preparing Intermediate 3-3 was used with the product from the previous step (4.8 g, 10.78 mmol), using 4 hr of reaction time at 90° C. The crude product was purified with silica gel chromatography using EtOAc/petroleum ether (1:1) to afford 3 g (49.78%) of the title compound as a yellow oil.

1-(4-Fluorobenzyl)-5-(3-hydroxypropyl)-3-(4-(methyl-sulfonyl)piperazin-1-yl)pyrazin-2(1H)-one The procedure for preparing Intermediate 33-5 was used with the product from the previous step (2 g, 3.72 mmol), to afford 360 mg (23%) of the title compound as a yellow oil.

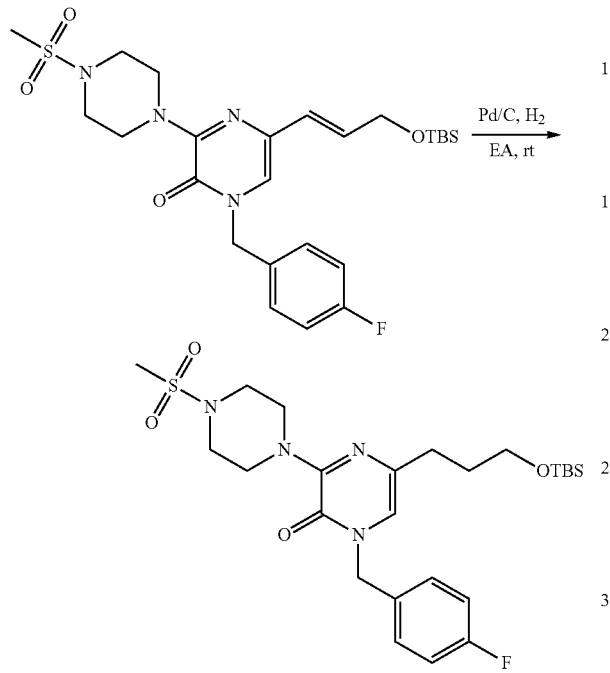

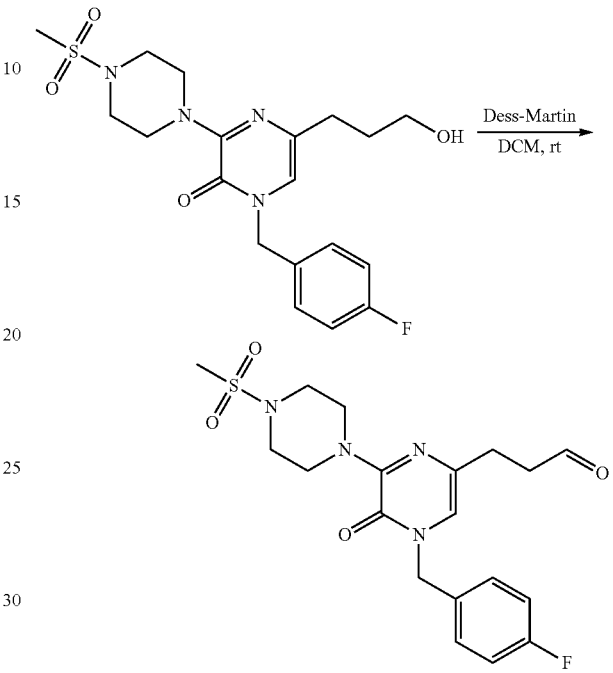

5-(3-((tert-Butyldimethylsilyl)oxy)propyl)-1-(4-fluo-robenzyl)-3-(4-(methyl-sulfonyl)piperazin-1-yl)pyrazin-2(1H)-one The procedure for preparing Intermediate 3-4 was used with the product from the previous step (3 g, 5.58 mmol, 1.0 equiv) to afford 2 g (63%) of the title compound as a yellow oil.

3-(4-(4-Fluorobenzyl)-6-(4-(methylsulfonyl)piperazin-1-yl)-5-oxo-4,5-dihydropyrazin-2-yl)propanal The procedure for preparing Intermediate 1-7 was used with the product from the previous step (360 mg, 0.85 mmol, 1 equiv). The crude product was purified with silica gel chromatography using EtOAc/petroleum ether (1:1) to afford 300 mg (83.73%) of the title compound as a white solid.

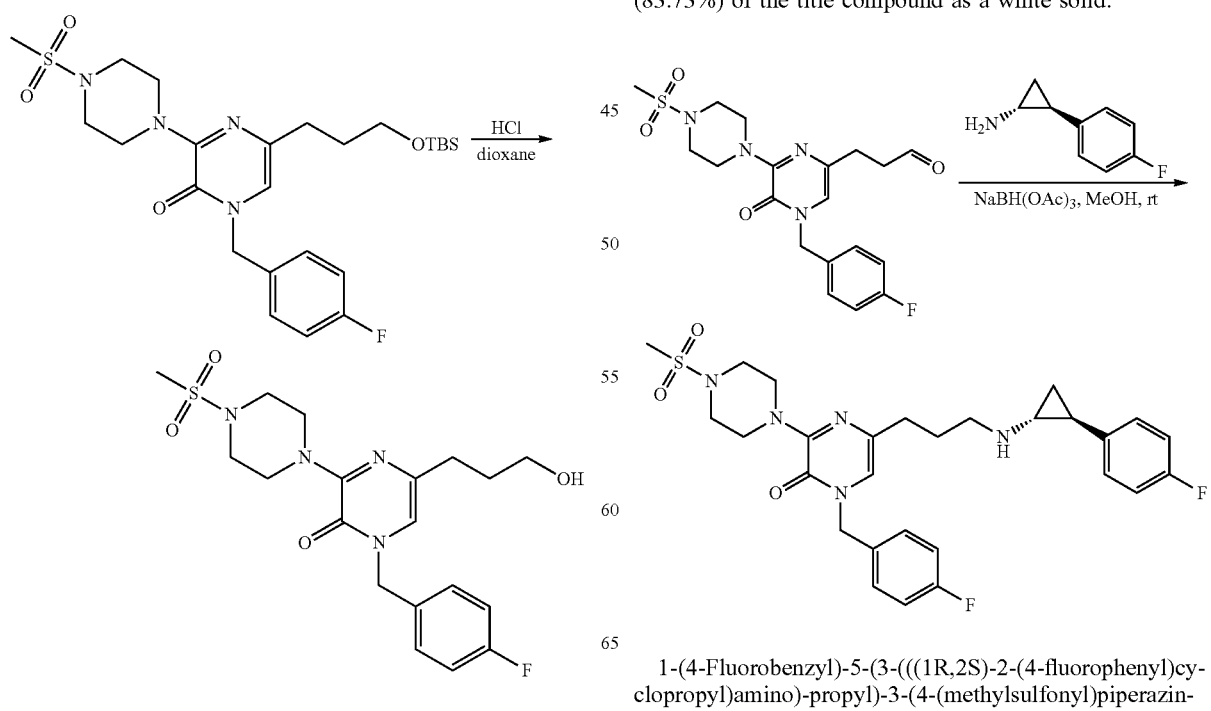

1-(4-Fluorobenzyl)-5-(3-(((1R,2S)-2-(4-fluorophenyl)cy-clopropyl)amino)-propyl)-3-(4-(methylsulfonyl)piperazin- 1-yl)pyrazin-2(1H)-one The reductive amination step for preparing Example 1 from Intermediate 1-7 was used with the product from the previous step (300 mg, 0.71 mmol, 1 equiv) and (1R,2S)-2-(4-fluorophenyl)-cyclopropan-1-amine (128.8 mg, 0.85 mmol, 1.20 equiv). The crude product was purified using chromatographic Procedure G (25% B to 37% CH₃CN in 8 min), to afford 135.7 mg (35.5%) of the title compound as brown oil.

LCMS: (ES, m/z): 558 [M+H]⁺. ¹H NMR (300 MHz, Methanol-d₄) δ ppm: 7.44-7.34 (m, 2H), 7.25-7.14 (m, 2H), 7.14-7.02 (m, 4H), 7.00 (s, 1H), 5.06 (s, 2H), 3.87-3.78 (m, 4H), 3.40-3.18 (m, 6H), 3.02-2.92 (m, 1H), 2.87 (s, 3H), 2.63-2.31 (m, 3H), 2.11-2.01 (m, 2H), 1.53-1.43 (m, 1H), 1.42-1.32 (m, 1H).

Example 40

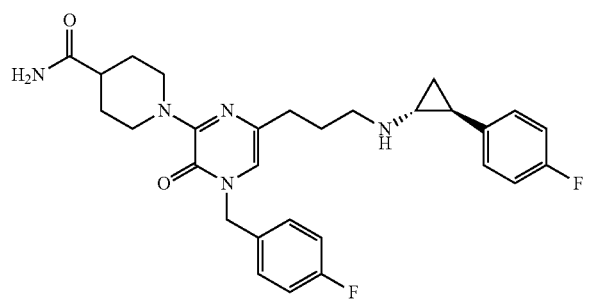 [SMILES: NC(=O)C1CCN(c2nc(CCCN[C@@H]3C[C@H]3c3ccc(F)cc3)cn(Cc3ccc(F)cc3)c2=O)CC1]

1-[4-(4-fluorobenzyl)-6-(3-(((1R,2S)-2-(4-fluorophenyl)cyclopropyl)amino)propyl)-3-oxo-3,4-dihydropyrazin-2-yl)piperidine-4-carboxamide

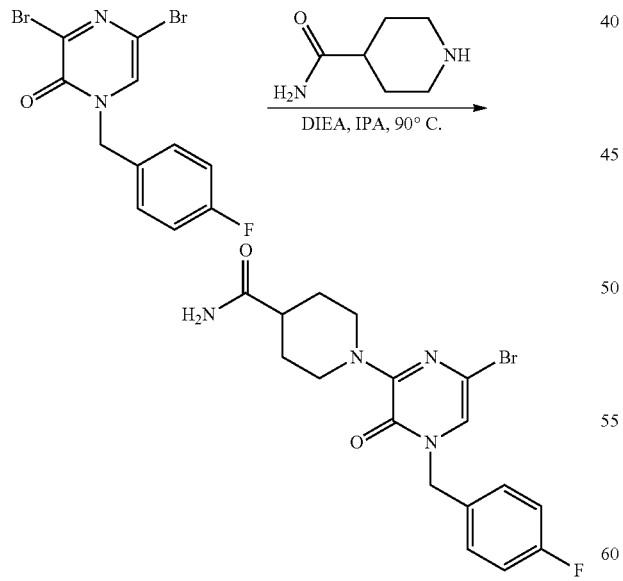

1-(6-Bromo-4-(4-fluorobenzyl)-3-oxo-3,4-dihydropyrazin-2-yl)piperidine-4-carboxamide The procedure for preparing Intermediate 2-1 was used with 3,5-dibromo-1-(4-fluorobenzyl)pyrazin-2(1H)-one (5 g, 13.81 mmol, 1.00 equiv) and piperidine-4-carboxamide (1.94 g, 15.19 mmol, 1.10 equiv), using 3 h reaction time at 90° C., to afford 5 g (88%) of the title compound as an off-white solid.

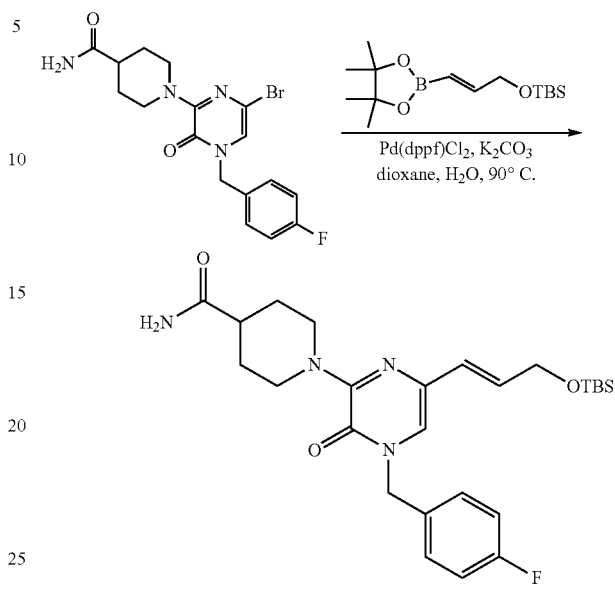

(E)-1-(6-(3-((tert-butyldimethylsilyl)oxy)prop-1-en-1-yl)-4-(4-fluorobenzyl)-3-oxo-3,4-dihydropyrazin-2-yl)piperidine-4-carboxamide The procedure for preparing Intermediate 3-3 was used with the product from the previous step (5 g, 12.2 mmol, 1.00 equiv) and tert-butyldimethyl([2E]-3-[tetramethyl-1,3,2-dioxaborolan-2-yl]prop-2-en-1-yl)oxy]silane (4.73 g, 15.88 mmol, 1.30 equiv), using 1 hr reaction time at 90° C. The crude product was purified with silica gel chromatography using EtOAc/petroleum ether (1:3) to afford 2.2 g (24%) of the title compound as a yellow solid.

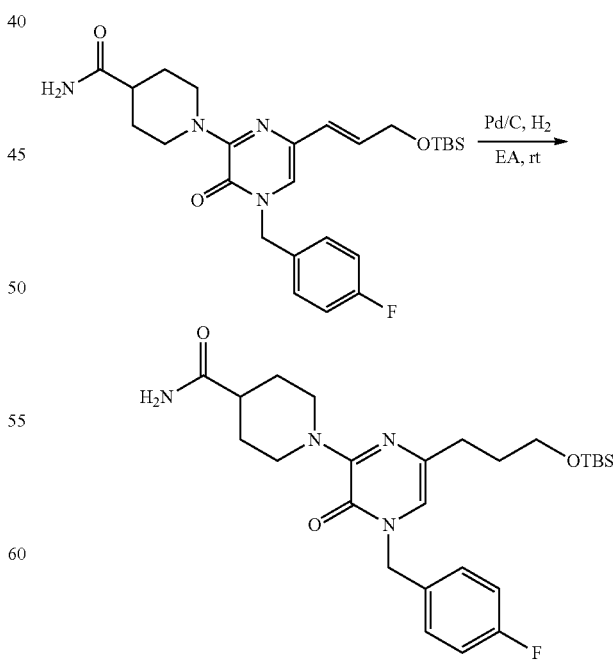

1-(6-(3-((tert-Butyldimethylsilyl)oxy)propyl)-4-(4-fluorobenzyl)-3-oxo-3,4-dihydropyrazin-2-yl)piperidine-4-carboxamide The procedure for preparing Intermediate 3-4 was used with the product from the previous step (2.2 g, 1.78 mmol, 1.00 equiv) to afford 2 g (80%) of the title compound as a light yellow solid.

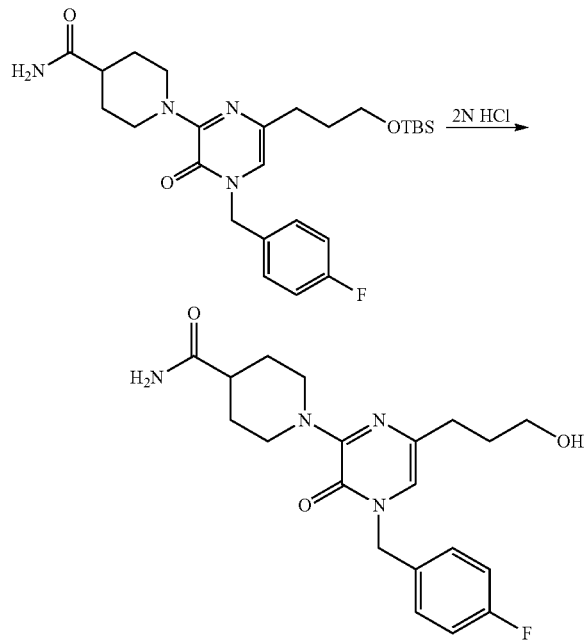

1-(4-(4-Fluorobenzyl)-6-(3-hydroxypropyl)-3-oxo-3,4-dihydropyrazin-2-yl)-piperidine-4-carboxamide The procedure for preparing Intermediate 33-5 was used with the product from the previous step (2 g, 1.42 mmol, 1.00 equiv), using 2 h of reaction time at 25° C. The crude product was purified with silica gel chromatography using EtOAc to afford 1.1 g (70%) of the title compound as a yellow solid.

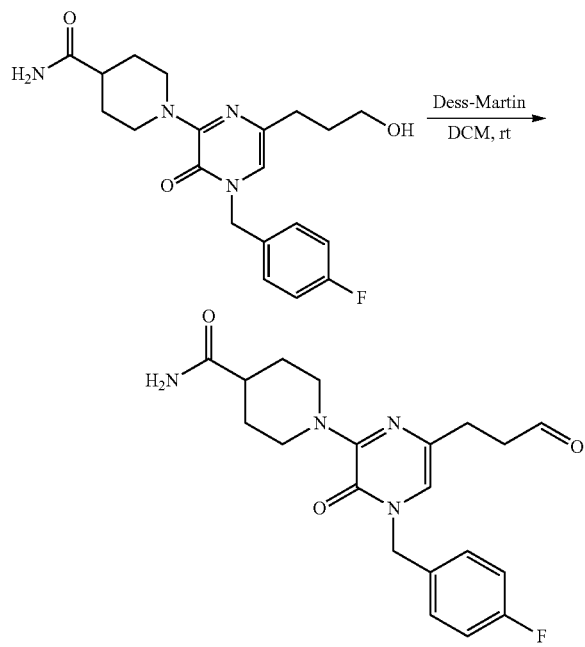

1-(4-(4-Fluorobenzyl)-3-oxo-6-(3-oxopropyl)-3,4-dihydropyrazin-2-yl)piperidine-4-carboxamide The procedure for preparing Intermediate 1-7 was used with the product from the previous step (1 g, 1.00 mmol, 1.00 equiv). The crude product was purified with silica gel chromatography using EtOAc/petroleum ether (2:1) to afford 310 mg (71%) of the title compound as a yellow solid.

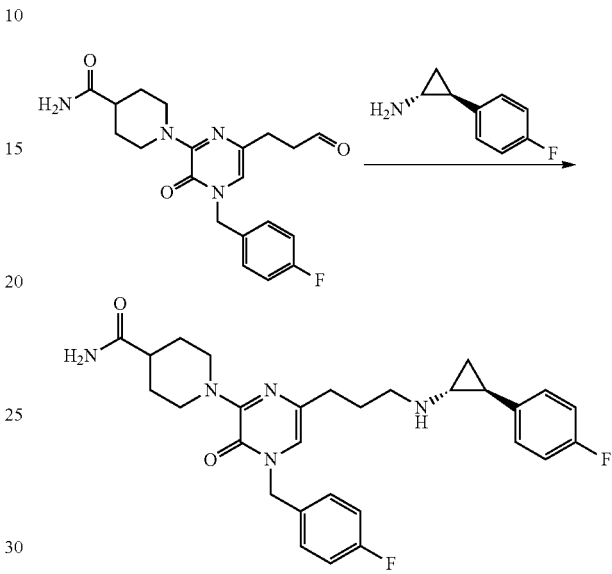

1-(4-(4-Fluorobenzyl)-6-(3-(((1R,2S)-2-(4-fluorophenyl)cyclopropyl)amino)-propyl)-3-oxo-3,4-dihydropyrazin-2-yl)piperidine-4-carboxamide The reductive amination step for preparing Example 1 from Intermediate 1-7 was used with the product from the previous step (310 mg, 0.71 mmol, 1.00 equiv) and (1R, 2S)-2-(4-fluoro-phenyl)cyclopropan-1-amine (162 mg, 1.07 mmol, 1.50 equiv). The crude product (4 mL) was purified using chromatographic Procedure F (22% to 32% $CH_3CN$ in 7 min), to afford 40 mg (22%) of the title compound as a yellow solid.

LC-MS: (ES, m/z): 522 [M+H]$^+$. $^1$H NMR (300 MHz, MeOD-$d_4$) δ ppm: 7.38-7.33 (m, 2H), 7.19-7.14 (m, 2H), 7.08-7.01 (m, 4H), 6.87 (s, 1H), 5.01 (s, 2H), 4.88-4.71 (m, 2H), 3.31-3.29 (m, 2H), 2.96-2.88 (m, 3H), 2.51-2.41 (m, 4H), 2.05-1.99 (m, 2H), 1.77-1.74 (m, 4H), 1.45-1.33 (m, 2H).

Example 41

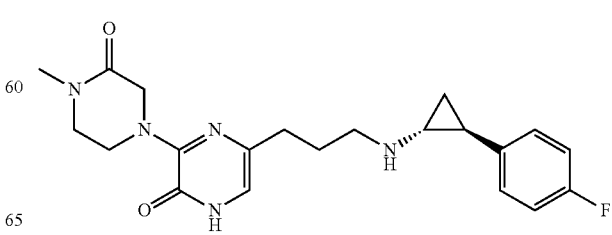

211

5-[3-([(1R,2S)-2-(4-fluorophenyl)cyclopropyl]amino)propyl]-3-[4-methyl-3-oxopiperazin-1-yl]pyrazin-2(1H)-one

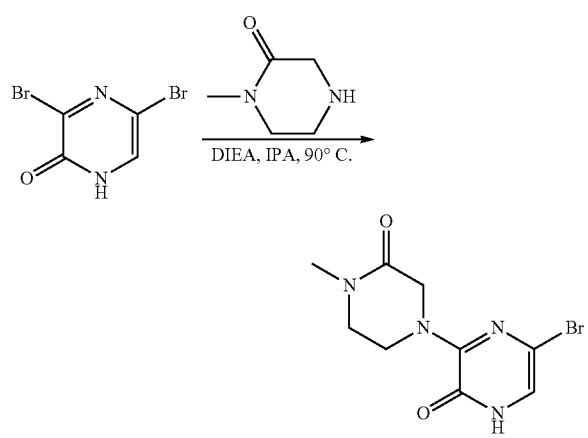

5-Bromo-3-(4-methyl-3-oxopiperazin-1-yl)pyrazin-2(1H)-one The procedure for preparing Intermediate 2-1 was used with 3,5-dibromo-1,2-dihydropyrazin-2-one (20 g, 78.78 mmol, 1 equiv) and 1-methylpiperazin-2-one (10.8 g, 94.54 mmol, 1.20 equiv), using 6 hr of reaction time at 90° C., to afford 18 g (80%) of the title compound as a yellow solid.

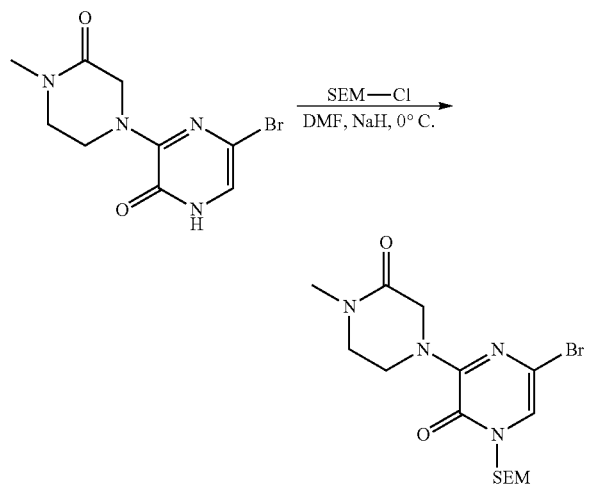

5-Bromo-3-(4-methyl-3-oxopiperazin-1-yl)-1-((2-(trimethylsilyl)ethoxy)-methyl)pyrazin-2(1H)-one A mixture of the product from the previous step (12 g, 41.80 mmol, 1 equiv) and NaH (5.0 g, 125.4 mmol, 3.0 equiv) in DMF (200 mL) was stirred for 1 h at 0° C., [2-(chloromethoxy)ethyl]trimethylsilane (10.5 g, 62.7 mmol, 1.5 equiv) was then added, and the mixture was stirred an additional hr at rt. The reaction was quenched and extracted with 5×500 ml EtOAc. The resulting mixture was concentrated, to afford 6 g (34%) of the title compound as a yellow oil.

212

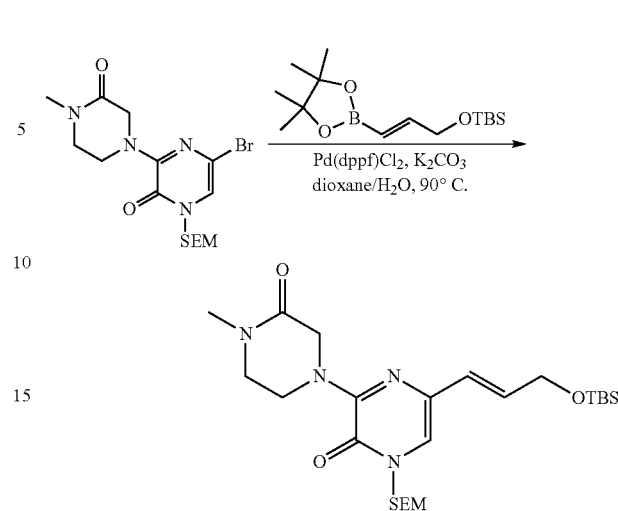

(E)-5-(3-((tert-butyldimethylsilyl)oxy)prop-1-en-1-yl)-3-(4-methyl-3-oxo-piperazin-1-yl)-1-((2-(trimethylsilyl)ethoxy)methyl)pyrazin-2(1H)-one The procedure for preparing Intermediate 3-3 was used with the product from the previous step (6 g, 14.38 mmol). The crude product was purified with silica gel chromatography using EtOAc/petroleum ether (1:3) (o afford 6 g (82%) of the title compound as a yellow oil.

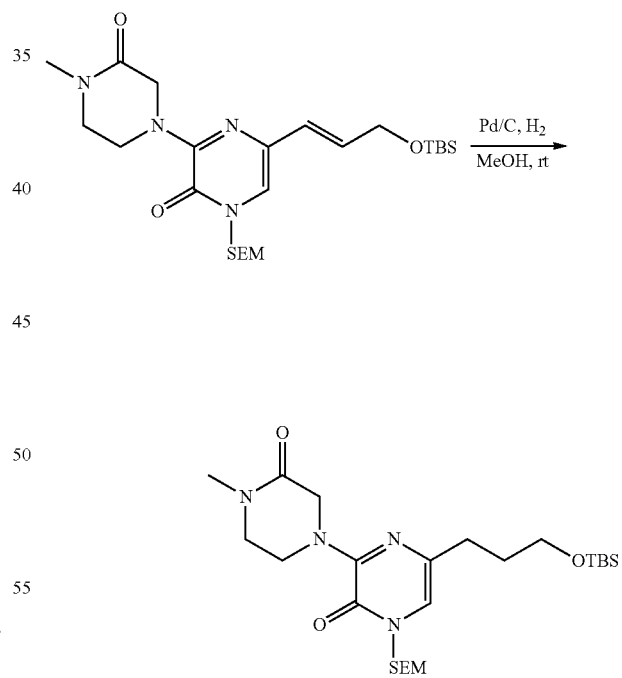

5-(3-((tert-Butyldimethylsilyl)oxy)propyl)-3-(4-methyl-3-oxopiperazin-1-yl)-1-((2-(trimethylsilyl)ethoxy)methyl)pyrazin-2(1H)-one The procedure for preparing Intermediate 1-5 was used with the product from the previous step (6 g, 11.81 mmol, 1.0 equiv) to afford 5.5 g (91%) of the title compound as a yellow oil.

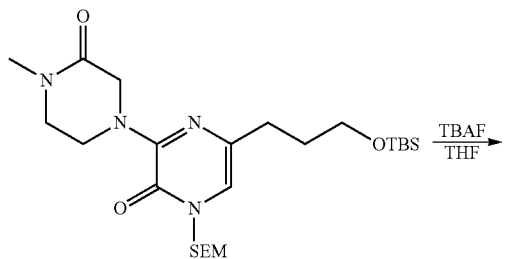

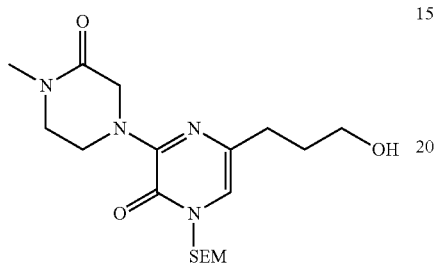

5-(3-Hydroxypropyl)-3-(4-methyl-3-oxopiperazin-1-yl)-1-((2-(trimethylsilyl)-ethoxy)methyl)pyrazin-2(1H)-one
The procedure for preparing Intermediate 22-4 was used with the product from the previous step (5.5 g, 10.78 mmol), using 6 hr of reaction time. The crude product was purified by HP-Flash with MeCN/H$_2$O to afford 4 g (63%) of the title compound as a yellow oil.

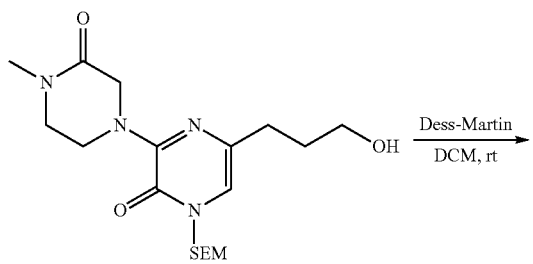

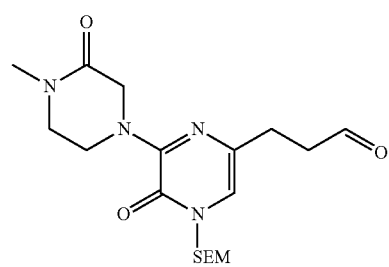

3-(6-(4-Methyl-3-oxopiperazin-1-yl)-5-oxo-4-((2-(trimethylsilyl)ethoxy)-methyl)-4,5-dihydropyrazin-2-yl)propanal The procedure for preparing Intermediate 1-7 was used with the product from the previous step (1.5 g, 3.78 mmol). The crude product was purified with silica gel chromatography using EtOAc/petroleum ether (1:1) to afford 800 mg (80.03%) of the title compound as a light yellow oil.

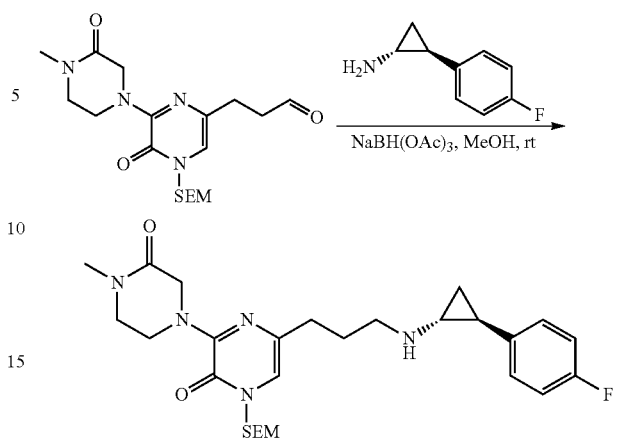

5-(3-(((1R,2S)-2-(4-fluorophenyl)cyclopropyl)amino)propyl)-3-(4-methyl-3-oxopiperazin-1-yl)-1-((2-(trimethylsilyl)ethoxy)methyl)pyrazin-2(1H)-one The reductive amination step for preparing Example 1 from Intermediate 1-7 was used with the product from the previous step (800 mg, 2.03 mmol, 1 equiv) and (1R,2S)-2-(4-fluorophenyl)cyclopropan-1-amine (551.8 mg, 3.65 mmol, 1.8 equiv). The crude product was purified by TLC with MeOH/CH$_2$Cl$_2$ (5:1) to afford 350 mg (32.62%) of the title compound as a yellow oil.

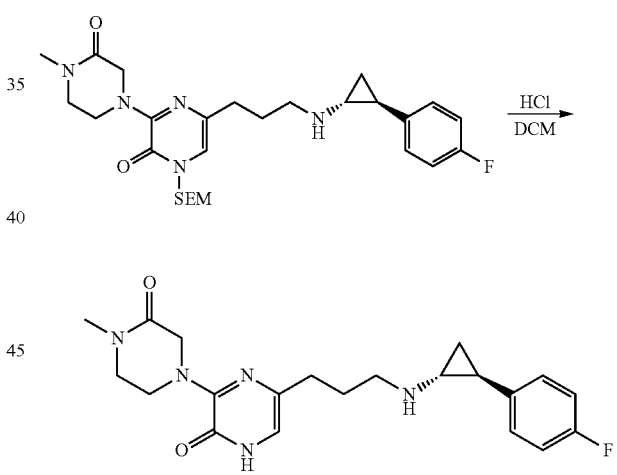

5-(3-(((1R,2S)-2-(4-fluorophenyl)cyclopropyl)amino)propyl)-3-(4-methyl-3-oxopiperazin-1-yl)pyrazin-2(1H)-one A solution of the product from the previous step (320 mg, 603 mmol, 1 equiv) in HCl (4N, 10 mL) and CH$_2$Cl$_2$ (20 mL) was stirred for 2 hr at rt. The pH was adjusted with Na$_2$CO$_3$ to 7. The resulting mixture was concentrated. The crude product was purified using chromatographic Procedure B (15% B to 43% CH$_3$CN in 7 min), to afford 85 mg (10.5%) of the title compound as a yellow oil.

LCMS: (ES, m/z): 400 [M+H]$^+$. $^1$H NMR (400 MHz, Methanol-d$_4$) δ ppm: 7.25-7.17 (m, 2H), 7.07 (t, J=6.8 Hz, 2H), 6.72 (s, 1H), 4.25 (s, 2H), 4.23-4.16 (m, 2H), 3.51-3.49 (t, J=5.6 Hz, 2H), 3.30-3.22 (m, 2H), 3.03-2.99 (m, 4H), 2.61-2.55 (m, 2H), 2.51-2.41 (m, 1H), 2.12-2.02 (m, 2H), 1.54-1.45 (m, 1H), 1.45-1.35 (m, 1H).

Example 42

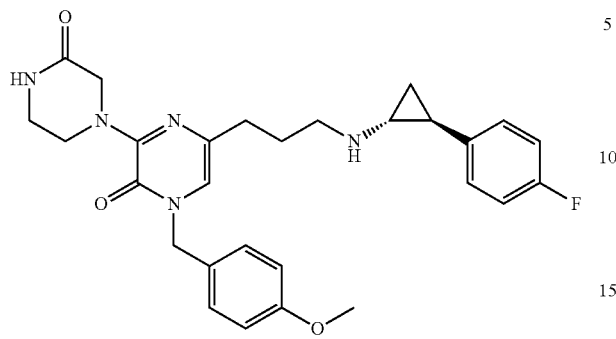

5-[3-([(1R,2S)-2-(4-fluorophenyl)cyclopropyl]amino)propyl]-1-[4-methoxybenzyl]-3-[3-oxopiperazin-1-yl]pyrazin-2(1H)-one

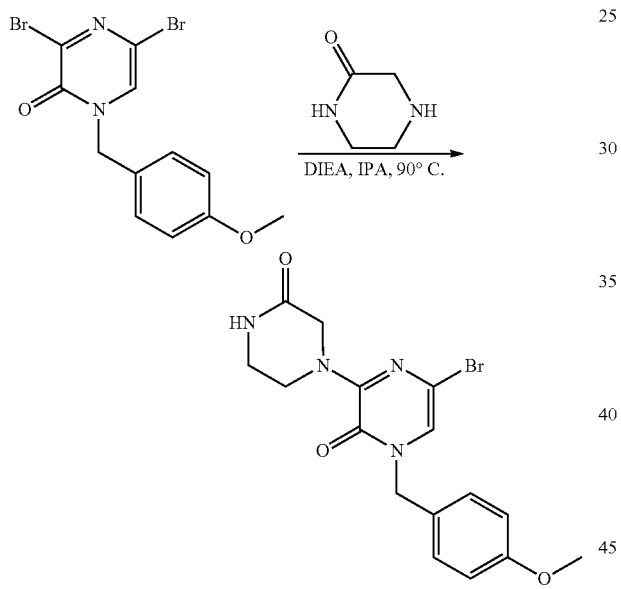

5-bromo-1-(4-methoxybenzyl)-3-(3-oxopiperazin-1-yl)pyrazin-2(1H)-one The procedure for preparing Intermediate 2-1 was used with 3,5-dibromo-1-(4-methoxy-benzyl)pyrazin-2(1H)-one (6 g, 16.04 mmol, 1.00 equiv) and piperazin-2-one (1.6 g, 19.28 mmol, 1.20 equiv), using 3 h of reaction time at 90° C., to afford 6.0 g (88%) of the title compound as a light yellow solid.

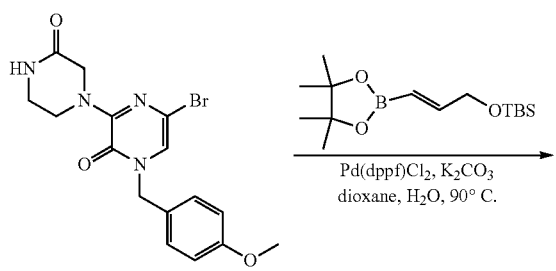

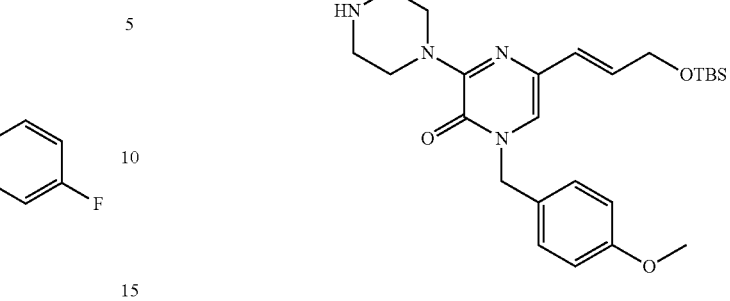

(E)-5-(3-((tert-butyldimethylsilyl)oxy)prop-1-en-1-yl)-1-(4-methoxybenzyl)-3-(3-oxopiperazin-1-yl)pyrazin-2(1H)-one The procedure for preparing Intermediate 3-3 was used with the product from the previous step (4.3 g, 11.14 mmol, 1.00 equiv), using 1 hr of reaction time at 90° C. The crude product was purified with silica gel chromatography using EtOAc/petroleum ether (1:1) to afford 1.7 g (24%) of the title compound as an orange solid.

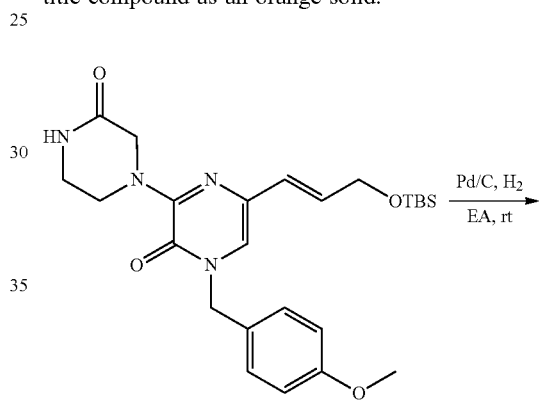

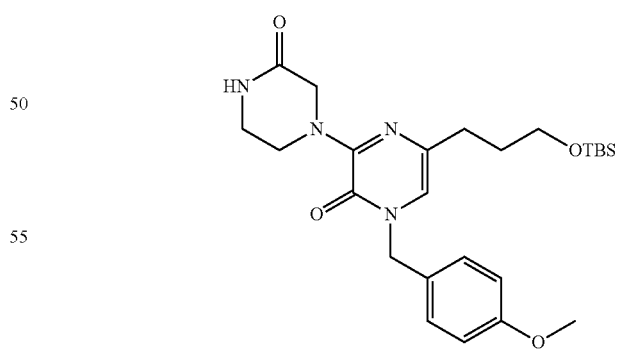

5-(3-((tert-Butyldimethylsilyl)oxy)propyl)-1-(4-methoxybenzyl)-3-(3-oxo-piperazin-1-yl)pyrazin-2(1H)-one The procedure for preparing Intermediate 3-4 was used with the product from the previous step (1.7 g, 1.78 mmol, 1.00 equiv) to afford 1.3 g (80%) of the title compound as a light yellow oil.

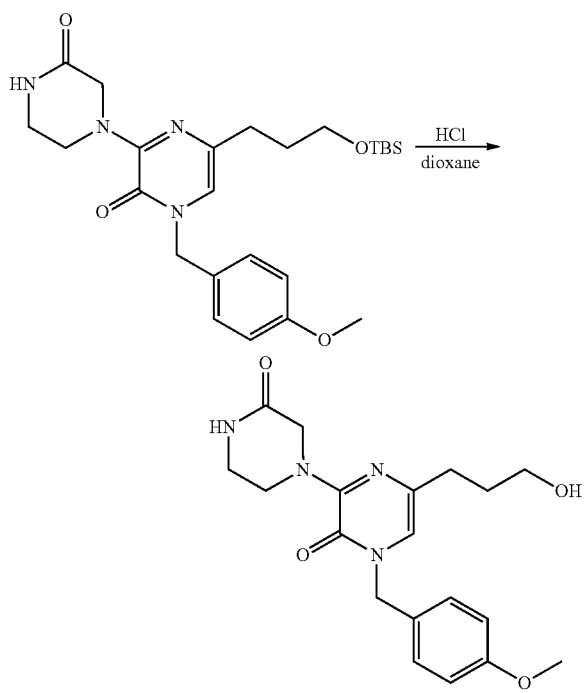

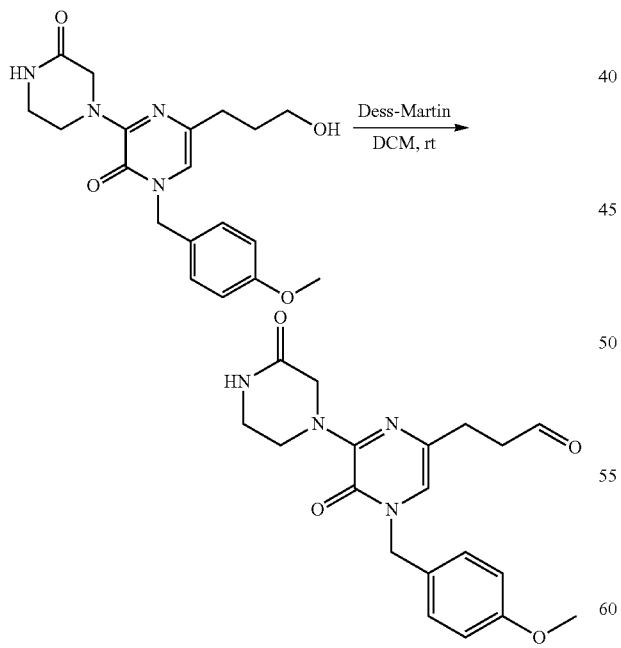

5-(3-Hydroxypropyl)-1-(4-methoxybenzyl)-3-(3-oxopiperazin-1-yl)pyrazin-2(1H₁)-one The procedure for preparing Intermediate 33-5 was used with the product from the previous step. The crude product was purified with silica gel chromatography using EtOAc to afford 500 mg (70%) of the title compound as yellow solid.

3-(4-(4-Methoxybenzyl)-5-oxo-6-(3-oxopiperazin-1-yl)-4,5-dihydropyrazin-2-yl)propanal The procedure for preparing Intermediate 1-7 was used with the product from the previous step (300 mg, 1.00 mmol). The crude product was purified with silica gel chromatography using EtOAc/petroleum ether (2:1) to afford 220 mg (71%) of the title compound as a yellow solid.

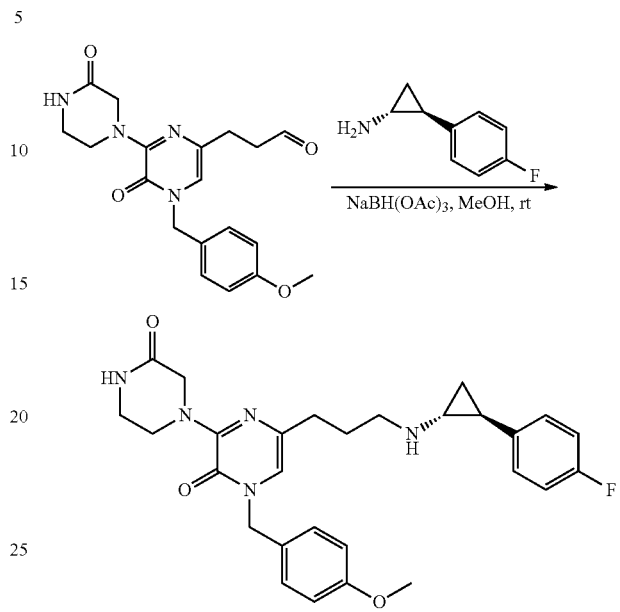

5-(3-(((1R,2S)-2-(4-fluorophenyl)cyclopropyl)amino)propyl)-1-(4-methoxy-benzyl)-3-(3-oxopiperazin-1-yl)pyrazin-2(1H)-one The reductive amination step for preparing Example 1 from Intermediate 1-7 was used with the product from the previous step (220 mg, 0.71 mmol, 1.00 equiv) and (1R, 2S)-2-(4-fluorophenyl) cyclopropan-1-amine (162 mg, 1.07 mmol, 1.50 equiv). The crude product was purified using chromatographic Procedure C (45% to 60% CH₃CN in 7 min), to afford 16.4 mg (22%) of the title compound as a yellow solid.

LC-MS: (ES, m/z): 506 [M+H]⁺. ¹H NMR (300 MHz, MeOD-d₄) δ ppm: 7.28-7.25 (d, J=9.0 Hz, 2H), 7.01-6.84 (m, 7H), 5.00 (s, 2H), 4.25 (s, 2H), 4.04-4.00 (td, J=5.0, 1.7 Hz, 2H), 3.74 (s, 3H), 3.42-3.38 (t, J=5.4 Hz, 2H), 2.70-2.65 (t, J=7.5 Hz, 2H), 2.44-2.39 (t, J=7.2 Hz, 2H), 2.26-2.21 (m, 1H), 1.88-1.79 (m, 3H), 1.14-0.90 (m, 2H).

Example 43

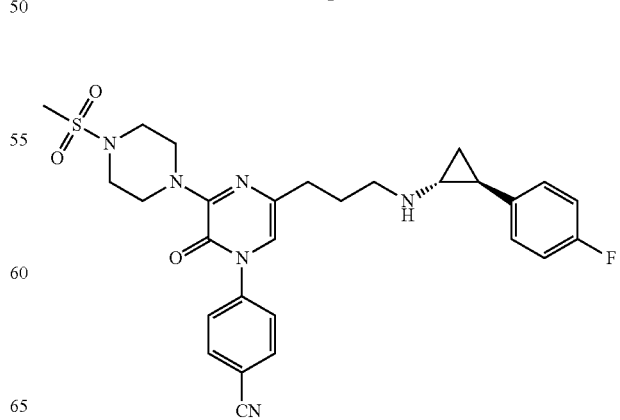

219

4-[5-(3-[([1R,2S]-2-[4-fluorophenyl]cyclopropyl)amino]propyl)-3-(4-[methylsulfonyl]piperazin-1-yl)-2-oxopyrazin-1(2H)-yl]benzonitrile

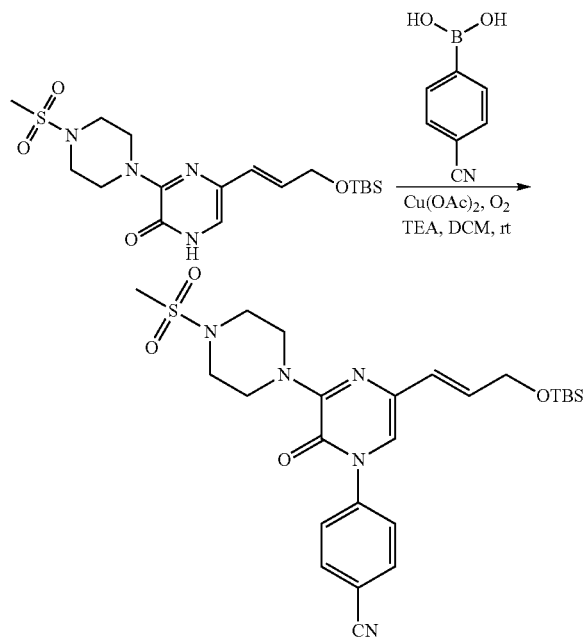

(E)-4-(5-(3-((tert-butyldimethylsilyl)oxy)prop-1-en-1-yl)-3-(4-(methylsulfonyl)piperazin-1-yl)-2-oxopyrazin-1(2H)-yl)benzonitrile The procedure for preparing Intermediate 8-9 was used with Intermediate 37-1 (9 g, 21.00 mmol, 1 equiv) and (4-cyanophenyl)boronic acid (3.6 g, 25.2 mmol, 1.2 equiv). The crude product was purified with silica gel chromatography using PE/EtOAc (3:1) to afford the title compound (1.2 g, 10.79%) as a dark brown semi-solid.

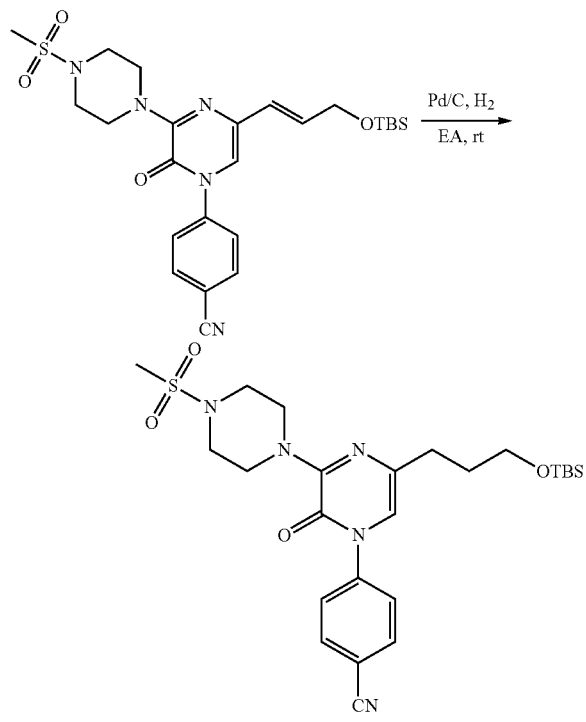

220

4-(5-(3-((tert-Butyldimethylsilyl)oxy)propyl)-3-(4-(methylsulfonyl)piperazin-1-yl)-2-oxopyrazin-1(2H)-yl)benzonitrile The procedure for preparing Intermediate 3-4 was used with the product from the previous step (900 mg, 1.0 equiv) (o afford 600 mg of the title compound as a yellow oil.

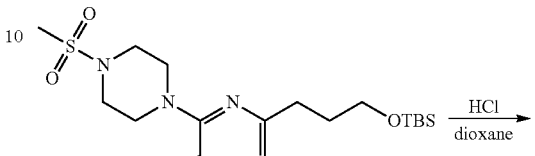

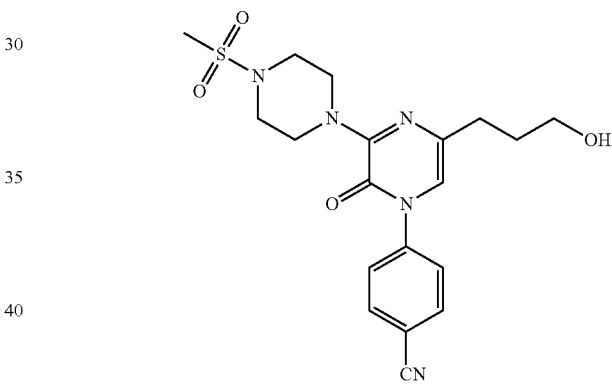

4-(5-(3-Hydroxypropyl)-3-(4-(methylsulfonyl)piperazin-1-yl)-2-oxopyrazin-1(2H)-yl)benzonitrile The procedure for preparing Intermediate 33-5 was used with the product from the previous step (600 mg, 1.0 equiv). The crude product was purified with silica gel chromatography using CHCl$_3$/MeOH (15:1) to afford 330 mg of the title compound as a yellow oil.

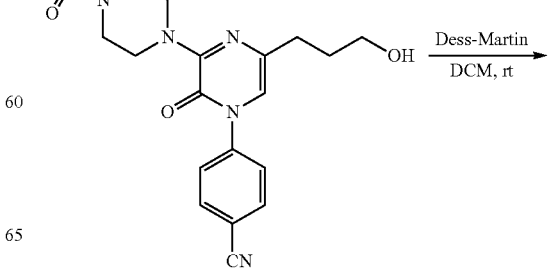

221
-continued

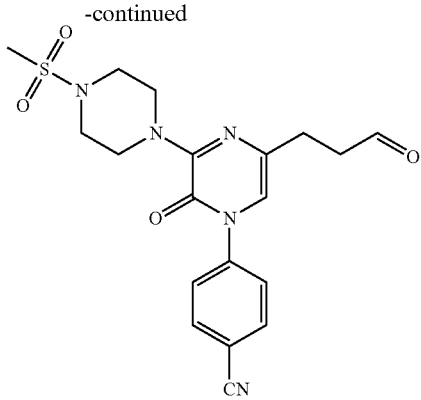

4-(3-(4-(Methylsulfonyl)piperazin-1-yl)-2-oxo-5-(3-oxo-propyl)pyrazin-1(2H)-yl)benzonitrile The procedure for preparing Intermediate 1-7 was used with the product from the previous step (300 mg, 0.72 mmol, 1 equiv) and Dess-Martin reagent (396.2 mg, 0.93 mmol, 1.300 equiv). The crude product was purified with silica gel chromatography using EtOAc/petroleum ether (1:1) to afford 230 mg (77.04%) of the title compound as a light yellow oil.

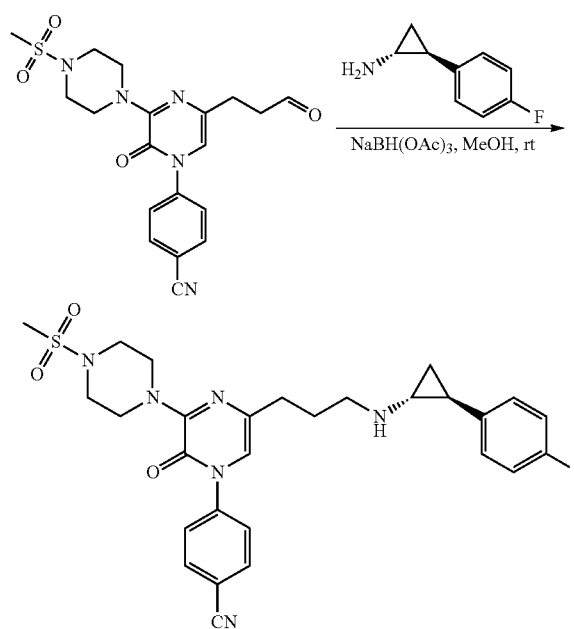

4-(5-(3-(((1R,2S)-2-(4-fluorophenyl)cyclopropyl)amino)propyl)-3-(4-(methylsulfonyl)piperazin-1-yl)-2-oxopyrazin-1(2H)-yl)benzonitrile The procedure for preparing Intermediate 4-7 was used with the product from the previous step (230 mg, 0.55 mmol, 1 equiv) and (1R,2S)-2-(4-fluorophenyl)cyclopropan-1-amine (125.5 mg, 0.83 mmol, 1.5 equiv). The crude product was purified using chromatographic Procedure E (44% to 74% CH$_3$CN in 8 min), to afford 78.5 mg (25.75%) of the title compound as a light yellow solid.

LC-MS: (ES, m/z): 551 [M+H]$^+$. $^1$H NMR (300 MHz, MeOD-d$_4$) δ ppm: 8.02-7.82 (d, J=6.0 Hz, 2H), 7.75-7.52 (d, J=6.0 Hz, 2H), 7.16-7.03 (m, 2H), 7.03-6.95 (m, 2H), 6.88 (s, 1H), 4.00-3.80 (m, 4H), 3.32-3.28 (m, 4H), 2.87 (s, 3H), 2.88-2.72 (t, J=7.2 Hz, 2H), 2.63-2.40 (t, J=7.2 Hz, 2H), 2.39-2.20 (m, 1H), 2.00-1.80 (m, 3H), 1.15-0.89 (m, 2H).

222
Example 44

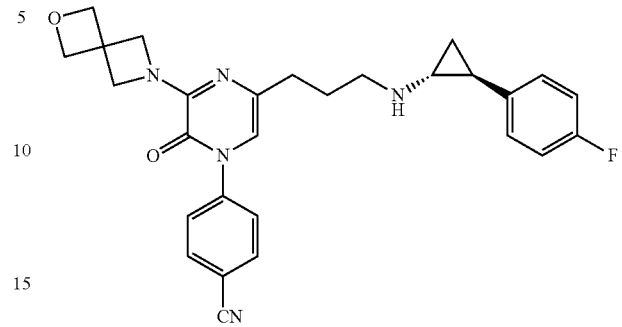

4-[5-(3-[([1R,2S]-2-[4-fluorophenyl]cyclopropyl)amino]propyl)-2-oxo-3-(2-oxa-6-azaspiro[3.3]heptan-6-yl)pyrazin-1(2H)-yl]benzonitrile

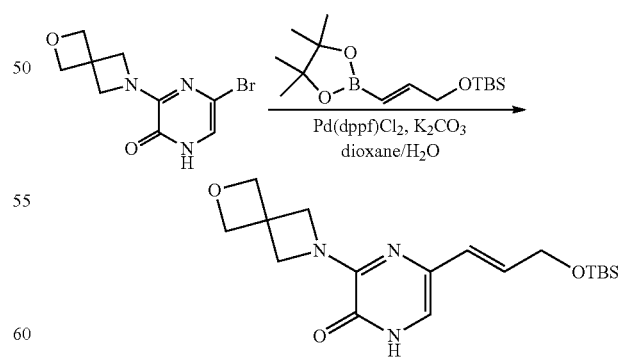

5-Bromo-3-(2-oxa-6-azaspiro[3.3]heptan-6-yl)pyrazin-2(1H)-one The procedure for preparing Intermediate 2-1 was used with 3,5-dibromo-1,2-dihydropyrazin-2-one (20 g, 78.78 mmol, 1 equiv) and 2-oxa-6-azaspiro[3.3]heptane (11.7 g, 118.17 mmol, 1.5 equiv), using 2 h of reaction time at 90° C., affording 18 g (83.97%) of the title compound as an off-white solid.

(E)-5-(3-((tert-butyldimethylsilyl)oxy)prop-1-en-1-yl)-3-(2-oxa-6-azaspiro-[3.3]heptan-6-yl)pyrazin-2(1H)-one The procedure for preparing Intermediate 3-3 was used with the product from the previous step (8 g, 29.40 mmol), using 2 hr of reaction time at 90° C. The crude product was purified with silica gel chromatography using EtOAc/petroleum ether (4:1) to afford 2.5 g (23.4%) of the title compound as a light yellow oil.

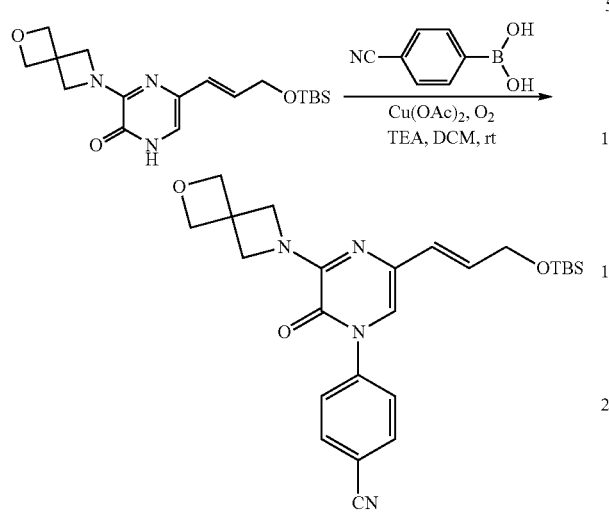

(E)-4-(5-(3-((tert-butyldimethylsilyl)oxy)prop-1-en-1-yl)-2-oxo-3-(2-oxa-6-azaspiro[3.3]heptan-6-yl)pyrazin-1(2H)-yl)benzonitrile The procedure for preparing Intermediate 8-9 was used with the product from the previous step (2.1 g, 5.78 mmol, 1 equiv) and (4-cyanophenyl)boronic acid (1.3 g, 0.01 mmol, 1.5 equiv), using 6 hr reaction time at rt. The crude product was purified with silica gel chromatography using EtOAc/petroleum ether (1:3) to afford 1.0 g (37.26%) of the title compound as a yellow solid.

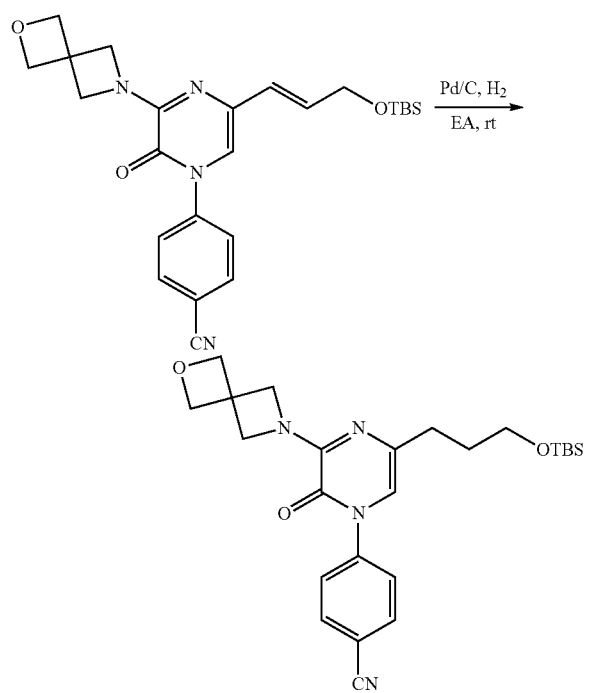

4-(5-(3-((tert-Butyldimethylsilyl)oxy)propyl)-2-oxo-3-(2-oxa-6-azaspiro[3.3]-heptan-6-yl)pyrazin-1(2H)-yl)benzonitrile The procedure for preparing Intermediate 3-4 was used with the product from the previous step (1 g, 1 equiv) to afford 800 mg (79%) of the title compound as a yellow oil.

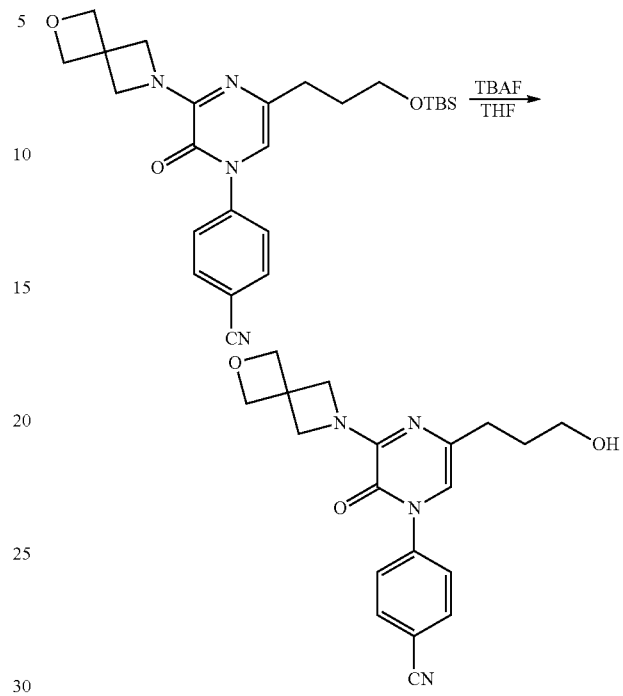

4-(5-(3-Hydroxypropyl)-2-oxo-3-(2-oxa-6-azaspiro[3.3]heptan-6-yl)pyrazin-1(2H)-yl)benzonitrile The procedure for preparing Intermediate 22-4 was used with the product from the previous step (800 mg). The resulting mixture was concentrated and purified by HP-Flash with MeCN/H₂O to afford 540 mg (53%) of the title compound as a yellow solid.

225

4-(2-Oxo-5-(3-oxopropyl)-3-(2-oxa-6-azaspiro[3.3]heptan-6-yl)pyrazin-1(2H)-yl)benzonitrile The procedure for preparing Intermediate 1-7 was used with the product from the previous step (470 mg, 1.33 mmol, 1 equiv) and Dess-Martin reagent (848.6 mg, 2.00 mmol, 1.5 equiv). The crude product was purified with silica gel chromatography using EtOAc/petroleum ether (1:3) to afford 280 mg (59.92%) of the title compound as a yellow oil.

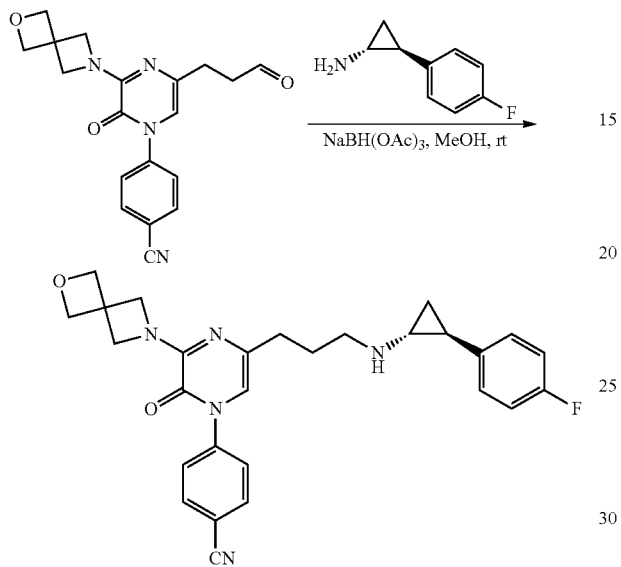

4-(5-(3-(((1R,2S)-2-(4-fluorophenyl)cyclopropyl)amino)propyl)-2-oxo-3-(2-oxa-6-azaspiro[3.3]heptan-6-yl)pyrazin-1(2H)-yl)benzonitrile The reductive amination step for preparing Example 1 from Intermediate 1-7 was used with the product from the previous step (280 mg, 0.80 mmol, 1 equiv) and (1R,2S)-2-(4-fluorophenyl)cyclopropan-1-amine (218.7 mg, 1.45 mmol, 1.8 equiv). The crude product was purified using chromatographic Procedure C (43% to 60% CH$_3$CN in 7 min), to afford 43.9 mg (11.25%) of the title compound as a yellow solid.

LCMS: (ES, m/z): 486 [M+H]$^+$. $^1$H NMR (400 MHz, Methanol-d$_4$) δ ppm: 7.94-7.87 (d, J=2.0 Hz, 2H), 7.68-7.61 (d, J=2.0 Hz, 2H), 7.12-7.04 (m, 2H), 7.03-6.92 (m, 2H), 6.65 (s, 1H), 4.82 (s, 4H), 4.46 (s, 4H), 2.77 (t, J=7.5 Hz, 2H), 2.43 (t, J=7.4 Hz, 2H), 2.36-2.26 (m, 1H), 1.98-1.81 (m, 3H), 1.12-1.04 (m, 1H), 1.04-0.96 (m, 1H).

Example 45

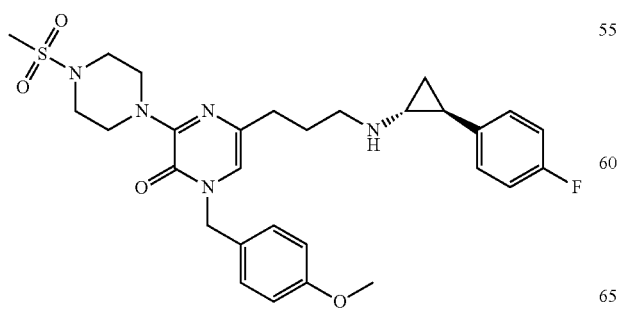

226

5-(3-(((1R,2S)-2-(4-Fluorophenyl)cyclopropyl)amino)propyl)-1-(4-methoxybenzyl)-3-(4-(methylsulfonyl)piperazin-1-yl)pyrazin-2(1H)-one

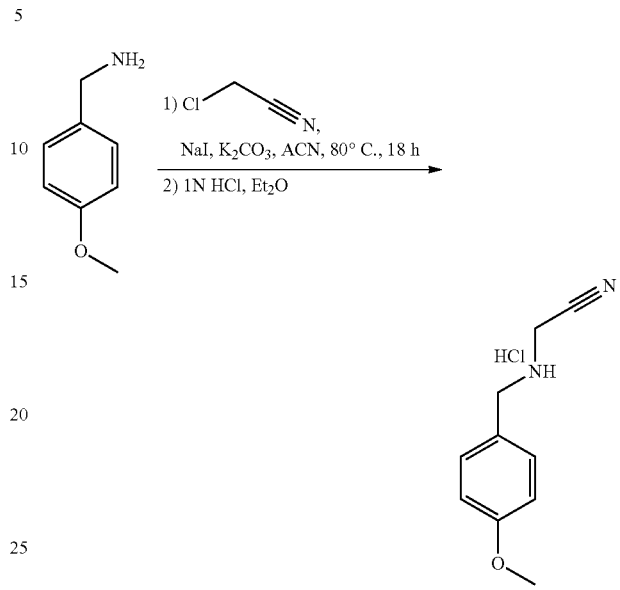

2-((4-Methoxybenzyl)amino)acetonitrile hydrochloride A mixture of (4-methoxyphenyl)methanamine (60 g, 437.37 mmol, 1 equiv), 2-chloroacetonitrile (39.6 g, 524.85 mmol, 1.2 equiv), NaI (6.57 g, 43.74 mmol, 0.1 equiv), and K$_2$CO$_3$ (78.6 g, 568.58 mmol, 1.3 equiv) in CH$_3$CN (400 mL) was stirred for 18 h at 80° C. The reaction was monitored by LCMS. The mixture was allowed to cool to rt. The resulting mixture was filtered; the filter cake was washed with CH$_3$CN (3×350 mL). The filtrate was concentrated under reduced pressure. The resulting mixture was diluted with Et$_2$O (400 mL). HCl (1N, 300 mL) was added to the solution. The precipitated solids were collected by filtration and washed with Et$_2$O (3×70 mL) to afford the title compound (51 g, 66.17%) as a grey solid.

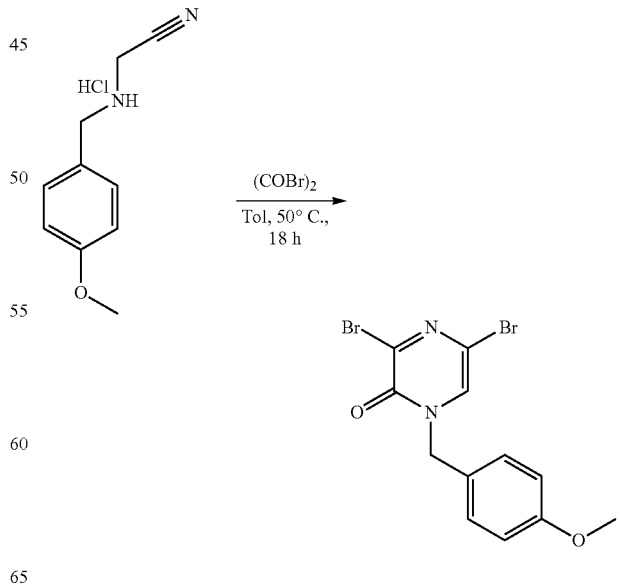

3,5-dibromo-1-(4-methoxybenzyl)pyrazin-2(1H)-one To a 500 mL round-bottom flask containing toluene (200 mL)

was added oxalic dibromide (150 g, 693.6 mmol, 3.0 equiv) dropwise over 30 min at rt. The resulting mixture was stirred for additional 15 min at this temperature. To the stirred solution was added the product from the previous step (49.2 g, 231.33 mmol, 1 equiv) in portions at rt. The resulting mixture was stirred for 18 h at 50° C. The reaction was monitored by LCMS. The mixture was allowed to cool to rt, and was then diluted with sat. NaH$_2$PO$_4$ (500 mL). The aqueous layer was extracted with EtOAc (4×400 mL). The combined organic layers were washed with 500 mL of brine and dried over Na$_2$SO$_4$. The resulting mixture was filtered; the filter cake was washed with EtOAc (2×400 mL). The filtrate was concentrated under reduced pressure. The residue was purified with silica gel chromatography using PE/EtOAc (5:1) to afford the title compound (9 g, 10.40%) as a dark yellow oil.

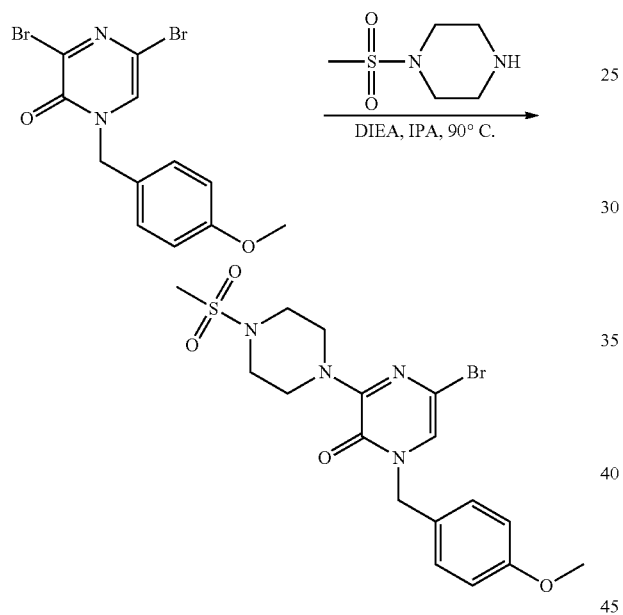

5-Bromo-1-(4-methoxybenzyl)-3-(4-(methylsulfonyl)piperazin-1-yl)pyrazin-2(1H)-one The procedure for preparing Intermediate 1-3 was used with the product from the previous step (6.9 g, 18.45 mmol, 1 equiv) and 1-methanesulfonylpiperazine (3.6 g, 22.14 mmol, 1.2 equiv), using 2 hr of reaction time at 90° C., to afford the title compound (6.6 g, crude) as a yellow solid.

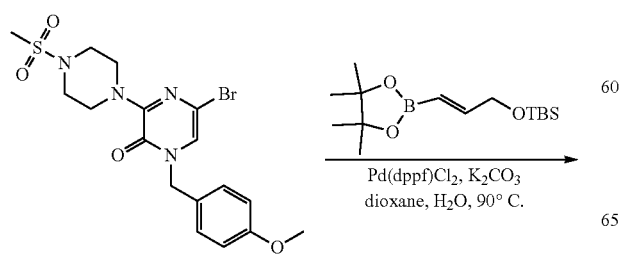

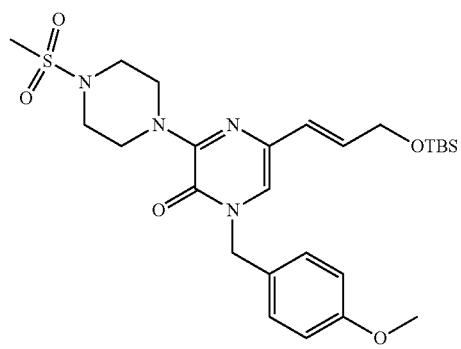

(E)-5-(3-((tert-butyldimethylsilyl)oxy)prop-1-en-1-yl)-1-(4-methoxybenzyl)-3-(4-(methylsulfonyl)piperazin-1-yl)pyrazin-2(1H)-one The procedure for preparing Intermediate 3-3 was used with the product from the previous step (4.5 g, 9.84 mmol), using 1 hr of reaction time at 90° C. The crude product was purified with silica gel chromatography using PE/EtOAc (5:1) to afford the title compound (3.9 g, 72.23%) as a yellow oil.

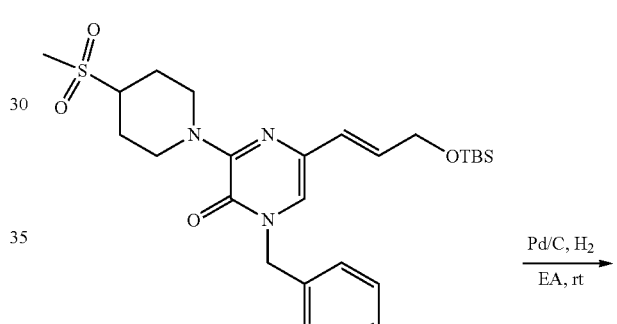

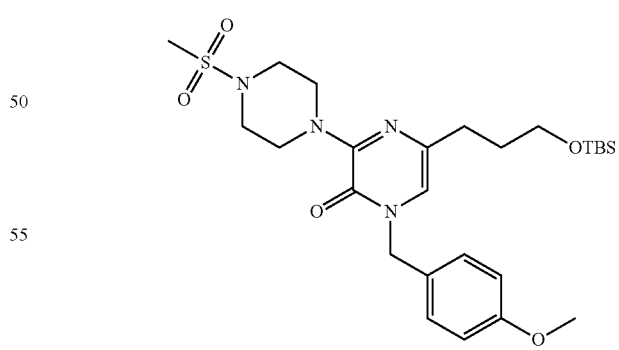

5-(3-((tert-Butyldimethylsilyl)oxy)propyl)-1-(4-methoxybenzyl)-3-(4-(methyl-sulfonyl)piperazin-1-yl)pyrazin-2(1H)-one The procedure for preparing Intermediate 3-4 was used with the product from the previous step (3.5 g, 6.38 mmol, 1 equiv) to afford the title compound (3.3 g, 93.94%) as a yellow oil.

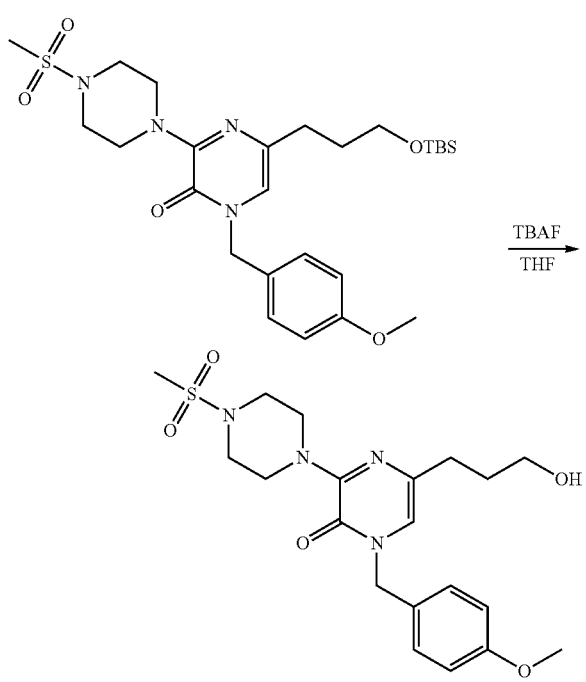

5-(3-Hydroxypropyl)-1-(4-methoxybenzyl)-3-(4-(methylsulfonyl)piperazin-1-yl)pyrazin-2(1H)-one The procedure for preparing Intermediate 22-4 was used with the product from the previous step (3.3 g, 5.99 mmol). The crude product was purified by MPLC with the following conditions (Mobile Phase A: Water, Mobile Phase B: CH$_3$CN; Flow rate: 100 mL/min; Gradient: 0 B to 100% B in 50 min; 220/254 nm; Rt: 31.26 min) to afford the title compound (1.1 g, 42.06%) as a yellow oil.

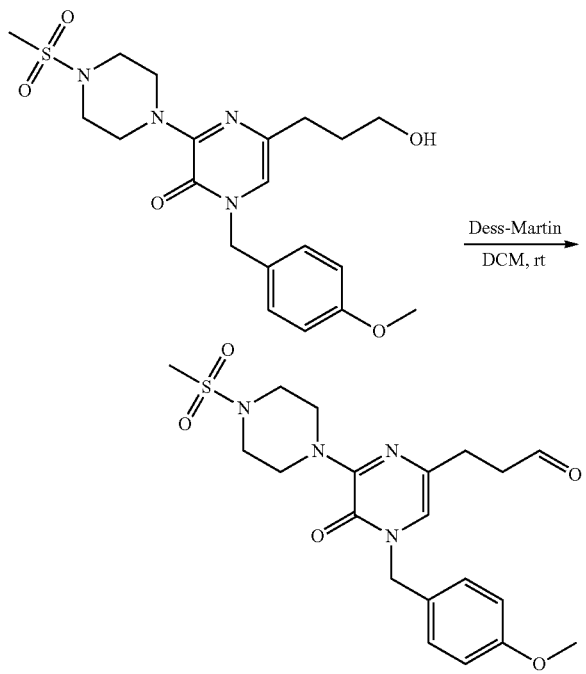

3-(4-(4-Methoxybenzyl)-6-(4-(methylsulfonyl)piperazin-1-yl)-5-oxo-4,5-dihydropyrazin-2-yl)propanal The procedure for preparing Intermediate 1-7 was used with the product from the previous step (500 mg, 1.15 mmol, 1 equiv) and Dess-Martin reagent (583.0 mg, 1.37 mmol, 1.2 equiv). The crude product was purified with silica gel chromatography using CH$_2$Cl$_2$/EtOAc (1:5) to afford the title compound (380 mg, 76%) as an off-white solid.

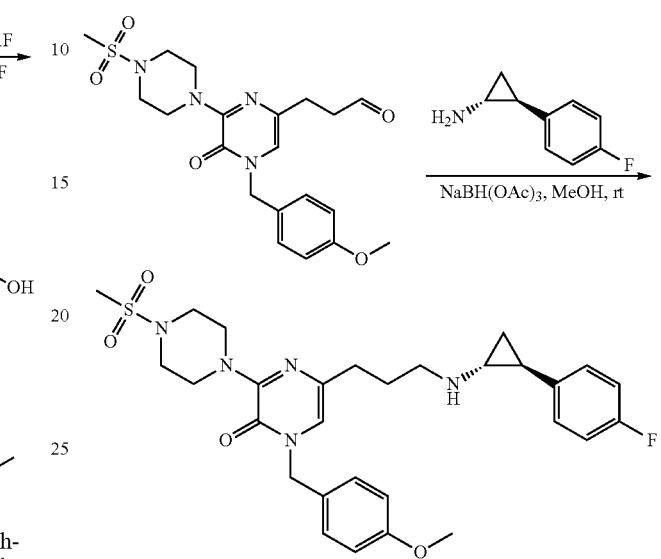

5-(3-(((1R,2S)-2-(4-fluorophenyl)cyclopropyl)amino)propyl)-1-(4-methoxy-benzyl)-3-(4-(methylsulfonyl)piperazin-1-yl)pyrazin-2(1H)-one The reductive amination step for preparing Example 1 from Intermediate 1-7 was used with the product from the previous step (380 mg, 0.87 mmol, 1 equiv) and (1R,2S)-2-(4-fluorophenyl)-cyclopropan-1-amine (246 mg, 1.63 mmol, 1.861 equiv). The crude product (380 mg) was purified using chromatographic Procedure C (44% to 54% CH$_3$CN 10 min), to afford the title compound (69.6 mg, 13.98%) as off-white solid.

LC-MS: (ES, m/z): 570 [M+H]$^+$. $^1$H NMR (300 MHz, MeOD-d$_4$) δ ppm: 7.30 (d, J=8.7 Hz, 2H), 7.07-6.88 (m, 7H), 5.01 (s, 2H), 3.84-3.80 (m, 4H), 3.78 (s, 3H), 3.35-3.29 (m, 4H), 2.87 (s, 3H), 2.71 (t, J=7.2 Hz, 2H), 2.45 (t, J=7.2 Hz, 2H), 2.29-2.24 (m, 1H), 1.90-1.82 (m, 3H), 1.06-0.96 (m, 2H).

Example 46

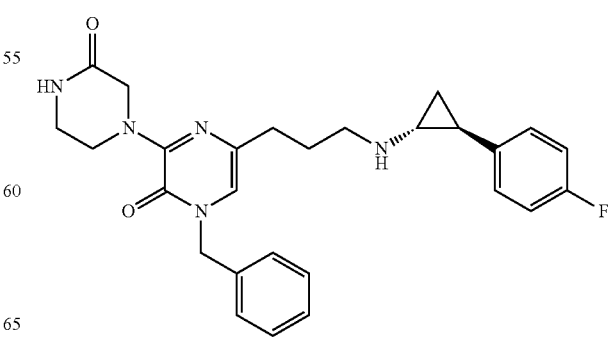

1-benzyl-5-[3-([(1R,2S)-2-(4-fluorophenyl)cyclopropyl]amino)propyl]-3-[3-oxopiperazin-1-yl]pyrazin-2(1H)-one

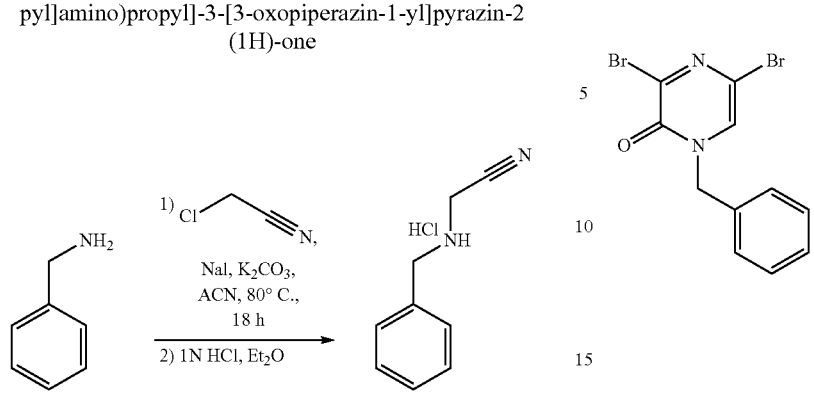

2-(Benzylamino)acetonitrile hydrochloride A mixture of benzylamine (40 g, 291.58 mmol, 1 equiv), 2-chloroacetonitrile (26.4 g, 349.9 mmol, 1.2 equiv), NaI (4.37 g, 29.16 mmol, 0.1 equiv), and K$_2$CO$_3$ (52.4 g, 379.06 mmol, 1.3 equiv) in CH$_3$CN (200 mL) was stirred for 18 h at 80° C. The reaction was monitored by LCMS. The mixture was allowed to cool down to rt. The resulting mixture was filtered; the filter cake was washed with CH$_3$CN (3×150 mL). The filtrate was concentrated under reduced pressure. The resulting mixture was diluted with Et$_2$O (200 mL). HCl (2 M, 100 mL) was then added to the solution. The solid that formed was collected by filtration and washed with Et$_2$O (3×70 mL) to afford the title compound (34 g, 66.17%) as a grey solid.

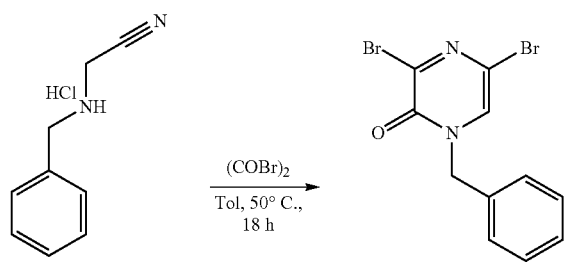 [SMILES: N#CCNCc1ccccc1 ; Cl ; "(COBr)2" ; O=c1c(Br)nc(Br)cn1Cc1ccccc1]

1-benzyl-3,5-dibromopyrazin-2(1H)-one To a 500 mL round-bottom flask containing toluene (200 mL) was added oxalic dibromide (100 g, 462.40 mol, 3.0 equiv) dropwise over 30 min at rt. The resulting mixture was stirred for additional 15 min at this temperature. To the stirred solution was added the product from the previous step (32.8 g, 154.22 mmol, 1 equiv) in portions at rt. The resulting mixture was stirred for 18 h at 50° C. The reaction was monitored by LCMS. The mixture was allowed to cool to rt. The resulting mixture was diluted with sat. NaH$_2$PO$_4$ (500 mL). The aqueous layer was extracted with EtOAc (4×200 mL). The combined organic layers were washed with 500 mL of brine and dried over Na$_2$SO$_4$. The resulting mixture was filtered; the filter cake was washed with EtOAc (2×200 mL). The filtrate was concentrated under reduced pressure. The residue was purified with silica gel chromatography using PE/EtOAc (5:1) to afford the title compound (6 g, 10%) as a dark yellow oil.

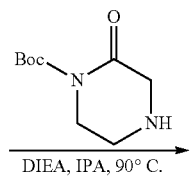
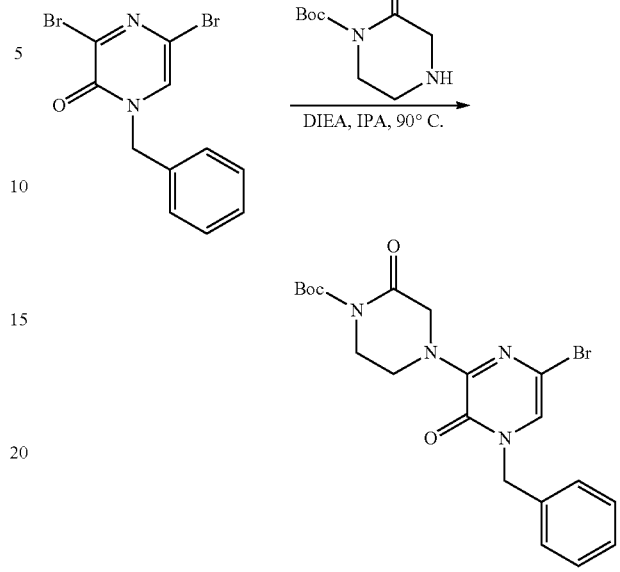

tert-Butyl 4-(4-benzyl-6-bromo-3-oxo-3,4-dihydropyrazin-2-yl)-2-oxopiperazine-1-carboxylate The procedure for preparing Intermediate 4-1 was used with the product from the previous step (5 g, 14.5 mmol, 1.00 equiv) and tert-butyl 2-oxopiperazine-1-carboxylate (4.36 g, 21.8 mmol, 1.50 equiv), affording 3.5 g (88%) of the title compound as a light yellow solid.

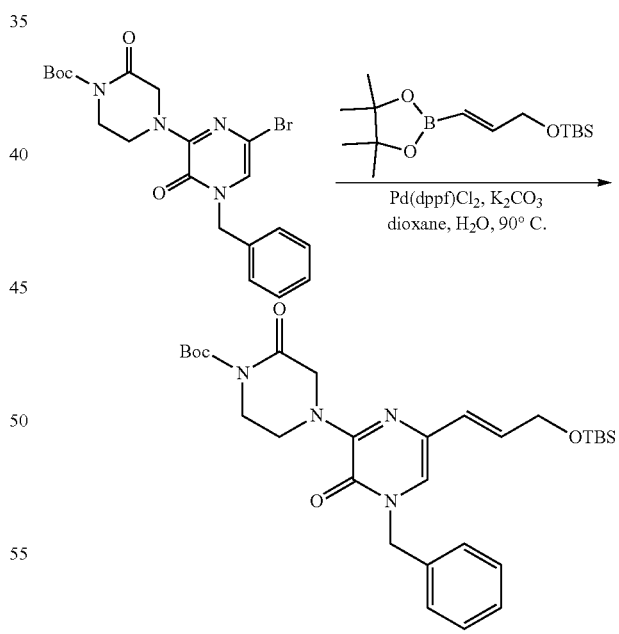

tert-Butyl(E)-4-(4-benzyl-6-(3-((tert-butyldimethylsilyl)oxy)prop-1-en-1-yl)-3-oxo-3,4-dihydropyrazin-2-yl)-2-oxopiperazine-1-carboxylate The procedure for preparing Intermediate 3-3 was used with the product from the previous step (3.5 g, 11.14 mmol, 1.00 equiv) and tert-butyldimethyl[((2E]-3-[tetramethyl-1,3,2-dioxaborolan-2-yl]pop-2-en-1-yl)oxy]silane (3.3 g, 14.60 mmol, 1.30 equiv), using 1 hr reaction time at 90° C. The crude product was purified with silica gel chromatography using EtOAc/petroleum ether (1:1) to afford 2.3 g (24%) of the title compound as orange oil.

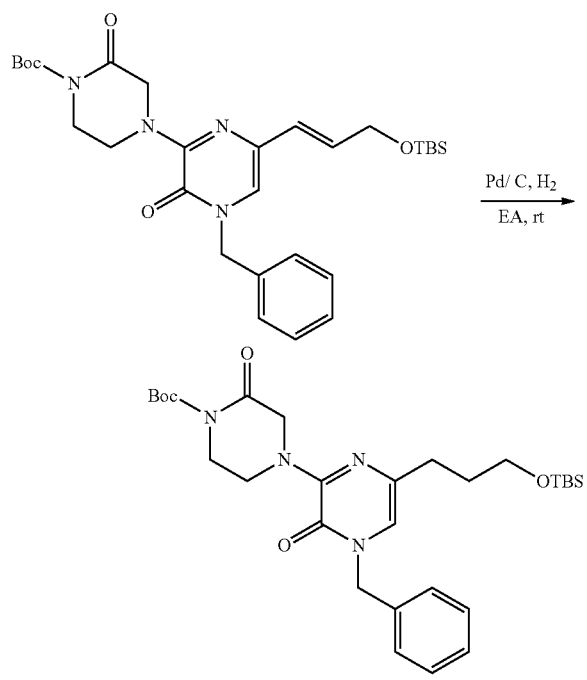

tert-Butyl 4-(4-benzyl-6-(3-((tert-butyldimethylsilyl)oxy)propyl)-3-oxo-3,4-dihydropyrazin-2-yl)-2-oxopiperazine-1-carboxylate The procedure for preparing Intermediate 3-4 was used with the product from the previous step (2.3 g, 1.78 mmol, 1.00 equiv) to afford 2 g (80%) of the title compound as a light yellow oil.

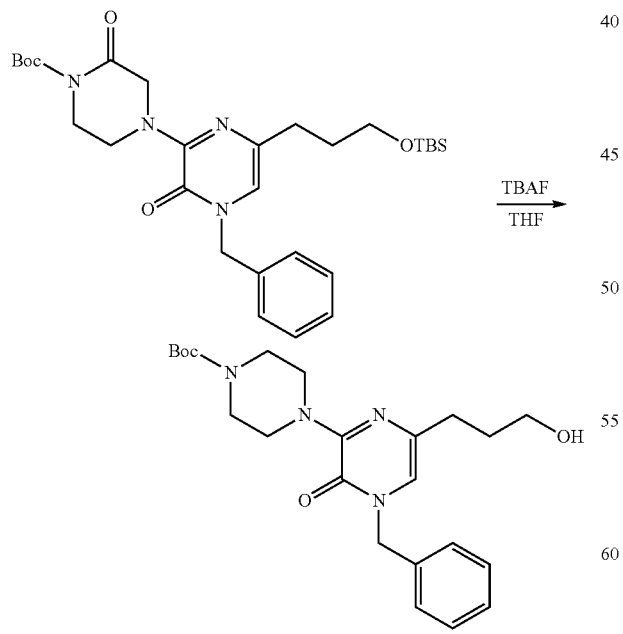

tert-Butyl 4-(4-benzyl-6-(3-hydroxypropyl)-3-oxo-3,4-dihydropyrazin-2-yl)piperazine-1-carboxylate The procedure for preparing Intermediate 22-4 was used with the product from the previous step (2 g, 1.42 mmol). The crude product was purified with silica gel chromatography using EtOAc/petroleum ether (1:2) to afford 1.1 g (70%) of the title compound as a yellow oil.

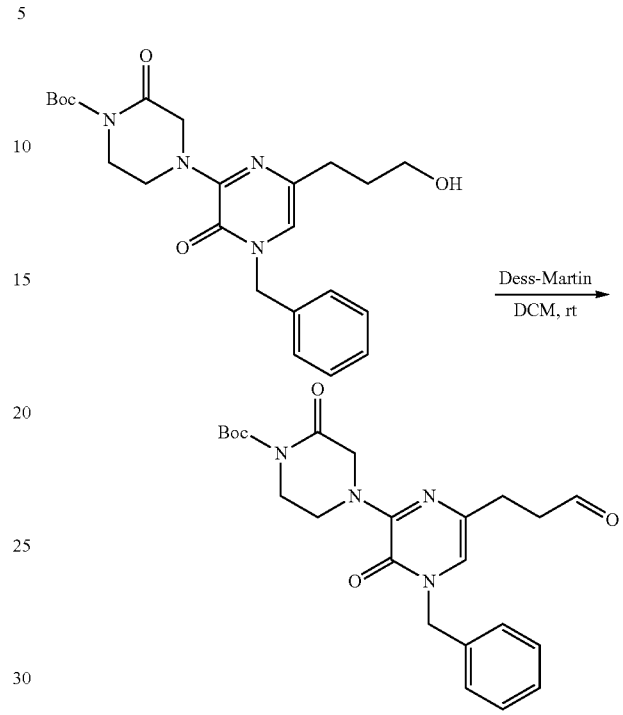

tert-Butyl 4-(4-benzyl-3-oxo-6-(3-oxopropyl)-3,4-dihydropyrazin-2-yl)-2-oxopiperazine-1-carboxylate The procedure for preparing Intermediate 1-7 was used with the product from the previous step (800 mg, 1.00 mmol, 1.00 equiv). The crude product was purified with silica gel chromatography using EtOAc/petroleum ether (2:1) to afford 400 mg (71%) of the title compound as a yellow solid.

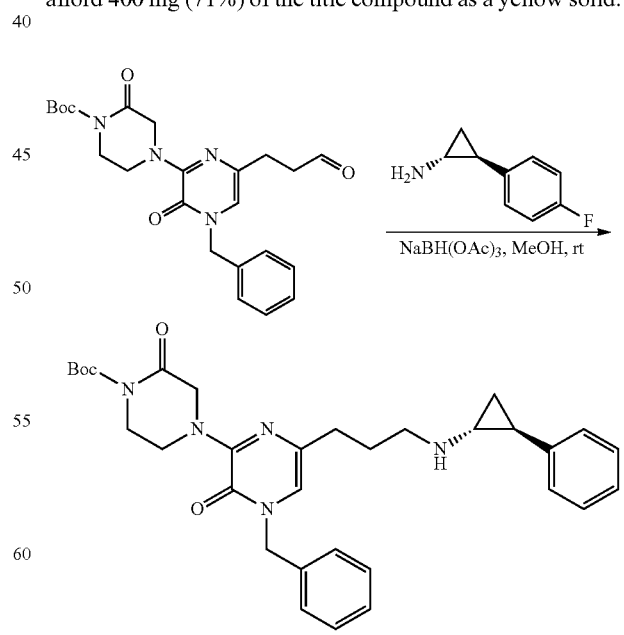

tert-Butyl 4-(4-benzyl-3-oxo-6-(3-(((1R,2S)-2-phenylcyclopropyl)amino)-propyl)-3,4-dihydropyrazin-2-yl)-2-oxopiperazine-1-carboxylate The reductive amination step for preparing Example 1 from Intermediate 1-7 was used with the product from the previous step (400 mg, 0.71 mmol, 1.00 equiv) and (1R,2S)-2-(4-fluorophenyl)-cyclopropan-1-amine (162 mg, 1.07 mmol, 1.50 equiv). The crude product was purified by Prep-TLC with EtOAc to afford 310 mg (22%) of the title compound as a yellow solid.

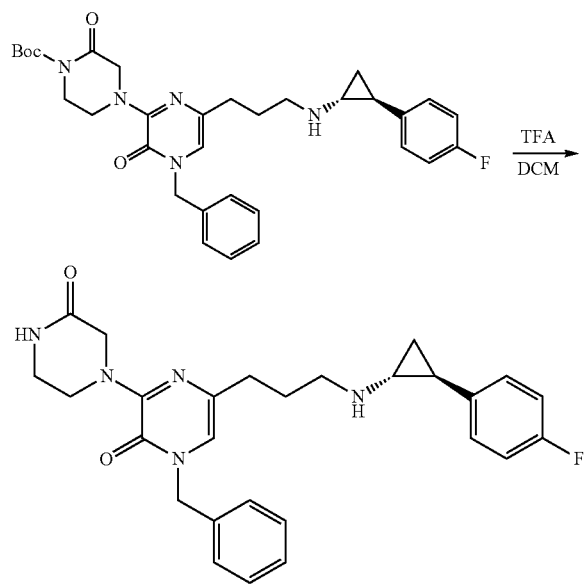

1-Benzyl-5-(3-(((1R,2S)-2-(4-fluorophenyl)cyclopropyl)amino)propyl)-3-(3-oxopiperazin-1-yl)pyrazin-2(1H)-one The deprotection step for preparing Example 14 from Intermediate 14-7 was used with the product from the previous step (100 mg, 0.71 mmol, 1.00 equiv). The crude product was purified using chromatographic Procedure F (22% to 32% CH$_3$CN), to afford 35.6 mg (22%) of the title compound as a yellow solid.

LC-MS: (ES, m/z): 476[M+H]$^+$. $^1$H NMR (300 MHz, MeOD-d$_4$) δ ppm: 7.32-7.30 (m, 5H), 7.29-6.99 (m, 4H), 6.94 (s, 1H), 5.10 (s, 2H), 4.22 (s, 2H), 4.13-4.09 (t, J=5.4 Hz, 2H), 3.42-3.40 (t, J=5.4 Hz, 2H), 3.24-3.18 (m, 2H), 2.96-2.93 (m, 1H), 2.53-2.50 (t, J=7.2 Hz, 2H), 2.50-2.37 (m, 1H), 2.05-2.0 (m, 2H), 1.47-1.34 (m, 2H).

Example 47

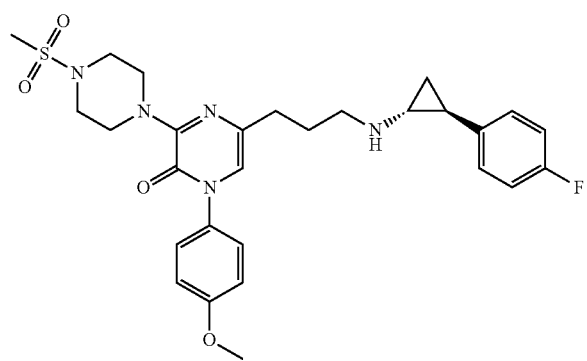 [SMILES: COc1ccc(-n2cc(CCCN[C@@H]3C[C@H]3c3ccc(F)cc3)nc(N3CCN(S(C)(=O)=O)CC3)c2=O)cc1]

5-[3-([(1R,2S)-2-(4-fluorophenyl)cyclopropyl]amino)propyl]-1-[4-methoxyphenyl]-3-[4-(methylsulfonyl)piperazin-1-yl]pyrazin-2(1H)-one

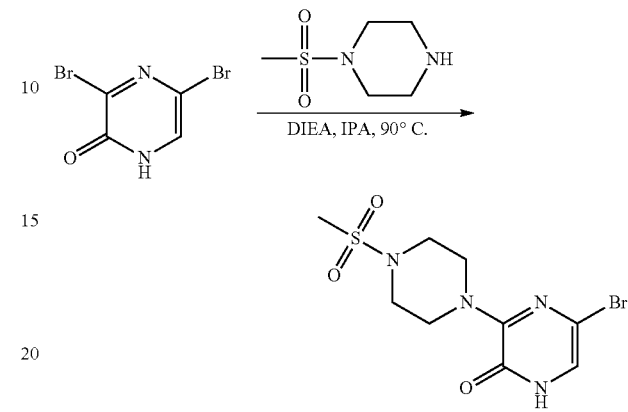

5-Bromo-3-(4-(methylsulfonyl)piperazin-1-yl)pyrazin-2(1H)-one The procedure for preparing Intermediate 4-1 was used with 3,5-dibromo-1,2-dihydropyrazin-2-one (20 g, 78.8 mmol, 1 equiv), 1-methanesulfonylpiperazine (15.6 g, 94.54 mmol, 1.2 equiv), to afford the title compound (16 g, 60%) as a dark yellow solid.

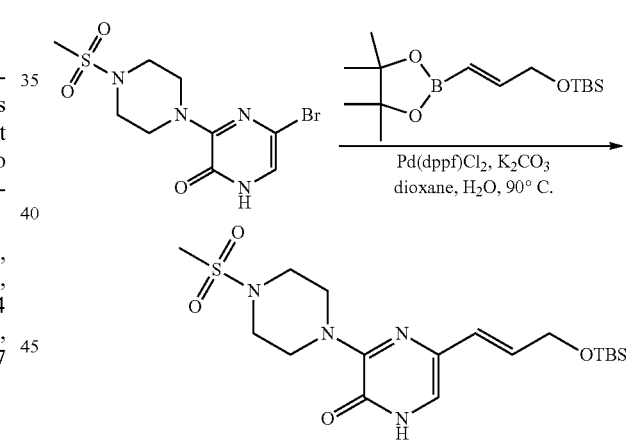

(E)-5-(3-((tert-butyldimethylsilyl)oxy)prop-1-en-1-yl)-3-(4-(methylsulfonyl)-piperazin-1-yl)pyrazin-2(1H)-one The procedure for preparing Intermediate 3-3 was used with the product from the previous step (8 g, 23.73 mmol), using 1 hr of reaction time at 90° C. The crude product was purified with silica gel chromatography using PE/EtOAc (1:1) to afford the title compound (4.26 g, 41.9%) as a yellow oil.

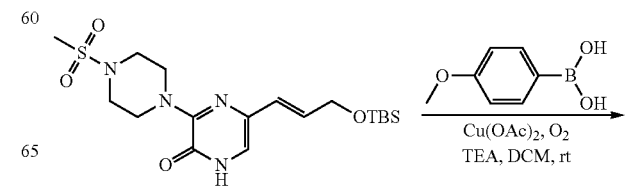

237
-continued

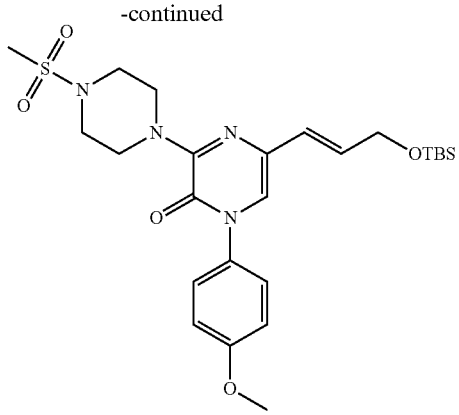

(E)-5-(3-((tert-butyldimethylsilyl)oxy)prop-1-en-1-yl)-1-(4-methoxyphenyl)-3-(4-(methylsulfonyl)piperazin-1-yl)pyrazin-2(1H)-one The procedure for preparing Intermediate 8-9 was used with the product from the previous step (3.5 g, 8.17 mmol, 1 equiv) and (4-methoxyphenyl)boronic acid (1.5 g, 9.80 mmol, 1.2 equiv). The crude product was purified with silica gel chromatography using PE/EtOAc (1:1) to afford the title compound (2.1 g, 48%) as a yellow solid.

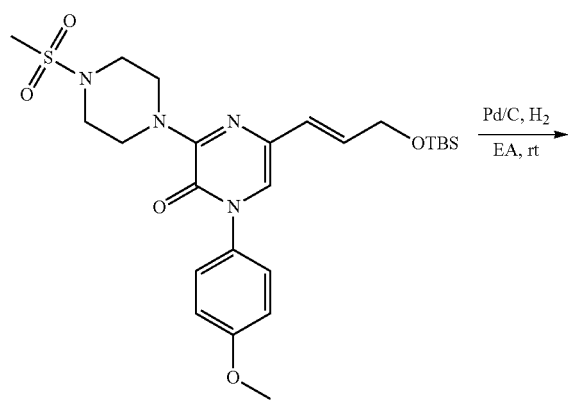

5-(3-((tert-Butyldimethylsilyl)oxy)propyl)-1-(4-methoxyphenyl)-3-(4-(methyl-sulfonyl)piperazin-1-yl)

238 pyrazin-2(1H)-one The procedure for preparing Intermediate 3-4 was used with the product from the previous step (2.1 g, 3.92 mmol, 1.0 equiv) to afford the title compound (1.9 g, 95%) as an off-white solid.

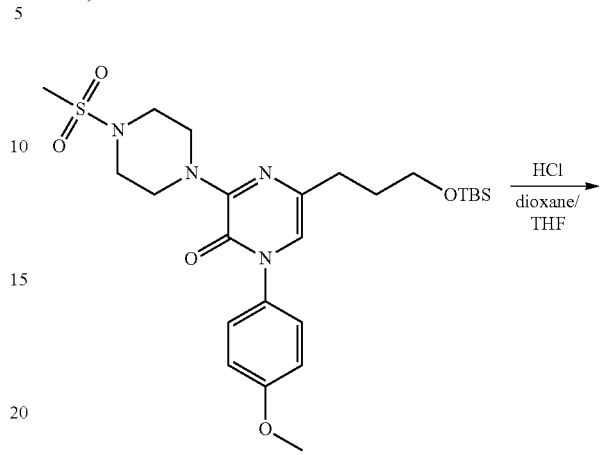

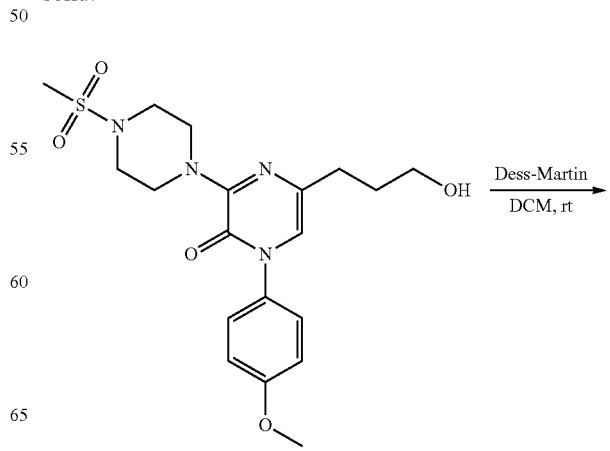

5-(3-hydroxypropyl)-1-(4-methoxyphenyl)-3-(4-(methylsulfonyl)piperazin-1-yl)pyrazin-2(1H)-one The procedure for preparing Intermediate 33-5 was used with the product from the previous step (1.9 g, 3.54 mmol, 1.0 equiv), affording 1.06 g (71%) of the title compound as an off-white solid.

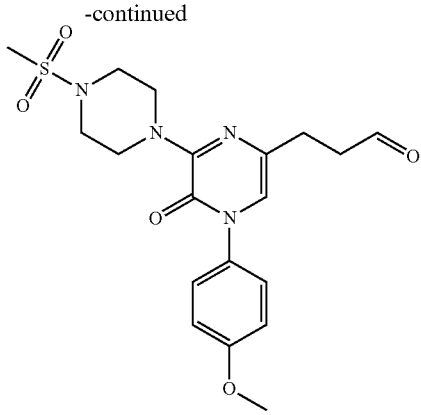

3-(4-(4-Methoxyphenyl)-6-(4-(methylsulfonyl)piperazin-1-yl)-5-oxo-4,5-dihydropyrazin-2-yl)propanal The procedure for preparing Intermediate 1-7 was used with the product from the previous step (500 mg, 1.18 mmol). The crude product was purified with silica gel chromatography using EtOAc/petroleum ether (1:1) to afford 380 mg (76%) of the title compound as a yellow oil.

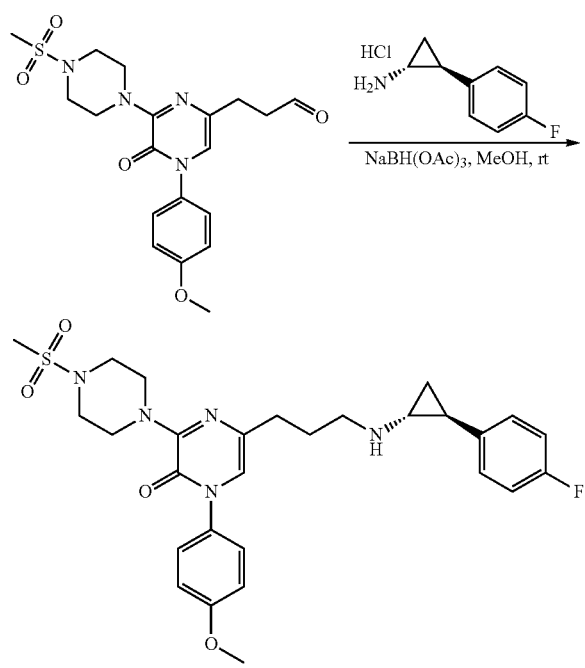

5-(3-(((1R,2S)-2-(4-fluorophenyl)cyclopropyl)amino)propyl)-1-(4-methoxy-phenyl)-3-(4-(methylsulfonyl)piperazin-1-yl)pyrazin-2(1H)-one The procedure for preparing Intermediate 4-7 was used with the product from the previous step (380 mg, 0.90 mmol, 1 equiv) and (1R,2S)-2-(4-fluorophenyl)cyclopropan-1-amine (204.9 mg, 1.36 mmol, 1.500 equiv). The crude product was purified using chromatographic Procedure C (49% B in 8 min), to afford 66.7 mg (13.3%) of the title compound as an off-white solid.

LCMS: (ES, m/z): 556 [M+H]+. 1H NMR (300 MHz, Methanol-d4) δ ppm: 7.36-7.26 (d, J=2.1 Hz, 2H), 7.13-6.91 (m, 6H), 6.85 (s, 1H), 3.90-3.80 (m, 7H), 3.30-3.20 (m, 4H), 2.87 (s, 3H), 2.84-2.73 (m, 2H), 2.49 (t, J=6.6 Hz, 2H), 2.36-2.26 (m, 1H), 1.95-1.85 (m, 3H), 1.14-0.93 (m, 2H).

Example 48

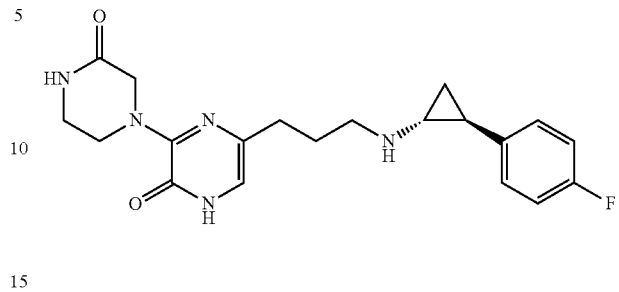

5-[3-([(1R,2S)-2-(4-fluorophenyl)cyclopropyl]amino)propyl]-3-[3-oxopiperazin-1-yl]pyrazin-2(1H)-one

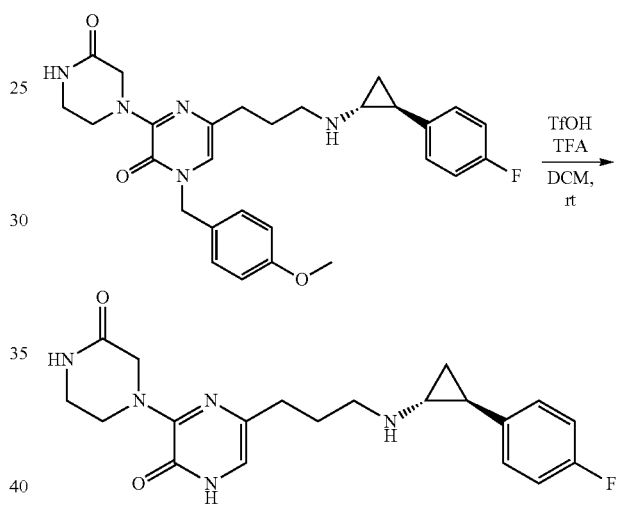

A solution of 5-(3-(((1R,2S)-2-(4-fluorophenyl)cyclopropyl)amino)propyl)-1-(4-methoxybenzyl)-3-(3-oxopiperazin-1-yl)pyrazin-2(1H)-one (Example 42, 400 mg, 0.79 mmol, 1 equiv), TFA (10 mL), and TfOH (5 mL) in CH2Cl2 (20 mL) was stirred for 1 h at 25° C. The resulting mixture was concentrated under vacuum. The residue was diluted with sat. NaHCO3 (100 mL). The aqueous layer was extracted with EtOAc (4×50 mL). The combined organic layers were washed with 1×100 mL of brine, dried over Na2SO4, and purified using chromatographic Procedure C (25% to 35% CH3CN in 7 min), to afford 78.5 mg (33%) of the title compound as white solid.

LC-MS: (ES, m/z): 386 [M+H]+. 1H NMR (300 MHz, MeOD-d4) δ ppm: 7.09-6.93 (m, 4H), 6.69-6.66 (m, 1H), 4.36 (s, 2H), 4.12-4.05 (m, 2H), 3.43-3.42 (t, J=5.4 Hz, 2H), 2.76-2.71 (t, J=7.5 Hz, 2H), 2.49-2.44 (t, J=7.3 Hz, 2H), 2.32-2.27 (m, 1H), 1.94-1.82 (m, 3H), 1.09-0.95 (m, 2H).

The activity of the compounds in Examples 1-32 as KDM1A inhibitors is illustrated in the following assay. The other compounds listed above, which have not yet been made and/or tested, are predicted to have activity in this assay as well.

Biological Activity Assay

The activity of the Examples above may be illustrated in the following assays. Compounds listed above, which may not yet have been made and/or tested, are predicted to have activity in these assays.

Assaying the inhibition of KDM1A can be determined in vitro, in cultured cells, and in animals. There are a variety of spectrophotometric methods to detect the results of demethylation of methylated lysines, viz., detecting the products of KDM1A demethylase oxidative activity on a peptide fragment of at least 18 amino acid representing the N-terminus of the histone $H_3$ substrate that contains a monomethyl at the fourth lysine residue. Hydrogen peroxide, one product of the KDM1A demethylase reaction, reacts with horseradish peroxidase and dihydroxyphenoxazine (ADHP) to produce the fluorescent compound resorufin (excitation=530-560 nm:emission=590 nm). The KDM1A demethylase enzyme activity can obtained from mammalian cells or tissues expressing KDM1A from an endogenous or recombinant gene and purified or assayed from a whole cell extract. These methods can be used to determine the concentration of the disclosed compounds can inhibit fifty percent of the enzyme activity ($IC_{50}$). In one aspect, the disclosed compounds exhibit inhibition fifty percent of the KDM1A enzyme activity at a concentration of less than 500 nM, less than 100 nM, less than 50 nM or less than 10 nM.

The association of KDM1A with other proteins can be determined by a variety of both in vitro and in vivo methods known to one skilled in the art. For example, the disruption of KDM1A with associated proteins can be determined in an electromobility shift assay (EMSA). In various aspects, the disruption of the physical association of KDM1A with CoRest by the disclosed compounds can be observed using EMSA. In another example, the disruption of KDM1A with associated proteins can be determined by immunoprecipitation followed by separation of the co-precipitated proteins by mass spectroscopy or by get electrophoresis. In another example, the disruption of KDM1A association with CoRest can be determined by the ability of KDM1A to act on a nucleosomal substrate containing K4 or K9 methylated histone $H_3$, a substrate that requires the presence of both KDM1A and CoRest. The disclosed compounds could be used to assay inhibition of CoRest association with KDM1A using nucleosomal substrate; such compounds may not inhibit KDM1A enzymatic activity as determined by the use of the histone H3 K4 methylated peptide substrate.

The inhibition of KDM1A can be determined in a cell-based assay. For example, KDM1A is an essential enzyme and prolonged inhibition of KDM1A will result in cell death, thus cell growth inhibition, arrest of cell growth or cell death can be assayed. In another aspect, genes induced by androgens and estrogens require KDM1A activity; inhibition by the disclosed compounds of KDM1A will abrogate the induction of gene expression in cells treated with androgens or estrogens. These effects can be measured, e.g., using quantitative PCR of mRNA to measure the magnitude of gene expression for androgen- and estrogen-dependent genes. KDM1A activity is required for the repression of transcription of specific genes. Inhibition of KDM1A by the disclosed compounds could de-repress the expression such genes in cell. These genes include Meis1, VEG-A, AIM1, HMOX1, VIM, SKAP1, BMP, EOMES, FOXA2, HNF4, SOX17, GH, PSA, pS2, GREB1, GR-1b, PRL, TSHB, SYN1, HBG, SCN1A, SCN2a, and SCN3A the expression of which can be assayed using quantitative PCR of mRNA before and at various time following the treatment of cells with the disclosed compounds. In another aspect, KDM1A is a regulator of leukemic stem cell potential and is required for oncogenic transformation of myeloid cells to acute myeloid leukemia (AML) by MLL-AF9. Inhibition of KDM1A in MLL-AF9-transformed cells grown in culture overcomes the arrest in differentiation to resulting in a more mature cell expressing the CD11b surface antigen, a monocytic cell antigen. Thus, inhibition of KDM1A can be assayed using an AML cell line such as THP-1 grown in culture quantifying the proportion of cells newly expressing the CD11b antigen using fluorescence activated cell sorting (FACS). A similar assay using FACS to count cells displaying the CD14 or CD86 can be also used, each of which are characteristic of more mature cells along the macrophage/monocytic lineage. Other cells lines derived from patients with acute myeloid leukemia such as MV4; 11 or MOLM-13 cells can be used for this assay. Other markers of differentiation along the macrophage/monocyte lineage can be similarly assayed by FACS such as CD14 and CD86. Other AML cell lines such as MPLM-13 or MV4; 11 can be assayed for the induction of either specific genes mentioned above or the differentiation markers as well as cell growth or apoptosis by Annexin V staining and FACS enumeration.

The selectivity of the disclosed compounds for KDM1A can be determined by assaying the $IC_{50}$ of the disclosed compounds for other FAD-dependent aminoxidases such as monoamine oxidase A (MAO-A), monoamine oxidase B (MAO-B), IL4I1, KDM1B, or SMOX. As such, a disclosed compound would inhibit KDM1A with an $IC_{50}$ that is 50-fold, or 100-fold or 250-fold or 500-fold less than for MAO-A or MAO-B.

Additional Demethylase Assays

The histone demethylase assay can be performed essentially as described in Shi, Y et al. Cell 199, 941-953 (2004). Briefly, bulk histones, histone peptides or nucleosomes are incubated with purified human recombinant KDM1A, in the histone demethylase activity (HDM) assay buffer 1 (50 mM Tris pH 8.5, 50 mM KCl, 5 mM MgCl, 0.5% BSA, and 5% glycerol) from 30 minutes to 4 hours at 37° C. A typical reaction is conducted in 100 microliters in which either 20 micrograms of purified bulk histones or 3 micrograms of modified histone peptides are used as substrates. Different amounts of KDM1A ranging from 1-20 micrograms are used in the reaction along with, as necessary, other co-factors such as FAD or CoREST, depending on the chosen substrate. The reaction mixture is analyzed by SDS-PAGE and Western blotting using histone methyl-specific antibodies or by formaldehyde formation assay to examine the removal and conversion of the methyl group to formaldehyde, or by mass spectrometry in the case of peptide substrates to identify the demethylated histone peptide.

Bulk histones (e.g., 4 mg) are incubated with the indicated amounts of recombinant proteins or complexes in histone demethylase (HDM) assay buffer A (50 mM Tris pH8.5, 50 mM KCl, 5 mM MgCl, 5% glycerol, 0.2 mM phenylmethylsulphonyl fluoride and 1 mM dithiothreitol) in a final volume of 10 ml for 12-16 h at 37 8 C. For nucleosomes (0.3 mg) or mononucleosome (0.3 mg), HDM buffer A containing 0.1% NP40 can be used. The reaction mixture can then be analyzed by SDS-PAGE followed by Western blotting. Antibodies against mono- or di-methyl K4 in histone $H_3$ and acetyl-K9/K14 of histone $H_3$ are used to detect the degree of methylation and acetylation, respectively. Western blots are then quantified by densitometry or by intensity of luminescence.

Alternatively, a standard flurogenic assay can be used in which the methylated histone substrate is tethered to the bottom of a 96 well plate (or to beads resting in the plate) using biotin conjugated to the histone methylated substrate and strepavidin (SA) on beads or SA attached to the plate to secure the biotinylated substrate. After incubation of the KDM1A enzyme in histone demethylase buffer A, the demethylated histone substrate can be detected using antibodies specific for demethylated $H_3K4$ substrate conjugated to a fluor or some other agent that can be detected. A variation on that assay method would employ an antibody directed against the methylated version of the histone in which the amount of substrate is quantified before and after incubation with the enzyme. Yet another version of a similar assay would employ a fluorescence resonance energy transfer (FRET) system of detection in which the antibody recognizing the methylated version is conjugated or otherwise linked to an entity, e.g., a bead or a large carrier molecule on which a fluorophore (donor) is attached and the fluorophore (acceptor) is bound to an entity linked to the substrate.

Alternatively, the production of $H_2O_2$ during the KDM1A reaction can be detected fluometrically. In this system, the production of $H_2O_2$ is detected in the HDM assay buffer after exposure to substrate, co-factor and enzyme using ADHP (10-Acetyl-3, 7-dihydroxyphenoxazine) as a fluorogenic substrate for horse radish peroxidase (HRP). ADHP (also known as Amplex Red Reagent) is the most stable and sensitive fluorogenic substrate for HRP. The florescent product is resorufin. Sensitivity can be as low as $10^{-15}$ M of target protein. The signal is read using a fluorescence microplate reader at excitation and emission wavelengths of 530-560 nm and 590 nm, respectively.

Additionally, the KDM1A reaction can include other factors which may influence the activity of KDM1A. Such factors might include CoREST, NuRD complexes, DNMT1, HDAC1, HDAC2, and HDAC3, for example, as proteins known to associate with KDM1A or KDM1A-containing complexes. Interactions that influence any aspect of the KDM1A activity including specificity for template, substrate, $K_m$, $K_{cat}$, or sensitivity to FAD concentrations can be assayed. For example, an in vitro interaction assay between KDM1A and CoREST can be performed adding recombinant KDM1A (e.g., 10 mg) and CoREST (e.g., 5 mg) mixed and incubated for 1 h at 4-8° C., fractionated by Superdex 200 gel filtration column in a buffer containing 20 mM Tris-HCl pH 7.9, 500 mM KCl, 10% glycerol, 0.2 mM EDTA, 1 mM dithiothreitol, 0.1% Nonidet P40 and 0.2 mM phenylmethylsulphonyl fluoride, and then analyzed by silver staining.

For co-immunoprecipation of mononucleosomes with KDM1A and CoREST, nucleosomes (1.5 mg) can be digested with micrococcal nuclease and incubated with recombinant KDM1A (e.g., 1 mg), CoREST (e.g., 500 ng) or both proteins in HDM buffer A containing 0.1% NP40 for 1 h at 4-8° C. Antibodies directed against KDM1A or CoREST attached to an affinity resin are added and after extensive washing with HDM buffer A containing 0.1% NP40, the bound proteins are eluted with a wash buffer. KDM1A activity can be assayed in the eluate or the concentration of KDM1A can be determined by quantitative Western blotting.

Compounds were tested in a 10-dose $IC_{50}$ mode fluorescence coupling enzyme assay with 3-fold serial dilution in duplicate starting at 100 μM. The production of FAD-dependent $H_2O_2$ as a result of demethylase activity of LSD1 on 10 M histone $H_3$(1-21)K4me2 peptide substrate was measured by coupling with HRP and Amplex Red to yield resorufin (fluorescence measured at Ex/Em=535/590 nm on EnVision, Perkin Elmer). Results are given below in Table 1.

TABLE 1

| LSD1 Activity | |
|---|---|
| Example # | RB LSD1 ave, nM |
| 1 | 2 |
| 2 | 28 |
| 3 | 7 |
| 4 | 7 |
| 5 | 12 |
| 6 | N.D. |
| 7 | 16 |
| 8 | 48 |
| 9 | 6 |
| 10 | 300 |
| 11 | 7 |
| 12 | 7 |
| 13 | 6 |
| 14 | 10 |
| 15 | 19 |
| 16 | 9 |
| 17 | 4 |
| 18 | 3 |
| 19 | 0.7 |
| 20 | 6 |
| 21 | 0.6 |
| 22 | 2 |
| 23 | 9 |
| 24 | 91 |
| 25 | 10 |
| 26 | 4 |
| 27 | 17 |
| 28 | 6 |
| 29 | 2 |
| 30 | 2 |
| 31 | 4 |
| 32 | 9 |
| 33 | 17 |
| 34 | 11 |
| 35 | 11 |
| 36 | 13 |
| 37 | 24 |
| 38 | 7 |
| 39 | 12 |
| 40 | 78 |
| 41 | 24 |
| 42 | 18 |
| 43 | <0.1 |
| 44 | 6 |
| 45 | 18 |
| 46 | 7 |
| 47 | 9 |
| 48 | 15 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this disclosure, and without departing from the spirit and scope thereof, can make various changes and modifications of the disclosure to adapt it to various usages and conditions.

What is claimed is:

1. A compound of structural Formula I:

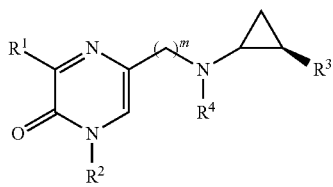

or a salt thereof, wherein:

m is chosen from 0, 1, 2, 3, and 4;

$R^1$ is a nitrogen-containing heterocycloalkyl or heteroaryl, either of which is optionally substituted with 1, 2, or 3 $R^5$ groups;

$R^2$ is H, or is chosen from alkyl, cycloalkyl, haloalkyl, heterocycloalkyl, aryl, and heteroaryl, any of which is optionally substituted with 1, 2, or 3 $R^6$ groups;

$R^3$ is chosen from aryl and heteroaryl, either of which is optionally substituted with 1, 2, or 3 $R^7$ groups;

$R^4$ is chosen from hydrogen, alkyl, alkenyl, alkynyl, and cycloalkyl;

each $R^5$ is independently chosen from halogen, alkyl, alkenyl, alkynyl, hydroxy, amino, oxo, cyano, $COR^8$, $CONR^8R^9$, $COOR^8$, $NHCOR^8$, $NHCONR^8R^9$, $SOR^8$, $SO_2R^8$, $NHSO_2R^8$, and $SO_2NR^8R^9$;

each $R^6$ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, $COR^8$, $SO_2R^8$, $NHSO_2R^8$, $NHSO_2NHR^8$, $SO_2NR^8R^9$, $NHCOR^8$, $NHCONHR^8$, $CONHR^8$, and $CONR^8R^9$;

each $R^7$ is independently chosen from alkyl, amino, cyano, halo, and hydroxy; and each $R^8$ and $R^9$ is independently chosen from hydrogen, aryl, and lower alkyl; or $R^8$ and $R^9$ may be taken together to form a nitrogen-containing heterocycloalkyl or heteroaryl ring, which is optionally substituted with lower alkyl.

2. The compound as recited in claim 1, or a salt thereof, wherein $R^4$ is hydrogen.

3. The compound as recited in claim 2, or a salt thereof, wherein $R^3$ is phenyl, and is optionally substituted with 1 or 2 $R^7$ groups.

4. The compound as recited in claim 3, or a salt thereof, wherein $R^7$ is fluorine.

5. The compound as recited in claim 1, or a salt thereof, having structural Formula II:

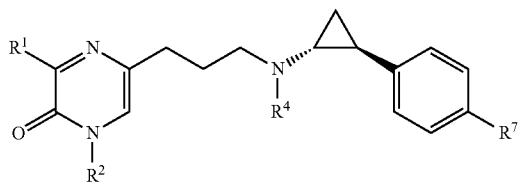

or a salt thereof, wherein:

$R^1$ is a nitrogen-containing heterocycloalkyl or heteroaryl, either of which is optionally substituted with 1, 2, or 3 $R^5$ groups;

$R^2$ is H, or is chosen from alkyl, cycloalkyl, haloalkyl, heterocycloalkyl, aryl, and heteroaryl, any of which is optionally substituted with 1, 2, or 3 $R^6$ groups;

$R^4$ is chosen from hydrogen, alkyl, alkenyl, alkynyl, and cycloalkyl;

each $R^5$ is independently chosen from halogen, alkyl, alkenyl, alkynyl, hydroxy, amino, oxo, cyano, $COR^8$, $CONR^8R^9$, $COOR^8$, $NHCOR^8$, $NHCONR^8R^9$, $SOR^8$, $SO_2R^8$, $NHSO_2R^8$, and $SO_2NR^8R^9$;

each $R^6$ is independently chosen from hydrogen, halogen, alkyl, alkylsulfonylaryl, alkenyl, alkynyl, cycloalkyl, haloalkyl, haloalkoxy, haloaryl, alkoxyaryl, aryl, aryloxy, aralkyl, heterocycloalkyl, heteroaryl, alkylheteroaryl, heteroarylalkyl, cyano, alkoxy, alkoxyaryl, amino, alkylamino, dialkylamino, oxo, $COR^8$, $SO_2R^8$, $NHSO_2R^8$, $NHSO_2NHR^8$, $SO_2NR^8R^9$, $NHCOR^8$, $NHCONHR^8$, $CONHR^8$, and $CONR^8R^9$;

each $R^7$ is independently chosen from hydrogen, alkyl, amino, cyano, halo, and hydroxy; and each $R^8$ and $R^9$ is independently chosen from hydrogen, aryl, and lower alkyl; or $R^8$ and $R^9$ may be taken together to form a nitrogen-containing heterocycloalkyl or heteroaryl ring, which is optionally substituted with lower alkyl.

6. The compound as recited in claim 5, or a salt thereof, wherein $R^4$ is hydrogen.

7. The compound as recited in claim 6, or a salt thereof, wherein $R^1$ is a nitrogen-containing heterocycloalkyl, which is optionally substituted with 1, 2, or 3 $R^5$ groups.

8. The compound as recited in claim 7, or a salt thereof, wherein $R^1$ is chosen from:

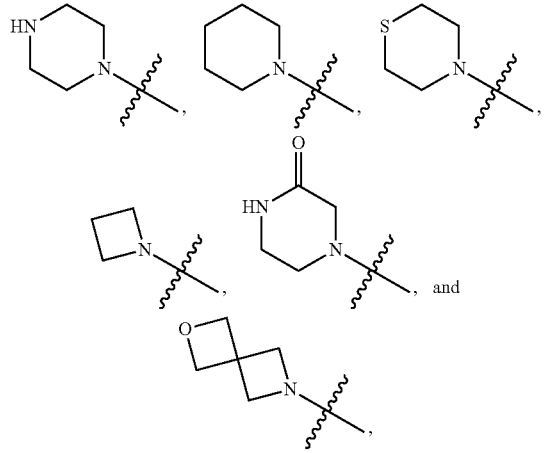

and is optionally substituted with 1, 2, or 3 $R^5$ groups.

9. The compound as recited in claim 8, or a salt thereof, wherein each $R^5$ is independently chosen from halogen, alkyl, hydroxy, amino, oxo, cyano, $COR^8$, $CONR^8R^9$, $COOR^8$, $NHCOR^8$, $NHCONR^8R^9$, $SOR^8$, $SO_2R^8$, $NHSO_2R^8$, and $SO_2NR^8R^9$.

10. The compound as recited in claim 9, or a salt thereof, wherein each $R^5$ is independently chosen from alkyl, oxo, $CONR^8R^9$, $COOR^8$, $SOR^8$, and $SO_2R^8$.

11. The compound as recited in claim 7, or a salt thereof, wherein $R^1$, with substitution $R^5$ where appropriate, and further with substitutions $R^8$ and $R^9$ where appropriate, is chosen from:

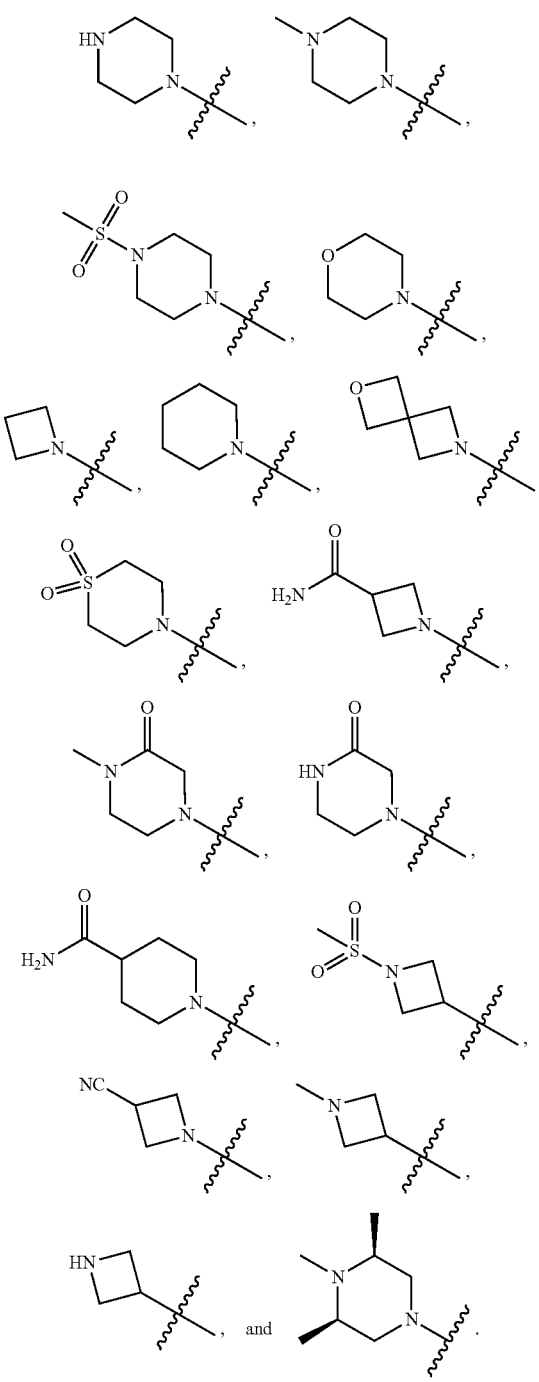

12. The compound as recited in claim 7, or a salt thereof, wherein $R^1$, with substitution $R^5$ where appropriate, and further with substitutions $R^8$ and $R^9$ where appropriate, is chosen from:

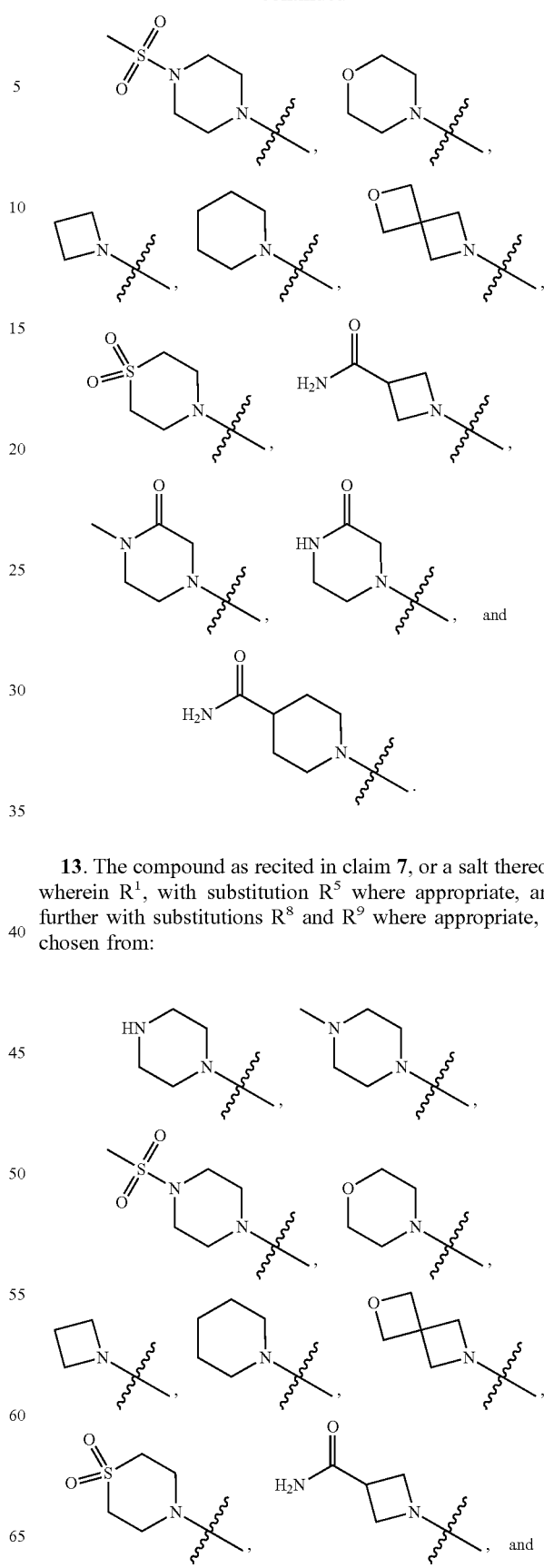

13. The compound as recited in claim 7, or a salt thereof, wherein $R^1$, with substitution $R^5$ where appropriate, and further with substitutions $R^8$ and $R^9$ where appropriate, is chosen from:

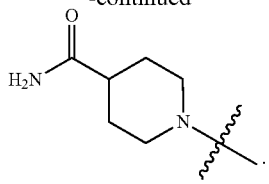

14. The compound as recited in claim 6, or a salt thereof, wherein $R^1$ is a nitrogen-containing heteroaryl, which is optionally substituted with 1, 2, or 3 $R^5$ groups.

15. The compound as recited in claim 14, or a salt thereof, wherein $R^1$ is chosen from:

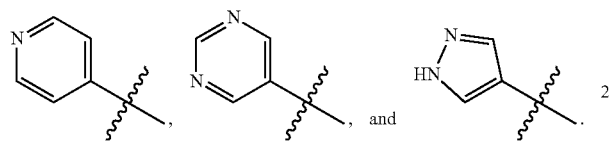

16. The compound as recited in claim 6, or a salt thereof, wherein $R^2$ is H.

17. The compound as recited in claim 16, or a salt thereof, wherein $R^1$ is chosen from piperidine, morpholine, thiomorpholine, piperazine, pyrrolidine, azetidine, 2-azaspiro[3.3]heptane, 2,6-diazaspiro[3.3]heptane, and 2-oxa-6-azaspiro[3.3]heptane, and is optionally substituted with 1, 2, or 3 $R^5$ groups.

18. The compound as recited in claim 17, or a salt thereof, wherein each $R^5$ is independently chosen from halogen, alkyl, hydroxy, amino, oxo, cyano, $COR^8$, $CONR^8R^9$, $COOR^8$, $NHCOR^8$, $NHCONR^8R^9$, $SOR^8$, $SO_2R^8$, $NHSO_2R^8$, and $SO_2NR^8R^9$.

19. The compound as recited in claim 18, or a salt thereof, wherein each $R^5$ is independently chosen from alkyl, oxo, $CONR^8R^9$, $COOR^8$, $SOR^8$, and $SO_2R^8$.

20. The compound as recited in claim 19, or a salt thereof, wherein $R^1$ is chosen from:

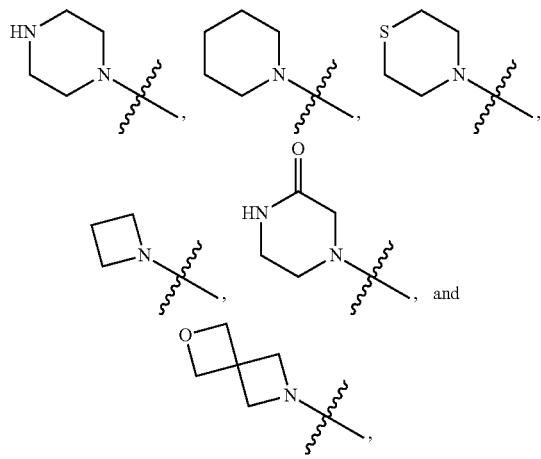

and is optionally substituted with 1, 2, or 3 $R^5$ groups.

21. The compound as recited in claim 16, or a salt thereof, wherein $R^1$, with substitution $R^5$ where appropriate, and further with substitutions $R^8$ and $R^9$ where appropriate, is chosen from:

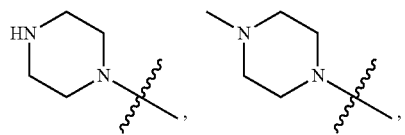

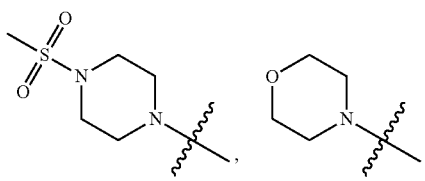

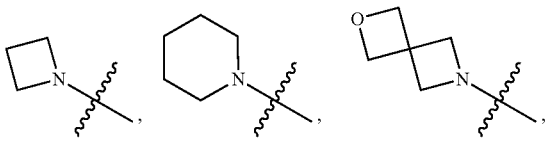

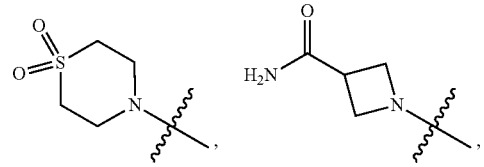

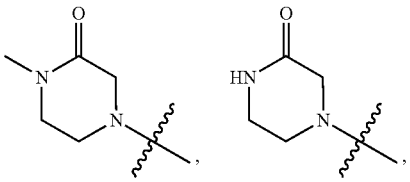

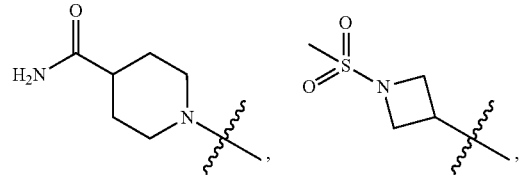

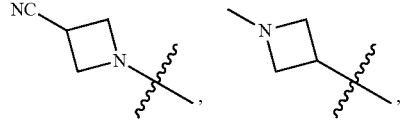

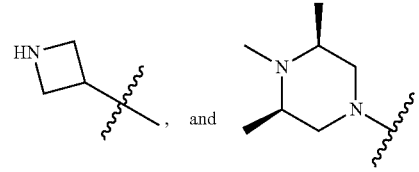

22. The compound as recited in claim 16, or a salt thereof, wherein $R^1$, with substitution $R^5$ where appropriate, and further with substitutions $R^8$ and $R^9$ where appropriate, is chosen from:

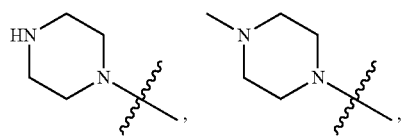

251
-continued
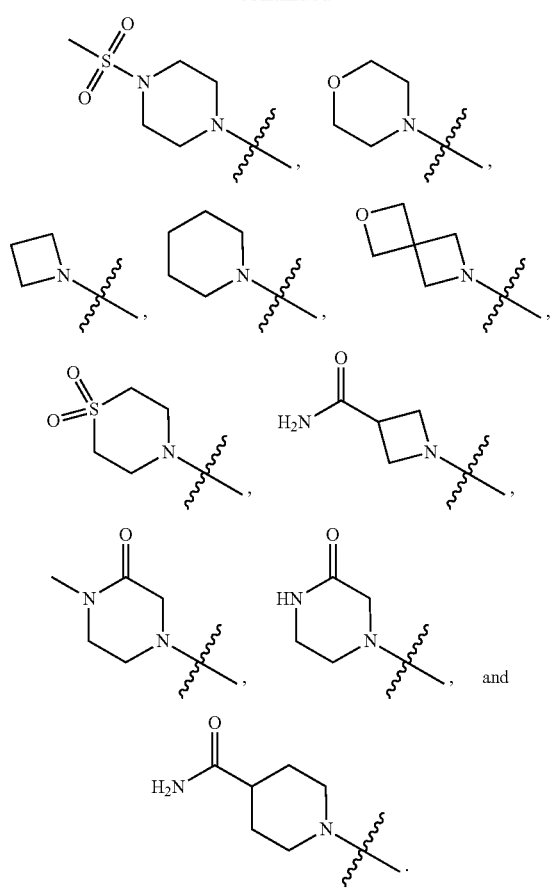
23. The compound as recited in claim 16, or a salt thereof, wherein $R^1$, with substitution $R^5$ where appropriate, and further with substitutions $R^8$ and $R^9$ where appropriate, is chosen from:
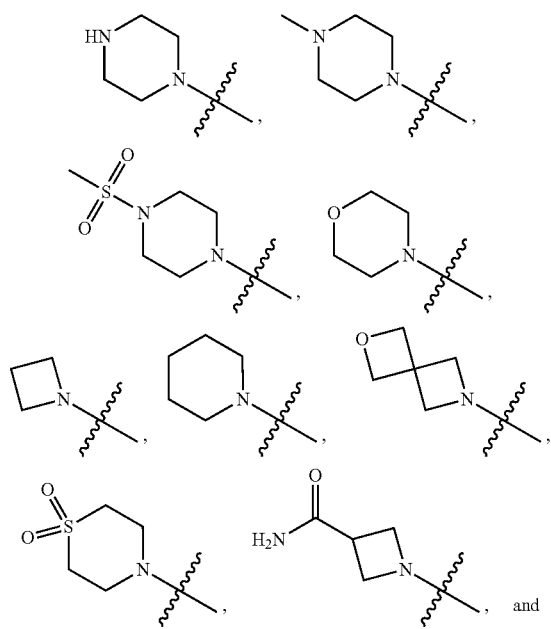
252
-continued
24. A compound chosen from:
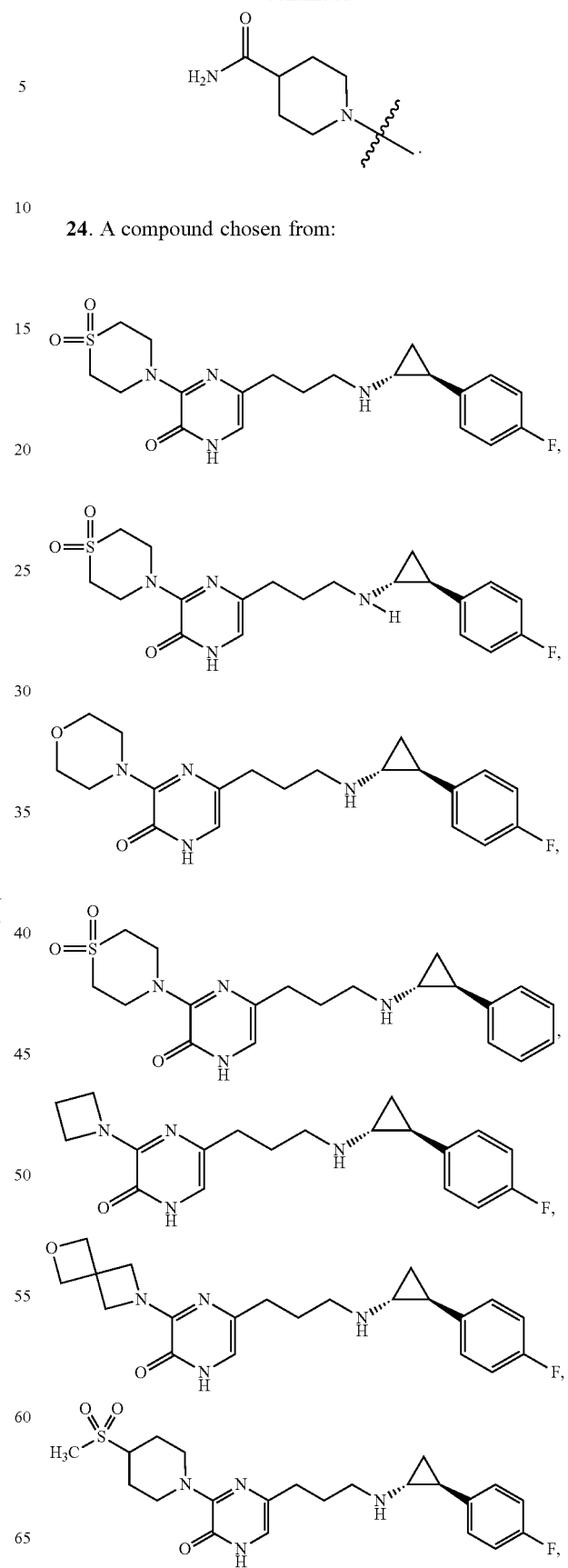

253
-continued
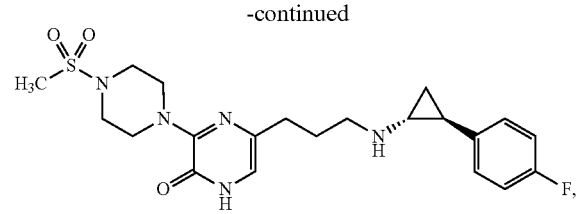
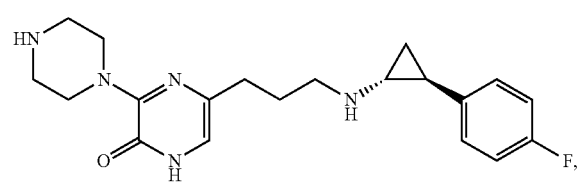
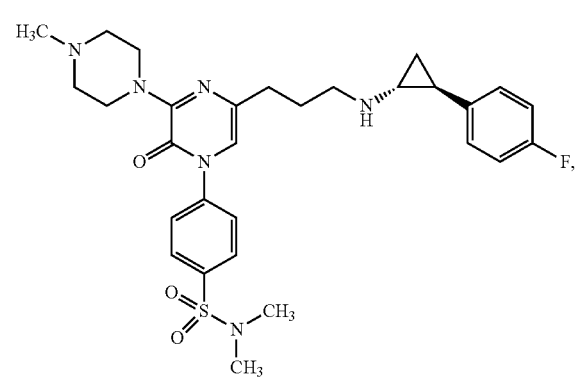
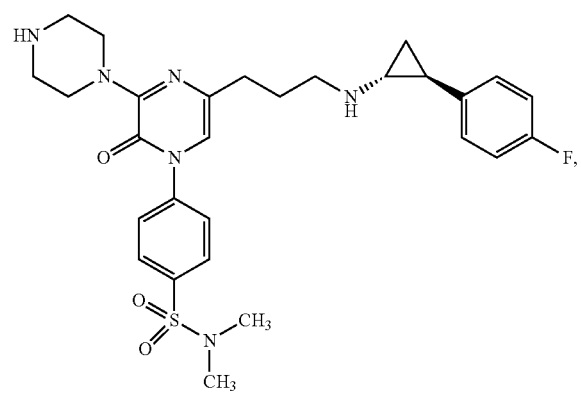
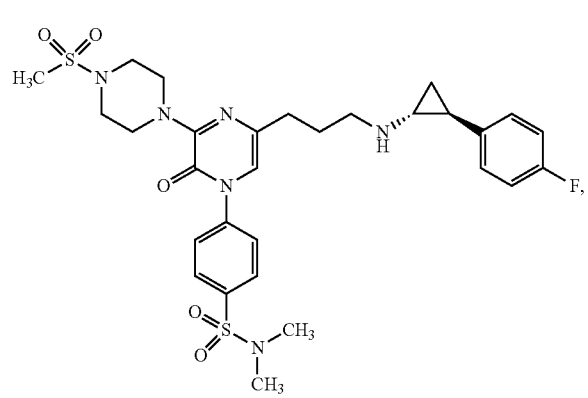
254
-continued
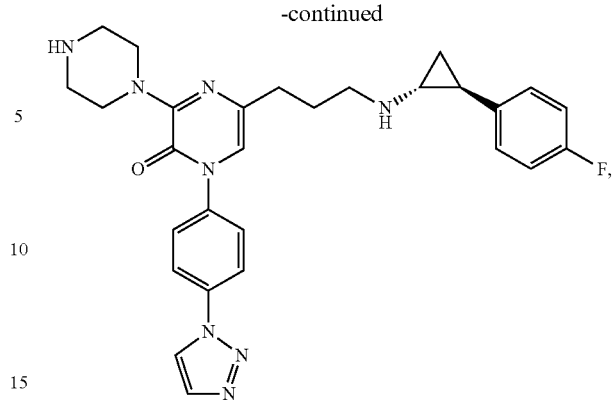
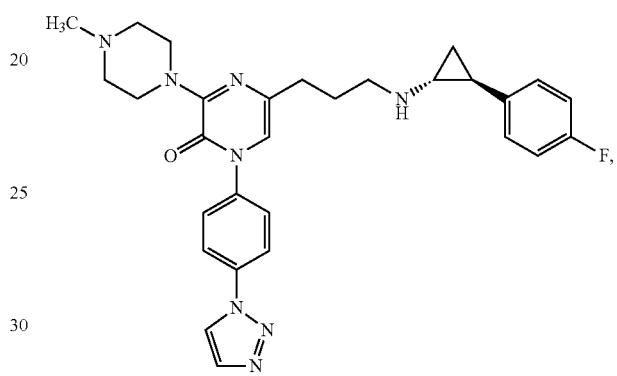
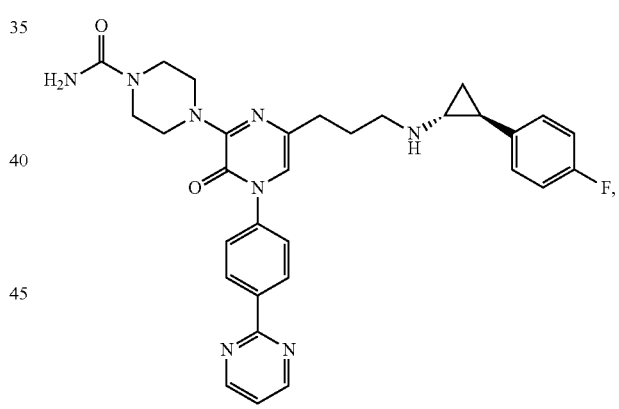

255
-continued
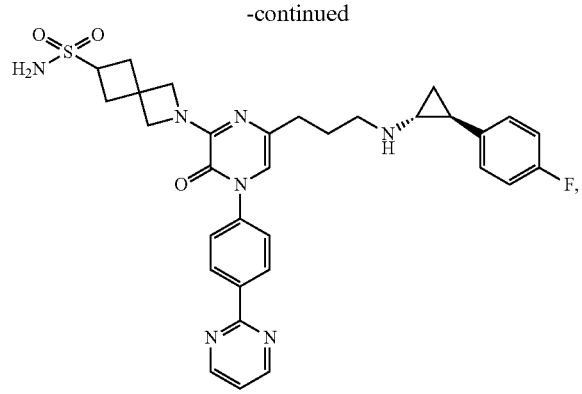
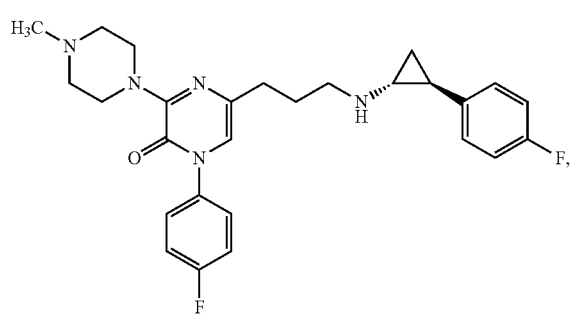
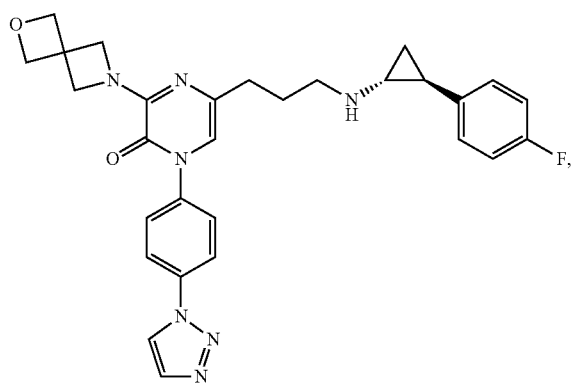
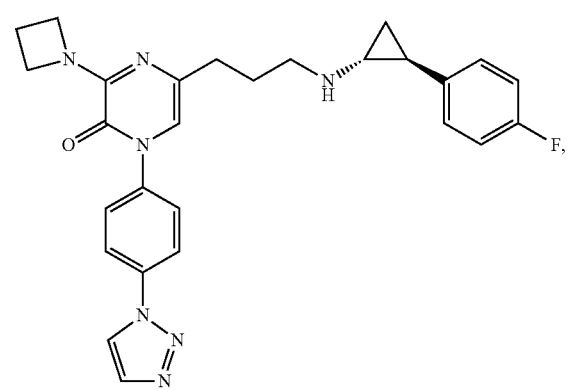
256
-continued
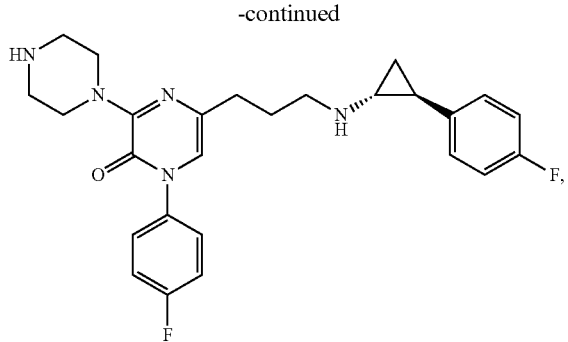
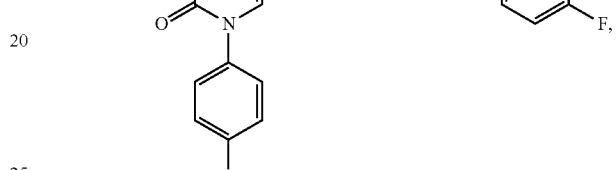
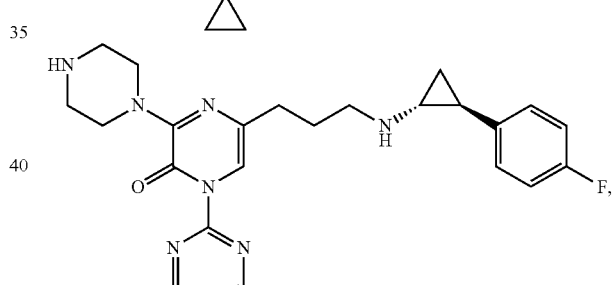
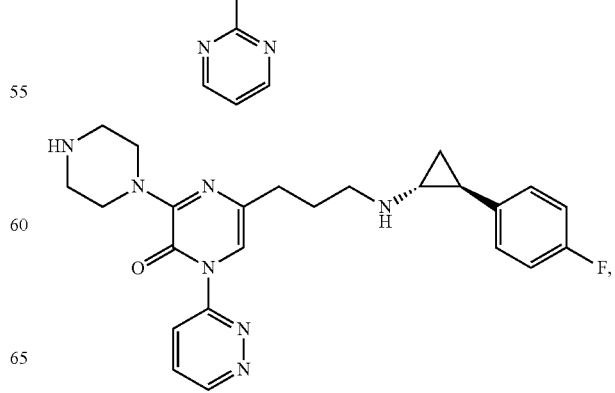

-continued

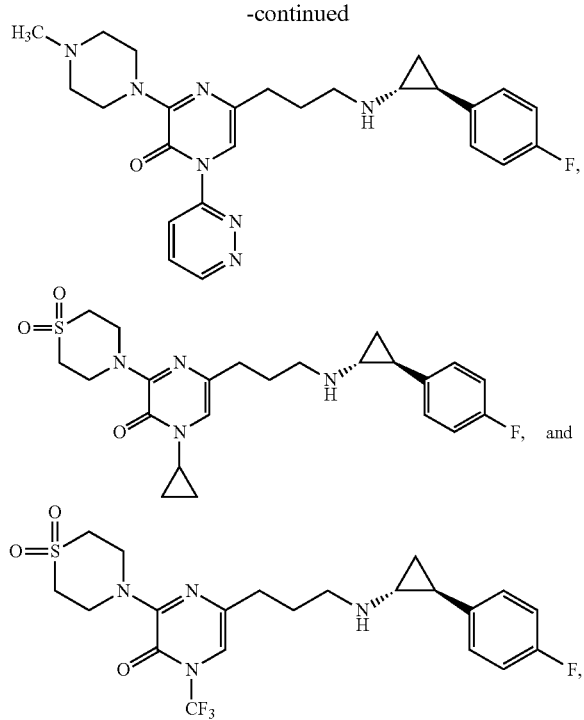

or a salt thereof.

25. A method of treatment of a KDM1A-mediated disease, comprising the administration of a therapeutically effective amount of a compound as recited in claim 1, or a salt thereof, to a patient having a KDM1A-mediated disease.

26. A method of treatment of a KDM1A-mediated disease, comprising the administration of:
a therapeutically effective amount of a compound as recited in claim 1, or a salt thereof; and
another therapeutic agent to a patient having a KDM1A-mediated disease.

27. A method of treatment of a globin-mediated disease comprising the administration of a therapeutically effective amount of a compound as recited in claim 1, or a salt thereof, to a patient having a globin-mediated disease.

28. A pharmaceutical composition comprising a compound as recited in claim 1, or a salt thereof, together with a pharmaceutically acceptable carrier.

29. A method for achieving an effect in a patient comprising the administration of a therapeutically effective amount of a compound, or a salt thereof, as disclosed herein, or a salt thereof, to a patient, wherein the effect is chosen from an elevation of red blood cell count, an elevation of the red blood cell count of red cells containing fetal hemoglobin, an elevation in the total concentration of fetal hemoglobin in red cells, an elevation in the total concentration of fetal hemoglobin in reticulocytes, an increase in the transcription of the gamma globin gene in bone marrow-derived red cell precursors, a reduction in the number of sickle cell crises a patient experiences over a unit period of time, a halt to or prevention of tissue damage in the heart, spleen, brain or kidney caused by sickling cells, a reduction in the proportion of red cells that undergo sickling under physiological conditions of relative hypoxia as measured using patient blood in an in vitro assay, an increase in the amount of histone 3 lysine methylation at lysine position 4 (H3K4me1 and H3K4me2), and/or a decrease in the amount of histone 3 methylation at lysine position 9 (H3K9me1 or H3K4me2) near or at the gamma globin promoter as assayed by ChIP using cells derived from a treated patient.

30. A method of inhibiting at least one KDM1A function comprising the step of contacting KDM1A with a compound as recited in claim 1, or a salt thereof, wherein the inhibition is measured by phenotype of red cells or their precursors, either cultured or in vivo, in humans or mouse or transgenic mice containing the human beta globin locus or portions thereof, the ability of cancer cells to proliferate, become differentiated, or induced to undergo apoptosis, the expression of specific genes known to be regulated by KDM1A activity, a change in the histone methylation states, a change in the methylation state of proteins known to be demethylated by KDM1A, expression of KDM1A-regulated genes, or binding of KDM1A with a natural binding partner.

* * * * *

UNITED STATES PATENT AND TRADEMARK OFFICE
CERTIFICATE OF CORRECTION

PATENT NO. : 11,578,059 B2
APPLICATION NO. : 17/054126
DATED : February 14, 2023
INVENTOR(S) : Amy E. Tapper et al.

It is certified that error appears in the above-identified patent and that said Letters Patent is hereby corrected as shown below:

In the Claims

At Column 252, Line 60, In Claim 24, replace:

"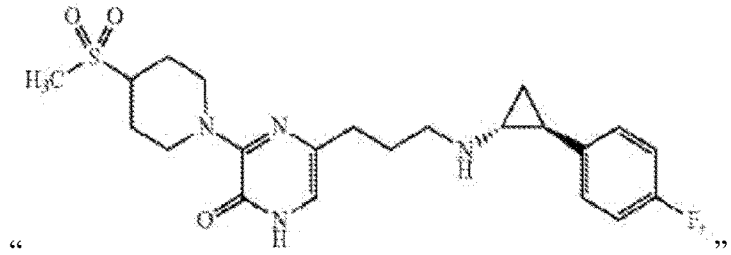"

With:

"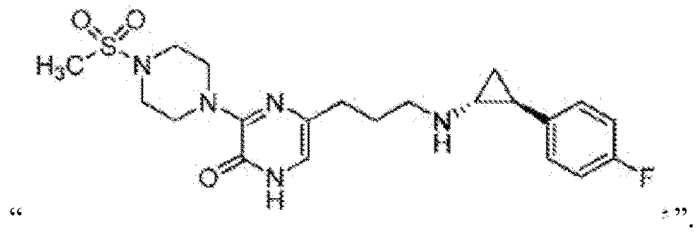".

Signed and Sealed this
Eighth Day of August, 2023

Katherine Kelly Vidal
*Director of the United States Patent and Trademark Office*

CERTIFICATE OF CORRECTION (continued)
U.S. Pat. No. 11,578,059 B2

At Column 254, Line 35, In Claim 24, replace:

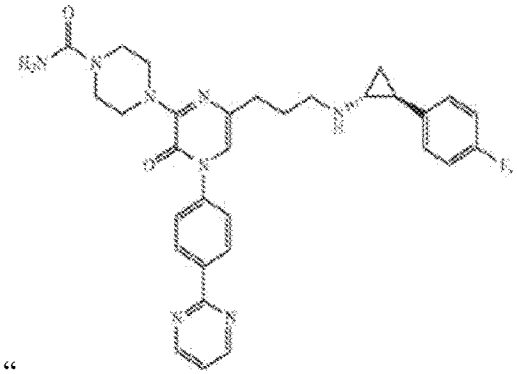

" "

With:

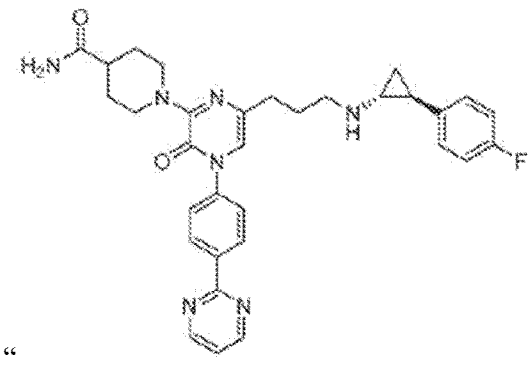

" ".